(12) United States Patent
Thorpe et al.

(10) Patent No.: US 7,056,509 B2
(45) Date of Patent: *Jun. 6, 2006

(54) ANTIBODY METHODS FOR SELECTIVELY INHIBITING VEGF

(75) Inventors: Philip E. Thorpe, Dallas, TX (US); Rolf A. Brekken, Seattle, WA (US)

(73) Assignee: Board of Regents The University of Texas System, Austin, TX (US)

( * ) Notice: Subject to any disclaimer, the term of this patent is extended or adjusted under 35 U.S.C. 154(b) by 379 days.

This patent is subject to a terminal disclaimer.

(21) Appl. No.: 10/373,561

(22) Filed: Feb. 24, 2003

(65) Prior Publication Data

US 2003/0175276 A1   Sep. 18, 2003

Related U.S. Application Data

(63) Continuation of application No. 09/561,499, filed on Apr. 28, 2000, now Pat. No. 6,524,583.

(60) Provisional application No. 60/131,432, filed on Apr. 28, 1999.

(51) Int. Cl.
  A61K 39/395 (2006.01)
  C12P 21/08 (2006.01)
  C07K 16/00 (2006.01)

(52) U.S. Cl. .............. 424/145.1; 424/130.1; 424/133.1; 424/184.1; 530/387.1; 530/388.1; 530/388.15; 530/388.25; 530/809; 530/864; 530/865; 530/866

(58) Field of Classification Search ......... 424/130.1, 424/145.1, 133.1, 184.1; 530/387.1, 338.1, 530/388.15, 388.25, 809, 864, 865, 866
See application file for complete search history.

(56) References Cited

U.S. PATENT DOCUMENTS

| | | | |
|---|---|---|---|
| 4,456,550 A | 6/1984 | Dvorak et al. |
| 4,925,922 A | 5/1990 | Byers et al. |
| 4,940,726 A | 7/1990 | Pettit et al. |
| 4,975,278 A | 12/1990 | Senter et al. |
| 5,008,196 A | 4/1991 | Connolly et al. |
| 5,036,003 A | 7/1991 | Olander et al. |
| 5,240,848 A | 8/1993 | Keck et al. |
| 5,354,778 A | 10/1994 | Ray et al. |
| 5,561,122 A | 10/1996 | Pettit |
| 5,569,786 A | 10/1996 | Pettit et al. |
| 5,587,297 A | 12/1996 | Jacobson et al. |
| 5,659,013 A | 8/1997 | Senger et al. |
| 5,660,827 A | 8/1997 | Thorpe et al. |
| 5,677,181 A | 10/1997 | Parish |
| 5,725,856 A | 3/1998 | Hudziak et al. |
| 5,730,977 A | 3/1998 | Ooka et al. |
| 5,776,427 A | 7/1998 | Thorpe et al. |
| 5,786,344 A | 7/1998 | Ratain et al. |
| 5,840,301 A | 11/1998 | Rockwell et al. |
| 5,854,205 A | 12/1998 | O'Reilly et al. |
| 5,855,866 A | 1/1999 | Thorpe et al. |
| 5,863,538 A | 1/1999 | Thorpe et al. |
| 5,866,127 A | 2/1999 | Senger et al. |
| 5,869,045 A | 2/1999 | Hellstrom et al. |
| 5,874,081 A | 2/1999 | Parish |
| 5,874,542 A | 2/1999 | Rockwell et al. |
| 5,877,289 A | 3/1999 | Thorpe et al. |
| 5,942,385 A | 8/1999 | Hirth |
| 5,965,132 A | 10/1999 | Thorpe et al. |
| 6,004,554 A | 12/1999 | Thorpe et al. |
| 6,004,555 A | 12/1999 | Thorpe et al. |
| 6,007,817 A | 12/1999 | Epstein et al. |
| 6,008,319 A | 12/1999 | Epstein et al. |
| 6,020,473 A | 2/2000 | Keyt et al. |
| 6,022,541 A | 2/2000 | Senger et al. |
| 6,024,955 A | 2/2000 | Asano et al. |
| 6,036,955 A | 3/2000 | Thorpe et al. |
| 6,051,230 A | 4/2000 | Thorpe et al. |
| 6,093,399 A | 7/2000 | Thorpe et al. |
| 6,121,230 A | 9/2000 | Charnock-Jones et al. |
| 6,291,667 B1 | 9/2001 | Gill et al. |
| 6,342,219 B1 | 1/2002 | Thorpe et al. |
| 6,342,221 B1 | 1/2002 | Thorpe et al. |
| 6,416,758 B1 | 7/2002 | Thorpe et al. |
| 6,524,583 B1 | 2/2003 | Thorpe et al. |
| 6,582,959 B1 | 6/2003 | Kim |
| 6,676,941 B1 | 1/2004 | Thorpe et al. |
| 6,703,020 B1 | 3/2004 | Thorpe et al. |
| 2002/0032315 A1 | 3/2002 | Baca et al. |
| 2002/0098187 A1 | 7/2002 | Ferrara et al. |

(Continued)

FOREIGN PATENT DOCUMENTS

EP       0 484 401 B1      9/1996

(Continued)

OTHER PUBLICATIONS

Storkebaum et al., "VEGF: Once Regarded as a Specific Angiogenic Factor, Now Implicated in Neuroprotection," *BioEssays*, 26:943-954, 2004.

(Continued)

*Primary Examiner*—Christina Chan
*Assistant Examiner*—Phuong N Huynh
(74) *Attorney, Agent, or Firm*—Shelley P. M. Fussey

(57) ABSTRACT

Disclosed are antibodies that specifically inhibit VEGF binding to only one (VEGFR2) of the two VEGF receptors. The antibodies effectively inhibit angiogenesis and induce tumor regression, and yet have improved safety due to their specificity. The present invention thus provides new antibody-based compositions, methods and combined protocols for treating cancer and other angiogenic diseases. Advantageous immunoconjugate and prodrug compositions and methods using the new VEGF-specific antibodies are also provided.

22 Claims, 4 Drawing Sheets

U.S. PATENT DOCUMENTS

| | | | |
|---|---|---|---|
| 2003/0086919 | A1 | 5/2003 | Rosenblum et al. |
| 2003/0190317 | A1 | 10/2003 | Baca et al. |
| 2003/0203409 | A1 | 10/2003 | Kim |
| 2003/0206899 | A1 | 11/2003 | Ferrara et al. |

FOREIGN PATENT DOCUMENTS

| | | |
|---|---|---|
| EP | 0 666 868 B1 | 4/2002 |
| WO | WO 90/13649 | 11/1990 |
| WO | WO 91/02058 | 2/1991 |
| WO | WO 92/14748 | 9/1992 |
| WO | WO 93/08210 | 4/1993 |
| WO | WO 93/17715 | 9/1993 |
| WO | WO 94/10202 | 5/1994 |
| WO | WO 94/11499 | 5/1994 |
| WO | WO 95/21868 | 8/1995 |
| WO | WO 96/01653 | 1/1996 |
| WO | WO 98/45331 | 10/1998 |
| WO | WO 98/45332 | 10/1998 |
| WO | WO99/40118 | 8/1999 |
| WO | WO 00/34337 | 6/2000 |
| WO | WO 00/37502 | 6/2000 |
| WO | WO 01/54723 A1 | 8/2001 |

OTHER PUBLICATIONS

Fishman et al., "Autoimmunity and Cancer—Beneficial Relationships: A New Concept for the Production of Human Monoclonal Antibodies (Review)," *Int. J. Oncol.*, 10:901-904, 1997.

Tschmelitsch et al., "Enhanced Antitumor Activity of Combination Radioimmunotherapy ($^{131}$1-Labeled Monoclonal Antibody A33) with chemotherapy (Fluorouracil)," *Cancer Res.*, 57:3181-3186, 1197.

Ben-Hur and Orenstein, "The Endothelium and Red Blood Cell as Potential Targets in PDT-Induced Vascular Stasis," *J. Radiat. Biol.*, 60(1/2):293-301, 1991.

Folkman, "Tumor Angiogenesis," *Adv. Cancer Res.*, 43:175-203, 1985.

Gschwind et al., "The Discovery of Receptor Tyrosine Kinases: Targets for Cancer Therapy," *Nature Reviews/Cancer*, 4:361-370, 2004.

Martiny-Baron and Marmé, "VEGF-Mediated Tumour Angiogenesis: A New Target for Cancer Therapy," *Curr. Opin. Biotech.*, 6:675-680, 1995.

McDonald and Baluk, "Significance of Blood Vessel Leakiness in Cancer," *Cancer Research*, 62:5381-5385, 2002.

Murata et al., "Immunohistochemical Detection of Extravasated Fibrinogen (Fibrin) in Human Diabetic Retina," *Graefe's Arch. Clin. Exp. Opthalmol.*, 230:428-431, 1992.

Risau, "What, if anything, is an Angiogenic Factor?" *Cancer Metastasis Rev.*, 15:149-151, 1996.

Senger et al., "Tumor Cells Secrete a Vascular Permeability Factor That Promotes Accumulation of Ascites Fluid," *Science*, 219:983-985, 1983.

Sioussat et al., "Inhibition of Vascular Permeability Factor (Vascular Endothelial Growth Factor) with Antipeptide Antibodies," *Arch. Biochem. Biophys.*, 301(1):15-20, 1993.

Wiig et al., "Interstitial Fluid Pressure in DMBA-Induced Rat Mammary Tumours," *Scand. J. Clin. Lab. Invest.*, 42:159-164, 1982.

Stephan et al., "Effect of Rapamycin Alone and in Combination with Antiangiogenesis Therapy in an Orthotopic Model of Human Pancreatic Cancer," *Clin. Can. Res.*, 10:6993-7000, 2004.

Aiello, "Suppression of Retinal Neovascularization In Vivo by Inhibition of Vascular Endothelial Growth Factor (VEGF) Using Soluble VEGF-Receptor Chimeric Proteins," *Proc. Natl. Acad. USA*, 92:10457-10461, 1995.

Broadley et al., "Monospecific Antibodies Implicate Basic Fibroblast Growth Factor in Normal Wound Repair," *Lab. Invest.*, 61(5):571-575, 1989.

Brock et al., "Tumor-Secreted Vascular Permeability Factor Increases Cytosolic $Ca^{2+}$ and von Willebrand Factor Release in Human Endothelial Cells," *Am. J. Path.*, 138(1):213-221, 1991.

Brown et al., "Leaky Vessels, Fibrin Deposition, and Fibrosis: A Sequence of Events Common to Solid Tumors and to Many Types of Disease," *Am. Rev. Respir. Dis.*, 140:1104-1107, 1989.

Clauss et al., "Vascular Permeability Factor: A Tumor-Derived Polypeptide that Induces Endothelial Cell and Monocyte Procoagulant Activity, and Promotes Monocyte Migration," *J. Exp. Med.*, 172:1535-1545, 1990.

Conn et al., "Purification of a Glycoprotein Vascular Endothelial Cell Mitogen from a Rat Glioma-Derived Cell Line," *Proc. Nat. Acad. Sci. USA*, 87:1323-1327, 1990.

Conn et al., "Amino Acid and cDNA Sequences of a Vascular Endothelial Cell Mitogen that is Homologous to Platelet-Derived Growth Factor," *Proc. Natl. Acad. Sci. USA*, 87:2628-2632, 1990.

Connolly, "Vascular Permeability Factor: A Unique Regulator of Blood Vessel Function," *J. Cell Biochem.*, 47:219-223, 1991.

Connolly, "Tumor Vascular Permeability Factor Stimulates Endothelial Cell Growth and Angiogenesis," *J. Clin. Invest.*, 84:1470-1478, 1989.

Denekamp, "Vasculature as a Target for Tumour Therapy," *Prog. Appl. Microcirc.*, 4:28-38, 1984.

Dennis and Rifkin, "Studies on the Role of Basic Fibroblast Growth Factor In Vivo: Inability of Neutralizing Antibodies to Block Tumor Growth," *J. Cell. Physiol.*, 144:84-98, 1990.

Dvorak et al., "Vascular Permeability Factor, Fibrin, and the Pathogenesis of Tumor Stroma Formation," *Ann. N.Y. Acad. Sci.*, 667:101-111, 1992.

Dvorak, "Leaky Tumor Vesssels: Consequences for Tumor Stroma Generation and for Solid Tumor Therapy," *Progress in Clinical and Bioilogical Research*, 354a: 317-330, 1990.

Dvorak, "Tumors: Wounds That Do Not Heal," *New Eng. J. Med.*, 315(26):1650-1659, 1986.

Dvorak et al., "Regulation of Extravascular Coagulation by Microvascular Permeability," *Science*, 227:1059-1061, 1985.

Dvorak et al., "Fibrin as a Component of the Tumor Stroma: Origins and Biological Significance," *Cancer Metastasis Reviews*, 2:41-73, 1983.

Ferrara et al., "Expression of Vascular Endothelial Growth Factor Does Not Promote Transformation but Confers a Growth Advantage In Vivo to Chinese Hamster Ovary Cells," *J. Clin. Invest.*, 91:160-170, 1993.

Ferrara et al., "The Vascular Endothelial Growth Factor Family of Polypeptides," *J. Cell. Biochem.*, 47:211-218, 1991.

Ferrara and Henzel, "Pituitary Follicular Cells Secrete A Novel Heparin Binding Growth Factor Specific for Vascular Endothelial Cells." *Biochem. Biophys. Res. Comm.*, 161(2):851-858, 1989.

Ferrara et al., "Molecular Characterization and Distribution of Vascular Endothelial Growth Factor," *J. Cell Biochem. Supp.*, 151(part F):p211, 1991, Abstract No. CF016.

Folkman and Ingber, "Inhibition of Angiogenesis," *Seminars in Cancer Biology*, 3:89-96, 1992.

Folkman and Shing, "Angiogenesis," *J. Biol. Chem.,* 267(16):10931-10934, 1992.

Folkman et al., "Induction of Angiogenesis During the Transition from Hyperplasia to Neoplasia," *Nature,* 339:58-61, 1989.

Folkman, "What is the Evidence that Tumors are Angiogenesis Dependent?," *J. Natl. Cancer Inst.,* 82(1):4-6, 1990.

Folkman and Klagsbrun, "Angiogenic Factors," *Science,* 235:442-447, 1987.

Gospodarowicz et al., "Isolation and Characterization of a Vascular Endothelial Cell Mitogen Produced by Pituitary-Derived Folliculo Stellate Cells," *Proc. Natl. Acad. Sci.,* 86:7311-7315, 1989.

Greenblatt and Shubi, "Tumor Angiogenesis: Transfilter Diffusion Studies in the Hamster by the Transparent Chamber Technique," *J. Natl. Cancer Inst.,* 41:111-124, 1968.

Houck et al., "The Vascular Endothelial Growth Factor Family: Identification of a Fourth Molecular Species and Characterization of Alternative Splicing of RNA," *Molecular Endocrinology,* 5:1806-1814, 1991.

Jain, "Haemodynamic and Transport Barriers to the Treatment of Solid Tumours," *Int. J. Radiat. Biol.,* 60(1/2):85-100, 1991.

Jakeman et al., "Binding Sites for Vascular Endothelial Growth Factor are Localized on Endothelial Cells in Adult Rat Tissues," *J. Clin. Invest.,* 89:244-253, 1992.

Keck et al., "Vascular Permeability Factor, an Endothelial Cell Mitogen Related to PDGF," *Science,* 246:1309-1312, 1989.

Kerbel, "Inhibition of Tumor Angiogenesis as a Strategy to Circumvent Acquired Resistance to Anti-Cancer Therapeutic Agents," *BioEssays,* 13(1):31-36, 1991.

Leung et al., "Cloning, Expression During Development, and Evidence for release of a Trophic Factor for Ciliary Ganglion Neurons," *Neuron,* 8:1045-1053, 1992.

Leung et al., "Vascular Endothelial Growth Factor is a Secreted Angiogenic Mitogen," *Science,* 246:1306-1308, 1989.

Li et al., "Monoclonal Antibodies to Recombinant Human Vascular Endothelial Growth Factor (rHuVEGF)," *J. Cell. Biochem.,* Supp. 15F:251, Abstract CF417, 1991.

Pepper et al., "Potent Synergism Between Vascular Endothelial Growth Factor and Basic Fibroblast Growth Factor in the Induction of Angiogenesis In Vitro" *Biochem. Biophys. Res. Comm.,* 189(2):824-831, 1992.

Plate, "Vascular Endothelial Growth Factor is a Potential Tumour Angiogenesis Factor in Human Gliomas *In Vivo,*" *Nature,* 359:845-848, 1992.

Plouet et al., "Isolation and Characterization of a Newly Identified Endothelial cell Mitogen Produced by AtT-20 Cells," *EMBO,* 8(12):3801-3806, 1989.

Roberts and Palade, "Increased Microvascular Permeability and Endothelial Fenestration Induced by Vascular Endothelial Growth Factor," *J. Cell Sci.,* 108;2369-2379, 1995.

Senger et al., "A Highly Conserved Vascular Permeability Factor Secreted by a Variety of Human and Rodent Tumor Cell Lines," *Cancer Research,* 46:5629-5632, 1986.

Senger et al., "Purification and $NH_2$-Terminal Amino Acid Sequence of Guinea Pig Tumor-Secreted Vascular Permeability Factor," *Cancer Research,* 50:1774-1778, 1990.

Shweiki et al., Vascular Endothelial Growth Factor Induced by Hypoxia May Mediate Hypoxia-Initiated Angiogenesis, *Nature,* 359:843-845, 1992.

Sioussat et al., "Anti-Peptide Antibodies to Vascular Permeability Factor," *J. Cell Biol.,* 115(3 part 2):p. 264a, Abstract No. 1528, 1991.

Tischer et al., "Vascular Endothelial Growth Factor: A New Member of the Platelet-Derived Growth Factor Gene Family," *Biochem. Biophys Res. Comm.,* 165(3):1198-1206, 1989.

Van Brugen et al., "VEGF Antagonism Reduces Edema Formation and Tissue Damage After Ischemia/Reperfusion Injury in the Mouse Brain," *J. Clin. Invest.,* 104(11):1613-1620, 1999.

Weidner, "Tumor Angiogenesis and Metastasis-Correlation in Invasive Breast Carcinoma," *New. Eng. J. Med.,* 324(1):1-7, 1991.

Yeo et al., Vascular Permeability Factor (Vascular Endothelial Growth Factor) in Guinea Pig and Human Tumor and Inflammatory Effusions, *Cancer Research,* 53:2912-2918, 1993.

Yeo et al., "Development of Time-Resolved Immunofluorometric Assay of Vascular Permeability," *Clin. Chem.,* 38(1):71-75, 1992.

Attwood, "The Babel of Bioinformatics," *Science,* 290(5491):471-473, 2000.

Mikayama et al., "Molecular Cloning and Functional Expression of a cDNA Encoding Glycosylation-Inhibiting Factor," *Proc. Natl. Acad. Sci. USA,* 90:10056-10060, 1993.

Voet et al., "Chemical Evolution," *In, Biochemistry* I, Voet & Voet, pp. 126-234, 1990.

Connolly et al., "Human Vascular Permeability Factor," *J. Biol. Chem.,* 264(33):20017-20024, 1989.

Ferrara et al., "Molecular and Biological Properties of the Vascular Endothelial Growth Factor Family of Proteins," *Endocrine Reviews,* 13(1):18-32, 1992.

Hori et al., "Suppression of Solid Tumor Growth by Immunoneutralizing Monoclonal Antibody Against Human Basic Fibroblast Growth Factor," *Cancer Res.,* 51:6180-6184, 1991.

Takahashi et al., "Inhibition of Cell Growth and Tumorigenesis of Human Glioblastoma Cells by a Neutralizing Antibody Against Human Basic Fibroblast Growth Factor," *FEBS Lett.,* 288(1,2):65-71, 1991.

Colman, "Effects of Amino Acid Sequence Changes on Antibody-Antigen Limitations," *In a Structural View of Immune Recognition by Antibodies,* 33-36, 1994.

Wang et al., "The Effect of Antibody Against Vascular Endothelial Growth Factor on Tumor Growth and Metastasis," *J. Can. Res. Clin. Oncol.,* 124(11):615-620, 1998 (Abstract only).

Abaza and Atassi, "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin,". *J. Protein Chem.,* 11(5):433-444, 1992.

Bodey et al., "Failure of Cancer Vaccines: The Significant Limitations of this Approach to Immunotherapy," *Anticancer Research,* 20:2665-2676, 2000.

Ezzell et al., "Cancer "Vaccines": An Idea Whose Time Has come?, " *J. NIH Research,* 7:46-49, 1995.

Ngo et al., "Computational Complexity, Protein Structure Prediction, and the Levinthal Paradox," *The Protein Folding Problem and Tertiary Structure Prediction,* 14:492-495, 1994.

Skolnick and Fetrow, "From Genes to Protein Structure and Function: Novel Applications of Computational Approaches in the Genomic Era," *TIBTECH,* 18:34-39, 2000.

Spitler, "Cancer Vaccines: The Interferon Analog," *Cancer Biotherapy,* 10(1):1-3, 1995.

Thorpe, "Vascular Targeting Agents as Cancer Therapeutics," *Clin. Can. Res.,* 10:415-427, 2004.

Hardman et al., In Goodman & Gilman's The Pharmacological Basis of Therapeutics Ninth Edition, pp. 51 and 57-58, 1996.

De Bandt et al., "Blockade of Vascular Endothelial Growth Factor Receptor I (VEGF-RI) but not VEGF-RII, Suppresses Joint Destruction in the K/BxN Model of Rheumatoid Arthritis," *J. Immunol.,* 171:4853-4859, 2003.

LeCouter et al., "Angiogenesis-Independent Endothelial Protection of Liver: Role of VEGFR-1," *Science,* 299:890-893, 2003.

Maes et al., "Soluble VEGF Isoforms are Essential for Establshing Epiphyseal Vascularization and Regulating Chondrocyte Development and Survival," *J. Clin. Invest.,* 113:188-199, 2004.

Pipp et al., "VEGFR-1-Selective VEGF Homologue PIGF is Arteriogenic Evidence for a Monocyte-Mediated Mechanism," *Circ. Res.,* 92:1-9, 2003.

Qi et al., "A Novel Function for Tissue Inhibitor of Metalloproteinases-3 (TIMP3): Inhibition of Angiogenesis by Blockage of VEGF Binding to VEGF Receptor-2," *Nature Medicine,* 9(4):407-415, 2003.

Shih et al., "Selective Stimulation of VEGFR-1 Prevents Oxygen-Induced Retinal Vascular Degeneration in Retinopathy of Prematurity," *J. Clin. Invest.,* 112:50-57, 2003.

Akuzawa, et al., "Zinc Finger Transcription Factor Egr-1 Activates Flt-1 Gene Expression in THP-1 Cells on Induction for Macrophage Differentiation", *Arteriosclerosis, Thrombosis, and Vascular Biology,* 20(2):377-84, 2000.

Asano et al., "Inhibition of Tumor Growth and Metastasis by an Immunoneutralizing Monoclonal Antibody to Human Vascular Endothelial Growth Factor/Vascular Permeability Factor," *Cancer Res.,* 55:5296-5301, 1995.

Asano, et al., "An Anti-human VEGF Monoclonal Antibody, MV833, that Exhibits Potent Anti-tumor Activity *in vivo*," *Hybridoma,* 17:185-90. 1998.

Baca et al , "Antibody Humanization using Monovalent Phage Fisplay," *J. Biol. Chem.,* 272(16):10678-84. 1997.

Benjamin et al., "Selective Ablation of Immature Blood Vessels in Established Human Tumors Follows Vascular Endothelial Growth Factor Withdrawal," *J. Clin. Invest.,* 103(2):159-165, 1999.

Borgstrom, et al., "Complete Inhibition of Angiogenesis and Growth of Microotumors by Anti-vascular Endothelial Growth Factor Neutralizing Antibody: Novel Concepts of Angiostatic Therapy from Intravital Videomicroscopy," *Cancer Res.,* 56(17):4032-1439, 1996.

Borgstrom, et al., "Neutralizing Anti-vascular Endothelial Growth Factor Antibody Completely Inhibits Angiogenesis and Growth of Human Prostate Carcinoma Micro Tumors *in vivo,*" *Prostate,* 35(1):1-10, 1998.

Borgstrom, et al., "Importance of VEGF for Breast Cancer Angiogenesis *in vivo*: Implications from Intravital Microscopy of Combination Treatments with an Anti-VEGF Neutralizing Monoclonal Antibody and Doxorubicin," *Anticancer Research,* 19(5B):4203-11, 1999.

Brekken, "Vascular Endothelial Growth Factor as a Target for the Therapy of Solid Tumors," *Ph.D. Dissertation, The University of Texas Southwestern Medical Center at Dallas,* Feb., 1999; vol. 60104-B of Dissertation Abstracts International, p. 1385.

Brekken, et al., "Vascular Endothelial Growth Factor as a Marker of Tumor Endothelium," *Cancer Res.,* 58(9):1952-1959, 1998.

Burrows and Thorpe, "Vascular Targeting-a New Approach to the Theraphy of Solid Tumors," *Pharmacol. Ther.,* 64:155-174, 1994.

Burrows et al., "A Murine Model for Antibody-Directed Targeting of Vascular Endothelial Cells in Solid Tumors," *Cancer Research,* 52:5954-5962, 1992.

Burrows and Thorpe, "Eradication of Large Solid Tumors in Mice with an Immunotoxin Directed Against Tumor Vasculature," *Proc. Natl. Acad. Sci. USA,* 90:8996-9000, 1993.

Claffey, et al., "Expression of Vascular Permeability Factor/Vascular Endothelial Growth Factor by Melanoma Cells Increases Tumor Growth, Angiogenesis, and Experimental Metastasis," *Cancer Res.,* 56:172-181, 1996.

Clauss et al., "The Vascular Endothelial Cell Growth Factor Receptor Flt-1 Mediates Biological Activities," *J. Biol. Chem.,* 271(30):17629-17634, 1996.

Davis and Yancopoulos, "The Angiopoietins: Yin and Yang in Angiogenesis", *Curr. Top. Microbiol. Immunol.,* 237:173-85, 1999.

Denekamp, "Vascular Attack as a Therapeutic Strategy for Cancer," *Cancer and Metastasis Reviews,* 9:267-282, 1990.

Dvorak et al., "Structure of Solid Tumors and Their Vasculature: Implications for Therapy with Monoclonal Antibodies," *Cancer Cells,* 3:77-85, 1991.

Dvorak, et al., "Distribution of Vascular Permeability Factor (Vascular Endothelial Growth Factor) in Tumors—Concentration in Tumor Blood Vessels." *J. Exp. Med.,* 174:1275-1278, 1991.

Fidler and Ellis, "The Implications of Angiogenesis for the Biology and Therapy of Cancer Metastasis [comment]," *Cell,* 79(2):185-188, 1994.

Fong, et al , "Role of the Flt-1 Receptor Tyrosine Kinase in Regulating the Assembly of Vascular Endothelium," *Nature,* 376:66-70, 1995.

Gerber, et al., "VEGF Couples Hypertrophic Cartilage Remodeling, Ossification and Angiogenesis During Endochondral Bone Formation"; *Nature Medicine,* 5(6):623-8, 1999.

Hagemeier et al., "A Monoclonal Antibody Reacting with Endothelial Cells of Budding Vessels in Tumors and Inflammatory Tissues, and Non-Reactive with Normal Adult Tissues," *Int. J. Cancer,* 38:481-488, 1986.

Hanahan and Folkman, "Patterns and Emerging Mechanisms of the Angiogenic Switch During Tumorigenesis," *Cell,* 86(3):353-364, 1996.

Hiratsuka, et al., "Flt-1 Lacking the Tyrosine Kinase Domain is Sufficient for Normal Development and Angiogenesis in Mice," *Proc. Natl. Acad. Sci. USA,* 95 (16):9349-9354, 1998.

Holash et al , "Vessel Cooption, Regression, and Growth in Tumors Mediated by Angiopoietins and VEGF". *Science,* 284:1994-1998, 1999.

Huang et al., "Tumor Infarction in Mice by Antibody-Directed Targeting of Tissue Factor to Tumor Vasculature," *Science,* 275:547-550, 1997.

Keyt et al., "Identification of Vascular Endothelial Growth Factor Determinants for Binding KDR and FLT-1 Receptors. Generation of Receptor-Selective VEGF Variants by Site- Directed Mutagenesis," *J. Biol. Chem.,* 271(10):5638-46, 1996.

Kim, et al., "The Vascular Endothelial Growth Factor Proteins: Identification of Biologically Relevant Regions by Neutralizing Monoclonal Antibodies," *Growth Factors,* 7:53-64, 1992.

Kim, et al., "Inhibition of Vascular Endothelial Growth Factor-Induced Angiogenesis Suppresses Tumor Growth *in vivo,*" *Nature,* 362:841-844, 1993.

Kondo, et al., "Significance of Vascular Endothelial Growth Factor/Vascular Permeability Factor for Solid Tumor Growth, and its Inhibition by the Antibody," *Biochem. Biophys. Res. Commun.,* 194:1234-1241, 1993.

Koukourakis, et al., "Vascular Endothelial Growth Factor/KDR Activated Microvessel Density versus CD31 Standard Microvessel Density in Non-Small Cell Lung Cancer," *Cancer Res.,* 60:3088-3095, 2000.

Kroll and Waltenberger, "The Vascular Endothelial Growth Factor Receptor KDR Activates Multiple Signal Transduction Pathways in Porcine Aortic Endothelial Cells", *J. Biol. Chem.,* 272:32521-7, 1997.

Lin, et al., "Preclinical Pharmacokinetics, Interspecies Scaling, and Tissue Distribution of a Humanized Monoclonal Antibody Against Vascular Endothelial Growth Factor", *J. Pharmacol. Exp. Therap.,* 288(1):371-8, 1999.

Lin-Ke, et al., "Vascular Targeting of Solid and Ascites Tumors with Antibodies to Vascular Endothelial Growth Factor," *Eur. J. Cancer,* 32A(14):2467-2473, 1996.

Luo, et al., "Differential Inhibition of Fluid Accumulation and Tumor Growth in Two Mouse Ascites Tumors by an Antivascular Endothelial Growth Factor/Permeability Factor Neutralizing Antibody," *Cancer Res.,* 58(12):2594-2600, 1998.

Luo, et al., "Significant Expression of Vascular Endothelial Growth Factor/Vascular Permeability Factor in Mouse Ascites Tumors," *Cancer Res.,* 58(12):2652-2660, 1998.

Mesiano, et al., "Role of Vascular Endothelial Growth Factor in Ovarian Cancer: Inhibition of Ascites Formation by Immunoneutralization," *Am. J. Pathol.,* 153(4):1249-1256, 1998.

Mordenti, et al., "Efficacy and Concentration-Response of Murine Anti-VEGF Monoclonal Antibody in Tumor-Bearing Mice and Extrapolation to Humans", *Toxicologic Pathology,* 27(1):14-21. 1999.

Muller, et al., "VEGF and the Fab Fragment of a Humanized Neutralizing Antibody: Crystal Structure of the Complex at 2.4 A Resolution and Mutational Analysis of the Interface," *Structure,* 6(9):1153-67, 1998.

Mustonen and Alitalo, "Endothelial Receptor Tyrosine Kinases Involved in Angiogenesis," *J. Cell Biol.,* 129:895-898, 1995.

Niida, et al., "Vascular Endothelial Growth Factor can Substitute for Macrophage Colony-Stimulating Factor in the Support of Osteoclastic Bone Resorption", *J. Exp. Med.,* 190(2):293-8, 1999.

Ohizumi et al., "Antibody-Based Therapy Targeting Tumor Vascular Endothelial Cells Suppresses Solid Tumor Growth in Rats," *Biochem. Biophys. Res. Comm.,* 236:493-496, 1997.

Presta, et al., "Humanization of an Anti-Vascular Endothelial Growth Factor Monoclonal Antibody for the Therapy of Solid Tumors and other Disorders," *Cancer Res.,* 57:4593-4599, 1997.

Ran et al., "Infarction of Solid Hodgkin's Tumors in Mice by Antibody-Directed Targeting of Tissue Factor to Tumor Vasculature," *Cancer Res.,* 58:4646-4653, 1998.

Ruf and Edgington, "Structural Biology of Tissue Factor, the Initiator of Thrombogenesis *in vivo,*" *FASEB J.,* 8: 385-390, 1994.

Ryan, et al., "Preclinical Safety Evaluation of rhuMAbVEGF, an Antiangiogenic Humanized Monoclonal Antibody", *Toxicologic Pathology,* 27(1):78-86, 1999.

Schlaeppi and Wood, "Targeting Vascular Endothelial Growth Factor (VEGF) for Anti-Tumor Therapy, by Anti-VEGF Neutralizing Monoclonal Antibodies or by VEGF Receptor Tyrosine-Kinase Inhibitors," *Cancer and Metastasis Rev.,* 18:473-481, 1999.

Shalaby, et al., "Failure of Blood-Island Formation and Vasculogenesis in Flk-1-Deficient Mice," *Nature,* 376:62-66, 1995.

Siemeister, et al., "The Pivotal Role of VEGF in Tumor Angiogenesis: Molecular Facts and Therapeutic Opportunities," *Cancer Metastasis Rev.,* 17(2):241-248, 1998.

Sioussat, et al., "Inhibition of Vascular Permeability Factor (Vascular Endothelial Growth Factor) with Antipeptide Antibodies," *Arch. Biochem. Biophys.,* 301:15-20, 1993.

Veikkola, et al., "Regulation of Angiogenesis via Vascular Endothelial Growth Factor Receptors," *Cancer Res.,* 60-203-212, 2000.

Waltenberger, et al., "Different Signal Transduction Properties of KDR and Flt1, Two Receptors for Vascular Endothelial Growth Factor," *J. Biol. Chem.,* 269(43):26988-26995, 1994.

Wiesmann, et al., "Crystal Structure at 1.7 A Resolution of VEGF in Complex with Domain 2 of the Flt-1 Receptor," *Cell,* 91(5):695-704, 1997.

Deonarain and Epenetos, "Targeting Enzymes for Cancer Therapy: Old Enzymes in New Roles," *Br. J. Cancer,* 70(5):786-794, 1994.

Giorgio et al., "Ellipticine Conjugated to Anti VEGFR2 Monoclonal Antibodies as Reagents for Targeting angiogenesis," *Proc. Amer. Assoc. Can. Ann.,* 41:387, 2000.

Haisma et al., "Analysis of a Conjugate between Anti-Carcinoembryonic Antigen Monoclonal Antibody and Alkaline Phosphatase for specific Activation of the Prodrug Etoposide Phosphate," *Cancer Immunol. Immunother.,* 34(5):343-348, 1992.

Huber et al., "Vascular Endothelial Growth Factor Receptor (VEFGR-2) Antibody Therapy Combined with Conventional Chemotherapy Inhibits Growth of Established Tumors in Mice," *Proc. Amer. Assoc. Cancer Res. Ann.,* 41:567, 2000.

Muller et al., "Vascular Endothelial Growth Factor: Crystal Structure and Functional Mapping of the Kinase Domain Receptor Binding Site," *Proc. Natl. Acad. Sci. USA,* 94(14):7192-7197, 1997.

Ortega et al., "Signal Relays in the VEGF System," *Frontiers in Bioscience,* 4:D141-152, 1999.

Witte et al., "Monoclonal Antibodies Targeting the VEGF Receptor-2 (Flk1/KDR) as an Anti-Angiogenic Therapeutic Strategy," *Cancer and Metastasis Reviews,* 17(2):155-161, 1998.

Kuby. "Antigens." *Immunology. Second Edition, Chapter 4,* 85-96, 1994.

Waldman, "Monoclonal Antibodies in Diagnosis and Therapy," *Science,* 252:1657-1662, 1991.

Heimbrook et al., "Transforming growth factor α-*Pseudomonas* exotoxin fusion protein prolongs survival of nude mice bearing tumor xenografts." *Proc. Natl. Acad. Sci. USA,* 87:4697-4701, 1990.

Hirota et al., "Suppression of an epidermal growth factor receptor-hyperproducing tumor by an immunotoxin conjugate of gelonin and a monoclonal anti-epidermal growth factor receptor antibody," *Cancer Research,* 49:7106-7109, 1989.

Plate et al., "Up-regulation of vascular endothelial growth factor and its cognate receptors in a rat glioma model of tumor angiogenesis," *Cancer Research,* 53(23):5822-5827,1993.

Denekamp, "Endothelial Cell Attack as a Novel Approach to Cancer Therapy," *Cancer Topics.* 6:6-8, 1986.

Denekamp, The Current Status of Targeting Tumor Vasculature as a Means of Cancer Therapy: An Overview, *Int. J. Radiat. Biol.,* 60:401-408. 1991.

Bicknell and Harris, "Anticancer Strategies Involving the Vasculature: Vascular Targeting and the Inhibition of Angiogenesis," *Seminars in Cancer Biology,* 3:399-407, 1992.

Bicknell and Harris, "Novel Growth Regulatory Factors and Tumour Angiogenesis," *Eur. J. Cancer,* 27(6):781-785, 1991.

Alvarez et al., "Localization of Basic Fibroblast Growth Factor and Vascular Endothelial Growth Factor in Human Glial Neoplasms," *Modern Pathology,* 5(3):303-307, 1992.

Auerbach, "Vascular Endothelial Cell Differentiation: Organ-Specificity and Selective Affinities as the Basis for Developing Anti-Cancer Strategies," *Int. J. Radiat. Biol.,* 60(1/2):Jan., 10, 1991.

Baird et al., "Immunoreactive Fibroblast Growth Factor (FGF) in a Transplantable Chondrosarcoma: Inhibition of Tumor Growth by Antibodies to FGF," *J. Cell. Biochem.,* 36:79-85, 1986.

Berse et al., "Vascular Permeability Factor (Vascular Endothelial Growth Factor) Gene is Expressed Differentially in Normal Tissues, Macrophages, and Tumors," *Molecular Biology Cell,* 3:211-220, 1992.

Berse et al., "Vascular Permeability Factor Vascular Endothelial Cell Growth Factor Expresssion in Normal Tissues and in Tumors," *J. Cell Biol.,* 115(3 part 2):421a, Abstract No. 2443, 1991.

Dvorak et al., "Vascular Permeability Facor, Fibrin, and the Pathogenesis of Tumor Stroma Formation," *Ann. N.Y. Acad. Sci.,* 667:101-111, 1992.

Dvorak, "Leaky Tumor Vessels: Consequences for Tumor Stroma Generation and for Solid Tumor Therapy," *Progress in Clinical and Bioilogical Research,* 354a: 317-330, 1990.

Keck et al., "Vascular.Permeability Factor, an Endothelial Cell Mitogen Related to PDGF," *Science,* 246:1309-1312, 1989.

ANTIBODY METHODS FOR SELECTIVELY INHIBITING VEGF

The present application is a continuation of U.S. patent application Ser. No. 09/561,499, filed Apr. 28, 2000, which issued as U.S. Pat. No. 6,524,583 on Feb. 25, 2003, which claims priority to U.S. provisional patent application Ser. No. 60/131,432, filed Apr. 28, 1999, the entire text and drawings of which applications are specifically incorporated by reference herein without disclaimer.

The U.S. Government owns rights in the present invention pursuant to grant numbers 1RO1 CA74951, 5RO CA54168 and T32 GM07062 from the National Institutes of Health.

BACKGROUND OF THE INVENTION

1. Field of the Invention

The present invention relates generally to the fields of antibodies, angiogenesis and tumor treatment. More particularly, it provides anti-VEGF antibodies that specifically inhibit VEGF binding to only one (VEGFR2) of the two VEGF receptors. Such antibodies inhibit angiogenesis and induce tumor regression, and yet have improved safety due to their specific blocking properties. The antibody-based compositions and methods of the invention also extend to the use of immunoconjugates and other therapeutic combinations, kits and methods, including those with prodrugs.

2. Description of the Related Art

Tumor cell resistance to chemotherapeutic agents represents a significant problem in clinical oncology. In fact, this is one of the main reasons why many of the most prevalent forms of human cancer still resist effective chemotherapeutic intervention, despite certain advances in this field.

Another tumor treatment strategy is the use of an "immunotoxin", in which an anti-tumor cell antibody is used to deliver a toxin to the tumor cells. However, in common with chemotherapeutic approaches, immunotoxin therapy also suffers from significant drawbacks when applied to solid tumors. For example, antigen-negative or antigen-deficient cells can survive and repopulate the tumor or lead to further metastases.

A further reason for solid tumor resistance to antibody-based therapies is that the tumor mass is generally impermeable to macromolecular agents such as antibodies and immunotoxins (Burrows et al., 1992; Dvorak et al., 1991a; Baxter and Jain, 1991). Both the physical diffusion distances and the interstitial pressure within the tumor are significant limitations to this type of therapy. Therefore, solid tumors, which make up over 90% of all human cancers, have thus far proven resistant to antibody and immunotoxin treatment.

A more recent strategy has been to target the vasculature of solid tumors. Targeting the blood vessels of the tumors, rather than the tumor cells themselves, has certain advantages in that it is not likely to lead to the development of resistant tumor cells, and that the targeted cells are readily accessible. Moreover, destruction of the blood vessels leads to an amplification of the anti-tumor effect, as many tumor cells rely on a single vessel for their oxygen and nutrients (Burrows and Thorpe, 1994a; 1994b). Exemplary vascular targeting strategies are described in U.S. Pat. Nos. 5,855,866 and 5,965,132, which particularly describe the targeted delivery of anti-cellular agents and toxins to markers of tumor vasculature.

Another effective version of the vascular targeting approach is to target a coagulation factor to a marker expressed or adsorbed within the tumor vasculature (Huang et al., 1997; U.S. Pat. Nos. 5,877,289, 6,004,555, and 6,093,399). The delivery of coagulants, rather than toxins, to tumor vasculature has the further advantages of reduced immunogenicity and even lower risk of toxic side effects. As disclosed in U.S. Patent No. 5,877,289, a preferred coagulation factor for use in such tumor-specific "coaguligands" is a truncated version of the human coagulation-inducing protein, Tissue Factor (TF), the major initiator of blood coagulation.

Although the specific delivery of toxins and coagulation factors to tumor blood vessels represents a significant advance in tumor treatment, certain peripheral tumor cells can survive the intratumoral destruction caused by such therapies. Anti-angiogenic strategies would therefore be of use in combination with the tumor destruction methods of U.S. Pat. Nos. 5,855,866 and 5,877,289.

Anti-angiogenic tumor treatment strategies are based upon inhibiting the proliferation of budding vessels, generally at the periphery of a solid tumor. These therapies are mostly applied to reduce the risk of micrometastasis or to inhibit further growth of a solid tumor after more conventional intervention (such as surgery or chemotherapy).

Angiogenesis is the development of new vasculature from preexisting blood vessels and/or circulating endothelial stem cells (Asahara et al., 1997; Springer et al., 1998; Folkman and Shing, 1992). Angiogenesis plays a vital role in many physiological processes, such as embryogenesis, wound healing and menstruation. Angiogenesis is also important in certain pathological events. In addition to a role in solid tumor growth and metastasis, other notable conditions with an angiogenic component are arthritis, psoriasis and diabetic retinopathy (Hanahan and Folkman, 1996; Fidler and Ellis, 1994).

Angiogenesis is regulated in normal and malignant tissues by the balance of angiogenic stimuli and angiogenic inhibitors that are produced in the target tissue and at distant sites (Fidler et al., 1998; McNamara et al., 1998). Vascular endothelial growth factor-A (VEGF, also known as vascular permeability factor, VPF) is a primary stimulant of angiogenesis. VEGF is a multifunctional cytokine that is induced by hypoxia and oncogenic mutations and can be produced by a wide variety of tissues (Kerbel et al., 1998; Mazure et al., 1996).

The recognition of VEGF as a primary stimulus of angiogenesis in pathological conditions has led to various attempts to block VEGF activity. Inhibitory anti-VEGF receptor antibodies, soluble receptor constructs, antisense strategies, RNA aptamers against VEGF and low molecular weight VEGF receptor tyrosine kinase (RTK) inhibitors have all been proposed for use in interfering with VEGF signaling (Siemeister et al., 1998). In fact, monoclonal antibodies against VEGF have been shown to inhibit human tumor xenograft growth and ascites formation in mice (Kim et al., 1993; Asano et al., 1998; Mesiano et al., 1998; Luo et al., 1998a; 1998b; Borgstrom et al., 1996; 1998).

Although the foregoing studies underscore the importance of VEGF in solid tumor growth, and its potential as a target for tumor therapy, the identification of additional agents that inhibit VEGF-induced angiogenesis would be of benefit in expanding the number of therapeutic options. The development of therapeutic agents that more specifically inhibit VEGF receptor binding would represent an important advance, so long as their anti-tumor effects were not substantially compromised by the improved specificity.

SUMMARY OF THE INVENTION

The present invention overcomes certain drawbacks in the prior art by providing new therapeutic compositions and methods for use in anti-angiogenic and anti-tumor treatment. The invention is based on antibodies that specifically inhibit VEGF binding to only one (VEGFR2) of the two primary VEGF receptors. Such antibodies inhibit angiogenesis and induce tumor regression as effectively as other anti-VEGF antibodies, including those already in clinical trials, and yet have improved safety due to their specific blocking properties. The compositions and methods of the invention also extend to the use of immunoconjugates and combinations, including prodrugs, using the specific category of antibodies provided.

A particular advantage of the present invention is that the antibodies provided inhibit VEGF binding only to VEGFR2, and not VEGFR1. This contrasts with the leading antibodies in the prior art, including A4.6.1, which inhibit VEGF binding to both VEGFR2 and VEGFR1. As VEGFR1 has important biological roles unconnected to angiogenesis, particularly in macrophage migration and chemotaxis, and osteoclast and chondroclast function, the present ability to inhibit only VEGFR2-mediated angiogenesis is a distinct advantage. This translates into notable clinical benefits in that macrophages are still able to mediate host anti-tumor responses and that bone metabolism, e.g., in the treatment of pediatric cancers, is not adversely affected.

A further advantage is that, as binding of VEGF to VEGFR1 is maintained in the presence of the antibodies of the invention, they can be used to specifically deliver attached therapeutic agents to tumor vasculature by virtue of binding to VEGF that is bound to VEGFR1, which is upregulated on tumor endothelium. In the context of immunoconjugates, therefore, the present invention provides agents that have both anti-angiogenic and tumor destructive properties within the same molecule.

Yet a further advantage exists in the ability of the compositions provided to neutralize the survival signal of VEGF, which is mediated through VEGFR2. The naked and conjugated antibodies of the invention thus form synergistic combinations with other therapies and/or attached agents, particularly those methods and agents that fail to achieve maximal effectiveness in vivo due to the ability of VEGF to counteract their destructive properties.

The present invention thus provides antibodies that specifically block VEGF binding to the VEGFR2 receptor, or that block VEGF binding to essentially only the VEGFR2 receptor. Such antibodies significantly inhibit VEGF binding to the VEGFR2 receptor (KDR/Flk-1) without significantly inhibiting VEGF binding to the VEGFR1 receptor (Flt-1). The antibodies thus inhibit VEGF binding to the VEGFR2 receptor (KDR/Flk-1), do not substantially inhibit VEGF binding to the VEGFR1 receptor (Flt-1), exhibit anti-angiogenic and anti-tumor effects in vivo and do not significantly inhibit macrophage chemotaxis, osteoclast or chondroclast functions The antibodies of the invention are thus succinctly termed "VEGFR2-blocking, non-VEGFR1-blocking, anti-VEGF antibodies". Even more succinctly, they are termed "VEGFR2-blocking, anti-VEGF antibodies", which is used for simplicity in reference to all compositions, uses and methods of the invention. A "VEGFR2-blocking, anti-VEGF antibody" is an antibody against VEGF that blocks VEGF binding to the VEGFR2 receptor. It will be clear that such antibodies are not antibodies against the VEGFR2 receptor itself.

Prior to the present invention, there was no motivation to generate anti-VEGF antibodies that specifically block VEGF binding to the VEGFR2 receptor, but not the VEGFR1, neither were any advantages of such antibodies envisioned. Importantly, as blocking antibodies need to physically prevent the interaction of a growth factor and its receptor(s), and as receptor binding sites on growth factors are limited in size, there was nothing to suggest that such specific VEGFR2-blocking, anti-VEGF antibodies could be developed.

However, in light of the inventors' surprising discoveries disclosed herein, the art is now provided with the knowledge that such specific inhibitory anti-VEGF antibodies can be prepared and have distinct advantages. The present application further describes the methodology for generating candidate VEGFR2-blocking, anti-VEGF antibodies and the routine technical aspects of the assays required to identify actual VEGFR2-blocking specific antibodies from the pool of candidates. In light of this invention, therefore, a range of VEGFR2-blocking, anti-VEGF antibodies can be made and used in a variety of embodiments, including in the inhibition of angiogenesis and the treatment of angiogenic diseases and tumors without inhibiting VEGF signaling via the VEGFR1 receptor and without the notable drawbacks and side effects associated therewith.

As used throughout the entire application, the terms "a" and "an" are used in the sense that they mean "at least one", "at least a first", "one or more" or "a plurality" of the referenced components or steps, except in instances wherein an upper limit is thereafter specifically stated. Therefore, an "antibody", as used herein, means "at least a first antibody". The operable limits and parameters of combinations, as with the amounts of any single agent, will be known to those of ordinary skill in the art in light of the present disclosure.

Antibodies that "specifically inhibit VEGF binding to the VEGF receptor VEGFR2 (KDR/Flk-1)" can now be identified by competition and/or functional assays. The preferred assays, for simplicity, are competition assays based upon an ELISA. In competition assays, one pre-mixes or admixes VEGF with varying amounts of the test antibodies (e.g., 100-fold to 1000-fold molar excess) and determines the ability of the test antibodies to reduce VEGF binding to VEGFR2. VEGF can be pre-labeled and detected directly, or can be detected using a (secondary) anti-VEGF antibody or a secondary and tertiary antibody detection system. An ELISA format of such a competition assay is a preferred format, but any type of immunocompetition assay may be conducted.

VEGF binding to VEGFR2 in the presence of a completely irrelevant antibody (including non-blocking anti-VEGF monoclonal antibodies) is the control high value (100%) in such a competition assay. In a test assay, a significant reduction in VEGF binding to VEGFR2 in the presence of a test antibody is indicative of a test antibody that significantly inhibits VEGF binding to the VEGF receptor VEGFR2 (KDR/Flk-1).

A significant reduction is a "reproducible", i.e., consistently observed, reduction in binding. A "significant reduction" in terms of the present application is defined as a reproducible reduction (in VEGF binding to VEGFR2) of at least about 45%, about 50%, about 55%, about 60% or about 65% at any amount between about 100 fold and about 1000 fold molar excess of antibody over VEGF.

As a preferred feature of the invention is that the antibodies provided do not substantially inhibit VEGF binding to VEGFR1, antibodies that exhibit a moderately significant reduction of VEGF binding to VEGFR2 will still be useful, so long as they do not substantially inhibit VEGF binding to VEGFR1. Nonetheless, more preferred antibodies will be those that have a more significant ability to inhibit VEGF binding to VEGFR2. These antibodies are those that exhibit a reproducible ability to reduce VEGF binding to VEGFR2 by at least about 70%, about 75% or about 80% at any amount between about 100 fold and about 1000 fold molar excess of antibody over VEGF. Although not required to practice the invention, antibodies that reduce VEGF binding to VEGFR2 by at least about 85%, about 90%, about 95% or even higher are by no means excluded.

Anti-VEGF antibodies, or antigen-binding fragments thereof, that inhibit VEGF binding to the VEGF receptor VEGFR2 (KDR/Flk-1) without significantly inhibiting VEGF binding to the VEGF receptor VEGFR1 (Flt-1) are readily confirmed by simple competition assays such as those described above, but using VEGFR1.

Absence of a significant reduction is a "reproducible", i.e., consistently observed, "substantial maintenance of binding". A "substantial maintenance of binding" in terms of the present application is defined as a reproducible maintenance (in VEGF binding to VEGFR1) of at least about 60%, about 75%, about 80% or about 85% at any amount between about 100 fold and about 1000 fold molar excess of antibody over VEGF.

The intention of using antibodies that do not substantially inhibit VEGF binding to VEGFR1 is to maintain the biological functions mediated by VEGFR1. Therefore, an antibody need only maintain sufficient VEGF binding to VEGFR1 so that a biological response is induced by VEGF. Nonetheless, more preferred antibodies will be those that have a more significant ability to maintain VEGF binding to VEGFR1. These antibodies are those that exhibit a reproducible ability to maintain VEGF binding to VEGFR1 at levels of at least about 88%, about 90%, about 92%, about 95% or of about 98–99% at any amount between about 100 fold and about 1000 fold molar excess of antibody over VEGF.

It will be understood that antibodies that more substantially inhibit VEGF binding to VEGFR2 can likely tolerate more reduction in binding VEGFR1. Equally, where an antibody has a moderate reduction in VEGF binding to VEGFR2, the maintenance of binding to VEGFR1 should be more stringently pursued.

Another preferred binding assay to identify and/or confirm that an antibody inhibits VEGF binding to the VEGF receptor VEGFR2 (KDR/Flk-1) is a co-precipitation assay. A co-precipitation assay tests the ability of an antibody to block the binding of VEGF to one or more receptors in solution. In such an assay, VEGF or detectably-labeled VEGF is incubated with a suitable form of the receptor.

There are many formats for conducting immunoprecipitation or co-precipitation assays. In the present case, a "suitable form of the receptor" may be the VEGFR2 receptor at issue or the extracellular domain of the receptor. Immunoprecipitation with then require, as well as the standard reagents, the presence of an antibody against the VEGFR2 receptor or an epitope on the extracellular domain of the receptor distinct from the site to which VEGF binds. The present invention provides other "suitable" forms of the VEGF receptors, namely the extracellular domains of the receptors linked to an Fc antibody portion. Such receptor/Fc constructs can be precipitated by incubation with an effective immunoprecipitating composition, such as a Protein A-based composition.

Irrespective of the suitable receptor, the immunoprecipitation or co-precipitation assays are preferably conducted with controls. The ability of VEGF alone to bind to the chosen receptor should be confirmed by precipitation in the absence of an anti-VEGF antibody. Preferably, parallel incubations are conducted in the presence or absence of an antibody with known binding properties to act as a control. Most preferably, assays using both a blocking control and non-blocking control antibody are run in parallel.

Any bound immunological species are then immunoprecipitated, e.g., by incubation with an effective immunoprecipitating composition, such as a Protein A composition or Protein A sepharose beads. The precipitate is then tested for the presence of VEGF. Where the VEGF in the initial incubation was detectably-labeled VEGF, such as radiolabeled VEGF, any VEGF in the immunoprecipitates can be detected directly. Any non-labeled VEGF in the immunoprecipitates may be detected by other suitable means, e.g., by gel separation and immunodetection with an anti-VEGF antibody.

The ability of an antibody to block VEGF binding to a VEGF receptor, such as VEGFR2, in such a co-precipitation assay can be readily quantitated, although qualitative results are also valuable. Quantification can be achieved by direct measurement of labeled VEGF or e.g., by densitometric analyses of immunodetected VEGF. Antibodies that exhibit a reproducible, i.e., consistently observed, ability to inhibit VEGF binding to VEGFR2 can thus be detected, and useful antibodies can be chosen according to the quantitative criteria outlined above.

Anti-VEGF antibodies that do not significantly inhibit VEGF binding to the VEGF receptor VEGFR1 (Flt-1) can also be readily identified by conducting co-precipitation assays as described above, but using VEGFR1 rather than VEGFR2. Therefore, anti-VEGF antibodies that inhibit VEGF binding to the VEGF receptor VEGFR2 (KDR/Flk-1) without significantly inhibiting VEGF binding to the VEGF receptor VEGFR1 (Flt-1) can also be readily identified using such methods.

The present application also provides various functional assays to identify and/or confirm that an antibody significantly inhibits VEGF binding to the VEGF receptor VEGFR2 (KDR/Flk-1). These are generally related to the identification of VEGFR2 as the receptor responsible for certain defined biological responses. Although less preferred than the foregoing competition-type assays, which are conducted in cell-free systems and are most reproducible, reliable, labor-saving and cost-effective, the following assays are nonetheless useful in the context of the present invention.

For example, a VEGFR2-blocking, anti-VEGF antibody may be identified by testing for the ability to inhibit VEGF-mediated endothelial cell growth (inhibiting the mitogenic activity of VEGF). Any suitable assay may be employed using any of a variety of endothelial cells in the presence of VEGF with or without test antibodies. Preferably, duplicate assays are run in parallel, such as those without VEGF and those with control antibodies of defined properties (both blocking and non-blocking). Endothelial cell growth may be determined and preferably accurately quantified by any acceptable means of determining cell number, including colorimetric assays.

An antibody with an ability to inhibit VEGF-mediated endothelial cell growth will generally exhibit a consistently observed inhibition of VEGF-mediated endothelial cell growth of about 25%, 30%, 35%, 40% 45% or 50% or so. Inhibition in such ranges will indicate an antibody with properties sufficient to inhibit angiogenesis in vivo. Antibodies with more significant inhibitory activity are not excluded from the invention.

Further functional assays to identify antibodies in accordance with the present invention are assays to test blocking of VEGF-induced phosphorylation. Any suitable assay may be employed using any of a variety of endothelial cells that express any form of native or recombinant phosphorylatable VEGFR2. Cells are incubated with VEGF in the presence or absence of the antibody to be tested for a suitable time period. Preferably, duplicate assays are run in parallel, such as those without VEGF and those with control antibodies of defined properties (both blocking and non-blocking).

VEGF-induced phosphorylation of VEGFR2 may be determined and preferably accurately quantified by any acceptable means. Generally, VEGFR2 is immunoprecipitated for further analyses. The degree of phosphorylation of VEGFR2 may be determined directly, for example, the cells may have been incubated with $^{32}$P-labelled ATP, allowing direct quantification of the $^{32}$P within the immunoprecipitated VEGFR2. Preferably, the immunoprecipitated VEGFR2 are analyzed by other means, e.g., by gel separation and immunodetection with an antibody that binds to phosphotyrosine residues. An antibody with an ability to inhibit VEGF-induced phosphorylation of VEGFR2 will generally exhibit a consistently observed reduction in the levels of phosphorylated VEGFR2.

Yet further functional assays to identify VEGFR2-blocking, anti-VEGF antibodies in accordance with the present invention are assays to test inhibition of VEGF-induced vascular permeability. Although any such assay may be used, a particularly suitable assay is the Miles permeability assay, wherein animals such as guinea pigs are injected with a dye, such as Evan's blue dye, and the appearance of the dye in the animal skin is determined after the provision of VEGF in the presence or absence of test antibodies. Preferably, duplicate studies are conducted in parallel, such as those without VEGF and those with control antibodies of defined properties (both blocking and non-blocking). The appearance of dye in the animal skin is typically as spots, such as blue spots, in the back of the animal, which can be photographed and measured.

VEGFR2-blocking, anti-VEGF antibodies will inhibit VEGF-induced-vascular permeability as a consistently observed inhibition at low concentrations, such as when provided at a 100-fold, or 1000-fold molar excess over VEGF. Antibodies that do not block VEGF binding to VEGFR2 will not show any significant inhibition of VEGF induced-vascular permeability. Generally, antibodies that block VEGF-induced permeability only at high concentrations, such as at a 10-fold molar excess over VEGF, will not be antibodies with properties in accordance with the present invention.

Widely accepted functional assays of angiogenesis and, hence, anti-angiogenic agents are the corneal micropocket assay of neovascularization and the chick chorio-allantoic membrane assay (CAM) assay. U.S. Pat. No. 5,712,291 is specifically incorporated herein by reference to show that the corneal micropocket and CAM assays are sufficiently predictive to identify agents for use in the treatment of an extremely wide range of angiogenic diseases.

U.S. Pat. No. 5,001,116 is also specifically incorporated herein by reference for purposes of describing the CAM assay. Essentially, fertilized chick embryos are removed from their shell on day 3 or 4, and a methylcellulose disc containing the test compound is implanted on the chorioallantoic membrane. The embryos are examined approximately 48 hours later and, if a clear avascular zone appears around the methylcellulose disc, the diameter of that zone is measured. As disclosed in U.S. Pat. No. 5,712,291, specifically incorporated herein by reference for this purpose, in the context of the present invention, the appearance of any avascular zone is sufficient to evidence an anti-angiogenic antibody. The larger the zone, the more effective the antibody.

The corneal micropocket assay of neovascularization may be practiced using rat or rabbit corneas. This in vivo model is widely accepted as being predictive of clinical usefulness, as evidenced by U.S. Pat. Nos. 5,712,291 and 5,871,723, each specifically incorporated herein by reference for evidence purposes. Although not believed to be particularly relevant the present invention, the corneal assays are preferable over the CAM assay because they will generally recognize compounds that are inactive per se but are metabolized to yield active compounds.

In the present invention, the corneal micropocket assay is used to identify an anti-angiogenic agent. This is evidenced by a significant reduction in angiogenesis, as represented by a consistently observed and preferably marked reduction in the number of blood vessels within the cornea. Such responses are preferably defined as those corneas showing only an occasional sprout and/or hairpin loop that displayed no evidence of sustained growth when contacted with the test substance.

Exemplary VEGFR2-blocking, anti-VEGF antibodies (and antigen-binding fragments) of the invention include those that:
  (a) significantly inhibit VEGF binding to the VEGF receptor VEGFR2 (KDR/Flk-1);
  (b) do not significantly inhibit VEGF binding to the VEGF receptor VEGFR1 (Flt-1);
  (c) inhibit, and preferably, significantly inhibit, VEGF-induced phosphorylation of VEGFR2;
  (d) inhibit, and preferably, significantly inhibit, VEGF-induced vascular permeability;
  (e) inhibit, and preferably, significantly inhibit, VEGF-mediated endothelial cell proliferation;
  (f) inhibit, and preferably, significantly inhibit, angiogenesis;
  (g) do not significantly inhibit VEGFR1-mediated stimulation or activation of macrophages, osteoclasts or chondroclasts; and
  (h) localize to tumor vasculature and tumor stroma upon administration to an animal with a vascularized tumor.

A particular aspect of the invention is based on the inventors' original, surprising discovery of antibodies that specifically inhibited VEGF binding to the VEGFR2 receptor, that had significant anti-tumor effects in vivo and that did not inhibit VEGF binding to the VEGFR1 receptor. In certain embodiments, the present invention thus provides antibodies of defined epitope-specificity, wherein such antibodies, or antigen-binding fragments thereof, bind to essentially the same epitope as the monoclonal antibody 2C3 (ATCC PTA 1595).

The invention as claimed is enabled in accordance with the present specification and readily available technological references, know-how and starting materials. Nonetheless, a sample of the hybridoma cell line producing the 2C3 monoclonal antibody was submitted March 27, for receipt Mar. 28, 2000, for deposit with the American Type Culture Collection (ATCC), 10801 University Blvd., Manassas, Va. 20110-2209, U.S.A. and given ATCC Accession number ATCC PTA 1595 on Apr. 11, 2000. This deposit was made under the provisions of the Budapest Treaty on the International Recognition of the Deposit of Microorganisms for the Purposes of Patent Procedure and the regulations thereof (Budapest Treaty). The hybridoma will be made available by the ATCC under the terms of the Budapest Treaty upon issue of a U.S. patent with pertinent claims. Availability of the deposited hybridoma is not to be construed as a license to practice the invention in contravention of the rights granted under the authority of any government in accordance with its patent laws.

Certain preferred compositions are therefore compositions comprising at least a first anti-VEGF antibody, or antigen-binding fragment thereof, or at least a first purified anti-VEGF antibody, or antigen-binding fragment thereof, that binds to substantially the same epitope as the monoclonal antibody 2C3 (ATCC PTA 1595); compositions comprising at least a first monoclonal antibody, or antigen-binding fragment thereof, that binds to VEGF at essentially the same epitope as the monoclonal antibody 2C3 (ATCC PTA 1595); and compositions comprising at least a first anti-VEGF monoclonal antibody, or antigen-binding fragment thereof, that binds to the same epitope as the monoclonal antibody 2C3 (ATCC PTA 1595).

Notwithstanding, certain other compositions, antibodies, methods, and particularly first and second medical uses of the invention, concern anti-VEGF antibodies, or antigen-binding fragments thereof, that bind to the same, or substantially the same, epitope as the monoclonal antibody 2C3 (ATCC PTA 1595) other than the monoclonal antibody 2C3 (ATCC PTA 1595) itself.

The terms "that bind to about, substantially or essentially the same, or the same, epitope as" the monoclonal antibody 2C3 (ATCC PTA 1595) mean that an antibody "cross-reacts" with the monoclonal antibody 2C3 (ATCC PTA 1595). "Cross-reactive antibodies" are those that recognize, bind to or have immunospecificity for substantially or essentially the same, or the same, epitope or "epitopic site" as the monoclonal antibody 2C3 (ATCC PTA 1595) such that are able to effectively compete with the monoclonal antibody 2C3 (ATCC PTA 1595) for binding to VEGF. "2C3-cross-reactive antibodies" are succinctly termed "2C3-like antibodies" and "2C3-based antibodies", and such terms are used interchangeably herein and apply to compositions, uses and methods.

The identification of one or more antibodies that bind(s) to about, substantially, essentially or at the same epitope as the monoclonal antibody 2C3 (ATCC PTA 1595) is a straightforward technical matter now that 2C3, with its advantageous properties, has been provided. As the identification of cross-reactive antibodies is determined in comparison to a reference antibody, it will be understood that actually determining the epitope to which the reference antibody (2C3) and the test antibody bind is not in any way required in order to identify an antibody that binds to the same or substantially the same epitope as the monoclonal antibody 2C3. However, considerable information on the epitope bound by 2C3 is included herein and epitope mapping can be further performed, as described by Champe et al. (1995, specifically incorporated herein by reference).

The identification of cross-reactive antibodies can be readily determined using any one of variety of immunological screening assays in which antibody competition can be assessed. All such assays are routine in the art and are further described herein in detail. U.S. Pat. No. 5,660,827, issued Aug. 26, 1997, is specifically incorporated herein by reference for purposes including even further supplementing the present teaching concerning how to make antibodies that bind to the same or substantially the same epitope as a given antibody, such as 2C3.

For example, where the test antibodies to be examined are obtained from different source animals, or are even of a different isotype, a simple competition assay may be employed in which the control (2C3) and test antibodies are admixed (or pre-adsorbed) and applied to a VEGF antigen composition. By "VEGF antigen composition" is meant any composition that contains a 2C3-binding VEGF antigen as described herein, such as free VEGF. Thus, protocols based upon ELISAs and Western blotting are suitable for use in such simple competition studies.

In certain embodiments, one would or pre-mix the control antibodies (2C3) with varying amounts of the test antibodies (e.g., 1:10 or 1:100) for a period of time prior to applying to an antigen composition. In other embodiments, the control and varying amounts of test antibodies can simply be admixed during exposure to the antigen composition. In any event, by using species or isotype secondary antibodies one will be able to detect only the bound control antibodies, the binding of which will be reduced by the presence of a test antibody that recognizes substantially the same epitope.

In conducting an antibody competition study between a control antibody and any test antibody (irrespective of species or isotype), one may first label the control (2C3) with a detectable label, such as, e.g., biotin or an enzymatic (or even radioactive) label to enable subsequent identification. In these cases, one would pre-mix or incubate the labeled control antibodies with the test antibodies to be examined at various ratios (e.g., 1:10 or 1:100) and (optionally after a suitable period of time) then assay the reactivity of the labeled control antibodies and compare this with a control value in which no potentially competing test antibody was included in the incubation.

The assay may again be any one of a range of immunological assays based upon antibody hybridization, and the control antibodies would be detected by means of detecting their label, e.g., using streptavidin in the case of biotinylated antibodies or by using a chromogenic substrate in connection with an enzymatic label (such as 3,3'5,5'-tetramethylbenzidine (TMB) substrate with peroxidase enzyme) or by simply detecting a radioactive label. An antibody that binds to the same epitope as the control antibodies will be able to effectively compete for binding and thus will significantly reduce control antibody binding, as evidenced by a reduction in bound label.

The reactivity of the (labeled) control antibodies in the absence of a completely irrelevant antibody would be the control high value. The control low value would be obtained by incubating the labeled (2C3) antibodies with unlabelled antibodies of exactly the same type (2C3), when competition would occur and reduce binding of the labeled antibodies. In a test assay, a significant reduction in labeled antibody reactivity in the presence of a test antibody is indicative of a test antibody that recognizes the same epitope, i.e., one that "cross-reacts" with the labeled (2C3) antibody.

A significant reduction is a "reproducible", i.e., consistently observed, reduction in binding. A "significant reduction" in terms of the present application is defined as a reproducible reduction (in 2C3 binding to VEGF in an ELISA) of at least about 70%, about 75% or about 80% at any ratio between about 1:10 and about 1:100. Antibodies with even more stringent cross-blocking activities will exhibit a reproducible reduction (in 2C3 binding to VEGF in an ELISA or other suitable assay) of at least about 82%, about 85%, about 88%, about 90%, about 92% or about 95% or so at any ratio between about 1:10 and about 1:100. Complete or near-complete cross-blocking, such as exhibiting a reproducible reduction in 2C3 binding to VEGF of about 99%, about 98%, about 97% or about 96% or so, although by no means required to practice the invention, is certainly not excluded.

The invention is exemplified by monoclonal antibody 2C3, produced by hybridoma ATCC PTA 1595, or an antigen-binding fragment of such a monoclonal antibody. A hybridoma that produces a monoclonal anti-VEGF antibody that binds to substantially the same epitope as the monoclonal antibody 2C3 (ATCC PTA 1595) is another aspect of the invention.

The invention further provides anti-VEGF antibodies that bind to substantially the same epitope as the monoclonal antibody 2C3 (ATCC PTA 1595), prepared by a process comprising immunizing an animal with at least a first immunogenic VEGF component and selecting from the immunized animal an antibody that substantially cross-reacts with the monoclonal antibody 2C3 (ATCC PTA 1595); and anti-VEGF antibodies that bind to substantially the same epitope as the monoclonal antibody 2C3 (ATCC PTA 1595), prepared by a process comprising immunizing an animal with at least a first immunogenic VEGF component and selecting a cross-reactive anti-VEGF antibody from the immunized animal by identifying an antibody that substantially reduces the binding of the 2C3 antibody to VEGF.

Anti-VEGF antibodies, or antigen-binding fragments thereof, that bind to substantially the same epitope as the monoclonal antibody 2C3 (ATCC PTA 1595) and that specifically inhibits VEGF binding to the VEGF receptor VEGFR2 (KDR/Flk-1); and anti-VEGF antibodies, or antigen-binding fragments thereof, that bind to substantially the same epitope as the monoclonal antibody 2C3 (ATCC PTA 1595) and that inhibits VEGF binding to the VEGF receptor VEGFR2 (KDR/Flk-1) without significantly inhibiting VEGF binding to the VEGF receptor VEGFR1 (Flt-1) form other aspects of the invention.

Antibodies with such combinations of properties can be readily identified by one or more or a combination of the receptor competition, ELISA, co-precipitation, and/or functional assays and the 2C3-crossreactivity assays described above. The guidance concerning the quantitative assessment of 2C3-like antibodies that consistently significantly reduce VEGF binding to VEGFR2 and that consistently do not significantly inhibit VEGF binding to VEGFR1 is as described above.

2C3 is herein shown reduce the amount VEGF that bound to VEGFR2-coated ELISA wells to about 26% and 19%, respectively, at 100 fold and 1000 fold molar excesses over VEGF. These figures equate to reductions in VEGF binding to VEGFR2 of about 74% and about 81%, respectively. 2C3 is herein shown maintain the amount-VEGF that bound to VEGFR2-coated ELISA wells at about 92% and 105%, respectively, at 100 fold and 1000 fold molar excesses over VEGF.

It will again be understood that 2C3-like or crossreactive antibodies that more substantially inhibit VEGF binding to VEGFR2 can likely tolerate more reduction in binding VEGFR1. Equally, where an antibody has a moderate reduction in VEGF binding to VEGFR2, the maintenance of binding to VEGFR1 should be more stringently pursued.

Additional exemplary anti-VEGF antibodies (and antigen-binding fragments) of the invention are therefore those that:
  (a) bind to a non-conformationally dependent VEGF epitope, as assessed by binding to VEGF in a Western blot;
  (b) bind to free VEGF;
  (c) significantly inhibit VEGF binding to the VEGF receptor VEGFR2 (KDR/Flk-1);
  (d) do not significantly inhibit VEGF binding to the VEGF receptor VEGFR1 (Flt-1);
  (e) inhibit, and preferably, significantly inhibit, VEGF-induced phosphorylation of VEGFR2;
  (f) inhibit, and preferably, significantly inhibit, VEGF-induced vascular permeability;
  (g) inhibit, and preferably, significantly inhibit, VEGF-mediated endothelial cell proliferation;
  (h) inhibit, and preferably, significantly inhibit, angiogenesis;
  (i) do not significantly inhibit VEGFR1-mediated stimulation or activation of macrophages, osteoclasts or chondroclasts;
  (j) localize to tumor vasculature and tumor stroma upon administration to an animal with a vascularized tumor; and
  (k) bind to the same or substantially the same epitope as the monoclonal antibody 2C3 (ATCC PTA 1595).

In the following descriptions of the compositions, immunoconjugates, pharmaceuticals, combinations, cocktails, kits, first and second medical uses and all methods in accordance with this invention, the terms "antibody" and "immunoconjugate", or an antigen-binding region thereof, unless otherwise specifically stated or made clear from the scientific terminology, refer to a range of VEGFR2-blocking, anti-VEGF antibodies as well as to specific 2C3-cross-reactive antibodies.

The terms "antibody" and "immunoglobulin", as used herein, refer broadly to any immunological binding agent, including polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. The heavy-chain constant domains that correspond to the difference classes of immunoglobulins are termed α, δ, ε, γ and μ, respectively. The subunit structures and three-dimensional configurations of different classes of immunoglobulins are well known.

Generally, where antibodies rather than antigen binding regions are used in the invention, IgG and/or IgM are preferred because they are the most common antibodies in the physiological situation and because they are most easily made in a laboratory setting.

The "light chain s" of mammalian antibodies are assigned to one of two clearly distinct types: kappa (κ) and lambda (λ), based on the amino acid sequences of their constant domains. There is essentially no preference to the use of κ or λ light chains in the antibodies of the present invention.

The use of monoclonal antibodies (MAbs) or derivatives thereof is much preferred. MAbs are recognized to have certain advantages, e.g., reproducibility and large-scale production, that makes them suitable for clinical treatment. The invention thus provides monoclonal antibodies of the murine, human, monkey, rat, hamster, rabbit and even frog or chicken origin. Murine, human or humanized monoclonal antibodies will generally be preferred.

As will be understood by those in the art, the immunological binding reagents encompassed by the term "antibody" extend to all antibodies from all species, and antigen binding fragments thereof, including dimeric, trimeric and multimeric antibodies; bispecific antibodies; chimeric antibodies; human and humanized antibodies; recombinant and engineered antibodies, and fragments thereof.

The term "antibody" is thus used to refer to any antibody-like molecule that has an antigen binding region, and this term includes antibody fragments such as Fab', Fab, F(ab')$_2$, single domain antibodies (DABs), Fv, scFv (single chain Fv), linear antibodies, diabodies, and the like. The techniques for preparing and using various antibody-based constructs and fragments are well known in the art (see Kabat et al., 1991, specifically incorporated herein by reference). Diabodies, in particular, are further described in EP 404,097 and WO 93/11161, each specifically incorporated herein by reference; whereas linear antibodies are further described in Zapata et al. (1995), specifically incorporated herein by reference.

In certain embodiments, the compositions of the invention comprise at least a first anti-VEGF antibody that comprises at least a first variable region that includes an amino acid sequence region of at least about 75%, more preferably, at least about 80%, more preferably, at least about 85%, more preferably, at least about 90% and most preferably, at least about 95% or so amino acid sequence identity to the amino acid sequence of SEQ ID NO:7 or SEQ ID NO:9; wherein said anti-VEGF antibody at least substantially maintains the biological properties of the VEGFR2-blocking, anti-VEGF antibodies of the present invention, as exemplified by the 2C3 antibody.

Identity or homology with respect to these and other anti-VEGF antibody sequences of the present invention is defined herein as the percentage of amino acid residues in a candidate sequence that are identical to the sequences of SEQ ID NO:7 or SEQ ID NO:9, or to the sequence of another anti-VEGF antibody of the invention, after aligning the sequences and introducing gaps, if necessary, to achieve the maximum percent sequence identity. The maintenance of substantially the same, or even more effective biological properties of the VEGFR2-blocking, anti-VEGF antibody used for the sequence comparison is particularly important. Such comparisons are easily conducted, e.g., using one or more of the various assays described in detail herein.

In certain preferred embodiments, anti-VEGF antibodies of the invention comprise at least a first variable region that includes an amino acid sequence region having the amino acid sequence of SEQ ID NO:7 or SEQ ID NO:9, as exemplified by variable regions that include an amino acid sequence region encoded by the nucleic acid sequences of SEQ ID NO:6 or SEQ ID NO:8. Such sequences are the sequences of Vh and Vκ of the 2C3 ScFv encompassing CDR1-3 (complementarity determining regions) of the variable regions of the heavy and light chains.

In other preferred embodiments, second generation antibodies are provided that have enhanced or superior properties in comparison to an original VEGFR2-blocking, anti-VEGF antibody, such as 2C3. For example, the second generation antibodies may have a stronger binding affinity, more effective blocking of VEGF binding to VEGFR2, more specific blocking of VEGF binding to VEGFR2, even less blocking of VEGF binding to VEGFR1, enhanced ability to inhibit VEGF-induced proliferation and/or migration of endothelial cells, superior ability to inhibit, VEGF-induced vascular permeability, and preferably, an increased ability to inhibit VEGF-induced angiogenesis in vivo, and to treat angiogenic diseases, including vascularized tumors.

Comparisons to identify effective second generation antibodies are readily conducted and quantified, e.g. using one or more of the various assays described in detail herein. Second generation antibodies that have an enhanced biological property or activity of at least about 10-fold, preferably, at least about 20-fold, and more preferably, at least about 50-fold, in comparison to the VEGFR2-blocking, anti-VEGF antibodies of the present invention, as exemplified by the 2C3 antibody, are encompassed by the present invention.

In certain embodiments, the antibodies employed will be "humanized", part-human or human antibodies. "Humanized" antibodies are generally chimeric monoclonal antibodies from mouse, rat, or other non-human species, bearing human constant and/or variable region domains ("part-human chimeric antibodies"). Various humanized monoclonal antibodies for use in the present invention will be chimeric antibodies wherein at least a first antigen binding region, or complementarity determining region (CDR), of a mouse, rat or other non-human monoclonal antibody is operatively attached to, or "grafted" onto, a human antibody constant region or "framework".

"Humanized" monoclonal antibodies for use herein may also be monoclonal antibodies from non-human species wherein one or more selected amino acids have been exchanged for amino acids more commonly observed in human antibodies. This can be readily achieved through the use of routine recombinant technology, particularly site-specific mutagenesis.

Entirely human, rather than "humanized", antibodies may also be prepared and used in the present invention. Such human antibodies may be obtained from healthy subjects by simply obtaining a population of mixed peripheral blood lymphocytes from a human subject, including antigen-presenting and antibody-producing cells, and stimulating the cell population in vitro by admixing with an immunogenically effective amount of a VEGF sample. The human anti-VEGF antibody-producing cells, once obtained, are used in hybridoma and/or recombinant antibody production.

Further techniques for human monoclonal antibody production include immunizing a transgenic animal, preferably a transgenic mouse, which comprises a human antibody library with an immunogenically effective amount of a VEGF sample. This also generates human anti-VEGF antibody-producing cells for further manipulation in hybridoma and/or recombinant antibody production, with the advantage that spleen cells, rather than peripheral blood cells, can be readily obtained from the transgenic animal or mouse.

VEGFR2-blocking, anti-VEGF antibodies in accordance with the invention may be readily prepared by processes and methods that comprise:

(a) preparing candidate antibody-producing cells; and (b) selecting from the candidate antibody-producing cells an antibody that significantly inhibits VEGF binding to VEGFR2 (KDR/Flk-1) and does not significantly inhibit VEGF binding to the VEGF receptor VEGFR1 (Flt-1).

Other antibodies in accordance with the invention may be readily prepared by selecting an antibody that substantially cross-reacts with the monoclonal antibody 2C3 (ATCC PTA 1595). Suitable preparative processes and methods comprise:

(a) preparing candidate antibody-producing cells; and
(b) selecting from the candidate antibody-producing cells an antibody that substantially cross-reacts with the monoclonal antibody 2C3 (ATCC PTA 1595).

One processes of preparing suitable antibody-producing cells and obtaining antibodies therefrom may be conduced in situ in a given patient. That is, simply providing an immunogenically effective amount of an immunogenic VEGF sample to a patient will result in appropriate antibody generation. Thus, the antibody is still "obtained" from the antibody-producing cell, but it does not have to be isolated away from a host and subsequently provided to a patient, being able to spontaneously localize to the tumor vasculature and exert its biological anti-tumor effects. However, such embodiments are not preferred due to the marked lack of specificity.

Suitable antibody-producing cells may also be obtained, and antibodies subsequently isolated and/or purified, by stimulating peripheral blood lymphocytes with VEGF in vitro.

Other methods comprise administering to an animal an immunizing composition comprising at least a first immunogenic VEGF component and selecting from the immunized animal an antibody that significantly inhibits VEGF binding to VEGFR2 (KDR/Flk-1) and does not significantly inhibit VEGF binding to the VEGF receptor VEGFR1 (Flt-1), and optionally that substantially cross-reacts with the monoclonal antibody 2C3 (ATCC PTA 1595). These methods generally comprise:

(a) immunizing an animal by administering to the animal at least one dose, and optionally more than one dose, of an immunogenically effective amount of an immunogenic VEGF sample (such as a first human VEGF component, a substantially full length VEGF component, or recombinant human VEGF); and
(b) obtaining a suitable antibody-producing cell from the immunized animal, such as an antibody-producing cell that produces an antibody that significantly inhibits VEGF binding to VEGFR2 (KDR/Flk-1) and does not significantly inhibit VEGF binding to the VEGF receptor VEGFR1 (Flt-1), and optionally that substantially cross-reacts with the monoclonal antibody 2C3 (ATCC PTA 1595).

The immunogenically effective amount of the VEGF sample or samples may be administered as VEGF conjugates, or in combination with any suitable adjuvant, such as Freund's complete adjuvant. Any empirical technique or variation may be employed to increase immunogenicity. Intact, substantially full length human VEGF is generally preferred as an immunogen.

Irrespective of the nature of the immunization process, or the type of immunized animal, suitable antibody-producing cells are obtained from the immunized animal and, preferably, further manipulated by the hand of man. "An immunized animal", as used herein, is a non-human animal, unless otherwise expressly stated. Although any antibody-producing cell may be used, most preferably, spleen cells are obtained as the source of the antibody-producing cells. The antibody-producing cells may be used in a preparative process that comprises:

(a) fusing a suitable anti-VEGF antibody-producing cell with an immortal cell to prepare a hybridoma that produces a monoclonal antibody in accordance with the present invention; and
(b) obtaining a suitable anti-VEGF antibody in accordance with the invention from the hybridoma.

"Suitable" anti-VEGF antibody-producing cells, hybridomas and antibodies are those that produce, or exist as, VEGFR2-blocking, anti-VEGF antibodies, i.e., antibodies that significantly inhibit VEGF binding to VEGFR2 (KDR/Flk-1) and do not significantly inhibit VEGF binding to the VEGF receptor VEGFR1 (Flt-1), and optionally, that substantially cross-react with the monoclonal antibody 2C3 (ATCC PTA 1595).

Hybridoma-based monoclonal antibody preparative methods thus include those that comprise:

(a) immunizing an animal by administering to the animal at least one dose, and optionally more than one dose, of an immunogenically effective amount of an immunogenic VEGF sample, preferably an intact human VEGF sample;
(b) preparing a collection of monoclonal antibody-producing hybridomas from the immunized animal;
(c) selecting from the collection at least a first hybridoma that produces at least a first VEGFR2-blocking, anti-VEGF monoclonal antibody in accordance with the invention, optionally an anti-VEGF antibody that substantially cross-reacts with the monoclonal antibody 2C3 (ATCC PTA 1595); and
(d) culturing the at least a first antibody-producing hybridoma to provide the at least a first VEGFR2-blocking, anti-VEGF monoclonal antibody; and preferably
(e) obtaining the at least a first VEGFR2-blocking, anti-VEGF monoclonal antibody from the cultured at least a first hybridoma.

In identifying an anti-VEGF antibody that substantially cross-reacts with the monoclonal antibody 2C3 (ATCC PTA 1595), the selecting step may comprise:

(a) contacting a VEGF sample with effective amounts of the monoclonal antibody 2C3 (ATCC PTA 1595) and a candidate antibody; and
(b) determining the ability of the candidate antibody to substantially reduce the binding of the 2C3 antibody to the VEGF sample; wherein the ability of a candidate antibody to substantially reduce the binding of the 2C3 antibody to the VEGF sample is indicative of an anti-VEGF antibody that binds to substantially the same epitope as the monoclonal antibody 2C3 (ATCC PTA 1595).

The selecting step may further comprise:

(a) contacting a first VEGF sample with an effective binding amount of the monoclonal antibody 2C3 (ATCC PTA 1595) and determining the amount of 2C3 that binds to VEGF;
(b) contacting a second VEGF sample with an effective binding amount of the monoclonal antibody 2C3 (ATCC PTA 1595) in combination with an effective competing amount of a candidate antibody and determining the amount of 2C3 that binds to VEGF in the presence of the candidate antibody; and
(c) identifying an anti-VEGF antibody that binds to substantially the same epitope as the monoclonal antibody 2C3 (ATCC PTA 1595) by selecting a candidate antibody that reduces the amount of 2C3 that binds to VEGF by, preferably, at least about 80%.

As non-human animals are used for immunization, the monoclonal antibodies obtained from such a hybridoma will often have a non-human make up. Such antibodies may be optionally subjected to a humanization process, grafting or mutation, as known to those of skill in the art and further disclosed herein. Alternatively, transgenic animals, such as mice, may be used that comprise a human antibody gene library. Immunization of such animals will therefore directly result in the generation of suitable human antibodies.

After the production of a suitable antibody-producing cell, most preferably a hybridoma, whether producing human or non-human antibodies, the monoclonal antibody-encoding nucleic acids may be cloned to prepare a "recombinant" monoclonal antibody. Any recombinant cloning technique may be utilized, including the use of PCR™ to prime the synthesis of the antibody-encoding nucleic acid sequences. Therefore, yet further appropriate monoclonal antibody preparative methods include those that comprise using the antibody-producing cells as follows:

(a) obtaining at least a first suitable anti-VEGF antibody-encoding nucleic acid molecule or segment from a suitable anti-VEGF antibody-producing cell, preferably a hybridoma; and (b) expressing the nucleic acid molecule or segment in a recombinant host cell to obtain a recombinant VEGFR2-blocking, anti-VEGF monoclonal antibody in accordance with the present invention.

However, other powerful recombinant techniques are available that are ideally suited to the preparation of recombinant monoclonal antibodies. Such recombinant techniques include the phagemid library-based monoclonal antibody preparative methods comprising:

(a) immunizing an animal by administering to the animal at least one dose, and optionally more than one dose, of an immunogenically effective amount of an immunogenic VEGF sample (such as an intact human VEGF sample);

(b) preparing a combinatorial immunoglobulin phagemid library expressing RNA isolated from the antibody-producing cells, preferably from the spleen, of the immunized animal;

(c) selecting from the phagemid library at least a first clone that expresses at least a first VEGFR2-blocking, anti-VEGF antibody, optionally one that substantially cross-reacts with the monoclonal antibody 2C3 (ATCC PTA 1595);

(d) obtaining VEGFR2-blocking, anti-VEGF antibody-encoding nucleic acids from the at least a first selected clone and expressing the nucleic acids in a recombinant host cell to provide the at least a first VEGFR2-blocking, anti-VEGF antibody; and preferably (e) obtaining the at least a first VEGFR2-blocking, anti-VEGF antibody expressed by the nucleic acids obtained from the at least a first selected clone.

Again, in such phagemid library-based techniques, transgenic animals bearing human antibody gene libraries may be employed, thus yielding recombinant human monoclonal antibodies.

Irrespective of the manner of preparation of a first VEGFR2-blocking, anti-VEGF antibody nucleic acid segment, further suitable antibody nucleic acid segments may be readily prepared by standard molecular biological techniques. In order to confirm that any variant, mutant or second generation VEGFR2-blocking, anti-VEGF antibody nucleic acid segment is suitable for use in the present invention, the nucleic acid segment will be tested to confirm expression of a VEGFR2-blocking, anti-VEGF antibody in accordance with the present invention. Preferably, the variant, mutant or second generation nucleic acid segment will also be tested to confirm hybridization under standard, more preferably, standard stringent hybridization conditions. Exemplary suitable hybridization conditions include hybridization in about 7% sodium dodecyl sulfate (SDS), about 0.5 M $NaPO_4$, about 1 mM EDTA at about 50° C.; and washing with about 1% SDS at about 42° C.

As a variety of recombinant monoclonal antibodies, whether human or non-human in origin, may be readily prepared, the treatment methods of the invention may be executed by providing to the animal or patient at least a first nucleic acid segment that expresses a biologically effective amount of at least a first VEGFR2-blocking, anti-VEGF antibody in the patient. The "nucleic acid segment that expresses a VEGFR2-blocking, anti-VEGF, 2C3-like or 2C3-based antibody" will generally be in the form of at least an expression construct, and may be in the form of an expression construct comprised within a virus or within a recombinant host cell. Preferred gene therapy vectors of the present invention will generally be viral vectors, such as comprised within a recombinant retrovirus, herpes simplex virus (HSV), adenovirus, adeno-associated virus (AAV), cytomegalovirus (CMV), and the like.

This invention further provides compositions comprising at least a first purified VEGFR2-blocking, anti-VEGF antibody, or antigen-binding fragment thereof, optionally one that binds to essentially the same epitope as the monoclonal antibody 2C3 (ATCC PTA 1595). Such compositions may be pharmaceutically acceptable compositions or compositions for use in laboratory studies. In terms of the pharmaceutical compositions, they may preferably be formulated for parenteral administration, such as for intravenous administration.

The present invention provides a number of methods and uses of the VEGFR2-blocking, anti-VEGF antibodies, including the 2C3-cross-reactive, 2C3-like or 2C3-based antibodies. Concerning all methods, the terms "a" and "an" are used to mean "at least one", "at least a first", "one or more" or "a plurality" of steps in the recited methods, except where specifically stated. This is particularly relevant to the administration steps in the treatment methods. Thus, not only may different doses be employed with the present invention, but different numbers of doses, e.g., injections, may be used, up to and including multiple injections. Combined therapeutics may be used, administered before, after or during administration of the anti-VEGF therapeutic antibody.

Various useful in vitro methods and uses are provided that have important biological implications. First provided are methods of, and uses in, binding VEGF, which generally comprise effectively contacting a composition comprising VEGF, preferably free (non-receptor bound) VEGF with at least a first VEGFR2-blocking, anti-VEGF antibody, or antigen-binding fragment thereof, optionally an antibody that binds to substantially the same epitope as the monoclonal antibody 2C3 (ATCC PTA 1595).

Methods of, and uses in, detecting VEGF are provided, which generally comprise contacting a composition suspected of containing VEGF with at least a first VEGFR2-blocking, anti-VEGF antibody, or antigen-binding fragment thereof, optionally one that binds to substantially the same epitope as the monoclonal antibody 2C3 (ATCC PTA 1595), under conditions effective to allow the formation of VEGF/antibody complexes and detecting the complexes so formed. The detection methods and uses may be used in connection with biological samples, e.g., in diagnostics for angiogenesis and tumors, and diagnostic kits based thereon are also provided.

The present invention provides methods of, and uses in, preferentially or specifically inhibiting VEGF binding to the VEGF receptor VEGFR2, which generally comprise contacting, in the presence of VEGF, a population of cells or tissues that includes endothelial cells that express VEGFR2 (KDR/Flk-1) with a composition comprising a biologically effective amount of at least a first VEGFR2-blocking, anti-VEGF antibody, optionally one that binds to substantially the same epitope as the monoclonal antibody 2C3 (ATCC PTA 1595), or an antigen-binding fragment thereof, under conditions effective to inhibit VEGF binding to the VEGF receptor VEGFR2.

Methods of, and uses in, significantly inhibiting VEGF binding to the VEGF receptor VEGFR2, without significantly inhibiting VEGF binding to the VEGF receptor VEGFR1 are provided. These methods comprise contacting, in the presence of VEGF, a population of cells or tissues that includes a population of endothelial cells that express VEGFR2 (KDR/Flk-1) and VEGFR1 (Flt-1) with a composition comprising a biologically effective amount of at least a first VEGFR2-blocking, anti-VEGF antibody, optionally an anti-VEGF antibody that binds to substantially the same epitope as the monoclonal antibody 2C3 (ATCC PTA 1595), or an antigen-binding fragment thereof, under conditions effective to inhibit VEGF binding to the VEGF receptor VEGFR2, without significantly inhibiting VEGF binding to the VEGF receptor VEGFR1.

Further methods and uses of the invention are in analyzing the biological roles of the VEGF receptors termed VEGFR2 and VEGFR1, comprising the steps of:

(a) contacting a biological composition or tissue that comprises VEGF and a population of cells that express VEGFR2 (KDR/Flk-1) and VEGFR1 (Flt-1) receptors with a composition comprising a biologically effective amount of at least a first VEGFR2-blocking, anti-VEGF antibody, optionally an anti-VEGF antibody that binds to substantially the same epitope as the monoclonal antibody 2C3 (ATCC PTA 1595), or an antigen-binding fragment thereof; and (b) determining the effect of the VEGFR2-blocking, anti-VEGF antibody on at least a first biological response to VEGF; wherein:

(i) an alteration in a biological response in the presence of the VEGFR2-blocking, anti-VEGF antibody is indicative of a response mediated by the VEGFR2 receptor; and (ii) the maintenance of a biological response in the presence of the VEGFR2-blocking, anti-VEGF antibody is indicative of a response mediated by the VEGFR1 receptor.

Proliferation inhibition methods and uses are provided, including those to specifically inhibit VEGF-induced endothelial cell proliferation and/or migration, which generally comprise contacting a population of cells or tissues that includes a population of endothelial cells and VEGF with a composition comprising a biologically effective amount of at least a first VEGFR2-blocking, anti-VEGF antibody, optionally one that binds to substantially the same epitope as the monoclonal antibody 2C3 (ATCC PTA 1595), or an antigen-binding fragment of the VEGFR2-blocking, anti-VEGF antibody, under conditions effective to inhibit VEGF-induced endothelial cell proliferation and/or migration.

Methods of, and uses in, inhibiting VEGF-induced endothelial cell proliferation and/or migration, without significantly inhibiting VEGF-induced macrophage chemotaxis are provided, which generally comprise contacting a population of cells or tissues that contains endothelial cells, macrophages and VEGF with a composition comprising a biologically effective amount of at least a first VEGFR2-blocking, anti-VEGF antibody, optionally one that binds to substantially the same epitope as the monoclonal antibody 2C3 (ATCC PTA 1595), or an antigen-binding fragment of the anti-VEGF antibody, under conditions effective to inhibit VEGF-induced endothelial cell proliferation and/or migration, without significantly inhibiting VEGF-induced macrophage chemotaxis.

Methods of, and uses in, inhibiting VEGF-induced endothelial cell proliferation and/or migration and, optionally, angiogenesis, without significantly inhibiting VEGF stimulation of macrophages, osteoclasts or chondroclasts are further provided. The methods generally comprise contacting a population of cells or tissues that contain endothelial cells and at least one of macrophages, osteoclasts or chondroclasts, with a composition comprising a biologically effective amount of at least a first VEGFR2-blocking, anti-VEGF antibody, optionally one that binds to substantially the same epitope as the monoclonal antibody 2C3 (ATCC PTA 1595), or an antigen-binding fragment of the antibody, under conditions effective to inhibit VEGF-induced endothelial cell proliferation and/or migration or angiogenesis, without significantly inhibiting VEGF stimulation of macrophages, osteoclasts or chondroclasts.

The foregoing methods and uses can be performed in vitro and in vivo, in the latter case, wherein the tissues or cells are located within an animal and the anti-VEGF antibody is administered to the animal. In both cases, the methods and uses become methods and uses for inhibiting angiogenesis, comprising contacting a tissue comprising, or a population of, potentially angiogenic blood vessels, i.e., those potentially exposed to VEGF, with an anti-angiogenic composition comprising a biologically effective amount of at least a first VEGFR2-blocking, anti-VEGF antibody, optionally one that binds to substantially the same epitope as the monoclonal antibody 2C3 (ATCC PTA 1595), or an antigen-binding fragment thereof, under conditions effective to inhibit angiogenesis.

Where populations of potentially angiogenic blood vessels are maintained ex vivo, the present invention has utility in drug discovery programs. In vitro screening assays, with reliable positive and negative controls, are useful as a first step in the development of drugs to inhibit or promoter angiogenesis, as well as in the delineation of further information on the angiogenic process. Where the population of potentially angiogenic blood vessels is located within an animal or patient, the anti-angiogenic composition is administered to the animal as a form of therapy.

"Biologically effective amounts", in terms of each of the foregoing inhibitory methods are therefore amounts of VEGFR2-blocking, anti-VEGF antibodies, optionally 2C3-based antibodies, effective to inhibit VEGF-induced endothelial cell proliferation and/or migration; to inhibit VEGF-induced endothelial cell proliferation and/or migration, without significantly inhibiting VEGF-induced macrophage chemotaxis; to inhibit VEGF-induced endothelial cell proliferation and/or migration or angiogenesis, without significantly inhibiting VEGF stimulation of macrophages, osteoclasts or chondroclasts; and, overall, to reduce vascular endothelial cell proliferation and/or migration in a manner effective to inhibit blood vessels growth or angiogenesis.

The invention thus provides methods of, and uses in, inhibiting VEGF-induced angiogenesis and, preferably, treating an angiogenic disease, without significantly inhibiting VEGF stimulation of macrophages, osteoclasts or chondroclasts. The methods generally comprise contacting a population of cells or tissues that contain endothelial cells and at least one of macrophages, osteoclasts or chondroclasts, with a composition comprising a biologically effective amount of at least a first VEGFR2-blocking, anti-VEGF antibody, optionally one that binds to substantially the same epitope as the monoclonal antibody 2C3 (ATCC PTA 1595), or an antigen-binding fragment of the antibody, under conditions effective to inhibit VEGF-induced angiogenesis and to treat an angiogenic disease without significantly inhibiting VEGF stimulation of macrophages, osteoclasts or chondroclasts.

Methods of, and uses in, inhibiting VEGF-induced angiogenesis and, preferably, treating an anti-angiogenic disease, without causing significant side effects on bone metabolism are further provided. The methods generally comprise contacting a tissue or a population of angiogenic vessels that contain vascular endothelial cells and at least one of macrophages, osteoclasts or chondroclasts, with a composition comprising a biologically effective amount of at least a first VEGFR2-blocking, anti-VEGF antibody, optionally one that binds to substantially the same epitope as the monoclonal antibody 2C3 (ATCC PTA 1595), or an antigen-binding fragment of the antibody, under conditions effective to inhibit VEGF-induced angiogenesis and to treat an angiogenic disease without causing significant side effects on bone metabolism by not significantly impairing the activities of macrophages, osteoclasts or chondroclasts.

Anti-angiogenic drug screening (in vitro) and therapy (in vivo) are provided in terms of animals and patients that have, or are at risk for developing, any disease or disorder characterized by undesired, inappropriate, aberrant, excessive and/or pathological vascularization. It is well known to those of ordinary skill in the art that as aberrant angiogenesis occurs in a wide range of diseases and disorders, a given anti-angiogenic therapy, once shown to be effective in any acceptable model system, can be used to treat the entire range of diseases and disorders connected with angiogenesis.

The methods and uses of the present invention are particularly intended for use in animals and patients that have, or are at risk for developing, any form of vascularized tumor; macular degeneration, including age-related macular degeneration; arthritis, including rheumatoid arthritis; atherosclerosis and atherosclerotic plaques; diabetic retinopathy and other retinopathies; thyroid hyperplasias, including Grave's disease; hemangioma; neovascular glaucoma; and psoriasis.

The methods and uses of the invention are further intended for the treatment of animals and patients that have, or are at risk for developing, arterioyenous malformations (AVM), meningioma, and vascular restenosis, including restenosis following angioplasty. Other intended targets of the therapeutic methods and uses are animals and patients that have, or are at risk for developing, angiofibroma, dermatitis, endometriosis, hemophilic joints, hypertrophic scars, inflammatory diseases and disorders, pyogenic granuloma, scleroderma, synovitis, trachoma and vascular adhesions.

As disclosed in U.S. Pat. No. 5,712,291, specifically incorporated herein by reference, each of the foregoing somewhat preferred treatment groups are by no means exhaustive of the types of conditions that are to be treated by the present invention. U.S. Pat. No. 5,712,291 is incorporated herein by reference for certain specific purposes, including the purpose of identifying a number of other conditions that may be effectively treated by an anti-angiogenic therapeutic; the purpose of showing that the treatment of all angiogenic diseases represents a unified concept, once a defined category of angiogenesis-inhibiting compounds have been disclosed and claimed (in the present case, VEGFR2-blocking, anti-VEGF antibodies, optionally those that bind to substantially the same epitope as the monoclonal antibody 2C3 (ATCC PTA 1595)); and the purpose of showing that the treatment of all angiogenic diseases is enabled by data from only a single model system.

In yet further aspects, and as disclosed in U.S. Pat. No. 5,712,291, incorporated herein by reference, the methods and uses of the present invention are intended for the treatment of animals and patients that have, or are at risk for developing, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, chemical burns, choroidal neovascularization, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratocon junctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, ocular neovascular disease, optic pits, Osler-Weber syndrome (Osler-Weber-Rendu, osteoarthritis, Pagets disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, seleritis, sickle cell anemia, Sogrens syndrome, solid tumors, Stargarts disease, Steven's Johnson disease, superior limbic keratitis, syphilis, systemic lupus, Terrien's marginal degeneration, toxoplasmosis, trauma, tumors of Ewing sarcoma, tumors of neuroblastoma, tumors of osteosarcoma, tumors of retinoblastoma, tumors of rhabdomyosarcoma, ulceritive colitis, vein occlusion, Vitamin A deficiency and Wegeners sarcoidosis.

The present invention further provides methods and uses for the treatment of animals and patients that have, or are at risk for developing, arthritis, in common with the treatment of arthritis using immunological agents described in U.S. Pat. No. 5,753,230, specifically incorporated herein by reference. U.S. Pat. No. 5,972,922 is also specifically incorporated herein by reference to even further exemplify the application of anti-angiogenic strategies to the treatment of undesired angiogenesis associated with diabetes, parasitic diseases, abnormal wound healing, hypertrophy following surgery, burns, injury or trauma, inhibition of hair growth, inhibition of ovulation and corpus luteum formation, inhibition of implantation and inhibition of embryo development in the uterus. All of the foregoing conditions are therefore contemplated for treatment by the methods and uses of the present invention.

U.S. Pat. No. 5,639,757 is further specifically incorporated herein by reference to exemplify the use of anti-angiogenic strategies to the general treatment of graft rejection. The treatment of lung inflammation, nephrotic syndrome, preeclampsia, pericardial effusion, such as that associated with pericarditis, and pleural effusion using anti-angiogenic strategies based upon VEGF inhibition is described in WO 98/45331, specifically incorporated herein by reference. Animals and patients that have, or are at risk for developing, any of the foregoing conditions are therefore contemplated for treatment by the methods and uses of the present invention.

As disclosed in WO 98/16551, specifically incorporated herein by reference, biological molecules that antagonize VEGF function are also suitable for use in treating diseases and disorders characterized by undesirable vascular permeability. Accordingly, the VEGF antagonizing antibodies, methods and uses of the present invention are applicable to the treatment of animals and patients that have, or are at risk for developing, diseases and disorders characterized by undesirable vascular permeability, e.g., edema associated with brain tumors, ascites associated with malignancies, Meigs' syndrome, lung inflammation, nephrotic syndrome, pericardial effusion and pleural effusion and the like.

Although the treatment of all the foregoing diseases is enabled within the present, unified invention, a particularly preferred aspect of the methods and uses of the present invention is application of anti-angiogenic therapy to animals and patients that have, or are at risk for developing, a vascularized solid tumor, a metastatic tumor or metastases from a primary tumor.

Methods of, and uses in, inhibiting VEGF-induced angiogenesis, and, preferably, exerting an anti-tumor or improved anti-tumor effect without significantly inhibiting VEGF stimulation of macrophages, osteoclasts or chondroclasts are further provided. The methods generally comprise contacting a tissue, tumor environment or population of angiogenic vessels that contain vascular endothelial cells and at least one of macrophages, osteoclasts or chondroclasts, with a composition comprising a biologically effective amount of at least a first VEGFR2-blocking, anti-VEGF antibody, optionally one that binds to substantially the same epitope as the monoclonal antibody 2C3 (ATCC PTA 1595), or an antigen-binding fragment of the antibody, under conditions effective to inhibit VEGF-induced angiogenesis and to exert an anti-tumor or improved anti-tumor effect without significantly inhibiting VEGF stimulation of macrophages, osteoclasts or chondroclasts.

The present invention thus further provides methods of, and uses in, treating a disease associated with angiogenesis, including all forms of cancer associated with angiogenesis, comprising administering to an animal or patient with such a disease or cancer a therapeutically effective amount of at least a first pharmaceutical composition that comprises a VEGFR2-blocking, anti-VEGF antibody, optionally one that binds to substantially the same epitope as the monoclonal antibody 2C3 (ATCC PTA 1595), or an antigen-binding fragment or immunoconjugate of such an anti-VEGF antibody.

This invention links both anti-angiogenic methods using unconjugated or naked antibodies and fragments thereof, and vascular targeting methods using immunoconjugates in which the antibody, or antigen-binding fragment thereof, is operatively attached to a therapeutic agent. Unless otherwise specifically stated or made clear in scientific terms, the terms "antibody and fragment thereof, as used herein, therefore mean an "unconjugated or naked" antibody or fragment, which is not attached to another agent, particularly a therapeutic or diagnostic agent. These definitions do not exclude modifications of the antibody, such as, by way of example only, modifications to improve the biological half life, affinity, avidity or other properties of the antibody, or combinations of the antibody with other effectors.

The anti-angiogenic treatment methods and uses of the invention also encompass the use of both unconjugated or naked antibodies and immunoconjugates. In the immunoconjugate-based anti-angiogenic treatment methods, the antibody, or antigen-binding fragment thereof, is preferably operatively attached to a second anti-angiogenic agent (the anti-VEGF antibody itself, being the first anti-angiogenic agent). The attached anti-angiogenic agents may be those that have a direct or indirect anti-angiogenic effect.

The anti-angiogenic treatment methods and uses comprise administering to an animal or patient with a disease associated with angiogenesis, including all forms of cancer associated with angiogenesis, a therapeutically effective amount of at least a first pharmaceutical composition that comprises at least a first unconjugated or naked VEGFR2-blocking, anti-VEGF antibody, or antigen-binding fragment thereof, optionally that binds to substantially the same epitope as the monoclonal antibody 2C3 (ATCC PTA 1595). Equally, the administered antibody may be operatively associated with a second anti-angiogenic agent.

Methods for, and uses in, treating metastatic cancer comprise administering to an animal or patient with metastatic cancer a therapeutically effective amount of at least a first pharmaceutical composition that comprises at least a first an unconjugated or naked VEGFR2-blocking, anti-VEGF antibody, or antigen-binding fragment thereof, optionally one that binds to substantially the same epitope as the monoclonal antibody 2C3 (ATCC PTA 1595). Further methods are those wherein the administered antibody may be operatively associated with a second anti-angiogenic agent.

Methods for, and uses in, reducing metastases from a primary cancer comprise administering a therapeutically effective amount of at least a first unconjugated or naked VEGFR2-blocking, anti-VEGF antibody, or antigen-binding fragment thereof, to an animal or patient that has, or was treated for, a primary cancer; wherein the unconjugated or naked VEGFR2-blocking, anti-VEGF antibody or fragment thereof optionally binds to substantially the same epitope as the monoclonal antibody 2C3 (ATCC PTA 1595). Similarly, the administered antibody may be operatively associated with a second anti-angiogenic agent.

Methods for, and uses in, treating a disease associated with angiogenesis, including all forms of cancer associated with angiogenesis, further comprise administering to an animal or patient with such a disease, e.g., a vascularized tumor, at least a first unconjugated or naked VEGFR2-blocking, anti-VEGF antibody, optionally one that binds to substantially the same epitope as the monoclonal antibody 2C3 (ATCC PTA 1595), or an antigen-binding fragment thereof, in an amount effective to inhibit angiogenesis within the disease site or vascularized tumor. Equally, the administered antibody may be operatively associated with a second anti-angiogenic agent.

The methods for, and uses in, treating a disease associated with angiogenesis, including all forms of cancer associated with angiogenesis, further comprise administering to an animal or patient with such a disease or cancer at least a first unconjugated or naked VEGFR2-blocking, anti-VEGF antibody, optionally one that binds to substantially the same epitope as the monoclonal antibody 2C3 (ATCC PTA 1595), or an antigen-binding fragment thereof, in an amount effective to inhibit VEGF binding to the VEGF receptor VEGFR2 (KDR/Flk-1), thereby inhibiting angiogenesis within the disease or cancerous site. The administered antibody may alternatively be operatively associated with a second anti-angiogenic agent.

Methods for, and uses in, treating a disease associated with angiogenesis, including all forms of cancer associated with angiogenesis, also comprise administering to an animal or patient with a vascularized tumor a therapeutically effective amount of at least a first unconjugated or naked VEGFR2-blocking, anti-VEGF antibody, optionally one that binds to substantially the same epitope as the monoclonal antibody 2C3 (ATCC PTA 1595), or antigen-binding fragment thereof; wherein the anti-VEGF antibody substantially inhibits VEGF binding to the VEGF receptor VEGFR2 (KDR/Flk-1) without significantly inhibiting VEGF binding to the VEGF receptor VEGFR1 (Flt-1). Equally, the administered antibody may be operatively associated with a second anti-angiogenic agent.

Yet further methods for, and uses in, treating a disease associated with angiogenesis, including all forms of cancer associated with angiogenesis, comprise administering to an animal or patient with such a disease, cancer or vascularized tumor a therapeutically effective amount of at least a first unconjugated or naked VEGFR2-blocking, anti-VEGF antibody, optionally one that binds to substantially the same epitope as the monoclonal antibody 2C3 (ATCC PTA 1595), or an antigen-binding fragment thereof; wherein the anti-VEGF antibody substantially inhibits VEGF binding to the VEGF receptor VEGFR2 (KDR/Flk-1) without significantly inhibiting VEGF binding to the VEGF receptor VEGFR1 (Flt-1), thereby inhibiting angiogenesis within the disease site, cancer or vascularized tumor without significantly impairing macrophage chemotaxis in the animal. The administered antibody may also be operatively associated with a second anti-angiogenic agent.

Still further methods for, and uses in, treating a disease associated with angiogenesis, including all forms of cancer associated with angiogenesis, comprise administering to an animal or patient with such a disease, cancer or vascularized tumor a therapeutically effective amount of at least a first unconjugated or naked VEGFR2-blocking, anti-VEGF antibody, optionally one that binds to substantially the same epitope as the monoclonal antibody 2C3 (ATCC PTA 1595), or an antigen-binding fragment thereof; wherein the anti-VEGF antibody substantially inhibits VEGF binding to the VEGF receptor VEGFR2 (KDR/Flk-1) without significantly inhibiting VEGF binding to the VEGF receptor VEGFR1 (Flt-1), thereby inhibiting angiogenesis within the disease site, cancer or vascularized tumor without significantly impairing macrophage, osteoclast and/or chondroclast activity in the animal. Equally, the administered antibody may be operatively associated with a second anti-angiogenic agent.

Methods for, and uses in, treating a disease associated with angiogenesis, including all forms of cancer associated with angiogenesis, further comprise administering to an animal or patient with such a disease, e.g., a vascularized tumor, at least a first unconjugated or naked VEGFR2-blocking, anti-VEGF antibody, optionally one that binds to substantially the same epitope as the monoclonal antibody 2C3 (ATCC PTA 1595), or an antigen-binding fragment thereof, in an amount effective to inhibit angiogenesis within the disease site or vascularized tumor without exerting a significant adverse on bone metabolism.

The foregoing anti-angiogenic treatment methods and uses will generally involve the administration of the pharmaceutically effective composition to the animal or patient systemically, such as by transdermal, intramuscular, intravenous injection and the like. However, any route of administration that allows the therapeutic agent to localize to the angiogenic site or sites, including tumor or intratumoral vascular endothelial cells, will be acceptable. Therefore, other suitable routes of delivery include oral, rectal, nasal, topical, and vaginal. U.S. Pat. No. 5,712,291, is specifically incorporated herein by reference for purposes including further describing the various routes of administration that may be included in connection with the treatment of an angiogenic disease or disorder.

For uses and methods for the treatment of arthritis, e.g., intrasynovial administration may be employed, as described for other immunological agents in U.S. Pat. No. 5,753,230, specifically incorporated herein by reference. For conditions associated with the eye, ophthalmic formulations and administration are contemplated.

"Administration", as used herein, means provision or delivery of VEGFR2-blocking, anti-VEGF antibody or 2C3-based therapeutics in an amount(s) and for a period of time(s) effective to exert anti-angiogenic and/or anti-tumor effects. The passive administration of proteinaceous therapeutics is generally preferred, in part, for its simplicity and reproducibility.

However, the term "administration" is herein used to refer to any and all means by which VEGFR2-blocking, anti-VEGF antibody or 2C3-based therapeutics are delivered or otherwise provided to the tumor vasculature. "Administration" therefore includes the provision of cells that produce the VEGFR2-blocking, anti-VEGF antibody or 2C3-based therapeutics in a manner effective to result in delivery to the tumor. In such embodiments, it may be desirable to formulate or package the cells in a selectively permeable membrane, structure or implantable device, generally one that can be removed to cease therapy. Exogenous VEGFR2-blocking, anti-VEGF antibody or 2C3-like administration will still generally be preferred, as this represents a non-invasive method that allows the dose to be closely monitored and controlled.

The therapeutic methods and uses of the invention also extend to the provision of nucleic acids that encode VEGFR2-blocking, anti-VEGF antibody or 2C3-based therapeutics in a manner effective to result in their expression in the vicinity of the tumor or their localization to the tumor. Any gene therapy technique may be employed, such as naked DNA delivery, recombinant genes and vectors, cell-based delivery, including ex vivo manipulation of patients' cells, and the like.

In yet further embodiments, the invention provides methods for, and uses in, delivering selected therapeutic or diagnostic agents to angiogenic blood vessels associated with disease. Such embodiments are preferably used for delivering selected therapeutic or diagnostic agents to tumor or intratumoral vasculature or stroma, and comprise administering to an animal or patient having a vascularized tumor a biologically effective amount of a composition comprising at least a first immunoconjugate in which a diagnostic or therapeutic agent is operatively attached to a VEGFR2-blocking, anti-VEGF antibody, or antigen-binding fragment thereof, optionally one that binds to substantially the same epitope as the monoclonal antibody 2C3 (ATCC PTA 1595).

Although understanding the mechanism of action underlying the targeting aspects of the invention is not required in order to practice such embodiments, it is believed that the antibodies of the invention deliver attached agents to angiogenic and tumor vasculature by virtue of binding to VEGF bound to the VEGFR1 expressed thereon. These methods and uses of the invention thus concern delivering selected therapeutic or diagnostic agents to angiogenic blood vessels, tumor or intratumoral vasculature, and comprise administering to an animal or patient in need of treatment a biologically effective amount of a composition comprising an immunoconjugate in which a diagnostic or therapeutic agent is operatively attached to at least a first VEGFR2-blocking, anti-VEGF antibody, or antigen-binding fragment thereof, optionally one that binds to substantially the same epitope as the monoclonal antibody 2C3 (ATCC PTA 1595), in a manner effective to allow binding of the antibody to VEGF bound to VEGFR1 expressed, overexpressed or upregulated on the angiogenic blood vessels, tumor or intratumoral vasculature, thus delivering the diagnostic or therapeutic agent to the VEGF-VEGFR1 on the angiogenic blood vessels, tumor or intratumoral vasculature.

The delivery of selected therapeutic agents to tumor or intratumoral vasculature or stroma acts to arrest blood flow, or specifically arrest blood flow, in tumor vasculature; to destroy, or specifically destroy, tumor vasculature; and to induce necrosis, or specific necrosis in a tumor. These methods and uses may thus be summarized as methods for treating an animal or patient having a vascularized tumor, comprising administering to the animal or patient a therapeutically effective amount of at least a first pharmaceutical composition comprising at least a first immunoconjugate that comprises a VEGFR2-blocking, anti-VEGF antibody, optionally one that binds to substantially the same epitope as the monoclonal antibody 2C3 (ATCC PTA 1595), or antigen-binding fragment thereof, operatively attached to a therapeutic agent.

The "therapeutically effective amounts" for use in the invention are amounts of VEGFR2-blocking, anti-VEGF antibody or 2C3-based immunoconjugates effective to specifically kill at least a portion of tumor or intratumoral vascular endothelial cells; to specifically induce apoptosis in at least a portion of tumor or intratumoral vascular endothelial cells; to specifically promote coagulation in at least a portion of tumor or intratumoral blood vessels; to specifically occlude or destroy at least a portion of blood transporting vessels of the tumor; to specifically induce necrosis in at least a portion of a tumor; and/or to induce tumor regression or remission upon administration to selected animals or patients. Such effects are achieved while exhibiting little or no binding to, or little or no killing of, vascular endothelial cells in normal, healthy tissues; little or no coagulation in, occlusion or destruction of blood vessels in healthy, normal tissues; and exerting negligible or manageable adverse side effects on normal, healthy tissues of the animal or patient.

The terms "preferentially" and "specifically", as used herein in the context of promoting coagulation in, or destroying, tumor vasculature, and/or in the context of binding to tumor stroma and/or causing tumor necrosis, thus mean that the VEGFR2-blocking, anti-VEGF antibody or 2C3-based immunoconjugates function to achieve stromal binding, coagulation, destruction and/or tumor necrosis that is substantially confined to the tumor stroma, vasculature and tumor site, and does not substantially extend to causing coagulation, destruction and/or tissue necrosis in normal, healthy tissues of the animal or subject. The structure and function of healthy cells and tissues is therefore maintained substantially unimpaired by the practice of the invention.

Although the antibodies of the invention effectively deliver agents to angiogenic and tumor vasculature by binding to VEGF in association with VEGFR1, other methods and uses operate on the basis of delivering a therapeutic agent to tumor stroma, wherein it exerts a therapeutic effect on the nearby vessels. These methods and uses comprise administering to an animal or patient with a vascularized tumor an immunoconjugate that comprises a therapeutic agent operatively attached to at least a first VEGFR2-blocking, anti-VEGF antibody, or antigen-binding fragment thereof, optionally one that binds to substantially the same epitope as the monoclonal antibody 2C3 (ATCC PTA 1595) in an amount effective to bind the immunoconjugate to non-receptor bound VEGF within the tumor stroma.

These methods and uses comprise administering to an animal or patient with a vascularized tumor an immunoconjugate that comprises a therapeutic agent operatively attached to at least a first VEGFR2-blocking, anti-VEGF antibody, or antigen-binding fragment thereof, optionally one that binds to substantially the same epitope as the monoclonal antibody 2C3 (ATCC PTA 1595) in an amount effective to localize the immunoconjugate within the tumor stroma such that the attached therapeutic agent exerts an anti-tumor effect on the surrounding tumor vasculature and/or tumor cells.

The compositions, as well as the methods and uses, of the invention thus extend to compositions comprising VEGFR2-blocking, anti-VEGF antibody or 2C3-based immunoconjugates comprising at least a first VEGFR2-blocking, anti-VEGF antibody, or antigen-binding fragment thereof, optionally one that binds to substantially the same epitope as the monoclonal antibody 2C3 (ATCC PTA 1595), operatively attached to at least a first therapeutic or diagnostic agent. VEGFR2-blocking, anti-VEGF antibody or 2C3-based therapeutic conjugates are preferably linked to radiotherapeutic agents, anti-angiogenic agents, apoptosis-inducing agents, anti-tubulin drugs, anti-cellular or cytotoxic agents, or coagulants (coagulation factors).

The invention thus provides a range of conjugated antibodies and fragments thereof in which the antibody is operatively attached to at least a first therapeutic or diagnostic agent. The term "immunoconjugate" is broadly used to define the operative association of the antibody with another effective agent and is not intended to refer solely to any type of operative association, and is particularly not limited to chemical "conjugation". Recombinant fusion proteins are particularly contemplated. So long as the delivery or targeting agent is able to bind to the target and the therapeutic or diagnostic agent is sufficiently functional upon delivery, the mode of attachment will be suitable.

Attachment of agents via the carbohydrate moieties on antibodies is also contemplated. Glycosylation, both O-linked and N-linked, naturally occurs in antibodies. Recombinant antibodies can be modified to recreate or create additional glycosylation sites if desired, which is simply achieved by engineering the appropriate amino acid sequences (such as Asn-X-Ser, Asn-X-Thr, Ser, or Thr) into the primary sequence of the antibody.

Currently preferred agents for use in VEGFR2-blocking, anti-VEGF antibody or 2C3-based therapeutic conjugates and related methods and uses are those that complement or enhance the effects of the antibody and/or those selected for a particular tumor type or patient. "Therapeutic agents that complement or enhance the effects of the antibody" include radiotherapeutic agents, anti-angiogenic agents, apoptosis-inducing agents and anti-tubulin drugs, any one or more of which are preferred for use herewith.

The attachment or association of the preferred agents with VEGFR2-blocking, anti-VEGF or 2C3-based antibodies gives "immunoconjugates", wherein such immunoconjugates often have enhanced and even synergistic anti-tumor properties. Currently preferred anti-angiogenic agents for use in this manner are angiostatin, endostatin, any one of the angiopoietins, vasculostatin, canstatin and maspin. Currently preferred anti-tubulin drugs include colchicine, taxol, vinblastine, vincristine, vindescine and one or more of the combretastatins.

The use of anti-cellular and cytotoxic agents results in VEGFR2-blocking, anti-VEGF antibody or 2C3-based "immunotoxins", whereas the use of coagulation factors results in VEGFR2-blocking, anti-VEGF antibody or 2C3- based "coaguligands". The use of at least two therapeutic agents is also contemplated, such as combinations of one or more radiotherapeutic agents, anti-angiogenic agents, apoptosis-inducing agents, anti-tubulin drugs, anti-cellular and cytotoxic agents and coagulation factors.

In certain applications, the VEGFR2-blocking, anti-VEGF antibody or 2C3-based therapeutics will be operatively attached to cytotoxic, cytostatic or otherwise anti-cellular agents that have the ability to kill or suppress the growth or cell division of endothelial cells. Suitable anti-cellular agents include chemotherapeutic agents, as well as cytotoxins and cytostatic agents. Cytostatic agents are generally those that disturb the natural cell cycle of a target cell, preferably so that the cell is taken out of the cell cycle.

Exemplary chemotherapeutic agents include: steroids; cytokines; anti-metabolites, such as cytosine arabinoside, fluorouracil, methotrexate or aminopterin; anthracyclines; mitomycin C; vinca alkaloids; antibiotics; demecolcine; etoposide; mithramycin; and anti-tumor alkylating agents, such as chlorambucil or melphalan. Indeed, any of the agents disclosed herein in Table C could be used. Certain preferred anti-cellular agents are DNA synthesis inhibitors, such as daunorubicin, doxorubicin, adriamycin, and the like.

In certain therapeutic applications, toxin moieties will be preferred, due to the much greater ability of most toxins to deliver a cell killing effect, as compared to other potential agents. Therefore, certain preferred anti-cellular agents for VEGFR2-blocking, anti-VEGF antibody or 2C3-based antibody constructs are plant-, fungus- or bacteria-derived toxins. Exemplary toxins include epipodophyllotoxins; bacterial endotoxin or the lipid A moiety of bacterial endotoxin; ribosome inactivating proteins, such as saporin or gelonin; α-sarcin; aspergillin; restrictocin; ribonucleases, such as placental ribonuclease; diphtheria toxin and *pseudomonas* exotoxin.

Preferred toxins are the A chain toxins, such as ricin A chain. The most preferred toxin moiety is often ricin A chain that has been treated to modify or remove carbohydrate residues, so called "deglycosylated A chain" (dgA). Deglycosylated ricin A chain is preferred because of its extreme potency, longer half-life, and because it is economically feasible to manufacture it a clinical grade and scale. Recombinant and/or truncated ricin A chain may also be used.

For tumor targeting and treatment with immunotoxins, the following patents and patent applications are specifically incorporated herein by reference for the purposes of even further supplementing the present teachings regarding anti-cellular and cytotoxic agents: U.S. application Ser. Nos. 07/846,349; 08/295,868 (U.S. Pat. No. 6,004,554); Ser. No. 08/205,330 (U.S. Pat. No. 5,855,866); Ser. No. 08/350,212 (U.S. Pat. No. 5,965,132); Ser. No. 08/456,495 (U.S. Pat. No. 5,776,427); Ser. No. 08/457,487 (U.S. Pat. No. 5,863, 538); Ser. Nos. 08/457,229 and 08/457,031 (U.S. Pat. No. 5,660,827) and Ser. No. 08/457,869 (U.S. Pat. No. 6,051, 230).

The 2C3-based or other VEGFR2-blocking, anti-VEGF antibody of the present invention may be linked to an anti-tubulin drug. "Anti-tubulin drug(s)", as used herein, means any agent, drug, prodrug or combination thereof that inhibits cell mitosis, preferably by directly or indirectly inhibiting tubulin activities necessary for cell mitosis, preferably tubulin polymerization or depolymerization.

Currently preferred anti-tubulin drugs for use herewith are colchicine; taxanes, such as taxol; vinca alkaloids, such as vinblastine, vincristine and vindescine; and combretastatins. Exemplary combretastatins are combretastatin A, B and/or D, including A-1, A-2, A-3, A-4, A-5, A-6, B-1, B-2, B-3, B-4, D-1 and D-2 and prodrug forms thereof.

The VEGFR2-blocking, anti-VEGF antibody or 2C3-based therapeutics may comprise a component that is capable of promoting coagulation, i.e., a coagulant. Here, the targeting antibody may be directly or indirectly, e.g., via another antibody, linked to a factor that directly or indirectly stimulates coagulation.

Preferred coagulation factors for such uses are Tissue Factor (TF) and TF derivatives, such as truncated TF (tTF), dimeric, trimeric, polymeric/multimeric TF, and mutant TF deficient in the ability to activate Factor VII. Other suitable coagulation factors include vitamin K-dependent coagulants, such as Factor II/IIa, Factor VII/VIIa, Factor IX/IXa and Factor X/Xa; vitamin K-dependent coagulation factors that lack the Gla modification; Russell's viper venom Factor X activator; platelet-activating compounds, such as thromboxane $A_2$ and thromboxane $A_2$ synthase; and inhibitors of fibrinolysis, such as α2-antiplasmin.

Tumor targeting and treatment with coaguligands is described in the following patents and patent applications, each of which are specifically incorporated herein by reference for the purposes of even further supplementing the present teachings regarding coaguligands and coagulation factors: U.S. applications Ser. Nos. 07/846,349; 08/205,330 (U.S. Pat. No. 5,855,866); Ser. No. 08/350,212 (U.S. Pat. No. 5,965,132); Ser. Nos. 08/273,567; 08/482,369 (U.S. Pat. No. 6,093,399); Ser. Nos. 08/485,482; 08/487,427 (U.S. Pat. No. 6,004,555); Ser. No. 08/479,733 (U.S. Pat. No. 5,877, 289); Ser. Nos. 08/472,631; and 08/479,727 and 08/48 1,904 (U.S. Pat. No. 6,036,955).

The preparation of immunoconjugates and immunotoxins is generally well known in the art (see, e.g., U.S. Pat. No. 4,340,535, incorporated herein by reference). Each of the following patents and patent applications are further incorporated herein by reference for the purposes of even further supplementing the present teachings regarding immunotoxin generation, purification and use: U.S. application Ser. No. 07/846,349; 08/295,868 (U.S. Pat. No. 6,004,554); Ser. No. 08/205,330 (U.S. Pat. No. 5,855,866); Ser. No. 08/350,212 (U.S. Pat. No. 5,965,132); Ser. No. 08/456,495 (U.S. Pat. No. 5,776,427); Ser. No. 08/457,487 (U.S. Pat. No. 5,863, 538); Ser. Nos. 08/457,229 and 08/457,031 (U.S. Pat. No. 5,660,827) and Ser. No. 08/457,869 (U.S. Pat. No. 6,051, 230).

In the preparation of immunoconjugates and immunotoxins, advantages may be achieved through the use of certain linkers. For example, linkers that contain a disulfide bond that is sterically "hindered" are often preferred, due to their greater stability in vivo, thus preventing release of the toxin moiety prior to binding at the site of action. It is generally desired to have a conjugate that will remain intact under conditions found everywhere in the body except the intended site of action, at which point it is desirable that the conjugate have good "release" characteristics.

Depending on the specific toxin compound used, it may be necessary to provide a peptide spacer operatively attaching the VEGFR2-blocking, anti-VEGF antibody or 2C3-based antibody and the toxin compound, wherein the peptide spacer is capable of folding into a disulfide-bonded loop structure. Proteolytic cleavage within the loop would then yield a heterodimeric polypeptide wherein the antibody and the toxin compound are linked by only a single disulfide bond.

When certain other toxin compounds are utilized, a non-cleavable peptide spacer may be provided to operatively attach the VEGFR2-blocking, anti-VEGF antibody or 2C3- based antibody and the toxin compound. Toxins that may be used in conjunction with non-cleavable peptide spacers are those that may, themselves, be converted by proteolytic cleavage, into a cytotoxic disulfide-bonded form. An example of such a toxin compound is a *Pseudonomas* exotoxin compound.

A variety of chemotherapeutic and other pharmacological agents can also be successfully conjugated to VEGFR2-blocking, anti-VEGF antibody or 2C3-based therapeutics. Exemplary antineoplastic agents that have been conjugated to antibodies include doxorubicin, daunomycin, methotrexate and vinblastine. Moreover, the attachment of other agents such as neocarzinostatin, macromycin, trenimon and α-amanitin has been described (see U.S. Pat. Nos. 5,660,827; 5,855,866; and 5,965,132; each incorporated herein.)

In light of one of the present inventors earlier work, the preparation of coaguligands is now also easily practiced. The operable association of one or more coagulation factors with a VEGFR2-blocking, anti-VEGF antibody or 2C3-based antibody may be a direct linkage, such as those described above for the immunotoxins. Alternatively, the operative association may be an indirect attachment, such as where the antibody is operatively attached to a second binding region, preferably an antibody or antigen binding region of an antibody, that binds to the coagulation factor. The coagulation factor should be attached to the VEGFR2-blocking, anti-VEGF antibody or 2C3-based antibody at a site distinct from its functional coagulating site, particularly where a covalent linkage is used to join the molecules.

Indirectly linked coaguligands are often based upon bispecific antibodies. The preparation of bispecific antibodies is also well known in the art. One preparative method involves the separate preparation of antibodies having specificity for the targeted tumor component, on the one hand, and the coagulating agent on the other. Peptic $F(ab'\gamma)_2$ fragments from the two chosen antibodies are then generated, followed by reduction of each to provide separate $Fab'\gamma_{SH}$ fragments. The SH groups on one of the two partners to be coupled are then alkylated with a cross-linking reagent, such as o-phenylenedimaleimide, to provide free maleimide groups on one partner. This partner may then be conjugated to the other by means of a thioether linkage, to give the desired $F(ab'\gamma)_2$ heteroconjugate (Glennie et al., 1987; incorporated herein by reference). Other approaches, such as cross-linking with SPDP or protein A may also be carried out.

Another method for producing bispecific antibodies is by the fusion of two hybridomas to form a quadroma. As used herein, the term "quadroma" is used to describe the productive fusion of two B cell hybridomas. Using now standard techniques, two antibody producing hybridomas are fused to give daughter cells, and those cells that have maintained the expression of both sets of clonotype immunoglobulin genes are then selected.

A preferred method of generating a quadroma involves the selection of an enzyme deficient mutant of at least one of the parental hybridomas. This first mutant hybridoma cell line is then fused to cells of a second hybridoma that had been lethally exposed, e.g., to iodoacetamide, precluding its continued survival. Cell fusion allows for the rescue of the first hybridoma by acquiring the gene for its enzyme deficiency from the lethally treated hybridoma, and the rescue of the second hybridoma through fusion to the first hybridoma. Preferred, but not required, is the fusion of immunoglobulins of the same isotype, but of a different subclass. A mixed subclass antibody permits the use if an alternative assay for the isolation of a preferred quadroma.

Microtiter identification embodiments, FACS, immunofluorescence staining, idiotype specific antibodies, antigen binding competition assays, and other methods common in the art of antibody characterization may be used to identify preferred quadromas. Following the isolation of the quadroma, the bispecific antibodies are purified away from other cell products. This may be accomplished by a variety of antibody isolation procedures, known to those skilled in the art of immunoglobulin purification (see, e.g., Antibodies: A Laboratory Manual, 1988; incorporated herein by reference). Protein A or protein G sepharose columns are preferred.

In the preparation of immunoconjugates, immunotoxins and coaguligands, recombinant expression may be employed. The nucleic acid sequences encoding the chosen VEGFR2-blocking, anti-VEGF antibody or 2C3-based antibody, and therapeutic agent, toxin or coagulant, are attached in-frame in an expression vector. Recombinant expression thus results in translation of the nucleic acid to yield the desired immunoconjugate. Chemical cross-linkers and avidin:biotin bridges may also join the therapeutic agents to the VEGFR2-blocking, anti-VEGF antibody or 2C3-based antibodies.

The following patents and patent applications are each incorporated herein by reference for the purposes of even further supplementing the present teachings regarding coaguligand preparation, purification and use, including bispecific antibody coaguligands: U.S. applications Ser. Nos. 07/846,349; 08/205,330 (U.S. Pat. No. 5,855,866); Ser. No. 08/350,212 (U.S. Pat. No. 5,965,132); Ser. Nos. 08/273,567; 08/482,369 (U.S. Pat. No. 6,093,399); Ser. Nos. 08/485,482; 08/487,427 (U.S. Pat. No. 6,004,555); Ser. No. 08/479,733 (U.S. Pat. No. 5,877,289); Ser. Nos. 08/472,63 1; and 08/479,727 and 08/481,904 (U.S. Pat. No. 6,036,955).

Immunoconjugates with radiotherapeutic agents, anti-angiogenic agents, apoptosis-inducing agents, anti-tubulin drugs, toxins and coagulants, whether prepared by chemical conjugation or recombinant expression, may employ a biologically-releasable bond and/or a selectively cleavable spacer or linker. Such compositions are preferably reasonably stable during circulation and are preferentially or specifically released upon delivery to the disease or tumor site.

Certain preferred examples are acid sensitive spacers, wherein VEGFR2-blocking, anti-VEGF antibodies linked to colchicine or doxorubicin are particularly contemplated. Other preferred examples are peptide linkers that include a cleavage site for peptidases and/or proteinases that are specifically or preferentially present or active within a disease site, such as a tumor environment. The delivery of the immunoconjugate to the disease or tumor site results in cleavage and the relatively specific release of the coagulation factor.

Peptide linkers that include a cleavage site for urokinase, pro-urokinase, plasmin, plasminogen, TGFβ, staphylokinase, Thrombin, Factor IXa, Factor Xa or a metalloproteinase (MMP), such as an interstitial collagenase, a gelatinase or a stromelysin, are particularly preferred, as described and enabled by U.S. Pat. No. 5,877,289, incorporated herein by reference for such purposes, and further exemplified herein in Table B2.

The VEGFR2-blocking, anti-VEGF antibody may also be derivatized to introduce functional groups permitting the attachment of the therapeutic agent(s) through a biologically releasable bond. The targeting antibody may thus be derivatized to introduce side chains terminating in hydrazide, hydrazine, primary amine or secondary amine groups.

Therapeutic agents may be conjugated through a Schiff's base linkage, a hydrazone or acyl hydrazone bond or a hydrazide linker (U.S. Pat. Nos. 5,474,765 and 5,762,918, each specifically incorporated herein by reference).

Whether primarily anti-angiogenic or vascular-targeting based, the compositions and methods of the present invention may be used in combination with other therapeutics and diagnostics. In terms of biological agents, preferably diagnostic or therapeutic agents, for use "in combination" with a VEGFR2-blocking, anti-VEGF antibody in accordance with the present invention, such as a 2C3-based antibody, the term "in combination" is succinctly used to cover a range of embodiments. The "in combination" terminology, unless otherwise specifically stated or made clear from the scientific terminology, thus applies to various formats of combined compositions, pharmaceuticals, cocktails, kits, methods, and first and second medical uses.

The "combined" embodiments of the invention thus include, for example, where the VEGFR2-blocking, anti-VEGF or 2C3-based antibody is a naked antibody and is used in combination with an agent or therapeutic agent that is not operatively attached thereto. In such cases, the agent or therapeutic agent may be used in a non-targeted or targeted form. In "non-targeted form", the agent, particularly therapeutic agents, will generally be used according to their standard use in the art. In "targeted form", the agent will generally be operatively attached to a distinct antibody or targeting region that delivers the agent or therapeutic agent to the angiogenic disease site or tumor. The use of such targeted forms of biological agents, both diagnostics and therapeutics, is also quite standard in the art.

In other "combined" embodiments of the invention, the VEGFR2-blocking, anti-VEGF or 2C3-based antibody is an immunoconjugate wherein the antibody is itself operatively associated or combined with the agent or therapeutic agent. In certain preferred examples, the agent, including diagnostic and therapeutic agents, will be a "2C3-targeted agent". The operative attachment includes all forms of direct and indirect attachment as described herein and known in the art.

The "combined" uses, particularly in terms of VEGFR2-blocking, anti-VEGF or 2C3-based antibodies in combination with therapeutic agents, also include combined compositions, pharmaceuticals, cocktails, kits, methods, and first and second medical uses wherein the therapeutic agent is in the form of a prodrug. In such embodiments, the activating component able to convert the prodrug to the functional form of the drug may again be operatively associated with the VEGFR2-blocking, anti-VEGF or 2C3-based antibodies of the present invention.

In certain preferred embodiments, the therapeutic compositions, combinations, pharmaceuticals, cocktails, kits, methods, and first and second medical uses will be "2C3-prodrug combinations". As will be understood by those of ordinary skill in the art, the term "2C3-prodrug combination", unless otherwise stated, means that the 2C3-based antibody is operatively attached to a component capable of converting the prodrug to the active drug, not that the 2C3-based antibody is attached to the prodrug itself. However, there is no requirement that the prodrug embodiments of the invention need to be used as 2C3-prodrug combinations. Accordingly, prodrugs may be used in any manner that they are used in the art, including in ADEPT and other forms.

Thus, where combined compositions, pharmaceuticals, cocktails, kits, methods, and first and second medical uses are described, preferably in terms of diagnostic agents, and more preferably therapeutic agents, the combinations include VEGFR2-blocking, anti-VEGF antibodies, such as 2C3-based antibodies, that are naked antibodies and immunoconjugates, and wherein practice of the in vivo embodiments of the invention involves the prior, simultaneous or subsequent administration of the naked antibodies or immunoconjugate and the biological, diagnostic or therapeutic agent; so long as, in some conjugated or unconjugated form, the overall provision of some form of the antibody and some form of the biological, diagnostic or therapeutic agent is achieved.

Particularly preferred combined compositions, methods and uses of the invention are those including VEGFR2-blocking, anti-VEGF antibodies and endostatin (U.S. Pat. No. 5,854,205, specifically incorporated herein by reference). These include where the VEGFR2-blocking, anti-VEGF antibody or 2C3 construct is a naked antibody or immunoconjugate; and when an immunoconjugate, wherein the VEGFR2-blocking, anti-VEGF antibody or 2C3 is linked to endostatin, optionally with angiostatin; wherein the combined therapeutic method or use involves the prior, simultaneous, or subsequent administration of endostatin, optionally with angiostatin; so long as, in some conjugated or unconjugated form, the overall provision of 2C3, endostatin and optionally angiostatin is achieved. VEGFR2-blocking, anti-VEGF or 2C3-based antibodies operatively associated with collagenase are also provided, as the collagenase, when specifically delivered to the tumor, will produce endostatin in situ, achieving similar benefits.

The foregoing and other explanations of the effects of the present invention on tumors are made for simplicity to explain the combined mode of operation, type of attached agent(s) and such like. This descriptive approach should not be interpreted as either an understatement or an oversimplification of the beneficial properties of the VEGFR2-blocking, anti-VEGF antibodies or 2C3-based antibodies of the invention. It will therefore be understood that such antibodies themselves have anti-angiogenic properties and VEGF neutralization properties (such as neutralizing the survival function of VEGF), that immunoconjugates of such antibodies will maintain these properties and combine them with the properties of the attached agent; and further, that the combined effect of the antibody and any attached agent will typically be enhanced and/or magnified.

The invention therefore provides compositions, pharmaceutical compositions, therapeutic kits and medicinal cocktails comprising, optionally in at least a first composition or container, a biologically effective amount of at least a first VEGFR2-blocking, anti-VEGF antibody, optionally one that binds to substantially the same epitope as the monoclonal antibody 2C3 (ATCC PTA 1595), or an antigen-binding fragment or immunoconjugate of such an anti-VEGF antibody; and a biologically effective amount of at least a second biological agent, component or system.

The "at least a second biological agent, component or system" will often be a therapeutic or diagnostic agent, component or system, but it not be. For example, the at least a second biological agent, component or system may comprise components for modification of the antibody and/or for attaching other agents to the antibody. Certain preferred second biological agents, components or systems are prodrugs or components for making and using prodrugs, including components for making the prodrug itself and components for adapting the antibodies of the invention to function in such prodrug or ADEPT embodiments.

Where therapeutic or diagnostic agents are included as the at least a second biological agent, component or system, such therapeutics and/or diagnostics will typically be those for use in connection with angiogenic diseases. Such agents are those suitable for use in treating or diagnosing a disease or disorder as disclosed in any one of U.S. Pat. Nos. 5,712,291, 5,753,230, 5,972,922, 5,639,757, WO 98/45331 and WO 98/16551, each specifically incorporated herein by reference.

Where the disease to be treated is cancer, "at least a second anti-cancer agent" will be included in the therapeutic kit or cocktail. The term "at least a second anti-cancer agent" is chosen in reference to the VEGFR2-blocking, anti-VEGF antibody or 2C3 construct being the first anti-cancer agent. The antibodies of the invention may thus be combined with chemotherapeutic agents, radiotherapeutic agents, cytokines, anti-angiogenic agents, apoptosis-inducing agents or anti-cancer immunotoxins or coaguligands.

"Chemotherapeutic agents", as used herein, refer to classical chemotherapeutic agents or drugs used in the treatment of malignancies. This term is used for simplicity notwithstanding the fact that other compounds may be technically described as chemotherapeutic agents in that they exert an anti-cancer effect. However, "chemotherapeutic" has come to have a distinct meaning in the art and is being used according to this standard meaning. A number of exemplary chemotherapeutic agents are described herein. Those of ordinary skill in the art will readily understand the uses and appropriate doses of chemotherapeutic agents, although the doses may well be reduced when used in combination with the present invention.

A new class of drugs that may also be termed "chemotherapeutic agents" are agents that induce apoptosis. Any one or more of such drugs, including genes, vectors, antisense constructs and ribozymes, as appropriate, may also be used in conjunction with the present invention. Currently preferred second agents are anti-angiogenic agents, such as angiostatin, endostatin, vasculostatin, canstatin and maspin.

Other exemplary anti-cancer agent include, e.g., neomycin, podophyllotoxin(s), TNF-α, $\alpha_v\beta_3$ antagonists, calcium ionophores, calcium-flux inducing agents, and any derivative or prodrug thereof. Currently preferred anti-tubulin drugs include colchicine, taxol, vinblastine, vincristine, vindescine, a combretastatin or a derivative or prodrug thereof.

Anti-cancer immunotoxins or coaguligands are further appropriate anti-cancer agents. "Anti-cancer immunotoxins or coaguligands", or targeting-agent/therapeutic agent constructs, are based upon targeting agents, including antibodies or antigen binding fragments thereof, that bind to a targetable or accessible component of a tumor cell, tumor vasculature or tumor stroma, and that are operatively attached to a therapeutic agent, including cytotoxic agents (immunotoxins) and coagulation factors (coaguligands). A "targetable or accessible component" of a tumor cell, tumor vasculature or tumor stroma, is preferably a surface-expressed, surface-accessible or surface-localized component, although components released from necrotic or otherwise damaged tumor cells or vascular endothelial cells may also be targeted, including cytosolic and/or nuclear tumor cell antigens.

Both antibody and non-antibody targeting agents may be used, including growth factors, such as VEGF and FGF; peptides containing the tripeptide. R-G-D, that bind specifically to the tumor vasculature; and other targeting components such as annexins and related ligands.

Anti-tumor cell immunotoxins or coaguligands may comprise antibodies exemplified by the group consisting of antibodies termed B3 (ATCC HB 10573), 260F9 (ATCC HB 8488), D612 (ATCC HB 9796) and KS1/4, said KS1/4 antibody obtained from a cell comprising the vector pGKC2310 (NRRL B-18356) or the vector pG2A52 (NRRL B-18357).

Anti-tumor cell targeting agents that comprise an antibody, or an antigen-binding region thereof, that binds to an intracellular component that is released from a necrotic tumor cell are also contemplated. Preferably such antibodies are monoclonal antibodies, or antigen-binding fragments thereof, that bind to insoluble intracellular antigen(s) present in cells that may be induced to be permeable, or in cell ghosts of substantially all neoplastic and normal cells, but are not present or accessible on the exterior of normal living cells of a mammal.

U.S. Pat. Nos. 5,019,368, 4,861,581 and 5,882,626, each issued to Alan Epstein and colleagues, are each specifically incorporated herein by reference for purposes of even further describing and teaching how to make and use antibodies specific for intracellular antigens that become accessible from malignant cells in vivo. The antibodies described are sufficiently specific to internal cellular components of mammalian malignant cells, but not to external cellular components. Exemplary targets include histones, but all intracellular components specifically released from necrotic tumor cells are encompassed.

Upon administration to an animal or patient with a vascularized tumor, such antibodies localize to the malignant cells by virtue of the fact that vascularized tumors naturally contain necrotic tumor cells, due to the process(es) of tumor re-modeling that occur in vivo and cause at least a proportion of malignant cells to become necrotic. In addition, the use of such antibodies in combination with other therapies that enhance tumor necrosis serves to enhance the effectiveness of targeting and subsequent therapy.

These types of antibodies may thus be used to directly or indirectly associate with angiopoietins and to administer the angiopoietins to necrotic malignant cells within vascularized tumors, as generically disclosed herein.

As also disclosed in U.S. Pat. Nos. 5,019,368, 4,861,581 and 5,882,626, each incorporated herein by reference, these antibodies may be used in combined diagnostic methods (see below) and in methods for measuring the effectiveness of anti-tumor therapies. Such methods generally involve the preparation and administration of a labeled version of the antibodies and measuring the binding of the labeled antibody to the internal cellular component target preferentially bound within necrotic tissue. The methods thereby image the necrotic tissue, wherein a localized concentration of the antibody is indicative of the presence of a tumor and indicate ghosts of cells that have been killed by the anti-tumor therapy.

Anti-tumor stroma immunotoxins or coaguligands will generally comprise antibodies that bind to a connective tissue component, a basement membrane component or an activated platelet component; as exemplified by binding to fibrin, RIBS or LIBS.

Anti-tumor vasculature immunotoxins or coaguligands may comprise ligands, antibodies, or fragments thereof, that bind to a surface-expressed, surface-accessible or surface-localized component of the blood transporting vessels, preferably the intratumoral blood vessels, of a vascularized tumor. Such antibodies include those that bind to surface-expressed components of intratumoral blood vessels of a vascularized tumor, including intratumoral vasculature cell surface receptors, such as endoglin (TEC-4 and TEC-11 antibodies), a TGFβ receptor, E-selectin, P-selectin, VCAM-1, ICAM-1, PSMA, a VEGF/VPF receptor, an FGF receptor, a TIE, $\alpha_v\beta_3$ integrin, pleiotropin, endosialin and MC Class II proteins. The antibodies may also bind to cytokine-inducible or coagulant-inducible components of intratumoral blood vessels. Certain preferred agents will bind to aminophospholipids, such as phosphatidylserine or phosphatidylethanolamine.

Other anti-tumor vasculature immunotoxins or coaguligands may comprise antibodies, or fragments thereof, that bind to a ligand or growth factor that binds to an intratumoral vasculature cell surface receptor. Such antibodies include those that bind to VEGF/VPF (GV39 and GV97 antibodies), FGF, TGFβ, a ligand that binds to a TIE, a tumor-associated fibronectin isoform, scatter factor/hepatocyte growth factor (HGF), platelet factor 4 (PF4), PDGF and TIMP. The antibodies, or fragments thereof, may also bind to a ligand:receptor complex or a growth factor:receptor complex, but not to the ligand or growth factor, or to the receptor, when the ligand or growth factor or the receptor is not in the ligand:receptor or growth factor:receptor complex.

Anti-tumor cell, anti-tumor stroma or anti-tumor vasculature antibody-therapeutic agent constructs may comprise anti-angiogenic agents, apoptosis-inducing agents, anti-tubulin drugs, cytotoxic agents such as plant-, fungus- or bacteria-derived toxins. Ricin A chain and deglycosylated ricin A chain will often be preferred. Anti-tumor cell, anti-tumor stroma or anti-tumor vasculature antibody-therapeutic agent constructs may comprise coagulants (direct and indirect acting coagulation factors) or second antibody binding regions that bind to coagulation factors. The operative association with Tissue Factor or Tissue Factor derivatives, such as truncated Tissue Factor, will often be preferred.

In terms of compositions, kits and/or medicaments of the invention, the combined effective amounts of the therapeutic agents may be comprised within a single container or container means, or comprised within distinct containers or container means. The cocktails will generally be admixed together for combined use. Agents formulated for intravenous administration will often be preferred. Imaging components may also be included. The kits may also comprise instructions for using the at least a first antibody and the one or more other biological agents included.

Speaking generally, the at least a second anti-cancer agent may be administered to the animal or patient substantially simultaneously with the VEGFR2-blocking, anti-VEGF antibody or 2C3-based therapeutic; such as from a single pharmaceutical composition or from two pharmaceutical compositions administered closely together.

Alternatively, the at least a second anti-cancer agent may be administered to the animal or patient at a time sequential to the administration of the VEGFR2-blocking, anti-VEGF antibody or 2C3-based therapeutic. "At a time sequential", as used herein, means "staggered", such that the at least a second anti-cancer agent is administered to the animal or patient at a time distinct to the administration of the VEGFR2-blocking, anti-VEGF antibody or 2C3-based therapeutic. Generally, the two agents are administered at times effectively spaced apart to allow the two agents to exert their respective therapeutic effects, i.e., they are administered at "biologically effective time intervals". The at least a second anti-cancer agent may be administered to the animal or patient at a biologically effective time prior to the VEGFR2-blocking, anti-VEGF antibody or 2C3-based therapeutic, or at a biologically effective time subsequent to that therapeutic.

Accordingly, the present invention provides methods for treating an animal or patient with a vascularized tumor, comprising:

(a) subjecting the animal or patient to a first treatment that substantially reduces the tumor burden; and (b) subsequently administering at least a first anti-angiogenic agent to the animal or patient in an amount effective to inhibit metastasis from any surviving tumor cells; wherein the first anti-angiogenic agent is at least a first VEGFR2-blocking, anti-VEGF antibody, or antigen-binding fragment thereof, optionally one that binds to substantially the same epitope as the monoclonal antibody 2C3 (ATCC PTA 1595); optionally wherein the antibody or fragment is operatively associated with a second anti-angiogenic agent.

Preferred first treatments include surgical resection and chemotherapeutic intervention. Combined anti-angiogenics can also be used, such as angiopoietin 2 or tumor-targeted angiopoietin 2 constructs.

Other treatment methods for animals or patients with vascularized tumors, comprise:

(a) administering a first antibody-therapeutic agent construct to the animal or patient in an amount effective to induce substantial tumor necrosis; wherein the first antibody-therapeutic agent construct comprises a therapeutic agent operatively linked to a first antibody, or antigen binding fragment thereof, that binds to a surface-expressed, surface-accessible or surface-localized component of a tumor cell, tumor vasculature or tumor stroma; and (b) subsequently administering a second antibody to the animal or patient in an amount effective to inhibit metastasis from any surviving tumor cells; wherein the second antibody is at least a first VEGFR2-blocking, anti-VEGF antibody, or antigen-binding fragment thereof, optionally one that binds to substantially the same epitope as the monoclonal antibody 2C3 (ATCC PTA 1595); and further optionally wherein the antibody or fragment is operatively associated with a second anti-angiogenic agent.

In particularly preferred embodiments, the present invention provides VEGFR2-blocking, anti-VEGF antibodies and 2C3-based antibodies for use in combination with prodrugs and ADEPT. In such compositions, combination, pharmaceuticals, kits, methods and uses, the VEGFR2-blocking, anti-VEGF antibody or 2C3-based antibody or fragment thereof will be modified to provide a converting or enzymatic capacity, or operatively associated with, preferably covalently linked or conjugated to, at least a first converting agent or enzyme capable of converting at least one prodrug to the active form of the drug.

The enzymatic or enzyme-conjugated antibody or fragment will combined with an initially separate formulation of the "prodrug". The prodrug will be an inactive or weakly active form of a drug that is that is converted to the active form of the drug on contact with the enzymatic capacity, converting function or enzyme associated with the VEGFR2-blocking, anti-VEGF or 2C3 antibody.

Accordingly, kits are provided that comprise, preferably in separate compositions and/or containers:

(a) a biologically effective amount of at least a first VEGFR2-blocking, anti-VEGF antibody or 2C3-based antibody, or fragment thereof, that has an enzymatic function, preferably where the antibody or fragment is operatively associated with, covalently linked or conjugated to, at least a first enzyme; and (b) a biologically effective amount of at least a first substantially inactive prodrug that is converted to a substantially active drug by the enzymatic function of, or enzyme associated with, linked to or conjugated to the VEGFR2-blocking, anti-VEGF or 2C3 antibody or fragment.

The present invention further provides advantageous methods and uses that comprise:

(a) administering to an animal or patient with a vascularized tumor a biologically effective amount of at least a first pharmaceutical composition comprising at least a first VEGFR2-blocking, anti-VEGF antibody or 2C3-based antibody, or antigen binding fragment thereof, wherein the antibody or fragment has an enzymatic function, preferably wherein the antibody or fragment is operatively associated with, covalently linked to, or conjugated to, at least a first enzyme; wherein said antibody or fragment localizes to the vasculature, intratumoral vasculature or stroma of the vascularized tumor after adminstration; and (b) subsequently administering to the animal or patient, after an effective time period, a biologically effective amount of at least a second pharmaceutical composition comprising a biologically effective amount of at least one substantially inactive prodrug; wherein the prodrug is converted to a substantially active drug by the enzymatic function of, or enzyme associated with, linked to, or conjugated to the VEGFR2-blocking, anti-VEGF or 2C3 antibody or fragment localized within the vasculature, intratumoral vasculature or stroma of said vascularized tumor.

In certain other embodiments, the antibodies and immunoconjugates of the invention may be combined with one or more diagnostic agents, typically diagnostic agents for use in connection with angiogenic diseases. A range of diagnostic compositions, kits and methods are thus included within the invention.

In terms of cancer diagnosis and treatment, the diagnostic and imaging compositions, kits and methods of the present invention include in vivo and in vitro diagnostics. For example, a vascularized tumor may be imaged using a diagnostically effective amount of a tumor diagnostic component that comprises at least a first binding region that binds to an accessible component of a tumor cell, tumor vasculature or tumor stroma, operatively attached to an in vivo diagnostic imaging agent.

The tumor imaging is preferably conducted to provide an image of the stroma and/or vasculature of a vascularized tumor using a diagnostic component that comprises at least a first binding region that binds to an accessible component of tumor vasculature or tumor stroma. Any suitable binding region or antibody may be employed, such as those described above in terms of the therapeutic constructs. Certain advantages will be provided by using a detectably-labeled VEGFR2-blocking, anti-VEGF antibody or 2C3-based antibody construct, wherein the image formed will be predictive the binding sites of the therapeutic to be used.

Detectably-labeled in vivo tumor diagnostics, whether VEGFR2-blocking, anti-VEGF antibody or 2C3-based or not, may comprise an X-ray detectable compound, such as bismuth (III), gold (III), lanthanum (III) or lead (II); a radioactive ion, such as copper$^{67}$, gallium$^{67}$, gallium$^{68}$, indium$^{111}$, indium$^{113}$, iodine$^{123}$, iodine$^{125}$, iodine$^{131}$, mercury$^{197}$, mercury$^{203}$rhenium$^{188}$, rubidium$^{97}$, rubidium$^{103}$, technetium$^{99m}$ or yttrium$^{90}$; a nuclear magnetic spin-resonance isotope, such as cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); or rhodamine or fluorescein.

Pre-imaging before tumor treatment may be carried out by:

(a) administering to the animal or patient a diagnostically effective amount of a pharmaceutical composition comprising a diagnostic agent operatively attached to at least a first binding region that binds to an accessible component of a tumor cell, tumor vasculature (preferably) or tumor stroma (preferably), including diagnostic agents operatively attached to VEGFR2-blocking, anti-VEGF antibody or 2C3-based antibody constructs; and (b) subsequently detecting the detectably-labeled first binding region (or VEGFR2-blocking, anti-VEGF antibody or 2C3-based antibody) bound to the tumor cells, tumor blood vessels (preferably) or tumor stroma (preferably); thereby obtaining an image of the tumor, tumor vasculature and/or tumor stroma.

Cancer treatment may also be carried out by:

(a) forming an image of a vascularized tumor by administering to an animal or patient having a vascularized tumor a diagnostically minimal amount of at least a first detectably-labeled tumor binding agent, preferably a VEGFR2-blocking, anti-VEGF antibody or 2C3-based antibody construct, comprising a diagnostic agent operatively attached to the tumor binding agent or VEGFR2-blocking, anti-VEGF antibody or 2C3-based antibody, thereby forming a detectable image of the tumor, tumor vasculature (preferably), or tumor stroma (preferably); and (b) subsequently administering to the same animal or patient a therapeutically optimized amount of at least a first naked VEGFR2-blocking, anti-VEGF antibody or 2C3 antibody or therapeutic agent-antibody construct using such an antibody, thereby causing an anti-tumor effect.

Imaging and treatment formulations or medicaments are thus provided, which generally comprise:

(a) a first pharmaceutical composition comprising a diagnostically effective amount of a detectably-labeled tumor binding agent, preferably a VEGFR2-blocking, anti-VEGF antibody or 2C3-based antibody construct, that comprises a detectable agent operatively attached to the tumor binding agent or VEGFR2-blocking, anti-VEGF antibody or 2C3-based antibody; and (b) a second pharmaceutical composition comprising a therapeutically effective amount of at least one naked VEGFR2-blocking, anti-VEGF antibody or 2C3 antibody or therapeutic agent-antibody construct using such an antibody.

The invention also provides in vitro diagnostic kits comprising at least a first composition or pharmaceutical composition comprising a biologically effective amount of at least one diagnostic agent that is operatively associated with at least a first VEGFR2-blocking, anti-VEGF antibody, optionally one that binds to substantially the same epitope as the monoclonal antibody 2C3 (ATCC PTA 1595), or an antigen-binding fragment thereof.

The invention still further provides combined kits in which the diagnostic agent is intended for use outside the body, preferably in connection with a test conducted on a biological sample obtained from an animal or patient. As such, the invention provides kits comprising, generally in at least two distinct containers, at least a first composition, pharmaceutical composition or medicinal cocktail comprising a biologically effective amount of at least a first VEGFR2-blocking, anti-VEGF antibody, optionally one that binds to substantially the same epitope as the monoclonal antibody 2C3 (ATCC PTA 1595), or an antigen-binding fragment or immunoconjugate of such an anti-VEGF antibody; and a biologically effective amount of at least one diagnostic agent, component or system for in vitro use.

The "diagnostic agent, component or system for in vitro use" will be any diagnostic agent or combination of agents that allow the diagnosis of one or more diseases that have an angiogenic component. The in vitro diagnostics thus include those suitable for use in generating diagnostic or prognostic information in relation to a disease or disorder as disclosed in any one of U.S. Pat. Nos. 5,712,291, 5,753,230, 5,972,922, 5,639,757, WO 98/45331 and WO 98/16551, each specifically incorporated herein by reference.

In terms of cancer diagnosis and treatment, the in vitro diagnostics will preferably include a diagnostic component that comprises at least a first binding region that binds to an accessible component of a tumor cell, tumor vasculature (preferably) or tumor stroma (preferably) operatively attached to a "detectable or reporter agent" directly or indirectly detectable by an in vitro diagnostic test. "Detectable or reporter agents" directly detectable in vitro include those such as radiolabels and reporter agents detectable by immunofluorescence.

"Detectable or reporter agents" indirectly detectable in vitro include those that function in conjunction with further exogenous agent(s), such as detectable enzymes that yield a colored product on contact with a chromogenic substrate. Indirect detection in vitro also extends to detectable or reporter components or systems that comprise the first binding region that binds to an accessible component of a tumor cell, tumor vasculature (preferably) or tumor stroma (preferably) in combination with at least one detecting antibody that has immunospecificity for the first binding region. The "detecting antibody" is preferably a "secondary antibody" that is attached to a direct or indirect detectable agent, such a radiolabel or enzyme. Alternatively, a "secondary and tertiary antibody detection system" may be used, including a first detecting antibody that has immunospecificity for the first binding region in combination with a second detecting antibody that has immunospecificity for the first detecting antibody, the second detecting antibody being attached to a direct or indirect detectable agent.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A: $1 \times 10^7$ NCI-H358 NSCLC cells were injected subcutaneously into nu/nu mice on day 0. FIG. 3B: $5 \times 10^6$ A673 rhabdomyosarcoma cells were injected subcutaneously into nu/nu mice on day 0. Mice were injected i.p. with the indicated IgG on day 1 and 2 times/week thereafter. 2C3 was given at a dose of 100, 10, or 1 µg/injection while a control IgG of irrelevant specificity (FIG. 3A) and 3E7 (FIG. 3B) were also given at 100 µg/injection. Tumors were measured 2–3 times per week. Mean and standard error is shown for the duration of the study in FIG. 3A, while data for the last day of the study (day 26) is shown in FIG. 3B.

FIG. 5A: Mice bearing subcutaneous NCI-H358 tumors, approximately 450 mm$^3$ in size, were treated with either 2C3 (n=6) or 3E7 (n=4). Treatments (T) were 100 µg of the IgG given i.p., except for the initial treatment that consisted of 500 µg of the IgG given i.v. Mean tumor volume along with the SEM is shown. At the end of the study (day 116), the mice were sacrificed and the tumors dissected out and weighed. The mean tumor weight for the 2C3 treated group was 0.054 g, while the 3E7 treated group had a mean tumor weight of 0.545 g. FIG. 5B: Mice bearing subcutaneous HT1080 tumors approximately 200–250 mm in size were treated i.p. with 100 µg of 2C3 (n=9), 3E7 (n=11), control IgG (n=11), or saline (n=1). The mice were treated every other day as indicated (T). The non-2C3 treated mice were sacrificed on day 26 due to more than 50% of each group having large ulcerated tumors. Mean tumor volume along with the SE is shown.

DESCRIPTION OF ILLUSTRATIVE EMBODIMENTS

Figure 1:
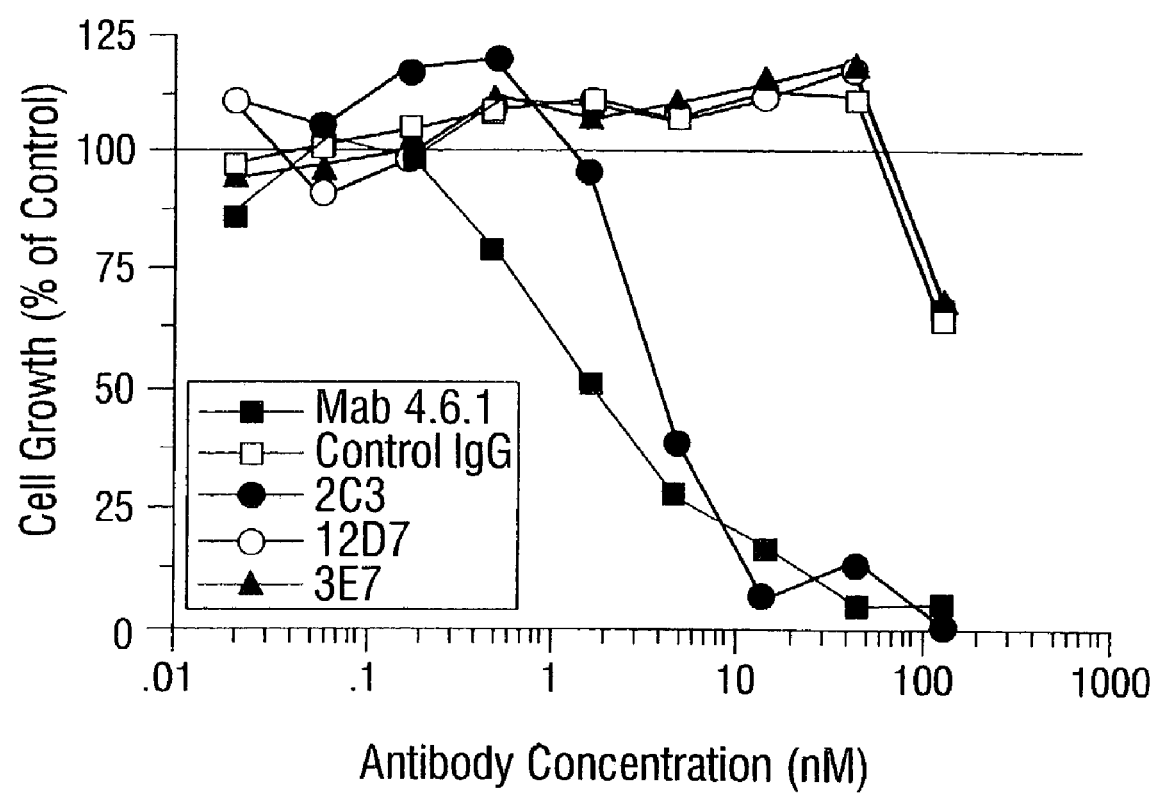
FIG. 1. 2C3 Inhibits VEGF-mediated growth of ABAE cells. ABAE cells were grown in the presence of the various indicated antibodies and 0.5 nM VEGF. Growth after 4 days was determined calorimetrically by the enzymatic conversion of MTS (Owen's reagent) to a yellow formazan. Results are displayed as a percentage of formazan production in control wells that were grown with VEGF alone. Background was determined by growing cells without VEGF or antibody and was subtracted from the control and sample wells. Results show the arithmetic mean of triplicate determinations, the standard deviations of which were always less than 20% of the mean. Shown are the growth curves for the anti-VEGF IgG antibodies including mAb 4.6.1 as a positive control and an IgG of irrelevant specificity (Control IgG) as a negative control.

Solid tumors and carcinomas account for more than 90% of all cancers in man. Although the use of monoclonal antibodies and immunotoxins has been investigated in the therapy of lymphomas and leukemias, these agents have been disappointingly ineffective in clinical trials against carcinomas and other solid tumors (Abrams and Oldham, 1985). A principal reason for the ineffectiveness of antibody-based treatments is that macromolecules are not readily transported into solid tumors. Even once within a tumor mass, these molecules fail to distribute evenly due to the presence of tight junctions between tumor cells, fibrous stroma, interstitial pressure gradients and binding site barriers (Dvorak et al., 1991 a).

In developing new strategies for treating solid tumors, the methods that involve targeting the vasculature of the tumor, rather than the tumor cells, offer distinct advantages. An effective destruction or blockade of the tumor vessels arrests blood flow through the tumor and results in an avalanche of tumor cell death. Antibody-toxin and antibody-coagulant constructs have already been effectively used in the specific targeting and destruction of tumor vessels, resulting in tumor necrosis (Burrows et al., 1992; Burrows and Thorpe, 1993; WO 93/17715; WO 96/01653; U.S. Pat. Nos. 5,855,866; 5,877,289; 5,965,132; 6,051,230; 6,004,555; U.S. Ser. No. 08/482,369, Issue Fee paid Oct. 20, 1998; each incorporated herein by reference).

Where antibodies, growth factors or other binding ligands are used to specifically deliver a coagulant to the tumor vasculature, such agents are termed "coaguligands". A currently preferred coagulant for use in coaguligands is truncated Tissue Factor (tTF) (Huang et al., 1997; WO 96/01653; U.S. Pat. No. 5,877,289). TF is the major initiator of blood coagulation. At sites of injury, Factor VII/VIIa in the blood comes into contact with, and binds to, TF on cells in the perivascular tissues. The TF:VIIa complex, in the presence of the phospholipid surface, activates factors IX and X. This, in turn, leads to the formation of thrombin and fibrin and, ultimately, a blood clot.

A range of suitable target molecules that are available on tumor endothelium, but largely absent from normal endothelium, have been described. For example, expressed targets may be utilized, such as endoglin, E-selectin, P-selectin, VCAM-1, ICAM-1, PSMA, a TIE, a ligand reactive with LAM-1, a VEGF/VPF receptor, an FGF receptor, $\alpha_v\beta_3$ integrin, pleiotropin or endosialin (U.S. Pat. Nos. 5,855,866; 5,877,289 and 6,004,555; Burrows et al., 1992; Burrows and Thorpe, 1993; Huang et al., 1997; each incorporated herein by reference).

Other targets inducible by the natural tumor environment or following intervention by man are also targetable entities, as described in U.S. Pat. Nos. 5,776,427 and 6,036,955; each incorporated herein by reference). When used in conjunction with prior suppression in normal tissues and tumor vascular induction, MHC Class II antigens may also be employed as targets (U.S. Pat. Nos. 5,776,427; 6,004,554 and 6,036,955; each incorporated herein by reference).

Adsorbed targets are another suitable group, such as VEGF, FGF, TGFβ, HGF, PF4, PDGF, TIMP, a ligand that binds to a TIE or a tumor-associated fibronectin isoform (U.S. Pat. Nos. 5,877,289 and 5,965,132; each incorporated herein by reference). Fibronectin isoforms are ligands that bind to the integrin family of receptors. Tumor-associated fibronectin isoforms are targetable components of both tumor vasculature and tumor stroma.

One currently preferred marker for such clinical targeting applications is receptor-associated VEGF. In fact, assemblies of VEGF:receptor complexes are one of the most specific markers of tumor vasculature observed to date (U.S. Pat. Nos. 5,877,289; 5,965,132 and 6,051,230; Lin-Ke et al., 1996; Dvorak et al., 1991b).

The VEGF:receptor complex presents an attractive target for the specific delivery of drugs or other effectors to tumor endothelium—as tumors are rich in cytokines and growth factors and as VEGF receptors are upregulated under the hypoxic conditions that are found in most solid tumors (Mazure et al., 1996; Forsythe et al., 1996; Waltenberger et al., 1996; Gerber et al., 1997; Kremer et al., 1997). Upregulation of both the ligand and its receptor specifically in the tumor microenvironment leads to a high concentration of occupied receptor on tumor vascular endothelium, as compared with the endotheliurn in normal tissue (U.S. Pat. Nos. 5,877,289 and 5,965,132). Dvorak and colleagues also showed that rabbit polyclonal antibodies directed against the N-terminus of VEGF selectively stain tumor blood vessels after injection into mice bearing syngeneic tumors (Lin-Ke et al., 1996).

The role of VEGF as a target for clinical intervention is not limited to immunotoxin or coaguligand therapies. Indeed, VEGF is one of the key factors involved in angiogenesis of solid tumors (Ferrara, 1995; Potgens et al., 1995), being both a potent permeability agent (Senger et al., 1983; Senger et al., 1990; Senger et al., 1986) and endothelial cell mitogen (Keck et al., 1989; Connolly et al., 1989; Thomas, 1996). The link between VEGF and angiogenesis has led to proposals of various therapeutic strategies aimed at VEGF intervention (Siemeister et al., 1998).

A. VEGF and VEGF Receptors

Vascular endothelial growth factor (VEGF) is a multifunctional cytokine that is induced by hypoxia and oncogenic mutations. VEGF is a primary stimulant of the development and maintenance of a vascular network in embryogenesis. It functions as a potent permeability-inducing agent, an endothelial cell chemotactic agent, an endothelial survival factor, and endothelial cell proliferation factor (Thomas, 1996; Neufeld et al., 1999). Its activity is required for normal embryonic development (Fong et al., 1995; Shalaby et al., 1995), as targeted disruption of one or both alleles of VEGF results in embryonic lethality (Carmeliet et al., 1996; Ferrara et al., 1996)

VEGF is an important factor driving angiogenesis or vasculogenesis in numerous physiological and pathological processes, including wound healing (Frank et al., 1995; Burke et al., 1995), diabetic retinopathy (Alon et al., 1995; Malecaze et al., 1994), psoriasis (Detmar et al., 1994), atherosclerosis (Inoue et al., 1998), rheumatoid arthritis (Harada et al., 1998; Nagashima et al., 1999), solid tumor growth (Plate et al., 1994; Claffey et al., 1996).

A wide variety of cells and tissues produce VEGF, which exists in at least five isoforms (121, 145, 165, 189, and 206 amino acids) that are splice variants encoded by the same gene (Houck et al., 1991; Ferrara et al., 1991; Tischer et al., 1991). The two smaller isoforms, 121 and 165, are secreted from cells (Houck et al., 1991; Anthony et al., 1994). Secreted VEGF is an obligate dimer of between 38–46 kDa in which the monomers are linked by two disulfide bonds.

VEGF dimers bind with high affinity to two well-characterized receptors, VEGFR1 (FLT-1) and VEGFR2 (KDR/Flk-1), which are selectively expressed on endothelial cells (Flt-1 and Flk-1 are the mouse homologues). The $K_d$ of VEGF binding to VEGFR1 and VEGFR2 is 15–100 pM and 400–800 pM, respectively (Terman et al., 1994). A recently identified third cell surface protein, neuropilin-1, also binds VEGF with high affinity (Olander et al., 1991; De Vries et al., 1992; Terman et al., 1992; Soker et al., 1998).

VEGFR1 and VEGFR2 are members of the Type III receptor tyrosine kinase (RTK III) family that is characterized by seven extracellular IgG-like repeats, a single spanning transmembrane domain, and an intracellular split tyrosine kinase domain (Mustonen and Alitalo, 1995). Until very recently, VEGFR1 and VEGFR2 were thought to be almost exclusively expressed on endothelial cells (Mustonen and Alitalo, 1995). Although VEGFR1 and VEGFR2 have been reported to have different functions with respect to stimulating endothelial cell proliferation, migration, and differentiation (Waltenberger et al, 1994; Guo et al., 1995), the precise role that each receptor plays in VEGF biology and endothelial cell homeostasis was not clearly defined prior to the present invention.

Recent studies using knockout mice have shown each of VEGF, VEGFR1 and VEGFR2 to be essential for vasculogenesis, angiogenesis and embryo development (Fong et al., 1995; Shalaby et al., 1995; Hiratsuka et al., 1998). In studies of lethal knockouts, the phenotypes associated with the lack of each receptor were different. Targeted disruption of VEGFR2 resulted in an embryo that lacked endothelial cell differentiation and failed to form yolk sac blood islands or go through vasculogenesis (Shalaby et al., 1995). VEGFR1 null mutants showed impaired vasculogenesis, disorganized assembly of endothelial cells, and dilated blood vessels (Fong et al., 1995; Hiratsuka et al., 1998). VEGFR1 evidently has a vital biological role.

VEGFR1 has a higher affinity for VEGF than VEGFR2, although it has a lower tyrosine kinase activity. This suggests that the extracellular domain of VEGFR1 is particularly important. This hypothesis was strongly supported by results from studies in knockout mice in which the tyrosine kinase domain of VEGFR1 was deleted whilst leaving the VEGF binding domain intact (Hiratsuka et al., 1998). The VEGFR1-tyrosine kinase deficient embryos developed normal blood vessels and survived to term (Hiratsuka et al., 1998).

In addition to the earlier knockouts (Fong et al., 1995; Shalaby et al., 1995), the Hiratsuka et al. (1998) studies indicate that VEGFR1 has a vital biological role. However, tyrosine kinase signaling does not seem to be the critical factor. It is interesting to note that macrophages from the VEGFR1 knockout mice did not exhibit VEGF-induced chemotaxis (Hiratsuka et al., 1998; incorporated herein by reference), thereby implicating VEGFR1 as the receptor responsible for mediating this important biological response to VEGF.

Certain groups have reported VEGFR2 to be the dominant signaling receptor in VEGF-induced mitogenesis, and permeability (Waltenberger et al., 1994; Zachary, 1998; Korpelainen and Alitalo, 1998). The role of VEGFR1 in endothelial cell function is much less clear, although functions in macrophage migration and chemotaxis were documented in the Hiratsuka et al. (1998) studies discussed above.

Clauss et al. (1996; incorporated herein by reference) also reported that VEGFR1 has important roles in monocyte activation and chemotaxis. In fact, cells of the macrophage/monocyte lineage express only VEGFR1, which is the receptor responsible for mediating monocyte recruitment and procoagulant activity (Clauss et al., 1996). VEGF binding to VEGFR1 on monocytes and macrophages also acts by raising intracellular calcium and inducing tyrosine phosphorylation (Clauss et al., 1996).

Binding of the VEGF dimer to the VEGF receptor is believed to induce receptor dimerization. Dimerization of the receptor then causes autotransphosphorylation of specific tyrosine residues, Y801 and Y1175, and Y1213 and Y1333 on the intracellular side of VEGFR2 and VEGFR1, respectively. This leads to a signal transduction cascade, which includes activation of phospholipase Cγ (PLCγ) and phosphatidylinositol 3-kinase (PI3K) and an increase in intracellular calcium ions (Hood and Meininger, 1998; Hood et al., 1998; Kroll and Waltenberger, 1998).

The intracellular events further downstream in VEGF-induced signaling are less clear, although a number of groups have shown that nitric oxide (NO) is produced after VEGF activation of VEGFR2 (Hood and Meininger, 1998; Hood et al., 1998; Kroll and Waltenberger, 1998). Activation of VEGFR2, but not VEGFR1, by VEGF has also been shown to activate Src and the Ras-MAP kinase cascade, including the MAP kinases, ERK 1 and 2 (Waltenberger et al., 1994, 1996; Kroll and Waltenberger, 1997).

The role of VEGFR1 in endothelial cell function is much less clear, particularly as Flt-1 tyrosine kinase-deficient mice are viable and develop normal vessels (Hiratsuka et al., 1998). It has been suggested that the main biological role of VEGFR1 on endothelial is as a non-signaling ligand-binding molecule, or "decoy" receptor that might be required to present VEGF to VEGFR2.

The connection between VEGF and pathological angiogenic conditions has prompted various attempts to block VEGF activity. These include the development of certain neutralizing antibodies against VEGF (Kim et al., 1992; Presta et al., 1997; Sioussat et al., 1993; Kondo et al., 1993; Asano et al., 1995). Antibodies against VEGF receptors have also been described, such as described in U.S. Pat. Nos. 5,840,301 and 5,874,542 and, subsequent to the present invention, in WO 99/40118. U.S. Pat. Nos. 5,840,301 and 5,874,542 would indeed suggest that blocking VEGF receptors rather than VEGF itself is advantageous for various reasons.

Soluble receptor constructs (Kendall and Thomas, 1993; Aiello et al., 1995; Lin et al., 1998; Millauer et al., 1996), tyrosine kinase inhibitors (Siemeister et al., 1998), antisense strategies, RNA aptamers and ribozymes against VEGF or VEGF receptors have also been reported (Saleh et al., 1996; Cheng et al., 1996; Ke et al., 1998; Parry et al., 1999; each incorporated herein by reference).

B. Anti-VEGF antibodies

B1. Range of Antibody Properties

The application of various inhibitory methods has been shown to be at least somewhat effective in either blocking angiogenesis and/or suppressing tumor growth by interfering with VEGF signaling. In fact, monoclonal antibodies against VEGF have been shown to inhibit human tumor xenograft growth and ascites formation in mice (Kim et al., 1993; Asano et al., 1995; 1998; Mesiano et al., 1998; Luo et al., 1998a; 1998b; Borgstrom et al., 1996; 1998).

The antibody A4.6.1 is a high affinity anti-VEGF antibody capable of blocking VEGF binding to both VEGFR1 and VEGFR2 (Kim et al., 1992; Wiesmann et al., 1997; Muller et al., 1998). Alanine scanning mutagenesis and X-ray crystallography of VEGF bound by the Fab fragment of A4.6.1 showed that the epitope on VEGF that A4.6.1 binds is centered around amino acids 89–94. This structural data demonstrates that A4.6.1 competitively inhibits VEGF from binding to VEGFR2, but inhibits VEGF from binding to VEGFR1 most likely by steric hindrance (Muller et al., 1998; Keyt et al., 1996; each incorporated herein by reference)

A4.6.1 is the most extensively utilized neutralizing anti-VEGF antibody in the literature to date. It has been shown to inhibit the growth and VEGF-induced vascular permeability of a variety of human tumors in mice (Brem, 1998; Baca et al., 1997; Presta et al., 1997; Mordenti et al., 1999; Borgstrom et al., 1999; Ryan et al., 1999; Lin et al., 1999; each specifically incorporated herein by reference). A4.6.1 also inhibits ascites formation in a well-characterized human ovarian carcinoma mouse model and tumor dissemination in a novel metastasis mouse model. A4.6.1 has recently been humanized by monovalent phage display techniques and is currently in Phase I clinical trials as an anti-cancer agent (Brem, 1998; Baca et al., 1997; Presta et al., 1997; each incorporated herein by reference).

Despite some success in the art with neutralizing antibodies against VEGF, the present inventors realized that new antibodies, particularly those with a more precisely defined mode of interaction with VEGFR1 (FLT-1) and/or VEGFR2 (KDR/Flk-1) would of benefit for a variety of reasons. For example, the development of anti-VEGF antibodies that selectively block the interaction of VEGF with only one of the two VEGF receptors would allow for a more precise dissection of the pathways activated by VEGF in cells that express both VEGFR1 and VEGFR2.

The present inventors believed that antibodies of defined epitope-specificity that blocked VEGF binding to only one receptor (VEGFR2s) may well have clinical benefits depending, of course, on the maintenance of their inhibitory effects in an in vivo environment. The knockout mice studies of Hiratsuka et al. (1998) show that both VEGFR1 and VEGFR2 have important biological roles. Prior to the present invention, realistic opportunities for therapeutic intervention aimed at inhibiting VEGF-mediated effects through only one of the two receptors were hampered by the lack of effective, tailored inhibitory agents.

The present inventors first developed a range of new anti-VEGF antibodies having various epitope-specificities and properties. Six groups of hybridomas that secrete monoclonal antibodies against the VEGF:receptor (Flk-1) complex or against VEGF itself are provided. Five of antibody groups do not interfere with the binding of VEGF to its receptor, while one blocked this interaction (2C3 group) and inhibited VEGF-mediated growth of endothelial cells.

Antibodies of the 3E7, GV39M, and 2C3 groups, all of which localize selectively to the tumor after intravenous injection into mice bearing human tumor xenografts, are currently preferred for use in targeting, imaging and treating the vasculature or connective tissue of solid tumors.

The monoclonal antibodies of the present invention that recognize the VEGF:receptor complex selectively localize to tumor endothelial cells after injection into mice bearing human tumor xenografts. The monoclonal antibodies of the 2C3 group localize conspicuously to the perivascular connective tissue of the tumor, and also to the surrounding tumor vessels.

The antibodies that recognize the N-terminus react with receptor bound VEGF by ELISA. GV39M and 11B5 display high specificity for receptor-bound VEGF, as opposed to non-receptor-bound VEGF. Presumably the epitope recognized by GV39M and 11B5 on the N-terminus is conformational and is created when VEGF binds to its receptor. The fact that the antibodies are both IgMs, and therefore large in size, may be important for their selectivity toward the VEGF:receptor complex.

The anti-N-terminal antibodies did not inhibit VEGF-mediated endothelial cell growth. This suggests that the N-terminus of VEGF is not involved in receptor interaction and that antibodies against the N-terminus of VEGF do not interfere with VEGF-mediated signaling.

In contrast, 2C3 inhibits VEGF-mediated growth of endothelial cells with an $IC_{50}$ of 3 nM. $^{125}$I-VEGF binding studies using KDR expressing endothelial cells (ABAE cells) demonstrated that 2C3 blocks VEGF from binding to KDR in a concentration dependent manner. Thus, 2C3 is capable of neutralizing KDR (VEGFR2) mediated VEGF activity in vitro by interfering with the binding of VEGF to its receptor.

Immunohistochemical analyses revealed that GV39M, 11B5, 3E7, and 7G3 react moderately to strongly with vascular endothelium when directly applied to the sections. GV39M displays the highest specificity for tumor endothelial cells with comparatively little staining of tumor cells or connective tissue. 11B5, 3E7, and 7G3 preferentially stain endothelial cells when applied at low concentrations, but stain tumor cells and connective tissue distinctly at higher concentrations.

The pattern of staining observed with 11B5, 3E7 and 7G3 is typical of the type of staining seen when using polyclonal antibodies against VEGF that do not have a preference for a particular conformation of VEGF (Lin-Ke et al., 1996; Plate et al., 1994; Claffey et al., 1996). The selective staining of endothelium by GV39M suggests that it binds to the VEGF:receptor complex on these cells and is consistent with the endothelial cell location of the receptors and the fact that GV39M binds selectively to VEGF:sFlk-1 in ELISA.

Similarly, the broader staining patterns of 3E7 and 7G3 are consistent with their ability to recognize both free and receptor bound VEGF. However, 11B5 was expected to have a staining pattern that was more restricted to endothelium because it strongly prefers VEGF:Flk-1 in the capture ELISA (see Table 2). It is possible that 11B5 is able to recognize VEGF that is bound to stromal components, giving it a broader reactivity pattern on tumor sections.

3E7 and GV39M selectively localize in vivo to vascular endothelial cells of tumor tissue, while 2C3 localizes to perivascular connective tissue of tumors, in addition to the endothelium. Twenty four hours after i.v. injection into tumor-bearing mice, 3E7 was not detectable on the endothelium of any tissue except the tumor. GV39M, on the other hand, also bound to endothelial cells or mesangial cells in the glomeruli of the kidney. The reason for reactivity of GV39M with the mouse kidney glomerulus is unclear. It could be that the antibody binds to the VEGF:receptor complex on the normal endothelial cells in the kidney (Takahashi et al., 1995). However, localization studies in guinea pigs bearing syngeneic Line 10 tumors have shown that GV39M localizes to tumor blood vessels but not to glomeruli or vessels in other normal tissues.

The ability of 3E7 and GV39M to localize specifically to tumor endothelium is probably a result of at least two factors. First, the VEGF:receptor complex is relatively abundant on tumor blood vessels because the hypoxic tumor microenvironment stimulates VEGF expression by tumor cells and VEGF receptor expression by endothelial cells. Second, tumor blood vessels are more permeable than normal blood vessels (Yuan et al., 1996), which may allow the antibody greater access to the VEGF:receptor complex that appears to be concentrated on the abluminal face of the vessels (Lin-Ke et al., 1996; Hong et al., 1995).

In a prior study by Lin-Ke and colleagues (1996), rabbit polyclonal antibodies directed against the N-terminus of rat VEGF were found to localize to tumor endothelial cells after injection into mice bearing TA3/St mouse mammary carcinoma or MOT ovarian carcinoma. In contrast, a rabbit polyclonal antibody (Ab-618) directed against the whole VEGF protein did not localize specifically to endothelial cells in these tumors or elsewhere in the tumors themselves.

Based on these results, Lin-Ke et al. (1996) concluded that the N-terminus of VEGF has the capacity to bind antibodies after VEGF has associated with microvascular endothelium and that the pool of free or non-endothelial cell associated VEGF is not sufficient to concentrate anti-VEGF antibodies directed against non-N-terminal epitopes (Lin-Ke et al., 1996). The present results with 3E7 and GV39M, directed against the N-terminus of VEGF support their conclusions.

However, the findings of the present invention that antibodies of the 2C3 group, directed against a non-N-terminal epitope on VEGF, localize both to the vasculature and to the perivascular connective tissue of solid tumors in mice are remarkably surprising over the Lin-Ke et al. (1996) work. The present invention suggests that a 'pool' of VEGF is present in the tumor stroma and does, in fact, allow for the concentration of 2C3 in the tumor mass. Such tumor stromal targeting could not have been predicted from a study of prior publications. The inventors contemplate that VEGF may bind to heparan sulfate proteoglycans (HSPGs) within the tumor, although understanding the mechanism of action is certainly not necessary to practicing the present invention.

An early conclusion of the present invention is that antibodies of the GV39M and 3E7 groups localize selectively to tumor endothelial cells in mice, whereas antibodies of the 2C3 group localize to the tumor endothelial cells and to the perivascular connective tissue of the tumor. Since the distribution of VEGF and its receptors are similar in the mouse and in man, these antibodies are contemplated to show similar patterns of localization in cancer patients. Thus, GV39M and 3E7 are envisioned for use in the delivery of therapeutic or diagnostic agents to tumor vasculature in man, while antibodies of the 2C3 group are contemplated as vehicles for targeting therapeutic or diagnostic agents to tumor vasculature and tumor connective tissue.

B2. VEGFR2-Blocking, Anti-VEGF and 2C3 Antibodies

Further studies on the antibodies of the 2C3 group revealed even further surprising properties, resulting in the effective compositions and uses of the present invention.

An important discovery of this invention, made using ELISA, receptor binding assays and receptor activation assays, is that monoclonal antibodies of the 2C3 group selectively block the interaction of VEGF with VEGFR2 (KDR/Flk-1), but not VEGFR1 (FLT-1). 2C3 antibodies inhibit VEGF-induced phosphorylation of VEGFR2 and block VEGF-induced permeability, implicating VEGFR2 as the receptor responsible for VEGF-induced permeability. 2C3 antibodies also have potent anti-tumor activity, arresting the growth of various established human solid tumors in art-accepted animal models of human cancer.

These discoveries demonstrate the usefulness of 2C3 in dissecting the pathways that are activated by VEGF in cells that express both VEGFR1 and VEGFR2, as well as highlighting the importance of VEGFR2 activity in the process of tumor growth and survival. More importantly, they provide a unique mode of therapeutic intervention, allowing specific inhibition of VEGFR2-induced angiogenesis, without concomitant inhibition of macrophage chemotaxis, osteoclast and chondroclast function (mediated by VEGFR1).

The discoveries concerning 2C3 thus provide, for the first time, the motivation and the means to make and use anti-VEGF antibodies that inhibit VEGF binding only to VEGFR2, and not VEGFR1. Such antibodies, succinctly termed "VEGFR2-blocking, anti-VEGF antibodies", represent an advance in the field and provide numerous advantages, both in terms of uses in unconjugated or "naked" form and when conjugated to or associated with other therapeutic agents.

The in vitro binding studies of the present invention, employing ELISA and co-precipitation assays with purified receptor proteins, demonstrated that 2C3 blocks the binding of VEGF to VEGFR2. Surprisingly, though 2C3 did not inhibit the binding of VEGF to VEGFR1 in any assay system. In order to confirm the initial results, binding ELISAs were repeated in different configurations. In each configuration, the results indicated that 2C3 does not interfere with the VEGF:VEGFR1 interaction. As a control for these studies the monoclonal antibody 3E7, an antibody directed against the $NH_2$-terminus of VEGF, was used, which did not block VEGF from binding to VEGFR1 or VEGFR2.

The 2C3 group of antibodies of the present invention are thus significantly improved over other blocking antibodies to VEGF, including A4.6.1. The A4.6.1 anti-VEGF antibody blocked the binding of VEGF to both VEGF receptors. Crystallographic and mutagenesis studies have shown that the binding epitopes for VEGFR2 and VEGFR1 are concentrated towards the two symmetrical poles of the VEGF dimer (Wiesmann et al., 1997; Muller et al., 1997). The binding determinants on VEGF that interact with the two receptors overlap partially and are distributed over four different segments that span across the dimer surface (Muller et al., 1998). Antibody 4.6.1 binds to a region of VEGF within the receptor binding region of both receptors (Muller et al., 1998). It is proposed that 2C3 binds to a region that lies close to the VEGFR2 binding site, but not to the VEGFR1 binding site.

Studies on the effect of 2C3 on VEGF-induced phosphorylation of the receptors showed that 2C3 does block VEGF-induced phosphorylation of VEGFR2. This also corresponds to data discussed above and further solidifies the role of VEGFR2 in VEGF-induced proliferation.

Similar to results from other studies, consistent VEGF-induced phosphorylation of VEGFR1 could not be demonstrated (De Vries et al., 1992; Waltenberger et al., 1994; Davis-Smyth et al., 1996; Landgren et al., 1998). Therefore, it could not be reliably judged whether 2C3 inhibits VEGF-induced phosphorylation of VEGFR1. The low activity of VEGF on VEGFR1 phosphorylation has lead others to suggest that VEGFR1 might not be a signaling receptor on endothelial cells, but that it might act as a decoy receptor to capture VEGF and amplify its signaling via VEGFR2 (Hiratsuka et al., 1998). However, tyrosine phosphorylation of VEGFR1 by VEGF binding has been reported by Kupprion et al. (1998) using human microvascular endothelial cells (HMEC) and by Sawano et al. (1996) using NIH 3T3 cells that overexpress VEGFR1. Additionally, Waltenberger et al. (1994) have shown that VEGF-induced VEGFR1 activation can be followed using an in vitro kinase assay. The effect of 2C3 on VEGF-induced phosphorylation of VEGFR1, or lack thereof, could be determined using one of the foregoing cell types or an in vitro kinase assay.

Figure 2:
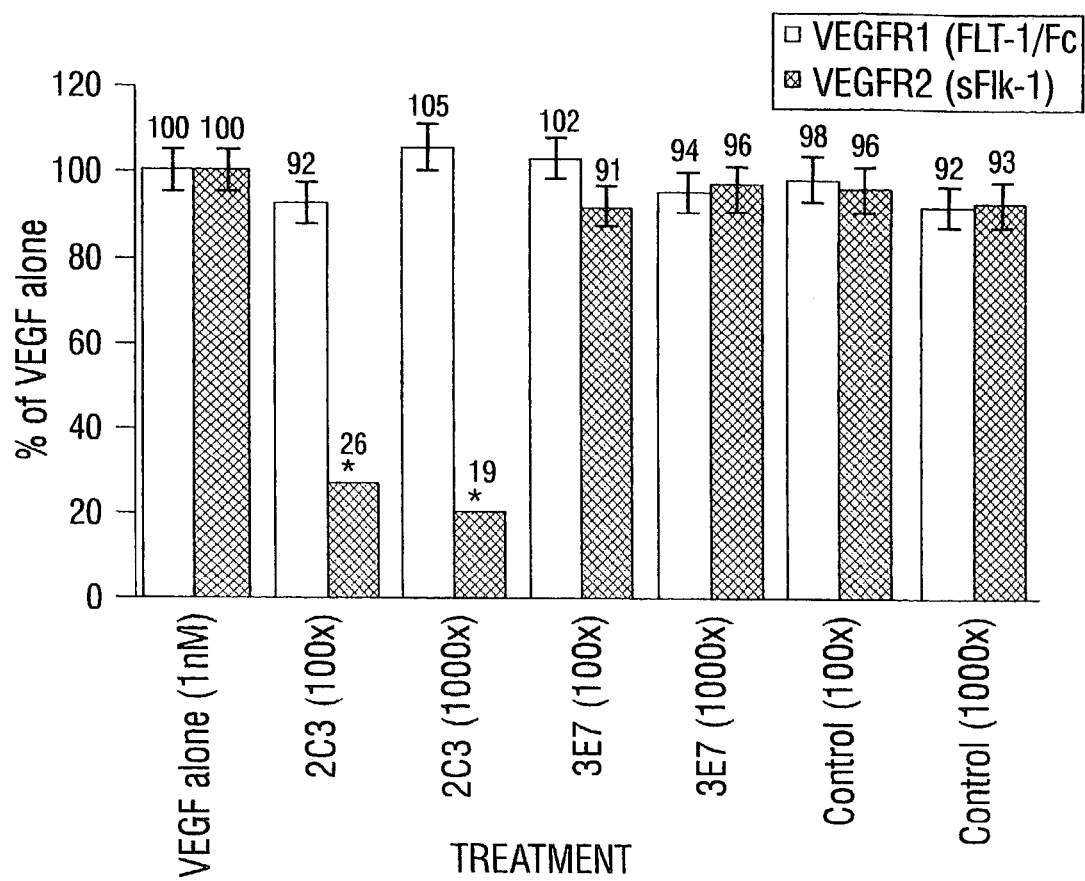
FIG. 2. 2C3 blocks VEGF binding to VEGFR2 but not VEGFR1 in ELISA. Wells were coated with the extracellular domain of VEGFR1 (Flt-1/Fc) or VEGFR2 (sFlk-1) and were then incubated with VEGF alone at 1 nM or VEGF in the presence of the indicated IgG at either 100 nM or 1000 nM. The plate was then incubated with rabbit anti-VEGF (A-20, Santa Cruz Biotechnology, Inc.) at 1 µg/ml and developed using a peroxidase conjugated goat anti-rabbit antibody. Assays were performed in triplicate. Mean percent binding in the absence of antibody is shown, together with the standard deviation. Asterisks indicate values that are statistically significantly different (p<0.002) from those in the absence of antibody by Student's paired T-test.

The present ELISA data of FIG. 2 and cell binding data demonstrate that 2C3 antibodies do not completely block VEGF from binding to cells that express both VEGFR1 and VEGFR2. The fact that 2C3 does not block VEGF binding to VEGFR1 means that 2C3 antibodies will be effective tools in delineating the role of VEGFR1 in the biology of endothelial cells and other cell types.

The functional consequences of the selectivity that 2C3 shows in blocking VEGF from activating its receptors was examined using the Miles permeability assay in guinea pigs. Both 2C3 and A4.6.1 inhibited VEGF-induced permeability when the IgG was in at least a 10-fold molar excess over VEGF. 3E7 and control antibodies did not inhibit VEGF-induced permeability even at a 1000-fold molar excess. These results show that VEGFR2 is involved in VEGF-induced permeability.

This finding accords with recent reports that a novel form of VEGF-C and two virus-derived VEGF-E variants bind VEGFR2 but not VEGFR1, yet retain the ability to enhance vascular permeability (Joukov et al., 1998; Ogawa et al., 1998; Meyer et al., 1999). Probably, the various forms of VEGF transmit signals via VEGFR2 that cause NO production, which, in turn, causes the increase in vascular permeability (Hood and Granger, 1998; Hood et al., 1998; Kroll and Waltenberger, 1998; Murohara et al., 1998; Kupprion et al., 1998; Sawano et al., 1996; Fujii et al., 1997; Parenti et al., 1998). This points indirectly at VEGFR2 involvement, as NO production has been shown to a consequence of VEGFR2 activation. However, there is also some evidence to the contrary, as Couper et al. (1997), found a strong correlation between increased vascular permeability induced by VEGF and VEGFR1 expression in vivo.

2C3 inhibited the growth of multiple different human tumor types in vivo. The effect of 100 μg of 2C3 given twice/wk was identical in mice-bearing subcutaneous NCI-H358 NSCLC and A673 rhabdomyosarcoma tumors, where it effectively limited the growth of the tumors to a small nodule of approximately 150 mm$^3$ in size. Similar responses were seen in other tumor models, such as HT29 and LS174T, both human adenocarcinomas of the colon.

The magnitude of tumor growth suppression by 2C3 is similar to that reported by other investigators using different neutralizing anti-VEGF antibodies (Asano et al., 1998; Mesiano et al., 1998). A monoclonal rat anti-mouse VEGFR2 antibody also strongly blocked the growth of malignant human keratinocytes in mice through an anti-angiogenic mechanism (Skobe et al., 1997). The effectiveness of 2C3, being similar to what other investigators have found using different anti-VEGF antibodies, further demonstrates the role of VEGF in tumor angiogenesis and tumor growth. However, 2C3 should provide a safer therapeutic, based on the specific inhibitory properties discussed herein.

To analyze the effect of inhibiting VEGF activity in a setting that would be closer to conditions in humans, mice that had established tumors were treated with 2C3. In this setting, 2C3 treatment significantly slowed the growth of two aggressive human tumors, A673 rhabdomyosarcoma and LS174T colon adenocarcinoma tumors. 2C3 antibodies caused significant tumor regressions in mice-bearing NCI-H358 NSCLC tumors.

Tumors treated with 2C3 or A4.6.1 regressed to 30% and 35%, respectively, of their original size after approximately 10 weeks of treatment. In a study where the treatment was allowed to extend past 100 days, even more significant regressions were observed. The results suggest that VEGF is providing more than just a mitotic signal for tumor endothelium.

The fact that regressions, rather than tumor stasis, was observed suggests that VEGF is providing more than just an angiogenic signal for tumor endothelium. Benjamin et al. (1999) recently reported that tumors contain a large fraction of immature blood vessels that have yet to establish contact with periendothelial cells and that these blood vessels are dependent upon VEGF for survival. It is possible that neutralization of VEGF causes these immature blood vessels to undergo apoptosis, thereby reducing the existing vascular network in the tumor. It is also possible that a dynamic process of vascular remodeling occurs in tumors, involving both vessel formation and vessel regression, and that neutralization of VEGF prevents vessel formation leading to a net shift towards vessel regression.

The finding that 2C3 suppressed tumor growth as completely as A4.6.1 (if not more so) indicates a dominant role for VEGFR2 in tumor angiogenesis. The multistep process of angiogenesis requires endothelial cell chemotaxis, metalloproteinase production, invasion, proliferation and differentiation. VEGFR1 may have no role in these processes, or may assist in the processes by binding VEGF and presenting it to the signaling receptor, VEGFR2.

The comparable figures for 2C3 and A4.6.1 in tumor treatment are highly relevant: 2C3 is slightly more effective as A4.6.1, although it only binds to VEGFR2 and not VEGFR1. The present studies therefore indicate that VEGFR1 does not play a notable role in VEGF-mediated tumor angiogenesis, and further suggest that VEGFR1 specific inhibitors may not influence tumor angiogenesis. These results also signify that 2C3 can be equally or more effective than A4.6.1, whilst causing less side-effects.

The ability to specifically block VEGF binding to and activation of VEGFR2 has importance in at two areas of clinical relevance. First, VEGFR1 (Flt-1) is believed to play an important role in the recruitment of macrophages and monocytes into the tumor, as these cells express VEGFR1 and respond chemotactically to VEGF via VEGFR1 signaling (Clauss et al., 1996; Hiratsuka et al., 1998; Akuzawa et al., 2000). Upon activation of macrophages, flt-1 gene transcription is stimulated through an induction of Egr-1, which binds to overlapping Egr-1/Sp1 transcription factor-binding sites in the human flt-1 promoter, providing evidence that the flt-1 gene is a direct target of Egr-1, the transcription factor primarily induced on macrophage differentiation (Akuzawa et al., 2000).

In order to maintain activation of macrophages, as required to produce a rigorous anti-tumor response, inhibition of VEGFR1 signaling should be avoided. The specific blocking of VEGFR1 afforded by the present invention thus provides important advantages over A4.6.1 in tumor therapy, as macrophage infiltration will not be impaired, enabling these cells to remove tumor cell debris from necrotic tumors and promote tumor shrinkage. Using VEGFR2 -blocking, anti-VEGF antibodies, such as 2C3, will also allow the infiltrating macrophages to contribute to the overall anti-tumor effect by having a direct cytocidal effect on tumor cells.

Indeed, the present invention provides uniquely advantageous agents for use in all forms of anti-angiogenic therapy, due to their ability to block VEGF angiogenic activity, but not to inhibit other beneficial actions of VEGF, mediated through VEGFR1 such as those on immune and bone cells. A second area of clinical importance concerns the ability of antibodies prepared in accordance with this invention to function in vivo without inhibiting the beneficial effects of osteoclasts and chondroclasts. This means that use of the present VEGFR2-blocking, anti-VEGF antibody therapeutics, including 2C3, will not be associated with side effects on bone and/or cartilage.

In vivo studies have shown that VEGF couples hypertrophic cartilage remodeling, ossification and angiogenesis during endochondral bone formation and that VEGF is essential for cartilage remodeling (Gerber et al., 1999; specifically incorporated herein by reference). Inactivation of VEGF signaling through VEGFR1, by administration of the soluble VEGFR1 receptor chimeric protein (Flt-(1-3)-IgG), was shown to impair trabecular bone formation and the expansion of the hypertrophic chondrocyte zone by decreasing the recruitment and/or differentiation of chondroclasts (Gerber et al., 1999).

It has further been shown that VEGF can substitute for macrophage colony-stimulating factor (M-CSF) in the support of osteoclast function in vivo (Niida et al., 1999;

specifically incorporated herein by reference). In studies using osteopetrotic (op/op) mice with a deficiency in osteoclasts resulting from a mutation in the M-CSF gene, injection of recombinant human M-CSF (rhM-CSF) allows osteoclast recruitment and survival. In recent studies, it was shown that a single injection of recombinant human VEGF can similarly induce osteoclast recruitment in op/op mice (Niida et al., 1999).

Niida et al. (1999) reported that as osteoclasts predominantly express VEGFR1, and the activity of recombinant human placenta growth factor 1 on osteoclast recruitment was comparable to that of rhVEGF, the beneficial effects of VEGF signaling in osteopetrotic (op/op) mice are mediated via the VEGF receptor 1 (VEGFR-1). These authors further showed that rhM-CSF-induced osteoclasts died after VEGF was inhibited (using a VEGFR1 receptor chimeric protein, VEGFR1/Fc), but that such effects were abrogated by concomitant injections of rhM-CSF. Osteoclasts supported by rhM-CSF or endogenous VEGF showed no significant difference in in vivo activity (Niida et al., 1999).

Mutant op/op mice undergo an age-related resolution of osteopetrosis accompanied by an increase in osteoclast number. In the Niida et al. (1999) studies, most of the osteoclasts disappeared after injections of anti-VEGF antibody, demonstrating that endogenously produced VEGF is responsible for the appearance of osteoclasts in the mutant mice. In addition, rhVEGF replaced rhM-CSF in the support of in vitro osteoclast differentiation. These results demonstrate that M-CSF and VEGF have overlapping functions in the support of osteoclast function and that VEGF acts through the VEGFR-1 receptor (Niida et al., 1999).

It can thus be concluded that 2C3, the first of the VEGFR2-blocking, anti-VEGF antibodies of the invention, does not block VEGF from binding and activating VEGFR1, but does block VEGF from binding and activating VEGFR2. The anti-tumor effects of such VEGFR2 inhibition are clearly demonstrated. These results show VEGFR2 to be the VEGF receptor that mediates permeability and highlight its role in tumor angiogenesis. This invention therefore further validates VEGF inhibition as therapy for the treatment of solid tumors. More importantly, the invention provides a range of new VEGFR2-blocking, anti-VEGF antibodies, such as those based upon 2C3, for therapeutic intervention and, in particular, for use as safe and effective drugs for inhibiting angiogenesis in tumors and other diseases.

The benefits of the present invention are not limited to the lack of side effects. Although these are important features that will have notable benefits, particularly in the treatment of children and patients with bone disorders, the antibodies of the invention have numerous other advantages.

For example, antibody conjugates based upon the VEGFR2-blocking, anti-VEGF or 2C3 antibodies can be used to deliver therapeutic agents to the tumor environment. In fact, 2C3 antibodies are shown herein to bind to both tumor vasculature and tumor stroma upon administration in vivo, but not to bind to vasculature or connective tissue in normal organs or tissues. Therapeutic constructs based upon the present antibodies therefore have the advantage of combining two functions within one molecule: the anti-angiogenic properties of the antibody or fragment thereof and the properties of the therapeutic agent selected for attachment.

As VEGFR2 is the key receptor on endothelium, blocking VEGF binding to VEGFR2 is critical for an anti-angiogenic effect. Although VEGFR1 is expressed on endothelium, it is non-signal transducing, or passive, in this context. Therefore, the inability of the antibodies of the present invention to block VEGF binding to VEGFR1 is without consequence to their effectiveness as anti-angiogenic and anti-tumor agents. In fact, rather than inhibiting VEGF binding to VEGFR1, which occurs with the blocking antibodies of the prior art, the ability of the present antibodies to bind to VEGF and yet to not substantially disturb VEGF-VEGFR1 interactions enhances the drug delivery properties of these new antibodies.

The present inventors realized that blocking antibodies would still be expected to function to deliver therapeutic agents to the tumor environment by binding to tumor-localized VEGF that is not bound to a receptor. Specifically, they understood that such antibodies will bind to VEGF in the tumor stroma and deliver therapeutic agents thereto. This provides a reservoir of drug around the endothelium, causing cytotoxic or other destructive effects on the vascular endothelial cells and exerting an anti-tumor effect.

The VEGF associated with the stroma or connective tissue is not bound to a VEGF receptor in a classic sense, i.e., a cell surface receptor. Rather, VEGF is bound to one or more connective tissue components, including proteoglycans, such as heparan sulfate proteoglycan, through a basic region of VEGF. These sequences (and the exons encoding them) are missing in VEGF121 protein (and underlying DNA), so this isoform should not be present in stroma in significant amounts. VEGF in the tumor stroma is often termed "free", although it is still localized within the tumor, so "free" essentially means non-receptor-bound.

The inventors further deduced that an antibody that blocks VEGF binding to one, but not both receptors, would still be able to deliver therapeutic agents to the tumor environment by binding to receptor bound VEGF on the vasculature. This is one of the most advantageous features of the present invention. Namely, the provision of antibodies that block VEGF binding to VEGFR2, and hence inhibit the angiogenic signal from VEGF, but that do not block VEGF binding to VEGFR1. In addition to reducing systemic side effects by maintaining VEGF signaling via VEGFR1 in other cell types and tissues, these antibodies are able to localize to VEGF-VEGFR1 complex on tumor vasculature and to deliver therapeutic agents directly thereto.

Both VEGFR1 and VEGFR2 are upregulated on tumor endothelial cells, as opposed to endothelial cells in normal tissues. VEGFR1 is highly expressed on tumor vascular endothelium, which makes the targeting aspects of the present invention particularly effective. In fact, VEGFR1, although "non-signaling" in endothelium, is expressed at least at the same levels as VEGFR2, if not at higher levels. A factor underlying this phenomenon is that VEGFR1 is upregulated in response to both hypoxia and VEGF, whereas VEGFR2 is only upregulated in response to VEGF and is not influenced by hypoxia.

Although the role of VEGFR1 on endothelium remains uncertain, VEGFR1 may act as a decoy receptor to "capture" VEGF and pass the ligand onto the signaling receptor, VEGFR2. For this to be true, one would expect the decoy receptor to have a higher affinity for VEGF than the signaling receptor, which is indeed the case. In light of this, and perhaps also due to enhanced expression levels, the VEGFR2-blocking, non-VEGFR1-blocking antibodies of this invention are ideal delivery agents for tumor treatment. Therapeutic conjugates of these antibodies are able to simultaneously inhibit angiogenesis through VEGFR2 and destroy the existing vasculature by delivering a therapeutic agent to VEGF-VEGFR1 receptor complex.

The inventors are by no means limited to the foregoing scientific reasoning as an explanation for the beneficial anti-angiogenic and tumor-localizing properties of the present antibodies. Although the utility of the invention is self-evident and needs no underlying theory to be put into practice, the inventors have considered alternative mechanisms by which VEGFR2-blocking, non-VEGFR1-blocking antibodies may effectively and specifically localize to tumor vasculature.

Such antibodies could bind to VEGF that is associated with Npn-1 or another, as yet, uncharacterized VEGF binding protein on the cell surface or could bind VEGF that is bound to heparan sulfate proteoglycans on the surface of endothelial cells. Antibody localization could also be enhanced by binding to another member of the VEGF family of proteins, i.e., VEGF-B, VEGF-C, VEGF-D, which are associated with the blood vessels, although this is less likely.

Another advantageous property of the VEGFR2-blocking, anti-VEGF or 2C3 antibodies of the invention is that these antibodies neutralize the survival signal or "protective effect" of VEGF, which is mediated through VEGFR2. In addition to making the antibodies more effective themselves, this property makes them particularly useful in combination with other agents that are hampered by VEGF's survival function.

For example, VEGF protects the endothelium from radiotherapy. Therefore, both the naked antibodies and immunoconjugates of the present invention are ideal for use in combination with radiotherapy. Even more benefits are provided by the use of such an antibody attached to a radiotherapeutic agent. This type of construct would have the triple advantages of: (1) exerting an anti-angiogenic effect through the antibody portion; (2) exerting a tumor vasculature destructive effect through delivery of the radiotherapeutic agent; and (3) preventing VEGF's typical survival signal from counteracting the effects of the radiotherapeutic agent.

Other constructs with similarly synergistic effects are VEGFR2-blocking, anti-VEGF antibodies in association with anti-tubulin drugs or prodrugs, anti-apoptopic agents and other anti-angiogenic agents. The actions of agents or drugs that cause apoptosis are antagonized by VEGF. The present invention therefore improves the effectiveness of such agents by neutralizing VEGF. VEGF survival signals also oppose endostatin, limiting this therapy. Therefore, in combined use with endostatin, the VEGFR2-blocking, anti-VEGF or 2C3 antibodies of the invention will neutralize VEGF and amplify the anti-tumor effects of endostatin. 2C3 or other VEGFR2-blocking, anti-VEGF antibodies may also be used to specifically delivery collagenase to the tumor, where the collagenase will produce endostatin in situ, achieving similar benefits.

In all such enhanced or synergistic combinations, the antibodies and other agents may be administered separately, or the second agents may be linked to the antibodies for specific delivery (i.e., targeted delivery to VEGFR1). In combinations with endostatin, chemical conjugates or recombinant fusion proteins will be preferred, as these will counteract the short half life of endostatin, which is currently a limitation of potential endostatin therapy. Combinations with, or targeted forms of, tissue plasminogen activator (tPA) may also be employed.

Further advantages of the therapeutics of the present invention include the ability to lower the interstitial pressure. As VEGF-mediated increased permeability contributes to the interstitial pressure, reduced signaling via VEFR2 will reduce both permeability and interstitial pressure. This, in turn, will reduce the barrier to drugs traversing the entirety of the tumor tissue, so that tumor cells distant from the vasculature can be killed. Prolonged therapy can also be achieved as the present compositions with have no, negligible or low immunogenicity.

B3. 2C3 Antibody CDR Sequences

The term "variable", as used herein in reference to antibodies, means that certain portions of the variable domains differ extensively in sequence among antibodies, and are used in the binding and specificity of each particular antibody to its particular antigen. However, the variability is not evenly distributed throughout the variable domains of antibodies. It is concentrated in three segments termed "hypervariable regions", both in the light chain and the heavy chain variable domains.

The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases, forming part of, the β-sheet structure.

The hypervariable regions in each chain are held together in close proximity by the FRs and, with the hypervariable regions from the other chain, contribute to the formation of the antigen-binding site of antibodies (Kabat et al., 1991, specifically incorporated herein by reference). The constant domains are not involved directly in binding an antibody to an antigen, but exhibit various effector functions, such as participation of the antibody in antibody-dependent cellular toxicity.

The term "hypervariable region", as used herein, refers to the amino acid residues of an antibody that are responsible for antigen-binding. The hypervariable region comprises amino acid residues from a "complementarity determining region" or "CDR" (i.e. residues 24–34 (L1), 50–56 (L2) and 89–97 (L3) in the light chain variable domain and 31–35 (H1), 50–56 (H2) and 95–102 (H3) in the heavy chain variable domain; Kabat et al., 1991, specifically incorporated herein by reference) and/or those residues from a "hypervariable loop" (i.e. residues 26–32 (L1), 50–52(L2) and 91–96 (L3) in the light chain variable domain and 26–32 (H1), 53–55 (H2) and 96–101 (H3) in the heavy chain variable domain). "Framework" or "FR" residues are those variable domain residues other than the hypervariable region residues as herein defined.

The DNA and deduced amino acid sequences of the Vh and Vκ chains of the 2C3 ScFv fragment are provided herein as SEQ ID NO:6, 7, 8 and 9. These sequences encompass CDR1–3 of the variable regions of the heavy and light chains of the antibody.

As described herein (Section C3), with the provision of structural and functional information for a biological molecule, a range of equivalent, or even improved molecules can be generated. This applies to the VEGFR2-blocking, anti-VEGF antibodies of the present invention, as exemplified by 2C3 antibodies. Although antigen-binding and other functional properties of an antibody must be conserved, there is an extremely high degree of skill in the art in making equivalent and even improved antibodies once a reference antibody has been provided. Such technical skill can, in light of the sequences and information provided herein, be applied to the production of further antibodies that have like, improved or otherwise desirable characteristics.

For equivalent antibodies, certain amino acids may substituted for other amino acids in the antibody constant or variable domain framework regions without appreciable loss of interactive binding capacity. It is preferably that such changes be made in the DNA sequences encoding the antibody portions and that the changes be conservative in nature (see Section C3, the codon information in Table A, and the supporting technical details on site-specific mutagenesis). Naturally, there is a limit to the number of changes that should be made, but this will be known those of ordinary skill in the art.

Other types of variants are antibodies with improved biological properties relative to the parent antibody from which they are generated. Such variants, or second generation compounds, are typically substitutional variants involving one or more substituted hypervariable region residues of a parent antibody. A convenient way for generating such substitutional variants is affinity maturation using phage display.

In affinity maturation using phage display, several hypervariable region sites (e.g. 6–7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identified hypervariable region residues contributing significantly to antigen binding.

Alternatively, or in addition, it is contemplated that the crystal structure of the antigen-antibody complex be delineated and analyzed to identify contact points between the antibody and VEGF. Such contact residues and neighboring residues are candidates for substitution. Once such variants are generated, the panel of variants is subjected to screening, as described herein, and antibodies with analogues but different or even superior properties in one or more relevant assays are selected for further development.

Further aspects of the invention therefore concern isolated DNA segments and recombinant vectors encoding CDR regions of VEGFR2-blocking, anti-VEGF antibody heavy and light chains, such as 2C3 heavy and light chains, and the creation and use of recombinant host cells through the application of DNA technology, that express such CDR regions.

The present invention thus concerns DNA segments, isolatable from any mammal, preferably, human or murine, that are free from total genomic DNA and are capable of expressing CDR regions of VEGFR2-blocking, anti-VEGF antibody heavy and light chains, such as 2C3 heavy and light chains. As used herein, the term "DNA segment" refers to a DNA molecule that has been isolated free of total genomic DNA of a particular species. Included within the term "DNA segment", are DNA segments and smaller fragments of such segments, and also recombinant vectors, including, for example, plasmids, cosmids, phage, viruses, and the like.

Similarly, a DNA segment comprising a coding segment or isolated gene portion encoding purified CDR regions of VEGFR2-blocking, anti-VEGF antibody heavy and light chains, such as 2C3 heavy and light chains, refers to a DNA segment including such coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes the native antibody-encoding sequences and smaller engineered segments that express, or may be adapted to express, suitable antigen binding proteins, polypeptides or peptides.

"Isolated substantially away from other coding sequences" means that the coding segment or isolated gene portion of interest forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated coding segments or isolated gene portions and recombinant vectors incorporating DNA sequences that encode CDR regions of VEGFR2-blocking, anti-VEGF antibody heavy and light chains, such as 2C3 heavy and light chains, that comprise at least a first sequence region that includes an amino acid sequence region of at least about 75%, more preferably, at least about 80%, more preferably, at least about 85%, more preferably, at least about 90% and most preferably, at least about 95% or so amino acid sequence identity to the amino acid sequence of SEQ ID NO:7 or SEQ ID NO:9; wherein said CDR regions at least substantially maintain the biological properties of the CDR regions of amino acid sequences SEQ ID NO:7 or SEQ ID NO:9.

As disclosed herein, the sequences may comprise certain biologically functional equivalent amino acids or "conservative substitutions". Other sequences may comprise functionally non-equivalent amino acids or "non-conservative substitutions" deliberately engineered to improve the properties of the CDR or antibody containing the CDR, as is known those of ordinary skill in the art and further described herein.

It will also be understood that amino acid and nucleic acid sequences may include additional residues, such as additional N- or C-terminal amino acids or 5' or 3' sequences, and yet still correspond to a sequence of the invention, so long as the sequence meets the criteria set forth above, preferably including the maintenance or improvement of biological protein activity where protein expression is concerned. The addition of terminal sequences includes various non-coding sequences flanking either of the 5' or 3' portions of the coding region, and also control regions.

The nucleic acid segments of the present invention may thus be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Recombinant vectors therefore form further aspects of the present invention. Particularly useful vectors are contemplated to be those vectors in which the coding portion of the DNA segment is positioned under the control of a promoter. Generally, although not exclusively, a recombinant or heterologous promoter will be employed, i.e., a promoter not normally associated with coding sequences in their natural environment. Such promoters may include bacterial, viral, eukaryotic and mammalian promoters, so long as the promoter effectively directs the expression of the DNA segment in the cell type, organism, or even animal, chosen for expression.

The use of promoter and cell type combinations for protein expression is known to those of skill in the art of molecular biology. The promoters employed may be constitutive, or inducible, and can be used under the appropriate conditions to direct high level expression of the introduced DNA segment, such as is advantageous in the large-scale production of recombinant proteins or peptides.

The expression of the nucleic acid sequences of the invention may be conveniently achieved by any one or more standard techniques known those of ordinary skill in the art and further described herein. For example, the later description of the recombinant expression of fusion proteins applies equally well to antibodies and antibody fragments that are not operatively associated with another coding sequence at the nucleic acid level.

B4. Polyclonal Antibodies

Means for preparing and characterizing antibodies are well known in the art (see, e.g., Antibodies: A Laboratory Manual, Cold Spring Harbor Laboratory, 1988; incorporated herein by reference). To prepare polyclonal antisera an animal is immunized with an immunogenic VEGF composition, and antisera collected from that immunized animal. A wide range of animal species can be used for the production of antisera. Typically the animal used for production of anti-antisera is a rabbit, mouse, rat, hamster, guinea pig or goat. Because of the relatively large blood volume of rabbits, a rabbit is a preferred choice for production of polyclonal antibodies.

The amount of VEGF immunogen composition used in the production of polyclonal antibodies varies upon the nature of the immunogen as well as the animal used for immunization. A variety of routes can be used to administer the present VEGF immunogen; subcutaneous, intramuscular, intradermal, intravenous, intraperitoneal and intrasplenic. The production of polyclonal antibodies may be monitored by sampling blood of the immunized animal at various points following immunization. A second, booster injection, may also be given. The process of boosting and titering is repeated until a suitable titer is achieved. When a desired titer level is obtained, the immunized animal can be bled and the serum isolated and stored. The animal can also be used to generate monoclonal antibodies.

As is well known in the art, the immunogenicity of a particular composition can be enhanced by the use of non-specific stimulators of the immune response, known as adjuvants. Exemplary adjuvants include complete Freund's adjuvant, a non-specific stimulator of the immune response containing killed *Mycobacterium tuberculosis*; incomplete Freund's adjuvant; and aluminum hydroxide adjuvant.

It may also be desired to boost the host immune system, as may be achieved by associating VEGF with, or coupling VEGF to, a carrier. Exemplary carriers are keyhole limpet hemocyanin (KLH) and bovine serum albumin (BSA). Other albumins such as ovalbumin, mouse serum albumin or rabbit serum albumin can also be used as carriers. As is also known in the art, a given composition may vary in its immunogenicity. However, the generation of antibodies against VEGF is not particularly difficult.

B5. Monoclonal Antibodies

Various methods for generating monoclonal antibodies (MAbs) are also now very well known in the art. The most standard monoclonal antibody generation techniques generally begin along the same lines as those for preparing polyclonal antibodies (Antibodies: A Laboratory Manual, Cold Spring Harbor Laboratory, 1988; incorporated herein by reference). A polyclonal antibody response is initiated by immunizing an animal with an immunogenic VEGF composition and, when a desired titer level is obtained, the immunized animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with the selected VEGF immunogen composition. The immunizing composition is administered in a manner effective to stimulate antibody-producing cells. Rodents such as mice and rats are preferred animals, however, the use of rabbit, sheep and frog cells is also possible. The use of rats may provide certain advantages (Goding, 1986, pp. 60–61; incorporated herein by reference), but mice are preferred, with the BALB/c mouse being most preferred as this is most routinely used and generally gives a higher percentage of stable fusions.

Following immunization, somatic cells with the potential for producing VEGF antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The anti-VEGF antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984; each incorporated herein by reference). For example, where the immunized animal is a mouse, one may use P3-X63/Ag8, X63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F, 4B210 or one of the above listed mouse cell lines; and U-266, GM1500-GRG2, LICR-LON-HMy2 and UC729-6, are all useful in connection with human cell fusions.

Methods for generating hybrids of antibody-producing spleen or lymph node cells and myeloma cells usually comprise mixing somatic cells with myeloma cells in a 4:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976; each incorporated herein by reference), and those using polyethylene glycol (PEG), such as 37% (v/v) PEG, by Gefter et al. (1977; incorporated herein by reference). The use of electrically induced fusion methods is also appropriate (Goding pp. 71–74, 1986; incorporated herein by reference).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired anti-VEGF reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual anti-VEGF antibody-producing cell lines, which clones can then be propagated indefinitely to provide MAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations.

MAbs produced by either means will generally be further purified, e.g., using filtration, centrifugation and various chromatographic methods, such as HPLC or affinity chromatography, all of which purification techniques are well known to those of skill in the art. These purification techniques each involve fractionation to separate the desired antibody from other components of a mixture. Analytical methods particularly suited to the preparation of antibodies include, for example, protein A-Sepharose and/or protein G-Sepharose chromatography.

B6. Antibodies from Phagemid Libraries

Recombinant technology now allows the preparation of antibodies having the desired specificity from recombinant genes encoding a range of antibodies (Van Dijk et al., 1989; incorporated herein by reference). Certain recombinant techniques involve the isolation of the antibody genes by immunological screening of combinatorial immunoglobulin phage expression libraries prepared from RNA isolated from the spleen of an immunized animal (Morrison et al., 1986; Winter and Milstein, 1991; each incorporated herein by reference).

For such methods, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination, which further increases the percentage of appropriate antibodies generated.

One method for the generation of a large repertoire of diverse antibody molecules in bacteria utilizes the bacteriophage lambda as the vector (Huse et al., 1989; incorporated herein by reference). Production of antibodies using the lambda vector involves the cloning of heavy and light chain populations of DNA sequences into separate starting vectors. The vectors are subsequently combined randomly to form a single vector that directs the co-expression of heavy and light chains to form antibody fragments. The heavy and light chain DNA sequences are obtained by amplification, preferably by PCR™ or a related amplification technique, of mRNA isolated from spleen cells (or hybridomas thereof) from an animal that has been immunized with a selected antigen. The heavy and light chain sequences are typically amplified using primers that incorporate restriction sites into the ends of the amplified DNA segment to facilitate cloning of the heavy and light chain segments into the starting vectors.

Another method for the generation and screening of large libraries of wholly or partially synthetic antibody combining sites, or paratopes, utilizes display vectors derived from filamentous phage such as M13, f1 or fd. These filamentous phage display vectors, referred to as "phagemids", yield large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries (Kang et al., 1991; Barbas et al., 1991; each incorporated herein by reference).

This general technique for filamentous phage display is described in U.S. Pat. No. 5,658,727, incorporated herein by reference. In a most general sense, the method provides a system for the simultaneous cloning and screening of pre-selected ligand-binding specificities from antibody gene repertoires using a single vector system. Screening of isolated members of the library for a pre-selected ligand-binding capacity allows the correlation of the binding capacity of an expressed antibody molecule with a convenient means to isolate the gene that encodes the member from the library.

Linkage of expression and screening is accomplished by the combination of targeting of a fusion polypeptide into the periplasm of a bacterial cell to allow assembly of a functional antibody, and the targeting of a fusion polypeptide onto the coat of a filamentous phage particle during phage assembly to allow for convenient screening of the library member of interest. Periplasmic targeting is provided by the presence of a secretion signal domain in a fusion polypeptide. Targeting to a phage particle is provided by the presence of a filamentous phage coat protein membrane anchor domain (i.e., a cpIII- or cpVIII-derived membrane anchor domain) in a fusion polypeptide.

The diversity of a filamentous phage-based combinatorial antibody library can be increased by shuffling of the heavy and light chain genes, by altering one or more of the complementarity determining regions of the cloned heavy chain genes of the library, or by introducing random mutations into the library by error-prone polymerase chain reactions. Additional methods for screening phagemid libraries are described in U.S. Pat. Nos. 5,580,717; 5,427,908; 5,403,484; and 5,223,409, each incorporated herein by reference.

Another method for the screening of large combinatorial antibody libraries has been developed, utilizing expression of populations of diverse heavy and light chain sequences on the surface of a filamentous bacteriophage, such as M13, f1 or fd (U.S. Pat. No. 5,698,426; incorporated herein by reference). Two populations of diverse heavy (Hc) and light (Lc) chain sequences are synthesized by polymerase chain reaction (PCR™). These populations are cloned into separate M13-based vector containing elements necessary for expression. The heavy chain vector contains a gene VIII (gVIII) coat protein sequence so that translation of the heavy chain sequences produces gVIII-Hc fusion proteins. The populations of two vectors are randomly combined such that only the vector portions containing the Hc and Lc sequences are joined into a single circular vector.

The combined vector directs the co-expression of both Hc and Lc sequences for assembly of the two polypeptides and surface expression on M13 (U.S. Pat. No. 5,698,426; incorporated herein by reference). The combining step randomly brings together different Hc and Lc encoding sequences within two diverse populations into a single vector. The vector sequences donated from each independent vector are necessary for production of viable phage. In addition, since the pseudo gVIII sequences are contained in only one of the two starting vectors, co-expression of functional antibody fragments as Lc associated gVIII-Hc fusion proteins cannot be accomplished on the phage surface until the vector sequences are linked in the single vector.

Surface expression of the antibody library is performed in an amber suppressor strain. An amber stop codon between the Hc sequence and the gVIII sequence unlinks the two components in a non-suppressor strain. Isolating the phage produced from the non-suppressor strain and infecting a suppressor strain will link the Hc sequences to the gVIII sequence during expression. Culturing the suppressor strain after infection allows the coexpression on the surface of M13 of all antibody species within the library as gVIII fusion proteins (gVIII-Fab fusion proteins). Alternatively, the DNA can be isolated from the non-suppressor strain and then introduced into a suppressor strain to accomplish the same effect.

The surface expression library is screened for specific Fab fragments that bind preselected molecules by standard affinity isolation procedures. Such methods include, for example, panning (Parmley and Smith, 1988; incorporated herein by reference), affinity chromatography and solid phase blotting procedures. Panning is preferred, because high titers of phage can be screened easily, quickly and in small volumes. Furthermore, this procedure can select minor Fab fragments species within the population, which otherwise would have been undetectable, and amplified to substantially homogenous populations. The selected Fab fragments can be characterized by sequencing the nucleic acids encoding the polypeptides after amplification of the phage population.

Another method for producing diverse libraries of antibodies and screening for desirable binding specificities is described in U.S. Pat. No. 5,667,988 and U.S. Pat. No. 5,759,817, each incorporated herein by reference. The method involves the preparation of libraries of heterodimeric immunoglobulin molecules in the form of phagemid libraries using degenerate oligonucleotides and primer extension reactions to incorporate the degeneracies into the CDR regions of the immunoglobulin variable heavy and light chain variable domains, and display of the mutagenized polypeptides on the surface of the phagemid. Thereafter, the display protein is screened for the ability to bind to a preselected antigen.

The method for producing a heterodimeric immunoglobulin molecule generally involves (1) introducing a heavy or light chain V region-coding gene of interest into the phagemid display vector; (2) introducing a randomized binding site into the phagemid display protein vector by primer extension with an oligonucleotide containing regions of homology to a CDR of the antibody V region gene and containing regions of degeneracy for producing randomized coding sequences to form a large population of display vectors each capable of expressing different putative binding sites displayed on a phagemid surface display protein; (3) expressing the display protein and binding site on the surface of a filamentous phage particle; and (4) isolating (screening) the surface-expressed phage particle using affinity techniques such as panning of phage particles against a preselected antigen, thereby isolating one or more species of phagemid containing a display protein containing a binding site that binds a preselected antigen.

A further variation of this method for producing diverse libraries of antibodies and screening for desirable binding specificities is described in U.S. Pat. No. 5,702,892, incorporated herein by reference. In this method, only heavy chain sequences are employed, the heavy chain sequences are randomized at all nucleotide positions which encode either the CDRI or CDRIII hypervariable region, and the genetic variability in the CDRs is generated independent of any biological process.

In the method, two libraries are engineered to genetically shuffle oligonucleotide motifs within the framework of the heavy chain gene structure. Through random mutation of either CDRI or CDRIII, the hypervariable regions of the heavy chain gene were reconstructed to result in a collection of highly diverse sequences. The heavy chain proteins encoded by the collection of mutated gene sequences possessed the potential to have all of the binding characteristics of an immunoglobulin while requiring only one of the two immunoglobulin chains.

Specifically, the method is practiced in the absence of the immunoglobulin light chain protein. A library of phage displaying modified heavy chain proteins is incubated with an immobilized ligand to select clones encoding recombinant proteins that specifically bind the immobilized ligand. The bound phage are then dissociated from the immobilized ligand and amplified by growth in bacterial host cells. Individual viral plaques, each expressing a different recombinant protein, are expanded, and individual clones can then be assayed for binding activity.

B7. Antibodies from Human Lymphocytes

In vitro immunization, or antigen stimulation, may also be used to generate a human anti-VEGF antibody. Such techniques can be used to stimulate peripheral blood lymphocytes from normal, healthy subjects, simply by stimulating antibody-producing cells with VEGF in vitro.

Such "in vitro immunization" involves antigen-specific activation of non-immunized B lymphocytes, generally within a mixed population of lymphocytes (mixed lymphocyte cultures, MLC). In vitro immunizations may also be supported by B cell growth and differentiation factors and lymphokines. The antibodies produced by these methods are often IgM antibodies (Borrebaeck et al., 1986; incorporated herein by reference).

Another method has been described (U.S. Pat. No. 5,681,729, incorporated herein by reference) wherein human lymphocytes that mainly produce IgG (or IgA) antibodies can be obtained. The method involves, in a general sense, transplanting human lymphocytes to an immunodeficient animal so that the human lymphocytes "take" in the animal body; immunizing the animal with a desired antigen, so as to generate human lymphocytes producing an antibody specific to the antigen; and recovering the human lymphocytes producing the antibody from the animal. The human lymphocytes thus produced can be used to produce a monoclonal antibody by immortalizing the human lymphocytes producing the antibody, cloning the obtained immortalized human-originated lymphocytes producing the antibody, and recovering a monoclonal antibody specific to the desired antigen from the cloned immortalized human-originated lymphocytes.

The immunodeficient animals that may be employed in this technique are those that do not exhibit rejection when human lymphocytes are transplanted to the animals. Such animals may be artificially prepared by physical, chemical or biological treatments. Any immunodeficient animal may be employed. The human lymphocytes may be obtained from human peripheral blood, spleen, lymph nodes, tonsils or the like.

The "taking" of the transplanted human lymphocytes in the animals can be attained by merely administering the human lymphocytes to the animals. The administration route is not restricted and may be, for example, subcutaneous, intravenous or intraperitoneal. The dose of the human lymphocytes is not restricted, and can usually be $10^6$ to $10^8$ lymphocytes per animal. The immunodeficient animal is then immunized with the desired VEGF antigen.

After the immunization, human lymphocytes are recovered from the blood, spleen, lymph nodes or other lymphatic tissues by any conventional method. For example, mononuclear cells can be separated by the Ficoll-Hypaque (specific gravity: 1.077) centrifugation method, and the monocytes removed by the plastic dish adsorption method. The contaminating cells originating from the immunodeficient animal may be removed by using an antiserum specific to the animal cells. The antiserum may be obtained by, for example, immunizing a second, distinct animal with the spleen cells of the immunodeficient animal, and recovering serum from the distinct immunized animal. The treatment with the antiserum may be carried out at any stage. The human lymphocytes may also be recovered by an immunological method employing a human immunoglobulin expressed on the cell surface as a marker.

By these methods, human lymphocytes mainly producing IgG and IgA antibodies specific to one or more selected VEGF epitopes can be obtained. Monoclonal antibodies are then obtained from the human lymphocytes by immortalization, selection, cell growth and antibody production.

B8. Transgenic Mice Containing Human Antibody Libraries

Recombinant technology is now available for the preparation of antibodies. In addition to the combinatorial immunoglobulin phage expression libraries disclosed above, another molecular cloning approach is to prepare antibodies from transgenic mice containing human antibody libraries. Such techniques are described in U.S. Pat. No. 5,545,807, incorporated herein by reference.

In a most general sense, these methods involve the production of a transgenic animal that has inserted into its germline genetic material that encodes for at least part of an immunoglobulin of human origin or that can rearrange to encode a repertoire of immunoglobulins. The inserted genetic material may be produced from a human source, or may be produced synthetically. The material may code for at least part of a known immunoglobulin or may be modified to code for at least part of an altered immunoglobulin.

The inserted genetic material is expressed in the transgenic animal, resulting in production of an immunoglobulin derived at least in part from the inserted human immunoglobulin genetic material. It is found the genetic material is rearranged in the transgenic animal, so that a repertoire of immunoglobulins with part or parts derived from inserted genetic material may be produced, even if the inserted genetic material is incorporated in the germline in the wrong position or with the wrong geometry.

The inserted genetic material may be in the form of DNA cloned into prokaryotic vectors such as plasmids and/or cosmids. Larger DNA fragments are inserted using yeast artificial chromosome vectors (Burke et al., 1987; incorporated herein by reference), or by introduction of chromosome fragments (Richer and Lo, 1989; incorporated herein by reference). The inserted genetic material may be introduced to the host in conventional manner, for example by injection or other procedures into fertilized eggs or embryonic stem cells.

In preferred aspects, a host animal that initially does not carry genetic material encoding immunoglobulin constant regions is utilized, so that the resulting transgenic animal will use only the inserted human genetic material when producing immunoglobulins. This can be achieved either by using a naturally occurring mutant host lacking the relevant genetic material, or by artificially making mutants e.g., in cell lines ultimately to create a host from which the relevant genetic material has been removed.

Where the host animal carries genetic material encoding immunoglobulin constant regions, the transgenic animal will carry the naturally occurring genetic material and the inserted genetic material and will produce immunoglobulins derived from the naturally occurring genetic material, the inserted genetic material, and mixtures of both types of genetic material. In this case the desired immunoglobulin can be obtained by screening hybridomas derived from the transgenic animal, e.g., by exploiting the phenomenon of allelic exclusion of antibody gene expression or differential chromosome loss.

Once a suitable transgenic animal has been prepared, the animal is simply immunized with the desired immunogen. Depending on the nature of the inserted material, the animal may produce a chimeric immunoglobulin, e.g. of mixed mouse/human origin, where the genetic material of foreign origin encodes only part of the immunoglobulin; or the animal may produce an entirely foreign immunoglobulin, e.g. of wholly human origin, where the genetic material of foreign origin encodes an entire immunoglobulin.

Polyclonal antisera may be produced from the transgenic animal following immunization. Immunoglobulin-producing cells may be removed from the animal to produce the immunoglobulin of interest. Preferably, monoclonal antibodies are produced from the transgenic animal, e.g., by fusing spleen cells from the animal with myeloma cells and screening the resulting hybridomas to select those producing the desired antibody. Suitable techniques for such processes are described herein.

In an alternative approach, the genetic material may be incorporated in the animal in such a way that the desired antibody is produced in body fluids such as serum or external secretions of the animal, such as milk, colostrum or saliva. For example, by inserting in vitro genetic material encoding for at least part of a human immunoglobulin into a gene of a mammal coding for a milk protein and then introducing the gene to a fertilized egg of the mammal, e.g., by injection, the egg may develop into an adult female mammal producing milk containing immunoglobulin derived at least in part from the inserted human immunoglobulin genetic material. The desired antibody can then be harvested from the milk. Suitable techniques for carrying out such processes are known to those skilled in the art.

The foregoing transgenic animals are usually employed to produce human antibodies of a single isotype, more specifically an isotype that is essential for B cell maturation, such as IgM and possibly IgD. Another preferred method for producing human anti-VEGF antibodies is to use the technology described in U.S. Pat. Nos. 5,545,806; 5,569,825; 5,625,126; 5,633,425; 5,661,016; and 5,770,429; each incorporated by reference, wherein transgenic animals are described that are capable of switching from an isotype needed for B cell development to other isotypes.

In the development of a B lymphocyte, the cell initially produces IgM with a binding specificity determined by the productively rearranged $V_H$ and $V_L$ regions. Subsequently, each B cell and its progeny cells synthesize antibodies with the same L and H chain V regions, but they may switch the isotype of the H chain. The use of mu or delta constant regions is largely determined by alternate splicing, permitting IgM and IgD to be coexpressed in a single cell. The other heavy chain isotypes (gamma, alpha, and epsilon) are only expressed natively after a gene rearrangement event deletes the C mu and C delta exons. This gene rearrangement process, termed isotype switching, typically occurs by recombination between so called switch segments located immediately upstream of each heavy chain gene (except delta). The individual switch segments are between 2 and 10 kb in length, and consist primarily of short repeated sequences.

For these reasons, it is preferable that transgenes incorporate transcriptional regulatory sequences within about 1–2 kb upstream of each switch region that is to be utilized for isotype switching. These transcriptional regulatory sequences preferably include a promoter and an enhancer element, and more preferably include the 5' flanking (i.e., upstream) region that is naturally associated (i.e., occurs in germline configuration) with a switch region. Although a 5' flanking sequence from one switch region can be operably linked to a different switch region for transgene construction, in some embodiments it is preferred that each switch region incorporated in the transgene construct have the 5' flanking region that occurs immediately upstream in the naturally occurring germline configuration. Sequence information relating to immunoglobulin switch region sequences is known (Mills et al., 1990; Sideras et al., 1989; each incorporated herein by reference).

In the method described in U.S. Pat. Nos. 5,545,806; 5,569,825; 5,625,126; 5,633,425; 5,661,016; and 5,770,429, the human immunoglobulin transgenes contained within the transgenic animal function correctly throughout the pathway of B-cell development, leading to isotype switching. Accordingly, in this method, these transgenes are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

An important requirement for transgene function is the generation of a primary antibody repertoire that is diverse enough to trigger a secondary immune response for a wide range of antigens. The rearranged heavy chain gene consists of a signal peptide exon, a variable region exon and a tandem array of multi-domain constant region regions, each of which is encoded by several exons. Each of the constant region genes encode the constant portion of a different class of immunoglobulins. During B-cell development, V region proximal constant regions are deleted leading to the expression of new heavy chain classes. For each heavy chain class, alternative patterns of RNA splicing give rise to both transmembrane and secreted immunoglobulins.

The human heavy chain locus consists of approximately 200 V gene segments spanning 2 Mb, approximately 30 D gene segments spanning about 40 kb, six J segments clustered within a 3 kb span, and nine constant region gene segments spread out over approximately 300 kb. The entire locus spans approximately 2.5 Mb of the distal portion of the long arm of chromosome 14. Heavy chain transgene fragments containing members of all six of the known $V_H$ families, the D and J gene segments, as well as the mu, delta, gamma 3, gamma 1 and alpha 1 constant regions are known (Berman et al., 1988; incorporated herein by reference). Genomic fragments containing all of the necessary gene segments and regulatory sequences from a human light chain locus is similarly constructed.

The expression of successfully rearranged immunoglobulin heavy and light transgenes usually has a dominant effect by suppressing the rearrangement of the endogenous immunoglobulin genes in the transgenic nonhuman animal. However, in certain embodiments, it is desirable to effect complete inactivation of the endogenous Ig loci so that hybrid immunoglobulin chains comprising a human variable region and a non-human (e.g., murine) constant region cannot be formed, for example by trans-switching between the transgene and endogenous Ig sequences. Using embryonic stem cell technology and homologous recombination, the endogenous immunoglobulin repertoire can be readily eliminated. In addition, suppression of endogenous Ig genes may be accomplished using a variety of techniques, such as antisense technology.

In other aspects of the invention, it may be desirable to produce a trans-switched immunoglobulin. Antibodies comprising such chimeric trans-switched immunoglobulins can be used for a variety of applications where it is desirable to have a non-human (e.g., murine) constant region, e.g., for retention of effector functions in the host. The presence of a murine constant region can afford advantages over a human constant region, for example, to provide murine effector functions (e.g., ADCC, murine complement fixation) so that such a chimeric antibody may be tested in a mouse disease model. Subsequent to the animal testing, the human variable region encoding sequence may be isolated, e.g., by PCR™ amplification or cDNA cloning from the source (hybridoma clone), and spliced to a sequence encoding a desired human constant region to encode a human sequence antibody more suitable for human therapeutic use.

B9. Humanized Antibodies

Human antibodies generally have at least three potential advantages for use in human therapy. First, because the effector portion is human, it may interact better with the other parts of the human immune system, e.g., to destroy target cells more efficiently by complement-dependent cytotoxicity (CDC) or antibody-dependent cellular cytotoxicity (ADCC). Second, the human immune system should not recognize the antibody as foreign. Third, the half-life in the human circulation will be similar to naturally occurring human antibodies, allowing smaller and less frequent doses to be given.

Various methods for preparing human anti-VEGF antibodies are provided herein. In addition to human antibodies, "humanized" antibodies have many advantages. "Humanized" antibodies are generally chimeric or mutant monoclonal antibodies from mouse, rat, hamster, rabbit or other species, bearing human constant and/or variable region domains or specific changes. Techniques for generating a so-called "humanized" anti-VEGF antibody are well known to those of skill in the art.

Humanized antibodies also share the foregoing advantages. First, the effector portion is still human. Second, the human immune system should not recognize the framework or constant region as foreign, and therefore the antibody response against such an injected antibody should be less than against a totally foreign mouse antibody. Third, injected humanized antibodies, as opposed to injected mouse antibodies, will presumably have a half-life more similar to naturally occurring human antibodies, also allowing smaller and less frequent doses.

A number of methods have been described to produce humanized antibodies. Controlled rearrangement of antibody domains joined through protein disulfide bonds to form new, artificial protein molecules or "chimeric" antibodies can be utilized (Konieczny et al., 1981; incorporated herein by reference). Recombinant DNA technology can also be used to construct gene fusions between DNA sequences encoding mouse antibody variable light and heavy chain domains and human antibody light and heavy chain constant domains (Morrison et al., 1984; incorporated herein by reference).

DNA sequences encoding the antigen binding portions or complementarity determining regions (CDR's) of murine monoclonal antibodies can be grafted by molecular means into the DNA sequences encoding the frameworks of human antibody heavy and light chains (Riechmann et al., 1988). The expressed recombinant products are called "reshaped" or humanized antibodies, and comprise the framework of a human antibody light or heavy chain and the antigen recognition portions, CDR's, of a murine monoclonal antibody.

Another method for producing humanized antibodies is described in U.S. Pat. No. 5,639,641, incorporated herein by reference. The method provides, via resurfacing, humanized rodent antibodies that have improved therapeutic efficacy due to the presentation of a human surface in the variable region. In the method: (1) position alignments of a pool of antibody heavy and light chain variable regions is generated to give a set of heavy and light chain variable region framework surface exposed positions, wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 Å of any atom of any residue of the complementarity determining regions of the rodent antibody; and (5) the humanized rodent antibody having binding specificity is produced.

A similar method for the production of humanized antibodies is described in U.S. Pat. Nos. 5,693,762; 5,693,761; 5,585,089; and 5,530,101, each incorporated herein by reference. These methods involve producing humanized immunoglobulins having one or more complementarity determining regions (CDR's) and possible additional amino acids from a donor immunoglobulin and a framework region from an accepting human immunoglobulin. Each humanized immunoglobulin chain usually comprises, in addition to the CDR's, amino acids from the donor immunoglobulin framework that are capable of interacting with the CDR's to effect binding affinity, such as one or more amino acids that are immediately adjacent to a CDR in the donor immunoglobulin or those within about 3 Å as predicted by molecular modeling. The heavy and light chains may each be designed by using any one, any combination, or all of the various position criteria described in U.S. Pat. Nos. 5,693,762; 5,693,761; 5,585,089; and 5,530,101, each incorporated herein by reference. When combined into an intact antibody, the humanized immunoglobulins are substantially non-immunogenic in humans and retain substantially the same affinity as the donor immunoglobulin to the original antigen.

An additional method for producing humanized antibodies is described in U.S. Pat. Nos. 5,565,332 and 5,733,743, each incorporated herein by reference. This method combines the concept of humanizing antibodies with the phagemid libraries also described in detail herein. In a general sense, the method utilizes sequences from the antigen binding site of an antibody or population of antibodies directed against an antigen of interest. Thus for a single rodent antibody, sequences comprising part of the antigen binding site of the antibody may be combined with diverse repertoires of sequences of human antibodies that can, in combination, create a complete antigen binding site.

The antigen binding sites created by this process differ from those created by CDR grafting, in that only the portion of sequence of the original rodent antibody is likely to make contacts with antigen in a similar manner. The selected human sequences are likely to differ in sequence and make alternative contacts with the antigen from those of the original binding site. However, the constraints imposed by binding of the portion of original sequence to antigen and the shapes of the antigen and its antigen binding sites, are likely to drive the new contacts of the human sequences to the same region or epitope of the antigen. This process has therefore been termed "epitope imprinted selection" (EIS).

Starting with an animal antibody, one process results in the selection of antibodies that are partly human antibodies. Such antibodies may be sufficiently similar in sequence to human antibodies to be used directly in therapy or after alteration of a few key residues. Sequence differences between the rodent component of the selected antibody with human sequences could be minimized by replacing those residues that differ with the residues of human sequences, for example, by site directed mutagenesis of individual residues, or by CDR grafting of entire loops. However, antibodies with entirely human sequences can also be created. EIS therefore offers a method for making partly human or entirely human antibodies that bind to the same epitope as animal or partly human antibodies respectively. In EIS, repertoires of antibody fragments can be displayed on the surface of filamentous phase and the genes encoding fragments with antigen binding activities selected by binding of the phage to antigen.

Additional methods for humanizing antibodies contemplated for use in the present invention are described in U.S. Pat. Nos. 5,750,078; 5,502,167; 5,705,154; 5,770,403;

5,698,417; 5,693,493; 5,558,864; 4,935,496; and 4,816,567, each incorporated herein by reference. WO 98/45331 and WO 98/45332 are believed to be particularly instructive and are incorporated herein by reference to further exemplify the principles of humanization as applied to anti-VEGF antibodies.

B10. Mutagenesis by PCR™

Site-specific mutagenesis is a technique useful in the preparation of individual antibodies through specific mutagenesis of the underlying DNA. The technique further provides a ready ability to prepare and test sequence variants, incorporating one or more of the foregoing considerations, whether humanizing or not, by introducing one or more nucleotide sequence changes into the DNA.

Although many methods are suitable for use in mutagenesis, the use of the polymerase chain reaction (PCR™) is generally now preferred. This technology offers a quick and efficient method for introducing desired mutations into a given DNA sequence. The following text particularly describes the use of PCR™ to introduce point mutations into a sequence, as may be used to change the amino acid encoded by the given sequence. Adaptations of this method are also suitable for introducing restriction enzyme sites into a DNA molecule.

In this method, synthetic oligonucleotides are designed to incorporate a point mutation at one end of an amplified segment. Following PCR™, the amplified fragments are blunt-ended by treating with Klenow fragments, and the blunt-ended fragments are then ligated and subcloned into a vector to facilitate sequence analysis.

To prepare the template DNA that one desires to mutagenize, the DNA is subcloned into a high copy number vector, such as pUC 19, using restriction sites flanking the area to be mutated. Template DNA is then prepared using a plasmid miniprep. Appropriate oligonucleotide primers that are based upon the parent sequence, but which contain the desired point mutation and which are flanked at the 5' end by a restriction enzyme site, are synthesized using an automated synthesizer. It is generally required that the primer be homologous to the template DNA for about 15 bases or so. Primers may be purified by denaturing polyacrylamide gel electrophoresis, although this is not absolutely necessary for use in PCR™. The 5' end of the oligonucleotides should then be phosphorylated.

The template DNA should be amplified by PCR™, using the oligonucleotide primers that contain the desired point mutations. The concentration of $MgCl_2$ in the amplification buffer will generally be about 15 mM. Generally about 20–25 cycles of PCR™ should be carried out as follows: denaturation, 35 sec. at 95° C.; hybridization, 2 min. at 50° C.; and extension, 2 min. at 72° C. The PCR™ will generally include a last cycle extension of about 10 min. at 72° C. After the final extension step, about 5 units of Klenow fragments should be added to the reaction mixture and incubated for a further 15 min. at about 30° C. The exonuclease activity of the Klenow fragments is required to make the ends flush and suitable for blunt-end cloning.

The resultant reaction mixture should generally be analyzed by nondenaturing agarose or acrylamide gel electrophoresis to verify that the amplification has yielded the predicted product. One would then process the reaction mixture by removing most of the mineral oils, extracting with chloroform to remove the remaining oil, extracting with buffered phenol and then concentrating by precipitation with 100% ethanol. Next, one should digest about half of the amplified fragments with a restriction enzyme that cuts at the flanking sequences used in the oligonucleotides. The digested fragments are purified on a low gelling/melting agarose gel.

To subclone the fragments and to check the point mutation, one would subclone the two amplified fragments into an appropriately digested vector by blunt-end ligation. This would be used to transform E. coli, from which plasmid DNA could subsequently be prepared using a miniprep. The amplified portion of the plasmid DNA would then be analyzed by DNA sequencing to confirm that the correct point mutation was generated. This is important as Taq DNA polymerase can introduce additional mutations into DNA fragments.

The introduction of a point mutation can also be effected using sequential PCR™ steps. In this procedure, the two fragments encompassing the mutation are annealed with each other and extended by mutually primed synthesis. This fragment is then amplified by a second PCR™ step, thereby avoiding the blunt-end ligation required in the above protocol. In this method, the preparation of the template DNA, the generation of the oligonucleotide primers and the first PCR™ amplification are performed as described above. In this process, however, the chosen oligonucleotides should be homologous to the template DNA for a stretch of between about 15 and about 20 bases and must also overlap with each other by about 10 bases or more.

In the second PCR™ amplification, one would use each amplified fragment and each flanking sequence primer and carry PCR™ for between about 20 and about 25 cycles, using the conditions as described above. One would again subclone the fragments and check that the point mutation was correct by using the steps outlined above.

In using either of the foregoing methods, it is generally preferred to introduce the mutation by amplifying as small a fragment as possible. Of course, parameters such as the melting temperature of the oligonucleotide, as will generally be influenced by the GC content and the length of the oligo, should also be carefully considered. The execution of these methods, and their optimization if necessary, will be known to those of skill in the art, and are further described in various publications, such as *Current Protocols in Molecular Biology*, 1995, incorporated herein by reference.

When performing site-specific mutagenesis, Table A can be employed as a reference.

TABLE A

| Amino Acids | | | Codons | | | |
|---|---|---|---|---|---|---|
| Alanine | Ala | A | GCA | GCC | GGG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

B11. Antibody Fragments and Derivatives

Irrespective of the source of the original VEGFR2-blocking, anti-VEGF antibody, either the intact antibody, antibody multimers, or any one of a variety of functional, antigen-binding regions of the antibody may be used in the present invention. Exemplary functional regions include diabodies, linear antibodies and scFv, Fv, Fab', Fab, F(ab')$_2$ fragments of the anti-VEGF antibodies. Techniques for preparing such constructs are well known to those in the art and are further exemplified herein.

The choice of antibody construct may be influenced by various factors. For example, prolonged half-life can result from the active readsorption of intact antibodies within the kidney, a property of the Fc piece of immunoglobulin. IgG based antibodies, therefore, are expected to exhibit slower blood clearance than their Fab' counterparts. However, Fab' fragment-based compositions will generally exhibit better tissue penetrating capability.

Antibody fragments can be obtained by proteolysis of the whole immunoglobulin by the non-specific thiol protease, papain. Papain digestion yields two identical antigen-binding fragments, termed "Fab fragments", each with a single antigen-binding site, and a residual "Fc fragment".

Papain must first be activated by reducing the sulfhydryl group in the active site with cysteine, 2-mercaptoethanol or dithiothreitol. Heavy metals in the stock enzyme should be removed by chelation with EDTA (2 mM) to ensure maximum enzyme activity. Enzyme and substrate are normally mixed together in the ratio of 1:100 by weight. After incubation, the reaction can be stopped by irreversible alkylation of the thiol group with iodoacetamide or simply by dialysis. The completeness of the digestion should be monitored by SDS-PAGE and the various fractions separated by protein A-Sepharose or ion exchange chromatography.

The usual procedure for preparation of F(ab')$_2$ fragments from IgG of rabbit and human origin is limited proteolysis by the enzyme pepsin. The conditions, 100×antibody excess w/w in acetate buffer at pH 4.5, 37° C., suggest that antibody is cleaved at the C-terminal side of the inter-heavy-chain disulfide bond. Rates of digestion of mouse IgG may vary with subclass and conditions should be chosen to avoid significant amounts of completely degraded IgG. In particular, IgG$_{2b}$ is susceptible to complete degradation. The other subclasses require different incubation conditions to produce optimal results, all of which is known in the art.

Pepsin treatment of intact antibodies yields an F(ab')$_2$ fragment that has two antigen-combining sites and is still capable of cross-linking antigen. Digestion of rat IgG by pepsin requires conditions including dialysis in 0.1 M acetate buffer, pH 4.5, and then incubation for four hours with 1% w/w pepsin; IgG$_1$ $_{and\ IgG2a}$ digestion is improved if first dialyzed against 0.1 M formate buffer, pH 2.8, at 4° C., for 16 hours followed by acetate buffer. IgG$_{2b}$ gives more consistent results with incubation in staphylococcal V8 protease (3% w/w) in 0.1 M sodium phosphate buffer, pH 7.8, for four hours at 37° C.

An Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. F(ab')$_2$ antibody fragments were originally produced as pairs of Fab' fragments that have hinge cysteines between them. Other chemical couplings of antibody fragments are also known.

An "Fv" fragment is the minimum antibody fragment that contains a complete antigen-recognition and binding site. This region consists of a dimer of one heavy chain and one light chain variable domain in tight, con-covalent association. It is in this configuration that the three hypervariable regions of each variable domain interact to define an antigen-binding site on the surface of the $V_H$–$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains that enables the sFv to form the desired structure for antigen binding.

The following patents and patent applications are specifically incorporated herein by reference for the purposes of even further supplementing the present teachings regarding the preparation and use of functional, antigen-binding regions of antibodies, including scFv, Fv, Fab', Fab and F(ab')$_2$ fragments of the anti-VEGF antibodies: U.S. Patent Nos. 5,855,866; 5,965,132; 6,051,230; 6,004,555; and 5,877,289; and U.S. application Ser. No. 08/482,369, Issue Fee Paid Oct. 20, 1998. WO 98/45331 is also incorporated herein by reference for purposes including even further describing and teaching the preparation of variable, hypervariable and complementarity determining (CDR) regions of antibodies.

"Diabodies" are small antibody fragments with two antigen-binding sites, which fragments comprise a heavy chain variable domain ($V_H$) connected to a light chain variable domain ($V_L$) in the same polypeptide chain ($V_H$–$V_L$). By using a linker that is too short to allow pairing between the two domains on the same chain, the domains are forced to pair with the complementary domains of another chain and create two antigen-binding sites. Diabodies are described in EP 404,097 and WO 93/11161, each specifically incorporated herein by reference. "Linear antibodies", which can be bispecific or monospecific, comprise a pair of tandem Fd segments ($V_H$–$C_H$1-$V_H$–$C_H$1) that form a pair of antigen binding regions, as described in Zapata et al. (1995), specifically incorporated herein by reference.

In using a Fab' or antigen binding fragment of an antibody, with the attendant benefits on tissue penetration, one may derive additional advantages from modifying the fragment to increase its half-life. A variety of techniques may be employed, such as manipulation or modification of the antibody molecule itself, and also conjugation to inert carriers. Any conjugation for the sole purpose of increasing half-life, rather than to deliver an agent to a target, should be approached carefully in that Fab' and other fragments are chosen to penetrate tissues. Nonetheless, conjugation to non-protein polymers, such PEG and the like, is contemplated.

Modifications other than conjugation are therefore based upon modifying the structure of the antibody fragment to render it more stable, and/or to reduce the rate of catabolism in the body. One mechanism for such modifications is the use of D-amino acids in place of L-amino acids. Those of ordinary skill in the art will understand that the introduction of such modifications needs to be followed by rigorous testing of the resultant molecule to ensure that it still retains the desired biological properties. Further stabilizing modifications include the use of the addition of stabilizing moieties to either the N-terminal or the C-terminal, or both, which is generally used to prolong the half-life of biological molecules. By way of example only, one may wish to modify the termini by acylation or amination.

Moderate conjugation-type modifications for use with the present invention include incorporating a salvage receptor binding epitope into the antibody fragment. Techniques for achieving this include mutation of the appropriate region of the antibody fragment or incorporating the epitope as a peptide tag that is attached to the antibody fragment. WO 96/32478 is specifically incorporated herein by reference for the purposes of further exemplifying such technology. Salvage receptor binding epitopes are typically regions of three or more amino acids from one or two loops of the Fc domain that are transferred to the analogous position on the antibody fragment. The salvage receptor binding epitopes of WO 98/45331 are incorporated herein by reference for use with the present invention.

B12. Binding and Functional Assays

Although the present invention has significant utility in animal and human treatment regimens, it also has many other practical uses, including many in vitro uses. Certain of these uses are related to the specific binding properties of the antibodies or immunoconjugates. In that all the compounds of the invention include at least one antibody component, they may be used in virtually all of the binding embodiments that the original antibody may be used.

The presence of an attached agent, where relevant, although providing advantageous properties, does not negate the utility of the first antibody regions in any binding assay. Suitably useful binding assays thus include those commonly employed in the art, such as in immunoblots, Western blots, dot blots, RIAs, ELISAs, immunohistochemistry, fluorescent activated cell sorting (FACS), immunoprecipitation, affinity chromatography, and the like, as further described herein.

Certain standard binding assays are those in which an antigen is immobilized onto a solid support matrix, e.g., nitrocellulose, nylon or a combination thereof, such as in immunoblots, Western blots and related assays. Other important assays are ELISAs. All such assays may be readily adapted for use in the detection of VEGF, as may be applied in the diagnosis of an angiogenic disease. The agents of the invention may also be used in conjunction with both fresh-frozen and formalin-fixed, paraffin-embedded tissue blocks in immunohistochemistry; in fluorescent activated cell sorting, flow cytometry or flow microfluorometry; in immunoprecipitation; in antigen purification embodiments, such as affinity chromatography, even including, in cases of bispecific antibodies, the one-step rapid purification of one or more antigens at the same time; and in many other binding assays that will be known to those of skill in the art given the information presented herein.

Further practical uses of the present antibodies are as controls in functional assays. These include many in vitro and ex vivo assays and systems, as well as animal model studies. As the binding and functional properties of the antibodies of the invention are particularly specific, i.e., they inhibit VEGF binding to and signaling via VEGFR2, but not VEGFR1, such "control" uses are actually extremely valuable. The assays that benefit from such a practical application of the present invention include, for example, assays concerning VEGF-mediated endothelial cell growth, VEGF-induced phosphorylation and VEGF-induced vascular permeability, as well as the corneal micropocket assay of neovascularization and the chick chorio-allantoic membrane assay (CAM) assay. These assays systems can also be developed into in vitro or ex vivo drug screening assays, wherein the present provision of biological materials with well defined properties is particularly important.

C. Immunoconjugates

Although the present invention provides surprisingly effective naked or unconjugated antibodies for use in anti-angiogenic methods, VEGFR2-blocking, anti-VEGF antibody or 2C3-based immunoconjugates, immunotoxins and coaguligands are also provided hereby. Currently preferred agents for use in VEGFR2-blocking, anti-VEGF antibody or 2C3-based therapeutic conjugates are radiotherapeutic agents (as exemplified by the radiodiagnostics disclosed herein), anti-angiogenic agents, apoptosis-inducing agents, anti-tubulin drugs, anti-cellular or cytotoxic agents and coagulants (coagulation factors).

To generate immunoconjugates, immunotoxins and coaguligands, recombinant expression may be employed to create a fusion protein, as is known to those of skill in the art and further disclosed herein. Equally, immunoconjugates, immunotoxins and coaguligands may be generated using avidin:biotin bridges or any of the chemical conjugation and cross-linker technologies developed in reference to antibody conjugates.

C1. Toxic and Anti-Cellular Agents

For certain applications, the therapeutic agents will be cytotoxic or pharmacological agents, particularly cytotoxic, cytostatic or otherwise anti-cellular agents having the ability to kill or suppress the growth or cell division of endothelial cells. In general, these aspects of the invention contemplate the use of any pharmacological agent that can be conjugated to a VEGFR2-blocking, anti-VEGF antibody or 2C3-like antibody, and delivered in active form to the targeted endothelium.

Exemplary anti-cellular agents include chemotherapeutic agents, as well as cytotoxins. Chemotherapeutic agents that may be used include: hormones, such as steroids; antimetabolites, such as cytosine arabinoside, fluorouracil, methotrexate or aminopterin; anthracyclines; mitomycin C; vinca alkaloids; demecolcine; etoposide; mithramycin; anti-tumor alkylating agents, such as chlorambucil or melphalan. Other embodiments may include agents such as cytokines. Basically, any anti-cellular agent may be used, so long as it can be successfully conjugated to, or associated with, an antibody in a manner that will allow its targeting, internalization, release and/or presentation to blood components at the site of the targeted endothelial cells.

There may be circumstances, such as when the target antigen does not internalize by a route consistent with efficient intoxication by the toxic compound, where one will desire to target chemotherapeutic agents, such as anti-tumor drugs, cytokines, antimetabolites, alkylating agents, hormones, and the like. A variety of chemotherapeutic and other pharmacological agents have now been successfully conjugated to antibodies and shown to function pharmacologically, including doxorubicin, daunomycin, methotrexate, vinblastine, neocarzinostatin, macromycin, trenimon and α-amanitin.

In other circumstances, any potential side-effects from cytotoxin-based therapy may be eliminated by the use of DNA synthesis inhibitors, such as daunorubicin, doxorubicin, adriamycin, and the like. These agents are therefore preferred examples of anti-cellular agents for use in the present invention.

In terms of cytostatic agents, such compounds generally disturb the natural cell cycle of a target cell, preferably so that the cell is taken out of the cell cycle.

A wide variety of cytotoxic agents are known that may be conjugated to VEGFR2-blocking, anti-VEGF antibody or 2C3-based antibodies. Examples include numerous useful plant-, fungus- or bacteria-derived toxins, which, by way of example, include various A chain toxins, particularly ricin A chain; ribosome inactivating proteins, such as saporin or gelonin; α-sarcin; aspergillin; restrictocin; ribonucleases, such as placental ribonuclease; diphtheria toxin; and *pseudomonas* exotoxin, to name just a few.

Of the toxins, ricin A chains are preferred. The most preferred toxin moiety for use herewith is toxin A chain that has been treated to modify or remove carbohydrate residues, so-called deglycosylated A chain (dgA). Deglycosylated ricin A chain is preferred because of its extreme potency, longer half-life, and because it is economically feasible to manufacture it in a clinical grade and scale.

It may be desirable from a pharmacological standpoint to employ the smallest molecule possible that nevertheless provides an appropriate biological response. One may thus desire to employ smaller A chain peptides that will provide an adequate anti-cellular response. To this end, it has been discovered that ricin A chain may be "truncated" by the removal of 30 N-terminal amino acids by Nagarase (Sigma), and still retain an adequate toxin activity. It is proposed that where desired, this truncated A chain may be employed in conjugates in accordance with the invention.

Alternatively, one may find that the application of recombinant DNA technology to the toxin A chain moiety will provide additional benefits in accordance the invention. In that the cloning and expression of biologically active ricin A chain has been achieved, it is now possible to identify and prepare smaller, or otherwise variant peptides, which nevertheless exhibit an appropriate toxin activity. Moreover, the fact that ricin A chain has now been cloned allows the application of site-directed mutagenesis, through which one can readily prepare and screen for A chain-derived peptides and obtain additional useful moieties for use in connection with the present invention.

C2. Coagulation Factors

The VEGFR2-blocking, anti-VEGF antibody or 2C3-based antibodies of the invention may be linked to a component that is capable of directly or indirectly stimulating coagulation, to form a coaguligand. Here, the antibodies may be directly linked to the coagulant or coagulation factor, or may be linked to a second binding region that binds and then releases the coagulant or coagulation factor. As used herein, the terms "coagulant" and "coagulation factor" are each used to refer to a component that is capable of directly or indirectly stimulating coagulation under appropriate conditions, preferably when provided to a specific in vivo environment, such as the tumor vasculature.

Preferred coagulation factors are Tissue Factor compositions, such as truncated TF (tTF), dimeric, multimeric and mutant TF molecules. "Truncated TF" (tTF) refers to TF constructs that are rendered membrane-binding deficient by removal of sufficient amino acid sequences to effect this change in property. A "sufficient amount" in this context is an amount of transmembrane amino acid sequence originally sufficient to enter the TF molecule in the membrane, or otherwise mediate functional membrane binding of the TF protein. The removal of such a "sufficient amount of transmembrane spanning sequence" therefore creates a truncated Tissue Factor protein or polypeptide deficient in phospholipid membrane binding capacity, such that the protein is substantially a soluble protein that does not significantly bind to phospholipid membranes. Truncated TF thus substantially fails to convert Factor VII to Factor VIIa in a standard TF assay, and yet retains so-called catalytic activity including activating Factor X in the presence of Factor VIIa.

U.S. Pat. No. 5,504,067 is specifically incorporated herein by reference for the purposes of further describing such truncated Tissue Factor proteins. Preferably, the Tissue Factors for use in these aspects of the present invention will generally lack the transmembrane and cytosolic regions (amino acids 220–263) of the protein. However, there is no need for the truncated TF molecules to be limited to molecules of the exact length of 219 amino acids.

Tissue Factor compositions may also be useful as dimers. Any of the truncated, mutated or other Tissue Factor constructs may be prepared in a dimeric form for use in the present invention. As will be known to those of ordinary skill in the art, such TF dimers may be prepared by employing the standard techniques of molecular biology and recombinant expression, in which two coding regions are prepared in-frame and expressed from an expression vector. Equally, various chemical conjugation technologies may be employed in connection with the preparation of TF dimers. The individual TF monomers may be derivatized prior to conjugation. All such techniques would be readily known to those of skill in the art.

If desired, the Tissue Factor dimers or multimers may be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metalloproteinase, such as collagenase, gelatinase or stromelysin.

In certain embodiments, the Tissue Factor dimers may further comprise a hindered hydrophobic membrane insertion moiety, to later encourage the functional association of the Tissue Factor with the phospholipid membrane, but only under certain defined conditions. As described in the context of the truncated Tissue Factors, hydrophobic membrane-association sequences are generally stretches of amino acids that promote association with the phospholipid environment due to their hydrophobic nature. Equally, fatty acids may be used to provide the potential membrane insertion moiety.

Such membrane insertion sequences may be located either at the N-terminus or the C-terminus of the TF molecule, or generally appended at any other point of the molecule so long as their attachment thereto does not hinder the functional properties of the TF construct. The intent of the hindered insertion moiety is that it remains non-functional until the TF construct localizes within the tumor environment, and allows the hydrophobic appendage to become accessible and even further promote physical association with the membrane. Again, it is contemplated that biologically-releasable bonds and selectively-cleavable sequences will be particularly useful in this regard, with the bond or sequence only being cleaved or otherwise modified upon localization within the tumor environment and exposure to particular enzymes or other bioactive molecules.

In other embodiments, the tTF constructs may be multimeric or polymeric. In this context a "polymeric construct" contains 3 or more Tissue Factor constructs. A "multimeric or polymeric TF construct" is a construct that comprises a first TF molecule or derivative operatively attached to at least a second and a third TF molecule or derivative. The multimers may comprise between about 3 and about 20 such TF molecules. The individual TF units within the multimers or polymers may also be linked by selectively-cleavable peptide linkers or other biological-releasable bonds as desired. Again, as with the TF dimers discussed above, the constructs may be readily made using either recombinant manipulation and expression or using standard synthetic chemistry.

Even further TF constructs useful in context of the present invention are those mutants deficient in the ability to activate Factor VII. Such "Factor VII activation mutants" are generally defined herein as TF mutants that bind functional Factor VII/VIIa, proteolytically activate Factor X, but are substantially free from the ability to proteolytically activate Factor VII. Accordingly, such constructs are TF mutants that lack Factor VII activation activity.

The ability of such Factor VII activation mutants to function in promoting tumor-specific coagulation is based upon their specific delivery to the tumor vasculature, and the presence of Factor VIIa at low levels in plasma. Upon administration of such a Factor VII activation mutant conjugate, the mutant will be localized within the vasculature of a vascularized tumor. Prior to localization, the TF mutant would be generally unable to promote coagulation in any other body sites, on the basis of its inability to convert Factor VII to Factor VIIa. However, upon localization and accumulation within the tumor region, the mutant will then encounter sufficient Factor VIa from the plasma in order to initiate the extrinsic coagulation pathway, leading to tumor-specific thrombosis. Exogenous Factor VIIa could also be administered to the patient.

Any one or more of a variety of Factor VII activation mutants may be prepared and used in connection with the present invention. There is a significant amount of scientific knowledge concerning the recognition sites on the TF molecule for Factor VII/VIIa. It will thus be understood that the Factor VII activation region generally lies between about amino acid 157 and about amino acid 167 of the TF molecule. However, it is contemplated that residues outside this region may also prove to be relevant to the Factor VII activating activity, and one may therefore consider introducing mutations into any one or more of the residues generally located between about amino acid 106 and about amino acid 209 of the TF sequence (WO 94/07515; WO 94/28017; each incorporated herein by reference).

A variety of other coagulation factors may be used in connection with the present invention, as exemplified by the agents set forth below. Thrombin, Factor V/Va and derivatives, Factor VIII/VIIIa and derivatives, Factor IX/IXa and derivatives, Factor X/Xa and derivatives, Factor XI/XIa and derivatives, Factor XII/XIIa and derivatives, Factor XIII/XIIIa and derivatives, Factor X activator and Factor V activator may be used in the present invention.

Russell's viper venom Factor X activator is contemplated for use in this invention. Monoclonal antibodies specific for the Factor X activator present in Russell's viper venom have also been produced, and could be used to specifically deliver the agent as part of a bispecific binding ligand.

Thromboxane $A_2$ is formed from endoperoxides by the sequential actions of the enzymes cyclooxygenase and thromboxane synthetase in platelet microsomes. Thromboxane $A_2$ is readily generated by platelets and is a potent vasoconstrictor, by virtue of its capacity to produce platelet aggregation. Both thromboxane $A_2$ and active analogues thereof are contemplated for use in the present invention.

Thromboxane synthase, and other enzymes that synthesize platelet-activating prostaglandins, may also be used as "coagulants" in the present context. Monoclonal antibodies to, and immunoaffinity purification of, thromboxane synthase are known; as is the cDNA for human thromboxane synthase.

$\alpha2$-antiplasmin, or $\alpha2$-plasmin inhibitor, is a proteinase inhibitor naturally present in human plasma that functions to efficiently inhibit the lysis of fibrin clots induced by plasminogen activator. $\alpha2$-antiplasmin is a particularly potent inhibitor, and is contemplated for use in the present invention.

As the cDNA sequence for $\alpha2$-antiplasmin is available, recombinant expression and/or fusion proteins are preferred. Monoclonal antibodies against $\alpha2$-antiplasmin are also available that may be used in the bispecific binding ligand embodiments of the invention. These antibodies could both be used to deliver exogenous $\alpha2$-antiplasmin to the target site or to garner endogenous $\alpha2$-antiplasmin and concentrate it within the targeted region.

C3. Anti-Tubulin Drugs

A range of drugs exert their effects via interfering with tubulin activity. As tubulin functions are essential to mitosis and cell viability, certain "anti-tubulin drugs" are powerful chemotherapeutic agents. Some of the more well known and currently preferred anti-tubulin drugs for use with the present invention are colchicine; taxanes, such as taxol; vinca alkaloids, such as vinblastine, vincristine and vindescine; and combretastatins. Other suitable anti-tubulin drugs are cytochalasins (including B, J, E), dolastatin, auristatin PE, paclitaxel, ustiloxin D, rhizoxin, 1069C85, colcemid, albendazole, azatoxin and nocodazole.

As described in U.S. Pat. Nos. 5,892,069, 5,504,074 and 5,661,143, each specifically incorporated herein by reference, combretastatins are estradiol derivatives that generally inhibit cell mitosis. Exemplary combretastatins that may be used in conjunction with the invention include those based upon combretastatin A, B and/or D and those described in U.S. Pat. Nos. 5,892,069, 5,504,074 and 5,661,143. Combretastatins A-1, A-2, A-3, A-4, A-5, A-6, B-1, B-2, B-3 and B-4 are exemplary of the foregoing types.

U.S. Pat. Nos. 5,569,786 and 5,409,953, are incorporated herein by reference for purposes of describing the isolation, structural characterization and synthesis of each of combretastatin A-1, A2, A-3, B-1, B-2, B-3 and B-4 and formulations and methods of using such combretastatins to treat neoplastic growth. Any one or more of such combretastatins may be used in conjunction with the present invention.

Combretastatin A-4, as described in U.S. Pat. Nos. 5,892,069, 5,504,074, 5,661,143 and 4,996,237, each specifically incorporated herein by reference, may also be used herewith. U.S. Pat. No. 5,561,122 is further incorporated herein by reference for describing suitable combretastatin A-4 pro-drugs, which are contemplated for combined use with the present invention.

U.S. Pat. No. 4,940,726, specifically incorporated herein by reference, particularly describes macrocyclic lactones denominated combretastatin D-1 and 'Combretastatin D-2', each of which may be used in combination with the compositions and methods of the present invention. U.S. Pat. No. 5,430,062, specifically incorporated herein by reference, concerns stilbene derivatives and combretastatin analogues with anti-cancer activity that may be used in combination with the present invention.

C4. Anti-Angiogenic Agents

The present invention particularly provides combined anti-angiogenics. The angiopoietins, in common with the members of the VEGF family, are growth factors specific for vascular endothelium (Davis and Yancopoulos, 1999; Holash et al., 1999; incorporated herein by reference). The angiopoietins first described were a naturally occurring receptor activator or agonist, angiopoietin-1 (Ang-1), and a naturally occurring receptor antagonist, angiopoietin-2 (Ang-2), both of which act by means of the endothelial cell tyrosine kinase receptor, Tie2.

Two new angiopoietins, angiopoietin-3 (mouse) and angiopoietin-4 (human) have also been identified (Valenzuela et al., 1999). Angiopoietin-3 appears to act as an antagonist (like Ang-2), whereas angiopoietin-4 appears to function as an agonist (like Ang-1) (Valenzuela et al., 1999). A protein termed angiopoietin-3 was also cloned from human heart and reported not to have mitogenic effects on endothelial cells (Kim et al., 1999).

Whereas VEGF is necessary for the early stages of vascular development, angiopoietin-1 is generally required for the later stages of vascularization. VEGF thus acts to promote endothelial cell differentiation, proliferation and primitive vessel formation. Angiopoietin-1 acts, via the Tie2 receptor, to promote maintenance and stabilization of mature vessels. Angiopoietin-1 is thus a maturation or stabilization factor, thought to convert immature vessels to immature vessels by promoting interactions between endothelial cells and surrounding support cells (Holash et al., 1999).

Angiopoietin-1 has been shown to augment revascularization in ischemic tissue (Shyu et al., 1998) and to increase the survival of vascular networks exposed to either VEGF or a form of aFGF (Papapetropoulos et al., 1999). These authors also showed that angiopoietin-1 prevents apoptotic death in HUVEC triggered by withdrawal of the same form of aFGF (Papapetropoulos et al., 1999). Such data are consistent with the direct role of angiopoietin-1 on human endothelial cells and its interaction with other angiogenic molecules to stabilize vascular structures by promoting the survival of differentiated endothelial cells.

As angiopoietin-1 imparts a maturity and stability signal, the inventors have carefully conceived those aspects of the present invention that relate to targeted angiopoietin-1 delivery. The inventors reasoned that as angiopoietin-1 is a maturity factor, it will render tumor blood vessels growth-factor independent. One aspect of this invention therefore concerns the use of tumor-targeted angiopoietin-1 in order to cement the VEGF-non-responsive properties of the target vessels.

It is reasoned that using a tumor-binding ligand to deliver angiopoietin-1 to tumor blood vessels would readily deliver on the order of 500,000 angiopoietin-1 molecules to a vessel lumen. This would overwhelm the Tie2 receptor system, totally saturating the Tie2 receptors with the angiopoietin-1 ligand. Angiopoietin-2 would thus be unable to bind, and so the combined effects of angiopoietin-2 and VEGF (see discussion below) would be inhibited.

The delivery of angiopoietin-1 to the tumor, preferably to the tumor vasculature, can also be used in conjunction with a variety of other anti-cancer strategies, as disclosed in detail herein, to achieve a combined therapeutic effect. The typical response of a tumor to therapies that induce at least some necrosis is to initiate vascular regeneration. As the angiopoietin-1 signal forces the blood vessels into maturity, they would be unable to remodel and could not compensate for the loss of tumor mass induced by the primary therapeutic agent. These observations therefore provide another preferred aspect of the angiopoietin delivery invention, namely the combined use of angiopoietin-1 targeting in combination with any one or more anti-cancer agents, including conventional chemotherapeutic drugs.

The action of the angiopoietin-1 upon delivery is fundamentally to prevent vascular remodeling. Whether this is used alone, or in combination therapies, the value of angiopoietin-1 targeting is particularly enhanced by the safety inherent in this therapeutic approach. There is no significant downside to angiopoietin-1 therapy. Even in the unlikely event that an amount of the targeted Ang-1 was misdirected to non-tumor tissues, all that would result would be that the vasculature in the targeted area would become more stable and/or quiescent. In this regard, Ang-1 could also be used as an anti-inflammatory agent.

Angiopoietin-2 is currently a preferred agent for use in tumor-targeted therapy, particularly in combination with the VEGF inhibition of the present invention. However, due to the differential effects of angiopoietin-2 under different conditions, particularly with varying VEGF levels, the inventors have again carefully conceived those aspects of the invention that relate to targeted angiopoietin-2 delivery.

Angiopoietin-2 is also a ligand for the Tie2 receptor, but generally counteracts blood vessel maturation/stability mediated by angiopoietin-1. It is thus an antagonist of angiopoietin-1 and acts to disturb capillary structure. Under appropriate conditions, angiopoietin-2 imparts a negative signal to the target cells and destabilization induced by angiopoietin-2 leads to vessel regression. This is the first feature of angiopoietin-2 sought to be exploited in the targeted delivery of angiopoietin-2 to tumors, preferably to tumor vasculature.

It is contemplated that simply delivering sufficient angiopoietin-2, which is readily achievable using VEGFR2-blocking, anti-VEGF antibodies, such as 2C3, would overwhelm any other signals that could be present in the tumor environment and would promote vessel regression. As there is a carefully controlled interplay between angiopoietins in the natural environment, an extreme biasing of the system in favor of regression, by perpetual angiopoietin-2 signaling, may well obliterate the effects of both angiopoietin-1 and VEGF.

The use of tumor-targeted angiopoietin-2 alone may therefore be used to advantage to induce tumor vessel regression, particularly as an early mechanism of therapeutic intervention. Generally, though, destabilization induced by angiopoietin-2 can lead to either vessel regression or regeneration. It is destabilization in the absence of other angiogenic stimuli, particularly VEGF, which leads to vessel regression; whereas destabilization in the presence of high levels of VEGF facilitates the angiogenic response (Holash et al., 1999).

Vessels that undergo destabilization in response to angiopoietin-2 can be "rescued" from regression by exposure to other stimuli. Angiopoietin-2 can therefore render endothelial cells responsive to other angiogenic stimuli and facilitate an angiogenic response under defined conditions. VEGF, in particular, can prompt ang-2-destabilized cells to proliferate and form primitive new vessels (Asahara et al., 1998; Holash et al., 1999). Indeed, angiopoietin-2 expression in tumor tissue has been reported (Tanaka et al., 1999), where it was presumed to act in combination with VEGF to promote angiogenesis (Stratmann et al., 1998). The neovascularization initiated by angiopoietin-2 and VEGF makes these molecules "co-angiogenic".

A coordinated model to explain the positive and negative effects of angiopoietin-2 on blood vessels in certain tumor types has now been reported (Holash et al., 1999). In this model, angiopoietin-2-induced destabilization initially causes significant vessel regression in tumors that originate by coopting blood vessels from surrounding host vasculature. The high levels of angiopoietin-2 produced by tumor-associated endothelial cells counter the survival signal apparently provided by low-level, constitutive expression of angiopoietin-1. Angiopoietin-2 thus marks coopted vessels for apoptopic regression (Holash et al., 1999). However, despite the resultant tumor necrosis, surviving tumor cells up-regulate VEGF to ensure their survival. The coincident expression of VEGF and angiopoietin-2 then results in robust angiogenesis at the tumor periphery, as VEGF nullifies the regressive signal from angiopoietin-2 and in fact promotes vascular development (Holash et al., 1999).

Although seemingly contradictory on first glance, the actions of angiopoietin-2 can be explained and largely predicted on the basis of other signals present, particularly VEGF. In the absence of another angiogenic signal, angiopoietin-2 causes vessels to destabilize and become immature, leading to regression. In the presence of a stimulus, particularly VEGF, the destabilization caused by angiopoietin-2 actually leads to angiogenesis as the vessels are "primed" to receive secondary angiogenic stimuli. The angiogenic effects of a number of regulators are thus believed to be achieved, at least in part, through the regulation of an autocrine loop of angiopoietin-2 activity in microvascular endothelial cells (Mandriota and Pepper, 1998).

The dual biological roles of angiopoietin-2 prompted the inventors to develop additional therapeutic strategies that account for other signals in the tumor environment, particularly VEGF. As angiopoietin-2 and VEGF act in concert to stimulate angiogenesis, a preferred aspect of the present invention is to use tumor-targeted angiopoietin-2 delivery in combination with the present VEGF inhibitory antibodies. This will ensure that angiopoietin-2 acts in regression and not in angiogenesis.

In light of the foregoing explanations, it will be understood that the present invention provides VEGFR2-blocking, anti-VEGF antibodies, such as 2C3, that are operatively attached to, or otherwise functionally associated, with any one or more of angiopoietin-1, angiopoietin-2, angiopoietin-3 and/or angiopoietin-4. Exemplary angiopoietin-1 compositions are those of SEQ ID NO:1 (DNA) and SEQ ID NO:2 (protein), whereas angiopoietin-2 compositions are exemplified by SEQ ID NO:3 (DNA) and SEQ ID NO:4 (protein). Angiopoietin-3, being an antagonist, will generally be used as angiopoietin-2; and the agonist angiopoietin-4 may be used in the manner of angiopoietin-1. The article by Valenzuela et al. (1999) is specifically incorporated herein by reference for purposes of further supplementing the present teaching regarding angiopoietin-3 and angiopoietin-4.

In addition, fusion proteins of angiopoietins are also envisioned for use in this invention. One example is the stable Ang-1-Ang-2 fusion protein included herein as SEQ ID NO:5. This protein contains the first 73 residues of angiopoietin-2, up to the DAPLEY sequence, fused to the angiopoietin-1 sequence beginning at amino acid 77. It also has a mutation at position 265 in the angiopoietin-1 sequence, where Cys is replaced by Ser.

Other anti-angiogenics for use herewith include angiostatin and endostatin. Angiostatin is disclosed in U.S. Pat. Nos. 5,776,704; 5,639,725 and 5,733,876, each incorporated herein by reference. Angiostatin is a protein having a molecular weight of between about 38 kD and about 45 kD, as determined by reducing polyacrylamide gel electrophoresis, which contains approximately Kringle regions 1 through 4 of a plasminogen molecule. Angiostatin generally has an amino acid sequence substantially similar to that of a fragment of murine plasminogen beginning at amino acid number 98 of an intact murine plasminogen molecule.

The amino acid sequence of angiostatin varies slightly between species. For example, in human angiostatin, the amino acid sequence is substantially similar to the sequence of the above described murine plasminogen fragment, although an active human angiostatin sequence may start at either amino acid number 97 or 99 of an intact human plasminogen amino acid sequence. Further, human plasminogen may be used, as it has similar anti-angiogenic activity, as shown in a mouse tumor model.

Angiostatin and endostatin have become the focus of intense study, as they are the first angiogenesis inhibitors that have demonstrated the ability to not only inhibit tumor growth but also cause tumor regressions in mice. There are multiple proteases that have been shown to produce angiostatin from plasminogen including elastase, macrophage metalloelastase (MME), matrilysin (MMP-7), and 92 kDa gelatinase B/type IV collagenase (MMP-9).

MME can produce angiostatin from plasminogen in tumors and granulocyte-macrophage colony-stimulating factor (GMCSF) upregulates the expression of MME by macrophages inducing the production of angiostatin. The role of MME in angiostatin generation is supported by the finding that MME is in fact expressed in clinical samples of hepatocellular carcinomas from patients. Another protease thought to be capable of producing angiostatin is stromelysin-1 (MMP-3). MMP-3 has been shown to produce angiostatin-like fragments from plasminogen in vitro. The mechanism of action for angiostatin is currently unclear, it is hypothesized that it binds to an unidentified cell surface receptor on endothelial cells inducing endothelial cell to undergo programmed cell death or mitotic arrest.

Endostatin appears to be an even more powerful anti-angiogenesis and anti-tumor agent and is particularly preferred for linking to VEGFR2-blocking, anti-VEGF antibodies, such as 2C3. Endostatin is effective at causing regressions in a number of tumor models in mice. Tumors do not develop resistance to endostatin and, after multiple cycles of treatment, tumors enter a dormant state during which they do not increase in volume. In this dormant state, the percentage of tumor cells undergoing apoptosis was increased, yielding a population that essentially stays the same size.

U.S. Pat. No. 5,854,205, to Folkinan and O'Reilly, specifically incorporated herein by reference, concerns endostatin and its use as an inhibitor of endothelial cell proliferation and angiogenesis. The endostatin protein corresponds to a C-terminal fragment of collagen type XVIII, and the protein can be isolated from a variety of sources. U.S. Pat. No. 5,854,205 also teaches that endostatin can have an amino acid sequence of a fragment of collagen type XVIII, a collasen type XV, or BOVMPE 1 pregastric esterase. Combinations of endostatin with other anti-angiogenic proteins, particularly angiostatin, are also described by U.S. Pat. No. 5,854,205, such that the combined compositions are capable of effectively regressing the mass of an angiogenesis-dependent tumor.

Endostatin and angiostatin are preferred agents for tumor delivery according to the present invention. Vasculostatin, canstatin and maspin are also preferred agents. Endostatin, in particular, is one of the most preferred agents. Endostatin-2C3 fusion proteins may be prepared, as described herein. Various forms of chemically linked endostatin-2C3 constructs are also described in the present application.

C5. Apoptosis-Inducing Agents

The present invention may also be used to deliver agents that induce apoptosis in any cells within the tumor, including tumor cells and tumor vascular endothelial cells. Although many anti-cancer agents may have, as part of their mechanism of action, an apoptosis-inducing effect, certain agents have been discovered, designed or selected with this as a primary mechanism, as described below.

Many forms of cancer have reports of mutations in tumor suppressor genes, such as p53. Inactivation of p53 results in a failure to promote apoptosis. With this failure, cancer cells progress in tumorigenesis, rather than become destined for cell death. Thus, delivery of tumor suppressors is also contemplated for use in the present invention to stimulate cell death. Exemplary tumor suppressors include, but are not limited to, p53, Retinoblastoma gene (Rb), Wilm's tumor (WTI), bax alpha, interleukin-1b-converting enzyme and family, MEN-1 gene, neurofibromatosis, type 1 (NF1), cdk inhibitor p16, colorectal cancer gene (DCC), familial adenomatosis polyposis gene (FAP), multiple tumor suppressor gene (MTS-1), BRCA1 and BRCA2.

Preferred for use are the p53 (U.S. Pat. Nos. 5,747,469; 5,677,178; and 5,756,455; each incorporated herein by reference), Retinoblastoma, BRCA1 (U.S. Pat. Nos. 5,750,400; 5,654,155; 5,710,001; 5,756,294; 5,709,999; 5,693,473; 5,753,441; 5,622,829; and 5,747,282; each incorporated herein by reference), MEN-1 (GenBank accession number U93236) and adenovirus E1A (U.S. Pat. No. 5,776,743; incorporated herein by reference) genes.

Other compositions that may be delivered by VEGFR2-blocking, anti-VEGF antibodies, such as 2C3, include genes encoding the tumor necrosis factor related apoptosis inducing ligand termed TRAIL, and the TRAIL polypeptide (U.S. Pat. No. 5,763,223; incorporated herein by reference); the 24 kD apoptosis-associated protease of U.S. Pat. No. 5,605,826 (incorporated herein by reference); Fas-associated factor 1, FAF1 (U.S. Pat. No. 5,750,653; incorporated herein by reference). Also contemplated for use in these aspects of the present invention is the provision of interleukin-1β-converting enzyme and family members, which are also reported to stimulate apoptosis.

Compounds such as carbostyril derivatives (U.S. Pat. Nos. 5,672,603; and 5,464,833; each incorporated herein by reference); branched apogenic peptides (U.S. Pat. No. 5,591,717; incorporated herein by reference); phosphotyrosine inhibitors and non-hydrolyzable phosphotyrosine analogs (U.S. Pat. Nos. 5,565,491; and 5,693,627; each incorporated herein by reference); agonists of RXR retinoid receptors (U.S. Pat. No. 5,399,586; incorporated herein by reference); and even antioxidants (U.S. Pat. No. 5,571,523; incorporated herein by reference) may also be used. Tyrosine kinase inhibitors, such as genistein, may also be linked to the agents of the present invention that target the cell surface receptor, VEGFR1 (as supported by U.S. Pat. No. 5,587,459; incorporated herein by reference).

C6. Biologically Functional Equivalents

Equivalents, or even improvements, of 2C3-based antibodies or any other VEGFR2-blocking, anti-VEGF antibody, can now be made, generally using the materials provided above as a starting point. Modifications and changes may be made in the structure of such an antibody and still obtain a molecule having like or otherwise desirable characteristics. For example, certain amino acids may substituted for other amino acids in a protein structure without appreciable loss of interactive binding capacity. These considerations also apply to toxins, anti-angiogenic agents, apoptosis-inducing agents, coagulants and the like.

Since it is the interactive capacity and nature of a protein that defines that protein's biological functional activity, certain amino acid sequence substitutions can be made in a protein sequence (or of course, the underlying DNA sequence) and nevertheless obtain a protein with like (agonistic) properties. It is thus contemplated that various changes may be made in the sequence of the antibodies or therapeutic agents (or underlying DNA sequences) without appreciable loss of their biological utility or activity. Biological functional equivalents made from mutating an underlying DNA sequence can be made using the codon information provided herein in Table A, and the supporting technical details on site-specific mutagenesis.

It also is well understood by the skilled artisan that, inherent in the definition of a "biologically functional equivalent" protein or peptide, is the concept that there is a limit to the number of changes that may be made within a defined portion of the molecule and still result in a molecule with an acceptable level of equivalent biological activity. Biologically functional equivalent proteins and peptides are thus defined herein as those proteins and peptides in which certain, not most or all, of the amino acids may be substituted. Of course, a plurality of distinct proteins/peptides with different substitutions may easily be made and used in accordance with the invention.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is thus understood that an amino acid can be substituted for another having a similar hydrophilicity value and still obtain a biologically equivalent protein. As detailed in U.S. Pat. No. 4,554,101 (incorporated herein by reference), the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (O); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon hydrophilicity values, the substitution of amino acids whose hydrophilicity values are within ±2 is preferred, those which are within ±1 are particularly preferred, and those within ±0.5 are even more particularly preferred.

C7. Fusion Proteins and Recombinant Expression

The VEGFR2-blocking, anti-VEGF antibody or 2C3-based immunoconjugates of the present invention may be readily prepared as fusion proteins using molecular biological techniques. Any fusion protein may be designed and made using any of the therapeutic agents disclosed herein and those known in the art. The fusion protein technology is readily adapted to prepare fusion proteins in which the two portions are joined by a selectively cleavable peptide sequence. Currently preferred fusion proteins are those containing endostatin. The endostatin, as with any other therapeutic, may be attached to the terminus of the antibody or to any point distinct from the CDRs. Therapeutics such as endostatin may also be prepared "integrally", wherein they are preferably associated with a selectively cleavable peptide to allow release of the agent after targeting.

The use of recombinant DNA techniques to achieve such ends is now standard practice to those of skill in the art. These methods include, for example, in vitro recombinant DNA techniques, synthetic techniques and in vivo recombination/genetic recombination. DNA and RNA synthesis may, additionally, be performed using an automated synthesizers (see, for example, the techniques described in Sambrook et al., 1989; incorporated herein by reference).

The preparation of such a fusion protein generally entails the preparation of a first and second DNA coding region and the functional ligation or joining of such regions, in frame, to prepare a single coding region that encodes the desired fusion protein. In the present context, the VEGFR2-blocking, anti-VEGF antibody or 2C3-like antibody DNA sequence will be joined in frame with a DNA sequence encoding a therapeutic agent. It is not generally believed to be particularly relevant which portion of the construct is prepared as the N-terminal region or as the C-terminal region.

Once the desired coding region has been produced, an expression vector is created. Expression vectors contain one or more promoters upstream of the inserted DNA regions that act to promote transcription of the DNA and to thus promote expression of the encoded recombinant protein. This is the meaning of "recombinant expression".

To obtain a so-called "recombinant" version of the VEGFR2-blocking, anti-VEGF antibody or 2C3-based immunoconjugate, it is expressed in a recombinant cell. The engineering of DNA segment(s) for expression in a prokaryotic or eukaryotic system may be performed by techniques generally known to those of skill in recombinant expression. It is believed that virtually any expression system may be employed in the expression of a VEGFR2-blocking, anti-VEGF antibody or 2C3-based immunoconjugate constructs.

Such proteins may be successfully expressed in eukaryotic expression systems, e.g., CHO cells, however, it is envisioned that bacterial expression systems, such as E. coli pQE-60 will be particularly useful for the large-scale preparation and subsequent purification of the VEGFR2-blocking, anti-VEGF antibody or 2C3-based immunoconjugates. cDNAs may also be expressed in bacterial systems, with the encoded proteins being expressed as fusions with β-galactosidase, ubiquitin, Schistosoma japonicum glutathione S-transferase, and the like. It is believed that bacterial expression will have advantages over eukaryotic expression in terms of ease of use and quantity of materials obtained thereby.

In terms of microbial expression, U.S. Pat. Nos. 5,583,013; 5,221,619; 4,785,420; 4,704,362; and 4,366,246 are incorporated herein by reference for the purposes of even further supplementing the present disclosure in connection with the expression of genes in recombinant host cells.

Recombinantly produced VEGFR2-blocking, anti-VEGF antibody or 2C3-based immunoconjugates may be purified and formulated for human administration. Alternatively, nucleic acids encoding the immunoconjugates may be delivered via gene therapy. Although naked recombinant DNA or plasmids may be employed, the use of liposomes or vectors is preferred. The ability of certain viruses to enter cells via receptor-mediated endocytosis and to integrate into the host cell genome and express viral genes stably and efficiently have made them attractive candidates for the transfer of foreign genes into mammalian cells. Preferred gene therapy vectors for use in the present invention will generally be viral vectors.

Retroviruses have promise as gene delivery vectors due to their ability to integrate their genes into the host genome, transferring a large amount of foreign genetic material, infecting a broad spectrum of species and cell types and of being packaged in special cell-lines. Other viruses, such as adenovirus, herpes simplex viruses (HSV), cytomegalovirus (CMV), and adeno-associated virus (AAV), such as those described by U.S. Pat. No. 5,139,941 (incorporated herein by reference), may also be engineered to serve as vectors for gene transfer.

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

In certain further embodiments, the gene therapy vector will be HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (e.g., temporal, strength) makes it possible to control expression to a greater extent than in other systems. It also is an advantage that the virus has relatively few spliced messages, further easing genetic manipulations. HSV also is relatively easy to manipulate and can be grown to high titers.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

C8. Antibody Conjugates

VEGFR2-blocking, anti-VEGF antibody or 2C3-based antibodies may be conjugated to anti-cellular or cytotoxic agents, to prepare "immunotoxins"; or operatively associated with components that are capable of directly or indirectly stimulating coagulation, thus forming a "coaguligand". In coaguligands, the antibody may be directly linked to a direct or indirect coagulation factor, or may be linked to a second binding region that binds and then releases a direct or indirect coagulation factor. The 'second binding region' approach generally uses a coagulant-binding antibody as a second binding region, thus resulting in a bispecific antibody construct. The preparation and use of bispecific antibodies in general is well known in the art, and is further disclosed herein.

In the preparation of immunotoxins, coaguligands and bispecific antibodies, recombinant expression may be employed. The nucleic acid sequences encoding the chosen antibody are attached, in-frame, to nucleic acid sequences encoding the chosen toxin, coagulant, or second binding region to create an expression unit or vector. Recombinant expression results in translation of the new nucleic acid, to yield the desired protein product. Although antibody-encoding nucleic acids are employed, rather than protein binding ligands, the recombinant approach is essentially the same as those described hereinabove.

Returning to conjugate technology, the preparation of immunotoxins is generally well known in the art. However, certain advantages may be achieved through the application of certain preferred technology, both in the preparation of the immunotoxins and in their purification for subsequent clinical administration. For example, while IgG based immunotoxins will typically exhibit better binding capability and slower blood clearance than their Fab' counterparts, Fab' fragment-based immunotoxins will generally exhibit better tissue penetrating capability as compared to IgG based immunotoxins.

Additionally, while numerous types of disulfide-bond containing linkers are known that can be successfully employed to conjugate the toxin moiety to the VEGFR2-blocking, anti-VEGF antibody or 2C3-based antibody, certain linkers will generally be preferred over other linkers, based on differing pharmacological characteristics and capabilities. For example, linkers that contain a disulfide bond that is sterically "hindered" are to be preferred, due to their greater stability in vivo, thus preventing release of the toxin moiety prior to binding at the site of action.

A wide variety of cytotoxic agents are known that may be conjugated to VEGFR2-blocking, anti-VEGF antibody or 2C3-based antibodies, including plant-, fungus- and bacteria-derived toxins, such as ricin A chain or deglycosylated A chain. The cross-linking of a toxin A chain to an antibody, in certain cases, requires a cross-linker that presents disulfide functions. The reason for this is unclear, but is likely due to a need for certain toxin moieties to be readily releasable from the antibody once the agent has "delivered" the toxin to the targeted cells.

Each type of cross-linker, as well as how the cross-linking is performed, will tend to vary the pharmacodynamics of the resultant conjugate. Ultimately, in cases where a releasable toxin is contemplated, one desires to have a conjugate that will remain intact under conditions found everywhere in the body except the intended site of action, at which point it is desirable that the conjugate have good "release" characteristics. Therefore, the particular cross-linking scheme, including in particular the particular cross-linking reagent used and the structures that are cross-linked, will be of some significance.

Depending on the specific toxin compound used as part of the fusion protein, it may be necessary to provide a peptide spacer operatively attaching the antibody and the toxin compound which is capable of folding into a disulfide-bonded loop structure. Proteolytic cleavage within the loop would then yield a heterodimeric polypeptide wherein the antibody and the toxin compound are linked by only a single disulfide bond. An example of such a toxin is a Ricin A-chain toxin.

When certain other toxin compounds are utilized, a non-cleavable peptide spacer may be provided to operatively attach the VEGFR2-blocking, anti-VEGF antibody or 2C3-based antibody and the toxin compound of the fusion protein. Toxins which may be used in conjunction with non-cleavable peptide spacers are those which may, themselves, be converted by proteolytic cleavage, into a cytotoxic disulfide-bonded form. An example of such a toxin compound is a *Pseudonomas* exotoxin compound.

There may be circumstances, such as when the target antigen does not internalize by a route consistent with efficient intoxication by immunotoxins, where one will desire to target chemotherapeutic agents such as anti-tumor drugs, other cytokines, antimetabolites, alkylating agents, hormones, and the like. A variety of chemotherapeutic and other pharmacological agents have now been successfully conjugated to antibodies and shown to function pharmacologically. Exemplary antineoplastic agents that have been investigated include doxorubicin, daunomycin, methotrexate, vinblastine, and various others. Moreover, the attachment of other agents such as neocarzinostatin, macromycin, trenimon and $\alpha$-amanitin has been described.

Where coagulation factors are used in connection with the present invention, any covalent linkage to the antibody should be made at a site distinct from its functional coagulating site. The compositions are thus "linked" in any operative manner that allows each region to perform its intended function without significant impairment. Thus, the antibody binds to VEGF, and the coagulation factor promotes blood clotting.

C9. Biochemical Cross-linkers

In additional to the general information provided above, VEGFR2-blocking, anti-VEGF antibody or 2C3-based antibodies may be conjugated to one or more therapeutic agents using certain preferred biochemical cross-linkers. Cross-linking reagents are used to form molecular bridges that tie together functional groups of two different molecules. To link two different proteins in a step-wise manner, hetero-bifunctional cross-linkers can be used that eliminate unwanted homopolymer formation. Exemplary hetero-bifunctional cross-linkers are referenced in Table B1.

TABLE B1

HETERO-BIFUNCTIONAL CROSS-LINKERS

| Linker | Reactive Toward | Advantages and Applications | Spacer Arm Length after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |

TABLE B1-continued

HETERO-BIFUNCTIONAL CROSS-LINKERS

| Linker | Reactive Toward | Advantages and Applications | Spacer Arm Length after cross-linking |
|---|---|---|---|
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

Hetero-bifunctional cross-linkers contain two reactive groups: one generally reacting with primary amine group (e.g., N-hydroxy succinimide) and the other generally reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the coagulant).

Compositions therefore generally have, or are derivatized to have, a functional group available for cross-linking purposes. This requirement is not considered to be limiting in that a wide variety of groups can be used in this manner. For example, primary or secondary amine groups, hydrazide or hydrazine groups, carboxyl alcohol, phosphate, or alkylating groups may be used for binding or cross-linking.

The spacer arm between the two reactive groups of a cross-linkers may have various length and chemical compositions. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents). The use of peptide spacers, such as L-Leu-L-Ala-L-Leu-L-Ala, is also contemplated.

It is preferred that a cross-linker having reasonable stability in blood will be employed. Numerous types of disulfide-bond containing linkers are known that can be successfully employed to conjugate targeting and toxic or coagulating agents. Linkers that contain a disulfide bond that is sterically hindered may prove to give greater stability in vivo, preventing release of the agent prior to binding at the site of action. These linkers are thus one preferred group of linking agents.

One of the most preferred cross-linking reagents for use in immunotoxins is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the tumor site. It is contemplated that the SMPT agent may also be used in connection with the bispecific ligands of this invention.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers can also be employed in accordance herewith. Other useful cross-linkers, not considered to contain or generate a protected disulfide, include SATA, SPDP and 2-iminothiolane. The use of such cross-linkers is well understood in the art.

Once conjugated, the conjugate is separated from unconjugated targeting and therapeutic agents and from other contaminants. A large a number of purification techniques are available for use in providing conjugates of a sufficient degree of purity to render them clinically useful. Purification methods based upon size separation, such as gel filtration, gel permeation or high performance liquid chromatography, will generally be of most use. Other chromatographic techniques, such as Blue-Sepharose separation, may also be used.

C10. Biologically Releasable Linkers

Although it is preferred that any linking moiety will have reasonable stability in blood, to prevent substantial release of the attached agent before targeting to the disease or tumor site, in certain aspects, the use of biologically-releasable bonds and/or selectively cleavable spacers or linkers is contemplated. "Biologically-releasable bonds" and "selectively cleavable spacers or linkers" still have reasonable stability in the circulation.

The VEGFR2-blocking, anti-VEGF antibodies of the present invention, such as 2C3-like antibodies, may thus be linked to one or more therapeutic agents via a biologically-releasable bond. Any form of VEGFR2-blocking, anti-VEGF antibody, or "targeting antibody or agent" may be employed, including intact antibodies, although ScFv fragments will be preferred in certain embodiments.

"Biologically-releasable bonds" or "selectively hydrolyzable bonds" include all linkages that are releasable, cleavable or hydrolyzable only or preferentially under certain conditions. This includes disulfide and trisulfide bonds and acid-labile bonds, as described in U.S. Pat. Nos. 5,474,765 and 5,762,918, each specifically incorporated herein by reference.

The use of an acid sensitive spacer for attachment of a therapeutic agent or drug to an antibody of the invention is particularly contemplated. In such embodiments, the therapeutic agents or drugs are released within the acidic compartments inside a cell. It is contemplated that acid-sensitive release may occur extracellularly, but still after specific targeting, preferably to the tumor site. Certain currently preferred examples include 2C3-like antibodies linked to colchicine or doxorubicin via an acid sensitive spacer. Attachment via the carbohydrate moieties of the antibodies is also contemplated. In such embodiments, the therapeutic agents or drugs are released within the acidic compartments inside a cell.

The targeting anti-VEGF antibody may also be derivatized to introduce functional groups permitting the attachment of the therapeutic agent(s) through a biologically releasable bond. The targeting antibody may thus be derivatized to introduce side chains terminating in hydrazide, hydrazine, primary amine or secondary amine groups. Therapeutic agents may be conjugated through a Schiff's base linkage, a hydrazone or acyl hydrazone bond or a hydrazide linker (U.S. Pat. Nos. 5,474,765 and 5,762,918, each specifically incorporated herein by reference).

Also as described in U.S. Pat. Nos. 5,474,765 and 5,762,918, each specifically incorporated herein by reference, the targeting anti-VEGF antibody may be operatively attached to the therapeutic agent(s) through one or more biologically releasable bonds that are enzyme-sensitive bonds, including peptide bonds, esters, amides, phosphodiesters and glycosides.

Preferred aspects of the invention concern the use of peptide linkers that include at least a first cleavage site for a peptidase and/or proteinase that is preferentially located within a disease site, particularly within the tumor environment. The antibody-mediated delivery of the attached therapeutic agent thus results in cleavage specifically within the disease site or tumor environment, resulting in the specific release of the active agent. Certain peptide linkers will include a cleavage site that is recognized by one or more enzymes involved in remodeling.

Peptide linkers that include a cleavage site for urokinase, pro-urokinase, plasmin, plasminogen, TGFβ, staphylokinase, Thrombin, Factor IXa, Factor Xa or a metalloproteinase, such as an interstitial collagenase, a gelatinase or a stromelysin, are particularly preferred. U.S. Pat. No. 6,004,555, U.S. Pat. No. 5,877,289, and U.S. application Ser. No. 08/482,369, Issue Fee paid Oct. 20, 1998, are specifically incorporated herein by reference for the purpose of further describing and enabling how to make and use targeting agent-therapeutic agent constructs comprising biologically-releasable bonds and selectively-cleavable linkers and peptides. U.S. Pat. No. 5,877,289, issued Mar. 2, 1999, in particular, is specifically incorporated herein by reference for the purpose of further describing and enabling how to make and use targeting agent-therapeutic agent constructs that comprise a selectively-cleavable peptide linker that is cleaved by urokinase, plasmin, Thrombin, Factor IXa, Factor Xa or a metalloproteinase, such as an interstitial collagenase, a gelatinase or a stromelysin, within a tumor environment.

Currently preferred selectively-cleavable peptide linkers are those that include a cleavage site for plasmin or a metalloproteinase (also known as "matrix metalloproteases" or MMPs"), such as an interstitial collagenase, a gelatinase or a stromelysin. Additional peptide linkers that may be advantageously used in connection with the present invention include, for example, those listed in Table B2.

TABLE B2

CLEAVABLE LINKER SEQUENCES

| Types of Cleavable Sequences | Amino Acid Sequence | SEQ ID NO: |
|---|---|---|
| Plasmin cleavable sequences | | |
| Pro-urokinase | PRFKIIGG | 15 |
| | PRFRIIGG | 16 |
| TGFβ | SSRHRRALD | 17 |
| Plasminogen | RKSSIIRMRDVVL | 18 |
| Staphylokinase | SSSFDKGKYKKGDDA | 19 |
| | SSSFDKGKYKRGDDA | 20 |
| Factor Xa cleavable sequences | IEGR | 21 |
| | IDGR | 22 |
| | GGSIDGR | 23 |
| MMP cleavable sequences | | |
| Gelatinase A | PLGLWA | 24 |
| Collagenase cleavable sequences | | |
| Calf skin collagen (α1(I) chain) | GPQGIAGQ | 25 |
| Calf skin collagen (α2(I) chain) | GPQGLLGA | 26 |
| Bovine cartilage collagen (α1(II) chain) | GIAGQ | 27 |
| Human liver collagen (α1(III) chain) | GPLGIAGI | 28 |
| Human α$_2$M | GPEGLRVG | 29 |
| Human PZP | YGAGLGVV | 30 |
| | AGLGVVER | 31 |
| | AGLGISST | 32 |
| Rat α$_1$M | EPQALAMS | 33 |
| | QALAMSAI | 34 |
| Rat α$_2$M | AAYHLVSQ | 35 |
| | MDAFLESS | 36 |
| Rat α$_1$I$_3$(2J) | ESLPVVAV | 37 |
| Rat α$_1$I$_3$(27J) | SAPAVESE | 38 |
| Human fibroblast collagenase (autolytic cleavages) | DVAQFVLT | 39 |
| | VAQFVLTE | 40 |
| | AQFVLTEG | 41 |
| | PVQPIGPQ | 42 |

C11. Bispecific Antibodies

Bispecific antibodies are particularly useful in the coaguligand and combined anti-angiogenic aspects of the present invention. However, bispecific antibodies in general may be employed, so long as one arm binds to VEGF, optionally at substantially the same epitope as 2C3, and the bispecific antibody is attached to a therapeutic agent, generally at a site distinct from the antigen binding site.

In general, the preparation of bispecific antibodies is also well known in the art. One method involves the separate preparation of antibodies having specificity for the targeted antigen, on the one hand, and (as herein) a coagulating agent on the other. Peptic F(ab'γ)$_2$ fragments are prepared from the two chosen antibodies, followed by reduction of each to provide separate Fab'γ$_{SH}$ fragments. The SH groups on one of the two partners to be coupled are then alkylated with a cross-linking reagent such as o-phenylenedimaleimide to provide free maleimide groups on one partner. This partner may then be conjugated to the other by means of a thioether linkage, to give the desired F(ab'γ)$_2$ heteroconjugate. Other techniques are known wherein cross-linking with SPDP or protein A is carried out, or a trispecific construct is prepared.

Another method for producing bispecific antibodies is by the fusion of two hybridomas to form a quadroma. As used herein, the term "quadroma" is used to describe the productive fusion of two B cell hybridomas. Using now standard techniques, two antibody producing hybridomas are fused to give daughter cells, and those cells that have maintained the expression of both sets of clonotype immunoglobulin genes are then selected.

A preferred method of generating a quadroma involves the selection of an enzyme deficient mutant of at least one of the parental hybridomas. This first mutant hybridoma cell line is then fused to cells of a second hybridoma that had been lethally exposed, e.g., to iodoacetamide, precluding its continued survival. Cell fusion allows for the rescue of the first hybridoma by acquiring the gene for its enzyme deficiency from the lethally treated hybridoma, and the rescue of the second hybridoma through fusion to the first hybridoma. Preferred, but not required, is the fusion of immunoglobulins of the same isotype, but of a different subclass. A mixed subclass antibody permits the use if an alternative assay for the isolation of a preferred quadroma.

In more detail, one method of quadroma development and screening involves obtaining a hybridoma line that secretes the first chosen mAb and making this deficient for the essential metabolic enzyme, hypoxanthine-guanine phosphoribosyltransferase (HGPRT). To obtain deficient mutants of the hybridoma, cells are grown in the presence of increasing concentrations of 8-azaguanine ($1 \times 10^{-7}$M to $1 \times 10^{-5}$M). The mutants are subcloned by limiting dilution and tested for their hypoxanthine/aminopterin/thymidine (HAT) sensitivity. The culture medium may consist of, for example, DMEM supplemented with 10% FCS, 2 mM L-Glutamine and 1 mM penicillin-streptomycin.

A complementary hybridoma cell line that produces the second desired mAb is used to generate the quadromas by standard cell fusion techniques. Briefly, $4.5 \times 10^7$ HAT-sensitive first cells are mixed with $2.8 \times 10^7$ HAT-resistant second cells that have been pre-treated with a lethal dose of the irreversible biochemical inhibitor iodoacetamide (5 mM in phosphate buffered saline) for 30 minutes on ice before fusion. Cell fusion is induced using polyethylene glycol (PEG) and the cells are plated out in 96 well microculture plates. Quadromas are selected using HAT-containing medium. Bispecific antibody-containing cultures are identified using, for example, a solid phase isotype-specific ELISA and isotype-specific immunofluorescence staining.

In one identification embodiment to identify the bispecific antibody, the wells of microtiter plates (Falcon, Becton Dickinson Labware) are coated with a reagent that specifically interacts with one of the parent hybridoma antibodies and that lacks cross-reactivity with both antibodies. The plates are washed, blocked, and the supernatants (SNs) to be tested are added to each well. Plates are incubated at room temperature for 2 hours, the supernatants discarded, the plates washed, and diluted alkaline phosphatase-anti-antibody conjugate added for 2 hours at room temperature. The plates are washed and a phosphatase substrate, e.g., P-Nitrophenyl phosphate (Sigma, St. Louis) is added to each well. Plates are incubated, 3N NaOH is added to each well to stop the reaction, and the $OD_{410}$ values determined using an ELISA reader.

In another identification embodiment, microtiter plates pre-treated with poly-L-lysine are used to bind one of the target cells to each well, the cells are then fixed, e.g. using 1% glutaraldehyde, and the bispecific antibodies are tested for their ability to bind to the intact cell. In addition, FACS, immunofluorescence staining, idiotype specific antibodies, antigen binding competition assays, and other methods common in the art of antibody characterization may be used in conjunction with the present invention to identify preferred quadromas.

Following the isolation of the quadroma, the bispecific antibodies are purified away from other cell products. This may be accomplished by a variety of protein isolation procedures, known to those skilled in the art of immunoglobulin purification. Means for preparing and characterizing antibodies are well known in the art (See, e.g., Antibodies: A Laboratory Manual, 1988).

For example, supernatants from selected quadromas are passed over protein A or protein G sepharose columns to bind IgG (depending on the isotype). The bound antibodies are then eluted with, e.g. a pH 5.0 citrate buffer. The elute fractions containing the BsAbs, are dialyzed against an isotonic buffer. Alternatively, the eluate is also passed over an anti-immunoglobulin-sepharose column. The BsAb is then eluted with 3.5 M magnesium chloride. BsAbs purified in this way are then tested for binding activity by, e.g., an isotype-specific ELISA and immunofluorescence staining assay of the target cells, as described above.

Purified BsAbs and parental antibodies may also be characterized and isolated by SDS-PAGE electrophoresis, followed by staining with silver or Coomassie. This is possible when one of the parental antibodies has a higher molecular weight than the other, wherein the band of the BsAbs migrates midway between that of the two parental antibodies. Reduction of the samples verifies the presence of heavy chains with two different apparent molecular weights.

D. Pharmaceutical Compositions

The pharmaceutical compositions of the present invention will generally comprise an effective amount of at least a first VEGFR2-blocking, anti-VEGF antibody or 2C3-based antibody or immunoconjugate, dissolved or dispersed in a pharmaceutically acceptable carrier or aqueous medium. Combined therapeutics are also contemplated, and the same type of underlying pharmaceutical compositions may be employed for both single and combined medicaments.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

D1. Injectable Formulations

The VEGFR2-blocking, anti-VEGF antibody-based and 2C3-based antibodies or immunoconjugates of the present invention will most often be formulated for parenteral administration, e.g., formulated for injection via the intravenous, intramuscular, sub-cutaneous, transdermal, or other such routes, including peristaltic administration and direct instillation into a tumor or disease site (intracavity administration). The preparation of an aqueous composition that contains such an antibody or immunoconjugate as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The VEGFR2-blocking, anti-VEGF antibody or 2C3-based antibody or immunoconjugate compositions can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the VEGFR2-blocking, anti-VEGF antibody or 2C3-based antibody or immunoconjugate should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the VEGFR2-blocking, anti-VEGF antibody or 2C3-based antibody or immunoconjugate admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards. Upon formulation, the antibody or immunoconjugate solutions will be administered in a manner compatible with the dosage formulation and in such amount as is therapeutically effective.

D2. Sustained Release Formulations

Formulations of VEGFR2-blocking, anti-VEGF antibody-based or 2C3-based antibodies or immunoconjugate solutions are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, topical formulations, liposomal forms and the like. The type of form for administration will be matched to the disease or disorder to be treated.

Pharmaceutical "slow release" capsules or "sustained release" compositions or preparations may be used and are generally applicable. Slow release formulations are generally designed to give a constant drug level over an extended period and may be used to deliver a VEGFR2-blocking, anti-VEGF antibody or 2C3-based antibody or immunoconjugate in accordance with the present invention. The slow release formulations are typically implanted in the vicinity of the disease site, for example, at the site of a tumor.

Suitable examples of sustained-release preparations include semipermeable matrices of solid hydrophobic polymers containing the antibody or immunoconjugate, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and γ ethyl-L-glutamate; non-degradable ethylene-vinyl acetate; degradable lactic acid-glycolic acid copolymers, such as the Lupron Depot™ (injectable microspheres composed of lactic acid-glycolic acid copolymer and leuprolide acetate); and poly-D-(-)-3-hydroxybutyric acid.

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thiodisulfide interchange, stabilization is achieved by modifying sulfhydryl residues, lyophilizing from acidic solutions, controlling moisture content, using appropriate additives, developing specific polymer matrix compositions, and the like.

D3. Liposomes and Nanoparticles

In certain embodiments, liposomes and/or nanoparticles may also be employed with the VEGFR2-blocking, anti-VEGF antibody or 2C3-based antibodies or immunoconjugates. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

D4. Ophthalmic Formulations

Many diseases with an angiogenic component are associated with the eye. For example, diseases associated with corneal neovascularization that can be treated according to the present invention include, but are not limited to, diabetic retinopathy, retinopathy of prematurity, corneal graft rejection, neovascular glaucoma and retrolental fibroplasia, epidemic keratocon junctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, trauma, rheumatoid arthritis, systemic lupus, polyarteritis, Wegeners sarcoidosis, Scleritis, Steven's Johnson disease, periphigoid radial keratotomy, and corneal graph rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

Other diseases that can be treated according to the present invention include, but are not limited to, diseases associated with rubeosis (neovascularization of the angle) and diseases caused by the abnormal proliferation of fibrovascular or fibrous tissue including all forms of proliferative vitreoretinopathy, whether or not associated with diabetes.

The VEGFR2-blocking, anti-VEGF antibody-based and 2C3-based antibodies and immunoconjugates of the present invention may thus be advantageously employed in the preparation of pharmaceutical compositions suitable for use as ophthalmic solutions, including those for intravitreal and/or intracameral administration. For the treatment of any of the foregoing or other disorders a VEGFR2-blocking, anti-VEGF antibody or 2C3-based antibody composition of the invention would be administered to the eye or eyes of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.).

The ophthalmic preparation will contain a VEGFR2-blocking, anti-VEGF antibody or 2C3-based antibody in a concentration from about 0.01 to about 1% by weight, preferably from about 0.05 to about 0.5% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

D5. Topical Formulations

In the broadest sense, formulations for topical administration include those for delivery via the mouth (buccal) and through the skin. "Topical delivery systems" also include transdermal patches containing the ingredient to be administered. Delivery through the skin can further be achieved by iontophoresis or electrotransport, if desired.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin include ointments, creams, gels and pastes comprising the ingredient to be administered in a pharmaceutical acceptable carrier. The formulation of VEGFR2-blocking, anti-VEGF or 2C3-based antibodies for topical use, such as in creams, ointments and gels, includes the preparation of oleaginous or water-soluble ointment bases, as is well known to those in the art. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Formulations for rectal administration may be presented as a suppository with a suitable base comprising, for example, cocoa butter or a salicylate. Formulations suitable for vaginal administration may be presented as pessaries, tampons, creams, gels, pastes, foams or spray formulations containing in addition to the active ingredient such carriers as are known in the art to be appropriate.

D6. Nasal Formulations

Local delivery via the nasal and respiratory routes is contemplated for treating various conditions. These delivery routes are also suitable for delivering agents into the systemic circulation. Formulations of active ingredients in carriers suitable for nasal administration are therefore also included within the invention, for example, nasal solutions, sprays, aerosols and inhalants. Where the carrier is a solid, the formulations include a coarse powder having a particle size, for example, in the range of 20 to 500 microns, which is administered, e.g., by rapid inhalation through the nasal passage from a container of the powder held close up to the nose.

Suitable formulations wherein the carrier is a liquid are useful in nasal administration. Nasal solutions are usually aqueous solutions designed to be administered to the nasal passages in drops or sprays and are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Inhalations and inhalants are pharmaceutical preparations designed for delivering a drug or compound into the respiratory tree of a patient. A vapor or mist is administered and reaches the affected area. This route can also be employed to deliver agents into the systemic circulation. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, comprises finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered does of the inhalation is propelled into the respiratory tract of the patient. Particle size is of major importance in the administration of this type of preparation. It has been reported that the optimum particle size for penetration into the pulmonary cavity is of the order of 0.5 to 7 µm. Fine mists are produced by pressurized aerosols and hence their use in considered advantageous.

E. Therapeutic Kits

This invention also provides therapeutic kits comprising a VEGFR2-blocking, anti-VEGF antibody or 2C3-based antibody or immunoconjugate for use in the present treatment methods. Such kits will generally contain, in suitable container means, a pharmaceutically acceptable formulation of at least one VEGFR2-blocking, anti-VEGF antibody or 2C3-based antibody or immunoconjugate. The kits may also contain other pharmaceutically acceptable formulations, either for diagnosis/imaging or combined therapy. For example, such kits may contain any one or more of a range of chemotherapeutic or radiotherapeutic drugs; anti-angiogenic agents; anti-tumor cell antibodies; and/or anti-tumor vasculature or anti-tumor stroma immunotoxins or coaguligands.

The kits may have a single container (container means) that contains the VEGFR2-blocking, anti-VEGF antibody or 2C3-based antibody or immunoconjugate, with or without any additional components, or they may have distinct containers for each desired agent. Where combined therapeutics are provided, a single solution may be pre-mixed, either in a molar equivalent combination, or with one component in excess of the other. Alternatively, each of the VEGFR2-blocking, anti-VEGF antibody or 2C3-based antibody or immunoconjugate and other anti-cancer agent components of the kit may be maintained separately within distinct containers prior to administration to a patient.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

The containers of the kit will generally include at least one vial, test tube, flask, bottle, syringe or other container means, into which the VEGFR2-blocking, anti-VEGF antibody or 2C3-based antibody or immunoconjugate, and any other desired agent, may be placed and, preferably, suitably aliquoted. Where separate components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the VEGFR2-blocking, anti-VEGF antibody or 2C3-based antibody or immunoconjugate to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

F. Anti-Angiogenic Therapy

The present invention may be used to treat animals and patients with aberrant angiogenesis, such as that contributing to a variety of diseases and disorders. The most prevalent and/or clinically important of these, outside the field of cancer treatment, include arthritis, rheumatoid arthritis, psoriasis, atherosclerosis, diabetic retinopathy, age-related macular degeneration, Grave's disease, vascular restenosis, including restenosis following angioplasty, arterioyenous malformations (AVM), meningioma, hemangioma and neovascular glaucoma. Other potential targets for intervention include angiofibroma, atherosclerotic plaques, corneal graft neovascularization, hemophilic joints, hypertrophic scars, osler-weber syndrome, pyogenic granuloma retrolental fibroplasia, scleroderma, trachoma, vascular adhesions, synovitis, dermatitis, various other inflammatory diseases and disorders, and even endometriosis. Further diseases and disorders that are treatable by the invention, and the unifying basis of such angiogenic disorders, are set forth below.

One disease in which angiogenesis is involved is rheumatoid arthritis, wherein the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Factors associated with angiogenesis also have a role in osteoarthritis, contributing to the destruction of the joint.

Harada et al. (1998, specifically incorporated herein by reference) showed that VEGF is involved in the pathogenesis of rheumatoid arthritis and, furthermore, that measurement of serum concentration of VEGF is a noninvasive, useful method for monitoring the disease activity of rheumatoid arthritis. This supports the therapeutic and diagnostic uses of the present invention in connection with rheumatoid arthritis.

Nagashima et al. (1999, specifically incorporated herein by reference) described the inhibitory effects of anti-rheumatic drugs on VEGF in cultured rheumatoid synovial cells. VEGF is constitutively expressed in the synovium of rheumatoid arthritis. The known anti-rheumatic drug, bucillamine (BUC), was shown to include within its mechanism of action the inhibition of VEGF production by synovial cells. Thus, the anti-rheumatic effects of BUC are mediated by suppression of angiogenesis and synovial proliferation in the arthritic synovium through the inhibition of VEGF production by synovial cells. The use of the present invention as an anti-arthritic therapy is supported by the VEGF inhibitory actions of this existing therapeutic.

Another example of a disease mediated by angiogenesis is ocular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia.

Other diseases associated with corneal neovascularization include, but are not limited to, epidemic keratocon junctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

Other diseases include, but are not limited to, diseases associated with rubeosis (neovascularization of the angle) and diseases caused by the abnormal proliferation of fibrovascular or fibrous tissue including all forms of proliferative vitreoretinopathy.

Chronic inflammation also involves pathological angiogenesis. Such disease states as ulcerative colitis and Crohn's disease show histological changes with the ingrowth of. new blood vessels into the inflamed tissues. Bartonellosis, a bacterial infection found in South America, can result in a chronic stage that is characterized by proliferation of vascular endothelial cells.

Another pathological role associated with angiogenesis is found in atherosclerosis. The plaques formed within the lumen of blood vessels have been shown to have angiogenic stimulatory activity. VEGF expression in human coronary atherosclerotic lesions was demonstrated by Inoue et al. (1998, specifically incorporated herein by reference). This evidences the pathophysiological significance of VEGF in the progression of human coronary atherosclerosis, as well as in recanalization processes in obstructive coronary diseases. The present invention provides an effective treatment for such conditions.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arterioyenous fistula.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Diseases and disorders characterized by undesirable vascular permeability can also be treated by the present invention. These include edema associated with brain tumors, ascites associated with malignancies, Meigs' syndrome, lung inflammation, nephrotic syndrome, pericardial effusion and pleural effusion, as disclosed in WO 98/16551, specifically incorporated herein by reference.

Each of the foregoing diseases and disorders, along with all types of tumors, as described in the following sections, can be effectively treated by the present invention in accordance with the knowledge in the art, as disclosed in, e.g., U.S. Pat. No. 5,712,291 (specifically incorporated herein by reference), that unified benefits result from the application of anti-angiogenic strategies to the treatment of angiogenic diseases.

The antibodies and/or immunoconjugates of the invention are most preferably utilized in the treatment of tumors. Tumors in which angiogenesis is important include malignant tumors, and benign tumors, such as acoustic neuroma, neurofibroma, trachoma and pyogenic granulomas. Angiogenesis is particularly prominent in solid tumor formation and metastasis. However, angiogenesis is also associated with blood-born tumors, such as leukemias, and various acute or chronic neoplastic diseases of the bone marrow in which unrestrained proliferation of white blood cells occurs, usually accompanied by anemia, impaired blood clotting, and enlargement of the lymph nodes, liver, and spleen. Angiogenesis also plays a role in the abnormalities in the bone marrow that give rise to leukemia-like tumors.

Angiogenesis is important in two stages of tumor metastasis. In the vascularization of the primary tumor, angiogenesis allows cells to enter the blood stream and to circulate throughout the body. After tumor cells have left the primary site, and have settled into the secondary, metastasis site, angiogenesis must occur before the new tumor can grow and expand. Therefore, prevention of angiogenesis can prevent metastasis of tumors and contain the neoplastic growth at the primary site, allowing treatment by other therapeutics, particularly, therapeutic agent-targeting agent constructs (see below).

The VEGFR2-blocking, anti-VEGF antibody and 2C3-based antibody or immunoconjugate methods provided by this invention are thus broadly applicable to the treatment of any malignant tumor having a vascular component. In using the antibodies and/or immunoconjugates of the invention in the treatment of tumors, particularly vascularized, malignant tumors, the agents may be used alone or in combination with, e.g., chemotherapeutic, radiotherapeutic, apoptopic, anti-angiogenic agents and/or immunotoxins or coaguligands.

Typical vascularized tumors for treatment are the solid tumors, particularly carcinomas, which require a vascular component for the provision of oxygen and nutrients. Exemplary solid tumors that may be treated using the invention include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, and the like. WO 98/45331 is also incorporated herein by reference to further exemplify the variety of tumor types that may be effectively treated using an anti-VEGF antibody.

Knowledge of the role of angiogenesis in the maintenance and metastasis of tumors has led to a prognostic indicator for cancers such as breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by the therapies of the present invention will reduce or negate the recurrence of such tumors.

The present invention is contemplated for use in the treatment of any patient that presents with a solid tumor. In light of the specific properties of the VEGFR2-blocking, anti-VEGF antibody-based compositions, the therapeutics of the present invention will have reduced side effects. Particular advantages will result in the maintenance or enhancement of host immune responses against the tumor, as mediated by macrophages, and in the lack of adverse effects on bone tissue. The invention will thus be the anti-angiogenic therapy of choice for the treatment of pediatric cancers and patients having, or at risk for developing, osteoporosis and other bone deficiencies.

Although all malignancies and solid tumors may be treated by the invention, the unconjugated VEGFR2-blocking, anti-VEGF and 2C3 antibodies of this invention are particularly contemplated for use in treating patients with more angiogenic tumors, or patients at risk for metastasis.

The present invention is also intended as a preventative or prophylactic treatment. These aspects of the invention include the ability of the invention to treat patients presenting with a primary tumor who may have metastatic tumors, or tumor cells in the earlier stages of metastatic tumor seeding. As an anti-angiogenic strategy, the present invention may also be used to prevent tumor development in subjects at moderate or high risk for developing a tumor, as based upon prognostic tests and/or close relatives suffering from a hereditary cancer.

The conjugated or immunotoxin forms of the VEGFR2-blocking, anti-VEGF and 2C3 antibodies of the invention are particularly contemplated for use in destroying or debulking solid tumors. These aspects of the invention may be used in conjunction with the unconjugated anti-angiogenic antibodies of the invention, or with other anti-angiogenic approaches.

It will be readily appreciated by those of skill in the art that the immunoconjugate and prodrug forms of the present treatment methods have the distinct advantage of providing a single therapeutic agent with two properties: the inherent anti-angiogenic property of the antibody and the therapeutic property of the attached agent (e.g., cytotoxic, coagulative, apoptopic, etc). The conjugated and prodrug treatment forms of the present antibodies thus have an incredibly wide utility throughout the field of cancer treatment.

The guidance provided herein regarding the more suitable patients for use in connection with the different aspects of the present invention is intended as teaching that certain patient's profiles may assist with the selection of patients for treatment by the present invention. The pre-selection of certain patients, or categories of patients, does not in any way negate the usefulness of the present invention in connection with the treatment of all patients having a vascularized tumor, or other angiogenic disease as described above. A further consideration is the fact that the assault on the tumor provided by the invention may predispose the tumor to further therapeutic treatment, such that the subsequent treatment results in an overall synergistic effect or even leads to total remission or cure.

It is not believed that any particular type of tumor should be excluded from treatment using the present invention. However, the type of tumor cells may be relevant to the use of the invention in combination with other therapeutic agents, particularly chemotherapeutics and anti-tumor cell immunotoxins. Both the unconjugated and conjugated aspects of the present therapies will include an anti-angiogenic effect that will inhibit tumor vasculature proliferation. The conjugated and prodrug treatment aspects will further destroy or occlude the tumor vasculature. As the vasculature is substantially or entirely the same in all solid tumors, the present methodology will be understood to be widely or entirely applicable to the treatment of all solid tumors, irrespective of the particular phenotype or genotype of the tumor cells themselves.

Therapeutically effective doses of VEGFR2-blocking, anti-VEGF antibodies or 2C3-based antibody or immunoconjugate constructs are readily determinable using data from an animal model, e.g., as shown in the studies detailed herein. Experimental animals bearing solid tumors are frequently used to optimize appropriate therapeutic doses prior to translating to a clinical environment. Such models are known to be very reliable in predicting effective anti-cancer strategies. For example, mice bearing solid tumors, such as used in the Examples, are widely used in pre-clinical testing. The inventors have used such art-accepted mouse models to determine working ranges of therapeutic agents that give beneficial anti-tumor effects with minimal toxicity.

In using unconjugated VEGFR2-blocking, anti-VEGF antibodies or 2C3-based antibodies in anti-angiogenic therapies, one can also draw on other published data in order to assist in the formulation of doses for clinical treatment. For instance, although the antibodies of the present invention have distinct advantages over those in the art, the information in the literature concerning treatment with other anti-VEGF antibodies can still be used in combination with the data and teaching in the present application to design and/or optimize treatment protocols and doses.

For example, Borgstrom et al. (1999), specifically incorporated herein by reference, described the importance of VEGF in breast cancer angiogenesis in vivo using MAb A4.6.1. As the 2C3-like antibodies of this invention exhibited equivalent or even improved anti-tumor responses in comparative studies with A4.6.1, these antibodies will also have significant utility in the treatment of breast cancer. The inventors further realized, as will be appreciated by those of ordinary skill in the art, that patients with breast cancer are typically women in the middle or later age groups, where concerns regarding osteoporosis are also apparent. The VEGFR2-blocking, anti-VEGF antibody and 2C3-based antibodies of the present invention will thus have the added advantage of not causing an adverse effect on bone metabolism, and so will not be preferred for use in breast cancer patients having or at risk for developing osteoporosis.

The same type of benefits make VEGFR2-blocking, anti-VEGF antibody and 2C3-based therapeutics the preferred drugs for the treatment of pediatric cancers. In children with cancer, the need to continue healthy and substantial bone growth is evident. As VEGFR2-blocking, anti-VEGF antibodies, such as 2C3, will not substantially impair the activities of osteoclasts and chondroclasts, which are important in developing bone, 2C3 will have important advantages over other antibodies, such as A4.6.1.

Borgstrom et al. (1999), specifically incorporated herein by reference, also reported that MAb A4.6.1 resulted in significant tumors regression when used in combination with doxorubicin. This further supports the combined use of VEGFR2-blocking, anti-VEGF antibodies and conventional cytotoxic or chemotherapeutic agents to achieve significant clinical results in treating a variety of cancers. Both unconjugated doxorubicin and doxorubicin prodrug combinations are contemplated.

Ferrara and colleagues also reported on the efficacy and concentration-response of a murine anti-VEGF monoclonal antibody in tumor-bearing mice and the extrapolation to human treatment (Mordenti et al., 1999, specifically incorporated herein by reference). The studies were designed to evaluate the concentration-response relationship of the murine anti-VEGF monoclonal antibody so that an efficacious plasma concentration of the recombinant humanized form of the antibody could be estimated in cancer patients. Mordenti et al. (1999) concluded that satisfactory tumor suppression in nude mice was achieved using doses of the murine antibody that could be readily applied to the human system in order to define clinical dosing regimens effective to maintain a therapeutic antibody for human use in the required efficacious range. Accordingly, the data from the present art-accepted mouse models can also be translated into appropriate human doses using the type of analyses reported in Mordenti et al. (1999), in addition to the techniques known to the skilled artisan as described herein.

Results from preclinical safety evaluations of a recombinant, humanized form of Genentech's anti-VEGF antibody in monkeys (Ryan et al., 1999, specifically incorporated herein by reference) serve to exemplify the drawbacks with that particular candidate therapeutic. Although the antibody has pharmacological activity in this animal, the monkeys in these studies exhibited physeal dysplasia characterized by a dose-related increase in hypertrophied chondrocytes, subchondral bony plate formation, and inhibition of vascular invasion of the growth plate. No such drawbacks will be evident in the use of the VEGFR2-blocking, anti-VEGF antibody and 2C3-based therapeutics, which do not inhibit VEGF binding and signaling in chondroclasts and chondrocytes, which is mediated by VEGFR1.

Data from a further study on the preclinical pharmacokinetics, interspecies scaling and tissue distribution of Genentech's humanized monoclonal anti-VEGF antibody was reported by Lin et al. (1999, specifically incorporated herein by reference). These studies were conducted in mice, rats, monkeys and rabbits, the latter using $^{125}$I-labelled antibody. The pharmacokinetic data from mice, rats and monkeys were used to predict the pharmacokinetics of the humanized counterpart antibody using allometric scaling in humans. Accordingly, appropriate dosage information can be developed for the treatment of human pathological conditions, such as rheumatoid arthritis, ocular neovascularization and cancer.

A humanized version of the anti-VEGF antibody A4.6.1 has been employed in clinical trials as an anti-cancer agent (Brem, 1998; Baca et al., 1997; Presta et al, 1997; each incorporated herein by reference). Therefore, such clinical data can also be considered as a reference source when designing therapeutic doses for the present VEGFR2-blocking, anti-VEGF antibody and 2C3 treatment. The present invention shows 2C3 to be as effective as A4.6.1 in studies in tumor-bearing mice, although the specificity for inhibiting only VEGFR2-mediated actions of VEGF is an advantage. WO 98/45331 is also incorporated herein by reference to further exemplify the doses of humanized anti-VEGF antibodies that may be used in treatment.

In terms of using conjugated VEGFR2-blocking, anti-VEGF antibodies or 2C3-based immunoconjugates in tumor therapy, one may refer to the scientific and patent literature on the success of delivering a wide range of therapeutics to tumor vasculature to achieve a beneficial effect. By way of example, each of U.S. Pat. Nos. 5,855,866; 5,877,289; 5,965,132; 6,051,230; 6,004,555; 5,776,427; 6,004,554; and 6,036,955; and U.S. Ser. No. 08/482,369, Issue Fee paid Oct. 20, 1998 are incorporated herein by reference for the purpose of further describing the use of such therapeutic agent-targeting agent constructs. In the present case, the therapeutic agent-targeting agent constructs include targeting agent portions that exert an anti-angiogenic effect, which will magnify or otherwise enhance the anti-tumor activity of the attached therapeutic agent.

As is known in the art, there are realistic objectives that may be used as a guideline in connection with pre-clinical testing before proceeding to clinical treatment. However, in light of the progress of other anti-VEGF antibodies to the clinic, the demonstrated anti-tumor effects in accepted models shown herein, and the enhanced safety of the present strategies, the current invention provides a therapeutic with a fast track to clinical treatment. Thus, pre-clinical testing may be employed to select the most advantageous antibodies, doses or combinations.

Any VEGFR2-blocking, anti-VEGF antibody or 2C3-based antibody or immunoconjugate dose, or combined medicament, that results in any consistently detectable anti-angiogenic effect, inhibition of metastasis, tumor vasculature destruction, tumor thrombosis, necrosis and/or general anti-tumor effect will define a useful invention. The present invention may also be effective against vessels downstream of the tumor, i.e., target at least a sub-set of the draining vessels, particularly as cytokines released from the tumor will be acting on these vessels, changing their antigenic profile.

It will also be understood that even in such circumstances where the anti-angiogenic and/or tumor effects of the VEGFR2-blocking, anti-VEGF antibody or 2C3-based antibody or immunoconjugate dose, or combined therapy, are towards the low end of the intended therapeutic range, it may be that this therapy is still equally or even more effective than all other known therapies in the context of the particular tumor target or patient. It is unfortunately evident to a clinician that certain tumors and conditions cannot be effectively treated in the intermediate or long term, but that does not negate the usefulness of the present therapy, particularly where it is at least about as effective as the other strategies generally proposed.

In designing appropriate doses of VEGFR2-blocking, anti-VEGF antibody or 2C3-based antibody or immunoconjugate constructs, or combined therapeutics, for the treatment of vascularized tumors, one may readily extrapolate from the animal studies described herein and the knowledge in the literature in order to arrive at appropriate doses for clinical administration. To achieve a conversion from animal to human doses, one would account for the mass of the agents administered per unit mass of the experimental animal and, preferably, account for the differences in the body surface area (m$^2$) between the experimental animal and the human patient. All such calculations are well known and routine to those of ordinary skill in the art.

For example, taking the successful doses of 2C3 in the mouse studies, and by applying standard calculations based upon mass and surface area, effective doses for use in human patients would be between about 1 mg/m$^2$ and about 1000 mg/m$^2$, preferably, between about 50 mg/m$^2$ and 500 mg/m$^2$10, and most preferably, between about 10 mg/m$^2$ and about 100 mg/m$^2$. These doses are appropriate for VEGFR2-blocking, anti-VEGF antibody or 2C3-based naked antibodies and VEGFR2-blocking, anti-VEGF antibody or 2C3-based immunoconjugates, although the doses are preferred for use in connection with naked or unconjugated antibodies for use as anti-angiogenics.

Accordingly, using this information, the inventors contemplate that useful low doses of VEGFR2-blocking, anti-VEGF antibody or 2C3-based antibodies or immunoconjugates for human administration will be about 1, 2, 3, 4, 5, 6, 7, 8, 9, 10, 12, 15, 20, 25, 30, 35, 40, 45 or about 50 mg/m$^2$; and that useful high doses of such antibodies or immunoconjugates for human administration will be about 600, 650, 700, 750, 800, 850, 900, 925, 950, 975 or about 1000 mg/m$^2$. Useful intermediate doses of VEGFR2-blocking, anti-VEGF antibody or 2C3-based antibodies or immunoconjugates for human administration are contemplated to be any dose between the low and high ranges, such as about 55, 60, 70, 80, 90, 100, 125, 150, 175, 200, 250, 300, 350, 400, 450, 500, 525, 550 or about 575 mg/m$^2$ or so.

Any particular range using any of the foregoing recited exemplary doses or any value intermediate between the particular stated ranges is contemplated. Where VEGFR2-blocking, anti-VEGF antibody or 2C3-based immunoconjugates are used, it will also be understood that coagulant immunoconjugates can generally be used at higher doses than toxin immunoconjugates.

In general, dosage ranges of between about 10–100 mg/m$^2$, about 10–90 mg/m$^2$, about 10–80 mg/m$^2$, about 20–100 mg/m$^2$, about 20–90 mg/m$^2$, about 20–80 mg/m$^2$, about 30–100 mg/m$^2$, about 30–90 mg/m$^2$, about 30–80 mg/m$^2$, about 15–100 mg/m$^2$, about 25–100 mg/m$^2$, about 35–100 mg/m$^2$, about 15–90 mg/m$^2$, about 25–90 mg/m$^2$, about 35–90 mg/ml$^2$, or so of VEGFR2-blocking, anti-VEGF antibody or 2C3-based antibodies or immunoconjugates will be preferred. Notwithstanding these stated ranges, it will be understood that, given the parameters and detailed guidance presented herein, further variations in the active or optimal ranges will be encompassed within the present invention.

Therefore, it will be understood that lower doses may be more appropriate in combination with other agents, and that high doses can still be tolerated, particularly given the enhanced safety of the VEGFR2-blocking, anti-VEGF antibody and 2C3-based antibodies that bind only to VEGFR2 and the yet further enhanced safety of VEGFR2-blocking, anti-VEGF antibody and 2C3-based coagulant and anti-angiogenic immunoconjugates. The use of human or humanized antibodies (and optionally, human coagulant or anti-angiogenic proteins) renders the present invention even safer for clinical use, further reducing the chances of significant toxicity or side effects in healthy tissues.

The intention of the therapeutic regimens of the present invention is generally to produce significant anti-tumor effects whilst still keeping the dose below the levels associated with unacceptable toxicity. In addition to varying the dose itself, the administration regimen can also be adapted to optimize the treatment strategy. One treatment protocol is to administer between about 1 mg/m$^2$ and about 1000 mg/m$^2$, preferably, between about 50 mg/m$^2$ and 500 mg/m$^2$10, and most preferably, between about 10 mg/m$^2$ and about 100 mg/m$^2$ of the VEGFR2-blocking, anti-VEGF antibody or 2C3-based antibody or immunoconjugate, or therapeutic cocktail containing such, about 1 to 3 times a week, preferably by intravenous or intramuscular administration, and most preferably, intravenously.

In administering the particular doses, one would preferably provide a pharmaceutically acceptable composition (according to FDA standards of sterility, pyrogenicity, purity and general safety) to the patient systemically. Intravenous injection is generally preferred. Continuous infusion over a time period of about 1 or 2 hours or so is also contemplated.

Naturally, before wide-spread use, clinical trials will be conducted. The various elements of conducting a clinical trial, including patient treatment and monitoring, will be known to those of skill in the art in light of the present disclosure. The following information is being presented as a general guideline for use in establishing such trials.

Patients chosen for the first VEGFR2-blocking, anti-VEGF antibody or 2C3-based treatment studies will have failed to respond to at least one course of conventional therapy, and will have objectively measurable disease as determined by physical examination, laboratory techniques, and/or radiographic procedures. Any chemotherapy should be stopped at least 2 weeks before entry into the study. Where murine monoclonal antibodies or antibody portions are employed, the patients should have no history of allergy to mouse immunoglobulin.

Certain advantages will be found in the use of an indwelling central venous catheter with a triple lumen port. The VEGFR2-blocking, anti-VEGF. antibody or 2C3-based agents should be filtered, for example, using a 0.22μ filter, and diluted appropriately, such as with saline, to a final volume of 100 ml. Before use, the test sample should also be filtered in a similar manner, and its concentration assessed before and after filtration by determining the A$_{280}$. The expected recovery should be within the range of 87% to 99%, and adjustments for protein loss can then be accounted for.

The VEGFR2-blocking, anti-VEGF antibody or 2C3-based antibodies or conjugates may be administered over a period of approximately 4–24 hours, with each patient receiving 2–4 infusions at 2–7 day intervals. Administration can also be performed by a steady rate of infusion over a 7 day period. The infusion given at any dose level should be dependent upon any toxicity observed. Hence, if Grade II toxicity was reached after any single infusion, or at a particular period of time for a steady rate infusion, further doses should be withheld or the steady rate infusion stopped unless toxicity improved. Increasing doses of VEGFR2-blocking, anti-VEGF antibody or 2C3-based therapeutics should be administered to groups of patients until approximately 60% of patients showed unacceptable Grade III or IV toxicity in any category. Doses that are 2/3 of this value are defined as the safe dose.

Physical examination, tumor measurements, and laboratory tests should, of course, be performed before treatment and at intervals up to 1 month later. Laboratory tests should include complete blood counts, serum creatinine, creatine kinase, electrolytes, urea, nitrogen, SGOT, bilirubin, albumin, and total serum protein. Serum samples taken up to 60 days after treatment should be evaluated by radioimmunoassay for the presence of the administered therapeutic, and antibodies against any portions thereof. Immunological analyses of sera, using any standard assay such as, for example, an ELISA or RIA, will allow the pharmacokinetics and clearance of the VEGFR2-blocking, anti-VEGF antibody or 2C3-based therapeutic agent to be evaluated.

To evaluate the anti-tumor responses, the patients should be examined at 48 hours to 1 week and again at 30 days after the last infusion. When palpable disease was present, two perpendicular diameters of all masses should be measured daily during treatment, within 1 week after completion of therapy, and at 30 days. To measure nonpalpable disease, serial CT scans could be performed at 1-cm intervals throughout the chest, abdomen, and pelvis at 48 hours to 1 week and again at 30 days. Tissue samples should also be evaluated histologically, and/or by flow cytometry, using biopsies from the disease sites or even blood or fluid samples if appropriate.

Clinical responses may be defined by acceptable measure. For example, a complete response may be defined by the disappearance of all measurable tumor 1 month after treatment. Whereas a partial response may be defined by a 50% or greater reduction of the sum of the products of perpendicular diameters of all evaluable tumor nodules 1 month after treatment, with no tumor sites showing enlargement. Similarly, a mixed response may be defined by a reduction of the product of perpendicular diameters of all measurable lesions by 50% or greater 1 month after treatment, with progression in one or more sites.

In light of results from clinical trials, such as those described above, an even more precise treatment regimen may be formulated. Even so, some variation in dosage may later be necessary depending on the condition of the subject being treated. The physician responsible for administration will, in light of the present disclosure, be able to determine the appropriate dose for the individual subject. Such optimization and adjustment is routinely carried out in the art and by no means reflects an undue amount of experimentation.

G. Combination Therapies

Whether used for treating angiogenic diseases, such as arthritis, psoriasis, atherosclerosis, diabetic retinopathy, age-related macular degeneration, Grave's disease, vascular restenosis, hemangioma and neovascular glaucoma (or other diseases described above), or solid tumors, the present invention can be combined with other therapies.

The VEGFR2-blocking, anti-VEGF antibody or 2C3-based treatment methods of the present invention may be combined with any other methods generally employed in the treatment of the particular tumor, disease or disorder that the patient exhibits. So long as a particular therapeutic approach is not known to be detrimental to the patient's condition in itself, and does not significantly counteract the VEGFR2- blocking, anti-VEGF antibody or 2C3-based treatment, its combination with the present invention is contemplated.

In connection solid tumor treatment, the present invention may be used in combination with classical approaches, such as surgery, radiotherapy, chemotherapy, and the like. The invention therefore provides combined therapies in which VEGFR2-blocking, anti-VEGF antibody or 2C3-based constructs are used simultaneously with, before, or after surgery or radiation treatment; or are administered to patients with, before, or after conventional chemotherapeutic, radiotherapeutic or anti-angiogenic agents, or targeted immunotoxins or coaguligands.

The combined use of the invention with radiotherapy, radiotherapeutics, anti-angiogenic agents, apoptosis-inducing agents and anti-tubulin drugs is particularly preferred. Many examples of such agents have been described above in conjunction with the immunoconjugates of the present invention. Any of the agents initially described for use as one part of a therapeutic conjugate may also be used separately, but still in operable combination with the present invention.

When one or more agents are used in combination with the VEGFR2-blocking, anti-VEGF antibody or 2C3-based therapy, there is no requirement for the combined results to be additive of the effects observed when each treatment is conducted separately. Although at least additive effects are generally desirable, any increased anti-tumor effect above one of the single therapies would be of benefit. Also, there is no particular requirement for the combined treatment to exhibit synergistic effects, although this is certainly possible and advantageous.

To practice combined anti-tumor therapy, one would simply administer to an animal a VEGFR2-blocking, anti-VEGF antibody or 2C3-based construct in combination with another anti-cancer agent in a manner effective to result in their combined anti-tumor actions within the animal. The agents would therefore be provided in amounts effective and for periods of time effective to result in their combined presence within the tumor vasculature and their combined actions in the tumor environment. To achieve this goal, the VEGFR2-blocking, anti-VEGF antibody or 2C3-based therapeutic and anti-cancer agents may be administered to the animal simultaneously, either in a single composition, or as two distinct compositions using different administration routes.

Alternatively, the VEGFR2-blocking, anti-VEGF antibody or 2C3-based treatment may precede, or follow, the anti-cancer agent treatment by, e.g., intervals ranging from minutes to weeks and months. One would ensure that the anti-cancer agent and VEGFR2-blocking, anti-VEGF antibody or 2C3-based agent exert an advantageously combined effect on the tumor.

Most anti-cancer agents would be given prior to VEGFR2-blocking, anti-VEGF antibody or 2C3-based anti-angiogenic therapy. However, where VEGFR2-blocking, anti-VEGF antibody or 2C3-based immunoconjugates are used, various anti-cancer agents may be simultaneously or subsequently administered.

The general use of combinations of substances in cancer treatment is well know. For example, U.S. Pat. No. 5,710,134 (incorporated herein by reference) discloses components that induce necrosis in tumors in combination with non-toxic substances or "prodrugs". The enzymes set free by necrotic processes cleave the non-toxic "prodrug" into the toxic "drug", which leads to tumor cell death. Also, U.S. Pat. No. 5,747,469 (incorporated herein by reference) discloses the combined use of viral vectors encoding p53 and DNA damaging agents. Any such similar approaches can be used with the present invention.

In some situations, it may even be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, such as surgery or chemotherapy, and another treatment was intended to prevent micrometastasis or tumor re-growth, such as anti-angiogenic based therapy. Anti-angiogenics should be administered at a careful time after surgery to allow effective wound healing.

It also is envisioned that more than one administration of either the VEGFR2-blocking, anti-VEGF antibody or 2C3-based agent or the anti-cancer agent will be utilized. The agents may be administered interchangeably, on alternate days or weeks; or a sequence of VEGFR2-blocking, anti-VEGF antibody or 2C3-based treatment may be given, followed by a sequence of anti-cancer agent therapy. In any event, to achieve tumor regression using a combined therapy, all that is required is to deliver both agents in a combined amount effective to exert an anti-tumor effect, irrespective of the times for administration.

In terms of surgery, any surgical intervention may be practiced in combination with the present invention. In connection with radiotherapy, any mechanism for inducing DNA damage locally within tumor cells is contemplated, such as $\gamma$-irradiation, X-rays, UV-irradiation, microwaves and even electronic emissions and the like. The directed delivery of radioisotopes to tumor cells is also contemplated, and this may be used in connection with a targeting antibody or other targeting means, and preferably, VEGFR2-blocking, anti-VEGF antibodies, such as 2C3.

Cytokine therapy also has proven to be an effective partner for combined therapeutic regimens. Various cytokines may be employed in such combined approaches. Examples of cytokines include IL-1$\alpha$ IL-1$\beta$, IL-2, IL-3, IL-4, IL-5, IL-6, IL-7, IL-8, IL-9, IL-10, IL-11, IL-12, IL-13, TGF-$\beta$, GM-CSF, M-CSF, G-CSF, TNF$\alpha$, TNF$\beta$, LAF, TCGF, BCGF, TRF, BAF, BDG, MP, LIF, OSM, TMF, PDGF, IFN-$\alpha$, IFN-$\beta$, IFN-$\gamma$. Cytokines are administered according to standard regimens, consistent with clinical indications such as the condition of the patient and relative toxicity of the cytokine. Uteroglobins may also be used to prevent or inhibit metastases (U.S. Pat. No. 5,696,092; incorporated herein by reference).

G1. Chemotherapeutics

In certain embodiments, the VEGFR2-blocking, anti-VEGF antibody or 2C3-based therapeutic agents of the present invention may be administered in combination with a chemotherapeutic agent. A variety of chemotherapeutic agents may be used in the combined treatment methods disclosed herein. Chemotherapeutic agents contemplated as exemplary include, e.g., adriamycin, dactinomycin, mitomycin, canninomycin, daunomycin, doxorubicin, tamoxifen, taxol, taxotere, vincristine, vinblastine, vinorelbine, etoposide (VP-16), 5-fluorouracil (5FU), cytosine arabinoside, cyclohohphamide, thiotepa, methotrexate, camptothecin, actinomycin-D, mitomycin C, cisplatin (CDDP), aminopterin, combretastatin(s) and derivatives and prodrugs thereof.

As will be understood by those of ordinary skill in the art, the appropriate doses of chemotherapeutic agents will be generally around those already employed in clinical therapies wherein the chemotherapeutics are administered alone or in combination with other chemotherapeutics. By way of example only, agents such as cisplatin, and other DNA alkylating may be used. Cisplatin has been widely used to treat cancer, with efficacious doses used in clinical applications of 20 mg/m² for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m² at 21 day intervals for adriamycin, to 35–50 mg/m² for etoposide intravenously or double the intravenous dose orally.

Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Exemplary chemotherapeutic agents for combined therapy are listed in Table C. Each of the agents listed are exemplary and not limiting. The skilled artisan is directed to "Remington's Pharmaceutical Sciences" 15th Edition, chapter 33, in particular pages 624–652. Variation in dosage will likely occur depending on the condition being treated. The physician administering treatment will be able to determine the appropriate dose for the individual subject.

TABLE C

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE |
|---|---|---|---|
| Alkylating Agents | Nitrogen Mustards | Mechlorethamine (HN₂) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan (L-sarcolysin) | Multiple myeloma, breast, ovary |
| | | Chlorambucil | Chronic lymphocytic leukemia, primary macroglobulinemia, Hodgkin's disease, non-Hodgkin's lymphomas |
| | Ethylenimenes and Methylmelamines | Hexamethylmelamine | Ovary |
| | | Thiotepa | Bladder, breast, ovary |
| | Alkyl Sulfonates | Busulfan | Chronic granulocytic leukemia |
| | Nitrosoureas | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |
| | | Semustine (methyl-CCNU) | Primary brain tumors, stomach, colon |
| | | Streptozocin (streptozotocin) | Malignant pancreatic insulinoma, malignant carcinoid |
| | Triazines | Dacarbazine (DTIC; dimethyltriazenoimidazolecarboxamide) | Malignant melanoma, Hodgkin's disease, soft-tissue sarcomas |
| Antimetabolites | Folic Acid Analogs | Methotrexate (amethopterin) | Acute lymphocytic leukemia, choriocarcinoma, mycosis fungoides, breast, head and neck, lung, osteogenic sarcoma |
| | Pyrimidine Analogs | Fluouracil (5-fluorouracil; 5-FU) | Breast, colon, stomach, pancreas, ovary, head and neck, urinary bladder, premalignant skin lesions (topical) |
| | | Floxuridine (fluorodeoxyuridine; FUdR) | |
| | | Cytarabine (cytosine arabinoside) | Acute granulocytic and acute lymphocytic leukemias |
| | | Mercaptopurine (6-mercaptopurine; 6-MP) | Acute lymphocytic, acute granulocytic and chronic granulocytic leukemias |
| | Purine Analogs and Related Inhibitors | Thioguanine (6-thioguanine; TG) | Acute granulocytic, acute lymphocytic and chronic granulocytic leukemias |
| | | Pentostatin (2-deoxycoformycin) | Hairy cell leukemia, mycosis fungoides, chronic lymphocytic leukemia |

TABLE C-continued

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE |
|---|---|---|---|
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | Epipodophyllotoxins | Etoposide | Testis, small-cell lung and other lung, breast, Hodgkin's disease, non-Hodgkin's lymphomas, acute granulocytic leukemia, Kaposi's sarcoma |
| | | Tertiposide | |
| | Antibiotics | Dactinomycin (actinomycin D) | Choriocarcinoma, Wilms' tumor, rhabdomyosarcoma, testis, Kaposi's sarcoma |
| | | Daunorubicin (daunomycin; rubidomycin) | Acute granulocytic and acute lymphocytic leukemias |
| | | Doxorubicin | Soft-tissue, osteogenic and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung and genitourinary tract; Hodgkin's disease, non-Hodgkin's lymphomas |
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon alfa | Hairy cell leukemia, Kaposi's sarcoma, melanoma, carcinoid, renal cell, ovary, bladder, non-Hodgkin's lymphomas, mycosis fungoides, multiple myeloma, chronic granulocytic leukemia |
| | Platinum Coordination Complexes | Cisplatin (cis-DDP) | Testis, ovary, bladder, head and neck, lung, thyroid, cervix, endometrium, neuroblastoma, osteogenic sarcoma |
| | | Carboplatin | |
| Miscellaneous Agents | Anthracenedione | Mitoxantrone | Acute granulocytic leukemia, breast |
| | Substituted Urea | Hydroxyurea | Chronic granulocytic leukemia, polycythemia vera, essental thrombocytosis, malignant melanoma |
| | Methyl Hydrazine Derivative | Procarbazine (N-methylhydrazine, MIH) | Hodgkin's disease |
| | Adrenocortical Suppressant | Mitotane (o,p'-DDD) | Adrenal cortex |
| | | Aminoglutethimide | Breast |
| Hormones and Antagonists | Adrenocorticosteroids | Prednisone (several other equivalent preparations available) | Acute and chronic lymphocytic leukemias, non-Hodgkin's lymphomas, Hodgkin's disease, breast |
| | Progestins | Hydroxyprogesterone caproate | Endometrium, breast |
| | | Medroxyprogesterone acetate | |
| | | Megestrol acetate | |
| | Estrogens | Diethylstilbestrol | Breast, prostate |
| | | Ethinyl estradiol (other preparations available) | |
| | Antiestrogen | Tamoxifen | Breast |
| | Androgens | Testosterone propionate | Breast |
| | | Fluoxymesterone (other preparations available) | |
| | Antiandrogen | Flutamide | Prostate |
| | Gonadotropin-releasing hormone analog | Leuprolide | Prostate |

G2. Anti-Angiogenics

Under normal physiological conditions, humans or animals undergo angiogenesis only in very specific restricted situations. For example, angiogenesis is normally observed in wound healing, fetal and embryonic development and formation of the corpus luteum, endometrium and placenta. Uncontrolled (persistent and/or unregulated) angiogenesis is related to various disease states, and occurs during tumor metastasis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

The present VEGFR2-blocking, anti-VEGF antibody or 2C3-based invention may be used in combination with any one or more other anti-angiogenic therapies. Combinations with other agents that inhibit VEGF are included, such as other neutralizing antibodies (Kim et al., 1992; Presta et al., 1997; Sioussat et al., 1993; Kondo et al., 1993; Asano et al., 1995), soluble receptor constructs (Kendall and Thomas, 1993; Aiello et al., 1995; Lin et al., 1998; Millauer et al., 1996), tyrosine kinase inhibitors (Siemeister et al., 1998), antisense strategies, RNA aptamers and ribozymes against VEGF or VEGF receptors (Saleh et al., 1996; Cheng et al., 1996; Ke et al., 1998; Parry et al., 1999; each incorporated herein by reference). Variants of VEGF with antagonistic properties may also be employed, as described in WO 98/16551, specifically incorporated herein by reference.

The anti-angiogenic therapies may be based upon the provision of an anti-angiogenic agent or the inhibition of an angiogenic agent. Inhibition of angiogenic—agents may be achieved by one or more of the methods described for inhibiting VEGF, including neutralizing antibodies, soluble receptor constructs, small molecule inhibitors, antisense, RNA aptamers and ribozymes may all be employed. For example, antibodies to angiogenin may be employed, as described in U.S. Pat. No. 5,520,914, specifically incorporated herein by reference. In that FGF is connected with angiogenesis, FGF inhibitors may also be used. Certain examples are the compounds having N-acetylglucosamine alternating in sequence with 2-O-sulfated uronic acid as their major repeating units, including glycosaminoglycans, such as archaran sulfate. Such compounds are described in U.S. Pat. No. 6,028,061, specifically incorporated herein by reference, and may be used in combination herewith.

Numerous tyrosine kinase inhibitors useful for the treatment of angiogenesis, as manifest in various diseases states, are now known. These include, for example, the 4-aminopyrrolo[2,3-d]pyrimidines of U.S. Pat. No. 5,639,757, specifically incorporated herein by reference, which may also be used in combination with the present invention. Further examples of organic molecules capable of modulating tyrosine kinase signal transduction via the VEGFR2 receptor are the quinazoline compounds and compositions of U.S. Pat. No. 5,792,771, which is specifically incorporated herein by reference for the purpose of describing further combinations for use with the present invention in the treatment of angiogenic diseases.

Compounds of other chemical classes have also been shown to inhibit angiogenesis and may be used in combination with the present invention. For example, steroids such as the angiostatic 4,9(11)-steroids and C21-oxygenated steroids, as described in U.S. Pat. No. 5,972,922, specifically incorporated herein by reference, may be employed in combined therapy. U.S. Pat. Nos. 5,712,291 and 5,593,990, each specifically incorporated herein by reference, describe thalidomide and related compounds, precursors, analogs, metabolites and hydrolysis products, which may also be used in combination with the present invention to inhibit angiogenesis. The compounds in U.S. Pat. Nos. 5,712,291 and 5,593,990 can be administered orally. Further exemplary anti-angiogenic agents that are useful in connection with combined therapy are listed in Table D. Each of the agents listed therein are exemplary and by no means limiting.

TABLE D

INHIBITORS AND NEGATIVE REGULATORS OF ANGIOGENESIS

| Substances | References |
| --- | --- |
| Angiostatin | O'Reilly et al., 1994 |
| Endostatin | O'Reilly et al., 1997 |
| 16 kDa prolactin fragment | Ferrara et al., 1991; Clapp et al., 1993; D'Angelo et al., 1995; Lee et al., 1998 |
| Laminin peptides | Kleinman et al., 1993; Yamamura et al., 1993; Iwamoto et al., 1996; Tryggvason, 1993 |
| Fibronectin peptides | Grant et al., 1998; Sheu et al., 1997 |
| Tissue metalloproteinase inhibitors (TIMP 1, 2, 3, 4) | Sang, 1998 |
| Plasminogen activator inhibitors (PAI-1, -2) | Soff et al., 1995 |
| Tumor necrosis factor α (high dose, in vitro) | Frater-Schroder et al., 1987 |
| TGF-β1 | RayChadhury and D'Amore, 1991; Tada et al., 1994 |
| Interferons (IFN-α, -β, γ) | Moore et al., 1998; Lingen et al., 1998 |
| ELR-CXC Chemokines: IL-12; SDF-1; MIG; Platelet factor 4 (PF-4); IP-10 | Moore et al., 1998; Hiscox and Jiang, 1997; Coughlin et al., 1998; Tanaka et al., 1997 |
| Thrombospondin (TSP) | Good et al., 1990; Frazier, 1991; Bornstein, 1992; Tolsma et al., 1993; Sheibani and Frazier, 1995; Volpert et al., 1998 |
| SPARC | Hasselaar and Sage, 1992; Lane et al., 1992; Jendraschak and Sage, 1996 |
| 2-Methoxyoestradiol | Fotsis et al., 1994 |
| Proliferin-related protein | Jackson et al., 1994 |
| Suramin | Gagliardi et al., 1992; Takano et al., 1994; Waltenberger et al., 1996; Gagliardi et al., 1998; Manetti et al., 1998 |
| Thalidomide | D'Amato et al., 1994; Kenyon et al., 1997 Wells, 1998 |
| Cortisone | Thorpe et al., 1993 Folkman et al., 1983 Sakamoto et al., 1986 |
| Linomide | Vukanovic et al., 1993; Ziche et al., 1998; Nagler et al., 1998 |
| Fumagillin (AGM-1470; TNP-470) | Sipos et al., 1994; Yoshida et al., 1998 |
| Tamoxifen | Gagliardi and Collins, 1993; Lindner and Borden, 1997; Haran et al., 1994 |
| Korean mistletoe extract (*Viscum album coloratum*) | Yoon et al., 1995 |
| Retinoids | Oikawa et al., 1989; Lingen et al., 1996; Majewski et al. 1996 |
| CM101 | Hellerqvist et al., 1993; Quinn et al., 1995; Wamil et al., 1997; DeVore et al., 1997 |

TABLE D-continued

INHIBITORS AND NEGATIVE REGULATORS
OF ANGIOGENESIS

| Substances | References |
|---|---|
| Dexamethasone | Hori et al., 1996; Wolff et al., 1997 |
| Leukemia inhibitory factor (LIF) | Pepper et al., 1995 |

Certain preferred components for use in inhibiting angiogenesis are angiostatin, endostatin, vasculostatin, canstatin and maspin. Such agents are described above in conjunction with the immunoconjugates of the present invention, but may be used in combined, but unconjugated form. Other preferred agents also described above in immunoconjugate form are the angiopoietins, particularly angiopoietin-2, which is contemplated for combined use with the present invention.

Certain anti-angiogenic therapies have already been shown to cause tumor regressions, including the bacterial polysaccharide CM101 and the antibody LM609. CM101 is a bacterial polysaccharide that has been well characterized in its ability to induce neovascular inflammation in tumors. CM101 binds to and cross-links receptors expressed on dedifferentiated endothelium that stimulates the activation of the complement system. It also initiates a cytokine-driven inflammatory response that selectively targets the tumor. It is a uniquely antipathoangiogenic agent that downregulates the expression VEGF and its receptors. CM101 is currently in clinical trials as an anti-cancer drug, and can be used in combination herewith.

Thrombospondin (TSP-1) and platelet factor 4 (PF4) may also be used in combination with the present invention. These are both angiogenesis inhibitors that associate with heparin and are found in platelet α-granules. TSP-1 is a large 450 kDa multi-domain glycoprotein that is constituent of the extracellular matrix. TSP-1 binds to many of the proteoglycan molecules found in the extracellular matrix including, HSPGs, fibronectin, laminin, and different types of collagen. TSP-1 inhibits endothelial cell migration and proliferation in vitro and angiogenesis in vivo. TSP-1 can also suppress the malignant phenotype and tumorigenesis of transformed endothelial cells. The tumor suppressor gene p53 has been shown to directly regulate the expression of TSP-1 such that, loss of p53 activity causes a dramatic reduction in TSP-1 production and a concomitant increase in tumor initiated angiogenesis.

PF4 is a 70aa protein that is member of the CXC ELR-family of chemokines that is able to potently inhibit endothelial cell proliferation in vitro and angiogenesis in vivo. PF4 administered intratumorally or delivered by an adenoviral vector is able to cause an inhibition of tumor growth.

Interferons and metalloproteinase inhibitors are two other classes of naturally occurring angiogenic inhibitors that can be combined with the present invention. The anti-endothelial activity of the interferons has been known since the early 1980s, however, the mechanism of inhibition is still unclear. It is known that they can inhibit endothelial cell migration and that they do have some anti-angiogenic activity in vivo that is possibly mediated by an ability to inhibit the production of angiogenic promoters by tumor cells. Vascular tumors in particular are sensitive to interferon, for example, proliferating hemangiomas can be successfully treated with IFNα.

Tissue inhibitors of metalloproteinases (TIMPs) are a family of naturally occurring inhibitors of matrix metalloproteases (MMPs) that can also inhibit angiogenesis and can be used in combined treatment protocols. MMPs play a key role in the angiogenic process as they degrade the matrix through which endothelial cells and fibroblasts migrate when extending or remodeling the vascular network. In fact, one member of the MMPs, MMP-2, has been shown to associate with activated endothelium through the integrin $\alpha v \beta 3$ presumably for this purpose. If this interaction is disrupted by a fragment of MMP-2, then angiogenesis is downregulated and in tumors growth is inhibited.

There are a number of pharmacological agents that inhibit angiogenesis, any one or more of which may be used in combination with the present invention. These include AGM-1470/TNP-470, thalidomide, and carboxyamidotriazole (CAI). Fumagillin was found to be a potent inhibitor of angiogenesis in 1990, and since then the synthetic analogues of fumagillin, AGM-1470 and TNP-470 have been developed. Both of these drugs inhibit endothelial cell proliferation in vitro and angiogenesis in vivo. TNP-470 has been studied extensively in human clinical trials with data suggesting that long-term administration is optimal.

Thalidomide was originally used as a sedative but was found to be a potent teratogen and was discontinued. In 1994 it was found that thalidomide is an angiogenesis inhibitor. Thalidomide is currently in clinical trials as an anti-cancer agent as well as a treatment of vascular eye diseases.

CAI is a small molecular weight synthetic inhibitor of angiogenesis that acts as a calcium channel blocker that prevents actin reorganization, endothelial cell migration and spreading on collagen IV. CAI inhibits neovascularization at physiological attainable concentrations and is well tolerated orally by cancer patients. Clinical trials with CAI have yielded disease stabilization in 49% of cancer patients having progressive disease before treatment.

Cortisone in the presence of heparin or heparin fragments was shown to inhibit tumor growth in mice by blocking endothelial cell proliferation. The mechanism involved in the additive inhibitory effect of the steroid and heparin is unclear although it is thought that the heparin may increase the uptake of the steroid by endothelial cells. The mixture has been shown to increase the dissolution of the basement membrane underneath newly formed capillaries and this is also a possible explanation for the additive angiostatic effect. Heparin-cortisol conjugates also have potent angiostatic and anti-tumor effects activity in vivo.

Further specific angiogenesis inhibitors, including, but not limited to, Anti-Invasive Factor, retinoic acids and paclitaxel (U.S. Pat. No. 5,716,981; incorporated herein by reference); AGM-1470 (Ingber et al., 1990; incorporated herein by reference); shark cartilage extract (U.S. Pat. No. 5,618,925; incorporated herein by reference); anionic polyamide or polyurea oligomers (U.S. Pat. No. 5,593,664; incorporated herein by reference); oxindole derivatives (U.S. Pat. No. 5,576,330; incorporated herein by reference); estradiol derivatives (U.S. Pat. No. 5,504,074; incorporated herein by reference); and thiazolopyrimidine derivatives (U.S. Pat. No. 5,599,813; incorporated herein by reference) are also contemplated for use as anti-angiogenic compositions for the combined uses of the present invention.

Compositions comprising an antagonist of an $\alpha_v \beta_3$ integrin may also be used to inhibit angiogenesis in combination with the present invention. As disclosed in U.S. Pat. No. 5,766,591 (incorporated herein by reference), RGD-containing polypeptides and salts thereof, including cyclic polypeptides, are suitable examples of $\alpha_v \beta_3$ integrin antagonists.

The antibody LM609 against the $\alpha_v \beta_3$ integrin also induces tumors regressions. Integrin $\alpha_v \beta_3$ antagonists, such as LM609, induce apoptosis of angiogenic endothelial cells leaving the quiescent blood vessels unaffected. LM609 or other $\alpha_v\beta_3$ antagonists may also work by inhibiting the interaction of $\alpha_v\beta_3$ and MMP-2, a proteolytic enzyme thought to play an important role in migration of endothelial cells and fibroblasts. U.S. Pat. No. 5,753,230 is specifically incorporated herein by reference to describe antibodies against $\alpha_v\beta_3$ (vitronectin $\alpha_v\beta_3$) for combined with the present invention for inhibiting angiogenesis.

Apoptosis of the angiogenic endothelium in this case may have a cascade effect on the rest of the vascular network. Inhibiting the tumor vascular network from completely responding to the tumor's signal to expand may, in fact, initiate the partial or full collapse of the network resulting in tumor cell death and loss of tumor volume. It is possible that endostatin and angiostatin function in a similar fashion. The fact that LM609 does not affect quiescent vessels but is able to cause tumor regressions suggests strongly that not all blood vessels in a tumor need to be targeted for treatment in order to obtain an anti-tumor effect.

Other methods of therapeutic intervention based upon altering signaling through the Tie2 receptor can also be used in combination with the present invention, such as using a soluble Tie2 receptor capable of blocking Tie2 activation (Lin et al., 1998). Delivery of such a construct using recombinant adenoviral gene therapy has been shown to be effective in treating cancer and reducing metastases (Lin et al., 1998).

G3. Apoptosis-Inducing Agents

VEGFR2-blocking, anti-VEGF antibody or 2C3-based therapeutic agents may also be advantageously combined with methods to induce apoptosis. Various apoptosis-inducing agents have been described above in connection with the immunoconjugates of the present invention. Any such apoptosis-inducing agent may be used in combination with the present invention without being linked to an antibody of the invention.

Aside from the apoptosis-inducing agents described above as immunoconjugates, a number of oncogenes have been identified that inhibit apoptosis, or programmed cell death. Exemplary oncogenes in this category include, but are not limited to, bcr-abl, bcl-2 (distinct from bcl-1, cyclin D1; GenBank accession numbers M14745, X06487; U.S. Pat. Nos. 5,650,491; and 5,539,094; each incorporated herein by reference) and family members including Bcl-x1, Mcl-1, Bak, A1, A20. Overexpression of bcl-2 was first discovered in T cell lymphomas. bcl-2 functions as an oncogene by binding and inactivating Bax, a protein in the apoptotic pathway. Inhibition of bcl-2 function prevents inactivation of Bax, and allows the apoptotic pathway to proceed.

Inhibition of this class of oncogenes, e.g., using antisense nucleotide sequences, is contemplated for use in the present invention to give enhancement of apoptosis (U.S. Pat. Nos. 5,650,491; 5,539,094; and 5,583,034; each incorporated herein by reference).

G4. Immunotoxins and Coaguligands

The treatment methods of the invention may be used in combination with [other] immunotoxins and/or coaguligands in which the targeting portion thereof, e.g., antibody or ligand, is directed to a relatively specific marker of the tumor cells, tumor vasculature or tumor stroma. In common with the chemotherapeutic and anti-angiogenic agents discussed above, the combined use of targeted toxins or coagulants will generally result in additive, markedly greater than additive or even synergistic anti-tumor results.

Generally speaking, antibodies or ligands for use in these additional aspects of the invention will preferably recognize accessible tumor antigens that are preferentially, or specifically, expressed in the tumor site. The antibodies or ligands will also preferably exhibit properties of high affinity; and the antibodies, ligands or conjugates thereof, will not exert significant in vivo side effects against life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The term "significant side effects", as used herein, refers- to an antibody, ligand or antibody conjugate, that, when administered in vivo, will produce only negligible or clinically manageable side effects, such as those normally encountered during chemotherapy.

At least one binding region of these second anti-cancer agents employed in combination with the invention will be a component that is capable of delivering a toxin or coagulation factor to the tumor region, i.e., capable of localizing within a tumor site. Such targeting agents may be directed against a component of a tumor cell, tumor vasculature or tumor stroma. The targeting agents will generally bind to a surface-expressed, surface-accessible or surface-localized component of a tumor cell, tumor vasculature or tumor stroma. However, once tumor vasculature and tumor cell destruction begins, internal components will be released, allowing additional targeting of virtually any tumor component.

Many tumor cell antigens have been described, any one which could be employed as a target in connection with the combined aspects of the present invention. Appropriate tumor cell antigens for additional immunotoxin and coaguligand targeting include those recognized by the antibodies B3 (U.S. Pat. No. 5,242,813); incorporated herein by reference; ATCC HB 10573); KSI/4 (U.S. Pat. No. 4,975,369); incorporated herein by reference; obtained from a cell comprising the vectors NRRL B-18356 and/or NRRL B-18357); 260F9 (ATCC HB 8488); and D612 (U.S. Pat. No. 5,183,756); incorporated herein by reference; ATCC HB 9796). One may also consult the ATCC Catalogue of any subsequent year to identify other appropriate cell lines producing anti-tumor cell antibodies.

For tumor vasculature targeting, the targeting antibody or ligand will often bind to a marker expressed by, adsorbed to, induced on or otherwise localized to the intratumoral blood vessels of a vascularized tumor. Appropriate expressed target molecules include, for example, endoglin, E-selectin, P-selectin, VCAM-1, ICAM-1, PSMA (Liu et al., 1997), a TIE, a ligand reactive with LAM-1, a VEGF/VPF receptor, an FGF receptor, $\alpha_v\beta_3$ integrin, pleiotropin and endosialin. Suitable adsorbed targets are those such as VEGF, FGF, TGFβ, HGF, PF4, PDGF, TIMP, a ligand that binds to a TIE and tumor-associated fibronectin isoforms. Antigens naturally and artificially inducible by cytokines and coagulants may also be targeted, such as ELAM-1, VCAM-1, ICAM-1, a ligand reactive with LAM-1, endoglin, and even MHC Class II (cytokine-inducible, e.g., by IL-1, TNF-α, IFN-γ, IL-4 and/or TNF-β); and E-selectin, P-selectin, PDGF and ICAM-1 (coagulant-inducible e.g., by thrombin, Factor IX/IXa, Factor X/Xa and/or plasmin).

The following patents and patent applications are specifically incorporated herein by reference for the purposes of even further supplementing the present teachings regarding the preparation and use of immunotoxins directed against expressed, adsorbed, induced or localized markers of tumor vasculature: U.S. application Ser. No. 08/482,369, Issue Fee paid Oct. 20, 1998; U.S. Pat. Nos. 5,855,866; 5,965,132;

6,051,230; 6,004,555; 5,877,289; 6,004,554; 5,776,427; 5,863,538; 5,660,827 and 6,036,955.

Further tumor vasculature targeting compositions and methods include those targeting aminophospholipids, such as phosphatidylserine and phosphatidylethanolamine, recently discovered to be accessible, specific markers of tumor blood vessels. Administration of anti-aminophospholipid antibodies alone is sufficient to induce thrombosis and tumor regression. The present invention can thus be effectively combined with unconjugated, anti-phosphatidylserine and/or phosphatidylethanolamine antibodies; or immunoconjugates of such antibodies can be used.

The following provisional patent applications are specifically incorporated herein by reference for the purposes of even further supplementing the present teachings regarding the preparation and use of anti-aminophospholipid antibodies and immunotoxins: provisional application Serial No. 60/092,672, filed Jul. 13, 1998, and provisional application Serial No. 60/092,589, filed Jul. 13, 1998. Application Serial No. 60/092,589 is further incorporated herein by reference for the purposes of further supplementing the present teachings regarding the use of aminophospholipid binding protein conjugates, such as annexin conjugates, for use in delivering toxins and coagulants to tumor blood vessels and for inducing thrombosis and tumor regression.

Suitable tumor stromal targets include components of the tumor extracellular matrix or stroma, or components those bound therein; including basement membrane markers, type IV collagen, laminin, heparan sulfate, proteoglycan, fibronectins, activated platelets, LIBS and tenascin. A preferred target for such uses is RIBS.

The following patents and patent applications are specifically incorporated herein by reference for the purposes of even further supplementing the present teachings regarding the preparation and use of tumor stromal targeting agents: U.S. applications Ser. No. 08/482,369 (U.S. Pat. No. 6,093,399); Ser. Nos. 08/485,482; 08/487,427 (U.S. Pat. No. 6,004,555); Ser. No. 08/479,733 (U.S. Pat. No. 5,877,289); Ser. Nos. 08/472,631; and 08/479,727 and 08/481,904 (U.S. Pat. No. 6,036,955).

The second anti-cancer therapeutics may be operatively attached to any of the cytotoxic or otherwise anti-cellular agents described herein for use in the VEGFR2-blocking, anti-VEGF antibody or 2C3-based immunotoxins. However, suitable anti-cellular agents also include radioisotopes. Toxin moieties will be preferred, such as ricin A chain and deglycosylated A chain (dgA).

The second, targeted agent for optional use with the invention may comprise a targeted component that is capable of promoting coagulation, i.e., a coaguligand. Here, the targeting antibody or ligand may be directly or indirectly, e.g., via another antibody, linked to any factor that directly or indirectly stimulates coagulation, including any of those described herein for use in the VEGFR2-blocking, anti-VEGF antibody or 2C3-based coaguligands. Preferred coagulation factors for such uses are Tissue Factor (TF) and TF derivatives, such as truncated TF (tTF), dimeric and multimeric TF, and mutant TF deficient in the ability to activate Factor VII.

Effective doses of immunotoxins and coaguligands for combined use in the treatment of cancer will be between about 0.1 mg/kg and about 2 mg/kg, and preferably, of between about 0.8 mg/kg and about 1.2 mg/kg, when administered via the IV route at a frequency of about 1 time per week. Some variation in dosage will necessarily occur depending on the condition of the subject being treated. The physician responsible for administration will determine the appropriate dose for the individual subject.

G5. ADEPT and Prodrug Therapy

The VEGFR2-blocking, anti-VEGF antibody or 2C3-based antibodies of the present invention may be used in conjunction with prodrugs, wherein the VEGFR2-blocking, anti-VEGF antibody or 2C3-based antibody is operatively associated with a prodrug-activating component, such as a prodrug-activating enzyme, which converts a prodrug to the more active form only upon contact with the antibody. This technology is generally termed "ADEPT", and is described in, e.g., WO 95/13095; WO 97/26918, WO 97/24143, and U.S. Pat. Nos. 4,975,278 and 5,658,568, each specifically incorporated herein by reference.

The term "prodrug", as used herein, refers to a precursor or derivative form of a biologically or pharmaceutically active substance that exerts reduced cytotoxic or otherwise anticellular effects on targets cells, including tumor vascular endothelial cells, in comparison to the parent drug upon which it is based. Preferably, the prodrug or precursor form exerts significantly reduced, or more preferably, negligible, cytotoxic or anticellular effects in comparison to the "native" or parent form. "Prodrugs" are capable of being activated or converted to yield the more active, parent form of the drug.

The technical capability to make and use prodrugs exists within the skill of the ordinary artisan. Willman et al. (1986) and Stella et al. (1985) are each specifically incorporated herein by reference for purposes of further supplementing the description and teaching concerning how to make and use various prodrugs. Exemplary prodrug constructs that may be used in the context of the present invention include, but are not limited to, phosphate-containing prodrugs (U.S. Pat. No. 4,975,278), thiophosphate-containing prodrugs, sulfate-containing prodrugs, peptide-based prodrugs (U.S. Pat. Nos. 5,660,829; 5,587,161; 5,405,990; WO 97/07118), D-amino acid-modified prodrugs, glycosylated prodrugs (U.S. Pat. Nos. 5,561,119; 5,646,298; 4,904,768, 5,041,424), β-lactam-containing prodrugs, optionally substituted phenoxyacetamide-containing prodrugs (U.S. Pat. No. 4,975,278), optionally substituted phenylacetamide-containing prodrugs, and even 5-fluorocytosine (U.S. Pat. No. 4,975,278) and 5-fluorouridine prodrugs and the like, wherein each of the patents are specifically incorporated herein by reference.

The type of therapeutic agent or cytotoxic drug that can be used in prodrug form is virtually limitless. The more cytotoxic agents will be preferred for such a form of delivery, over, e.g., the delivery of coagulants, which are less preferred for use as prodrugs. All that is required in forming the prodrug is to design the construct so that the prodrug is substantially inactive and the "released" or activated drug has substantial, or at least sufficient, activity for the intended purpose.

Various improvements on the original prodrugs are also known and contemplated for use herewith, as disclosed in WO 95/03830; EP 751,144 (anthracyclines); WO 97/07097 (cyclopropylindoles); and WO 96/20169. For example, prodrugs with reduced Km are described in U.S. Pat. No. 5,621,002, specifically incorporated herein by reference, which may be used in the context of the present invention. Prodrug therapy that be conducted intracellularly is also known, as exemplified by WO 96/03151, specifically incorporated herein by reference, and can be practiced herewith.

For use in ADEPT, the agent that activates or converts the prodrug into the more active drug is operatively attached to the VEGFR2-blocking, anti-VEGF antibody or 2C3-like antibody. The VEGFR2-blocking, anti-VEGF antibody or 2C3-like antibody thus localizes the prodrug converting capability within the angiogenic site, preferably, within the tumor vasculature and stroma, so that active drug is only produced in such regions and not in circulation or in healthy tissues.

Enzymes that may be attached to VEGFR2-blocking, anti-VEGF antibody or 2C3-based antibodies to function in prodrug activation include, but are not limited to, alkaline phosphatase for use in combination with phosphate-containing prodrugs (U.S. Pat. No. 4,975,278); arylsulfatase for use in combination with sulfate-containing prodrugs (U.S. Pat. No. 5,270,196); peptidases and proteases, such as serratia protease, thermolysin, subtilisin, carboxypeptidase (U.S. Pat. Nos. 5,660,829; 5,587,161; 5,405,990) and cathepsins (including cathepsin B and L), for use in combination with peptide-based prodrugs; D-alanylcarboxypeptidases for use in combination with D-amino acid-modified prodrugs; carbohydrate-cleaving enzymes such as β-galactosidase and neuramimidase for use in combination with glycosylated prodrugs (U.S. Pat. Nos. 5,561,119; 5,646,298); β-lactamase for use in combination with β-lactam-containing prodrugs; penicillin amidases, such as penicillin V amidase (U.S. Pat. No. 4,975,278) or penicillin G amidase, for use in combination with drugs derivatized at their amino nitrogens with phenoxyacetamide or phenylacetamide groups; and cytosine deaminase (U.S. Pat. Nos. 5,338,678; 5,545,548) for use in combination with 5-fluorocytosine-based prodrugs (U.S. Pat. No. 4,975,278), wherein each of the patents are specifically incorporated herein by reference.

Antibodies with enzymatic activity, known as catalytic antibodies or "abzymes", can also be employed to convert prodrugs into active drugs. Abzymes based upon VEGFR2-blocking, anti-VEGF antibody or 2C3-like antibodies thus form another aspect of the present invention. The technical capacity to make abzymes also exists within one of ordinary skill in the art, as exemplified by Massey et al. (1987), specifically incorporated herein by reference for purposes of supplementing the abzyme teaching. Catalytic antibodies capable of catalyzing the breakdown of a prodrug at the carbamate position, such as a nitrogen mustard aryl carbamate, are further contemplated, as described in EP 745,673, specifically incorporated herein by reference.

H. Diagnostics and Imaging

The present invention further provides in vitro and in vivo diagnostic and imaging methods. Such methods are applicable for use in generating diagnostic, prognostic or imaging information for any angiogenic disease, as exemplified by arthritis, psoriasis and solid tumors, but including all the angiogenic diseases disclosed herein. Outside the field of tumor diagnostics and imaging, these aspects of the invention are most preferred for use in in vitro diagnostic tests, preferably either where samples can be obtained non-invasively and tested in high throughput assays and/or where the clinical diagnosis in ambiguous and confirmation is desired.

H1. Immunodetection Methods and Kits

In still further embodiments, the present invention concerns immunodetection methods for binding, purifying, removing, quantifying or otherwise generally detecting VEGF and for diagnosing angiogenic diseases. The VEGFR2-blocking, anti-VEGF antibodies of the present invention, such as 2C3, may be employed to detect VEGF in vivo (see below), in isolated tissue samples, biopsies or swabs and/or in homogenized tissue samples. Such immunodetection methods have evident diagnostic utility, but also have applications to non-clinical samples, such as in the titering of antigen samples, and the like.

The steps of various useful immunodetection methods have been described in the scientific literature, such as, e.g., Nakamura et al. (1987, incorporated herein by reference). In general, the immunobinding methods include obtaining a sample suspected of containing VEGF and contacting the sample with VEGFR2-blocking, anti-VEGF antibodies, such as 2C3, under conditions effective to allow the formation of immunocomplexes. In such methods, the antibody may be linked to a solid support, such as in the form of a column matrix, and the sample suspected of containing VEGF will be applied to the immobilized antibody.

More preferably, the immunobinding methods include methods for detecting or quantifying the amount of VEGF in a sample, which methods require the detection or quantification of any immune complexes formed during the binding process. Here, one would obtain a sample suspected of containing VEGF and contact the sample with an antibody in accordance herewith and then detect or quantify the amount of immune complexes formed under the specific conditions.

The biological sample analyzed may be any sample that is suspected of containing VEGF, generally from an animal or patient suspected of having an angiogenic disease. The samples may be a tissue section or specimen, a biopsy, a swab or smear test sample, a homogenized tissue extract or separated or purified forms of such.

Contacting the chosen biological sample with the antibody under conditions effective and for a period of time sufficient to allow the formation of immune complexes (primary immune complexes) is generally a matter of simply adding an antibody composition to the sample and incubating the mixture for a period of time lone enough for the antibodies to form immune complexes with, i.e., to bind to, any VEGF present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

The detection of immunocomplex formation is well known in the art and may be achieved through the application of numerous approaches. These methods are generally based upon the detection of a label or marker, such as any radioactive, fluorescent, biological or enzymatic tags or labels known in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. The use of enzymes that generate a colored product upon contact with a chromogenic substrate are generally preferred. Secondary binding ligand, such as a second antibody or a biotin/avidin ligand binding arrangement, may also be used, as is known in the art.

The VEGFR2-blocking, anti-VEGF antibodies, such as 2C3, employed in the detection may themselves be linked to a detectable label, wherein one would then simply detect this label, thereby allowing the amount of the primary immune complexes in the composition to be determined.

Preferably, the primary immune complexes are detected by means of a second binding ligand that has binding affinity for the antibodies of the invention. In such cases, the second binding ligand may be linked to a detectable label. The second binding ligand is itself often an antibody, and may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the first antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if desired.

In the clinical diagnosis or monitoring of patients with an angiogenic disease, the detection of VEGF, or an increase in the levels of VEGF, in comparison to the levels in a corresponding biological sample from a normal subject is indicative of a patient with an angiogenic disease.

However, as is known to those of skill in the art, such a clinical diagnosis would not likely be made on the basis of this method in isolation. Those of skill in the art are very familiar with differentiating between significant expression of a biomarker, which represents a positive identification, and low level or background expression of a biomarker. Indeed, background expression levels are often used to form a "cut-off" above which increased staining will be scored as significant or positive.

H2. Imaging

These aspects of the invention are preferred for use in tumor imaging methods and combined tumor treatment and imaging methods. VEGFR2-blocking, anti-VEGF antibodies or 2C3-based antibodies that are linked to one or more detectable agents are envisioned for use in imaging per se, or for pre-imaging the tumor to form a reliable image prior to treatment. Such compositions and methods can also be applied to the imaging and diagnosis of any other angiogenic disease or condition, particularly non-malignant tumors, atherosclerosis and conditions in which an internal image is desired for diagnostic or prognostic purposes or to design treatment.

VEGFR2-blocking, anti-VEGF antibody or 2C3-based imaging antibodies will generally comprise a VEGFR2-blocking, anti-VEGF antibody or 2C3-based antibody operatively attached, or conjugated to, a detectable label. "Detectable labels" are compounds or elements that can be detected due to their specific functional properties, or chemical characteristics, the use of which allows the component to which they are attached to be detected, and further quantified if desired. In antibody conjugates for in vivo diagnostic protocols or "imaging methods" labels are required that can be detected using non-invasive methods.

Many appropriate imaging agents are known in the art, as are methods for their attachment to antibodies and binding ligands (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

An example of detectable labels are the paramagnetic ions. In this case, suitable ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III). Fluorescent labels include rhodamine, fluorescein and renographin. Rhodamine and fluorescein are often linked via an isothiocyanate intermediate.

In the case of radioactive isotopes for diagnostic applications, suitable examples include $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technetium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled VEGFR2-blocking, anti-VEGF antibody or 2C3-based antibodies for use in the present invention may be produced according to well-known methods in the art. For instance, intermediary functional groups that are often used to bind radioisotopic metallic ions to antibodies are diethylenetriaminepentaacetic acid (DTPA) and ethylene diaminetetracetic acid (EDTA).

Monoclonal antibodies can also be iodinated by contact with sodium or potassium iodide and a chemical oxidizing agent such as sodium hypochlorite, or an enzymatic oxidizing agent, such as lactoperoxidase. Antibodies according to the invention may be labeled with technetium-$^{99}$m by ligand exchange process, for example, by reducing pertechnate with stannous solution, chelating the reduced technetium onto a Sephadex column and applying the antibody to this column; or by direct labeling techniques, e.g., by incubating pertechnate, a reducing agent such as SNCl$_2$, a buffer solution such as sodium-potassium phthalate solution, and the antibody.

Any of the foregoing type of detectably labeled VEGFR2-blocking, anti-VEGF antibody or 2C3-based antibodies may be used in the imaging or combined imaging and treatment aspects of the present invention. They are equally suitable for use in in vitro diagnostics. Dosages for in vivo imaging embodiments are generally less than for therapy, but are also dependent upon the age and weight of a patient. One time doses should be sufficient.

The in vivo diagnostic or imaging methods generally comprise administering to a patient a diagnostically effective amount of a VEGFR2-blocking, anti-VEGF antibody or 2C3-based antibody that is conjugated to a marker that is detectable by non-invasive methods. The antibody-marker conjugate is allowed sufficient time to localize and bind to VEGF within the tumor. The patient is then exposed to a detection device to identify the detectable marker, thus forming an image of the tumor.

H3. Diagnostic Kits

In still further embodiments, the present invention provides diagnostic kits, including both immunodetection and imaging kits, for use with the immunodetection and imaging methods described above. Accordingly, the VEGFR2-blocking, anti-VEGF antibodies, such as 2C3, are provided in the kit, generally comprised within a suitable container.

For immunodetection, the antibodies may be bound to a solid support, such as a well of a microtitre plate, although antibody solutions or powders for reconstitution are preferred. The immunodetection kits preferably comprise at least a first immunodetection reagent. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present invention. These kits may contain antibody-label conjugates either in fully conjugated form, in the form of intermediates, or as separate moieties to be conjugated by the user of the kit.

The imaging kits will preferably comprise a VEGFR2-blocking, anti-VEGF antibody, such as 2C3, that is already attached to an in vivo detectable label. However, the label and attachment means could be separately supplied.

Either kit may further comprise control agents, such as suitably aliquoted compositions of VEGF, whether labeled or unlabeled, as may be used to prepare a standard curve for a detection assay. The components of the kits may be packaged either in aqueous media or in lyophilized form.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits may also include other diagnostic reagents for use in the diagnosis of any one or more angiogenic diseases. Preferably, second diagnostics not based upon VEGF binding will be used.

The kits of the present invention will also typically include a means for containing the antibody, and any other reagent containers in close confinement for commercial sale. Such containers may include injection or blow-molded plastic containers into which the desired vials are retained.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Generation and Unique Characteristics of Anti-VEGF Antibody 2C3

A. Materials and Methods

1. Immunogens

Peptides corresponding to the N-terminal 26 amino acids of human VEGF (huVEGF; SEQ ID NO:10) and the N-terminal 25 amino acids of guinea pig VEGF (gpVEGF; SEQ ID NO:11) were synthesized by the Biopolymers Facility of the Howard Hughes Medical Institute at UT Southwestern Medical Center at Dallas. The peptides had the following sequences (N to C):

```
APMAEGGGQNHHEVVKFMDVYQRSYC;     SEQ ID NO:10;

and

APMAEGEQKPREVVKIFMDVYKRSYC;     SEQ ID NO:11.
```

Peptides were conjugated via the C-terminal cysteine to thyroglobulin using succinimidyl 4-(N-maleimidomethyl) cyclohexane-1-carboxylate (SMCC) linker (Pierce, Rockford, Ill.). Control conjugates were also prepared that consisted of L-cysteine linked to thyroglobulin. Conjugates were separated from free peptide or linker by size exclusion chromatography.

Recombinant human VEGF was also separately used as an immunogen (obtained from Dr. S. Ramakrishnan, University of Minnesota, Minneapolis, Minn.).

2. Hybridomas

For the production of anti-gpVEGF antibody producing hybridomas, C57/B1–6 mice were immunized with the gpVEGF-peptide-thyroglobulin conjugate in TiterMax adjuvant (CytRX Co., Norcross, Ga.). For the production of anti-human VEGF antibodies, BALB/c mice were immunized with either the huVEGF-peptide-thyroglobulin conjugate or recombinant human VEGF in TiterMax. Three days after the final boost spleenocytes were fused with myeloma P3X63AG8.653 (American Type Culture Collection, Rockville, Md.) cells and were cultured as described by Morrow et al. (1990; incorporated herein by reference).

3. Antibody Purification

IgG antibodies (2C3, 12D7, 3E7) were purified from tissue culture supernatant by ammonium sulfate precipitation and Protein A chromatography using the Pierce ImmunoPure Binding/Elution buffering system (Pierce).

IgM antibodies (GV39M, 11B5, 7G3) were purified from tissue culture supernatant by 50% saturated ammonium sulfate precipitation, resuspension of the pellet in PBS (pH 7.4) and dialysis against dH$_2$O to precipitate the euglobulin. The dH$_2$O precipitate was resuspended in PBS and fractionated by size-exclusion chromatography on a Sepharose S300 column (Pharmacia). The IgM fraction was 85–90% pure, as judged by SDS-PAGE.

4. Control Antibodies

Various control antibodies have been used throughout these studies including mAb 4.6.1 (mouse anti-human VEGF from Genentech, Inc.), Ab-3 (mouse anti-human VEGF from OncogeneScience, Inc.), A-20 (rabbit anti-human VEGF from Santa Cruz Biotechnology, Inc., Santa Cruz, Calif.), OX7 (mouse anti-rat Thy1.1 from Dr. A. F. Williams, MRC Cellular Immunology Unit, Oxford, UK), MTSA (a mouse myeloma IgM of irrelevant specificity from Dr. E. S. Vitetta, UT-Southwestern, Dallas, Tex.), 1A8

(mouse anti-mouse Flk-1; Philip E. Thorpe and colleagues), MECA 32 (rat anti-mouse endothelium from Dr. E. Butcher, Stanford University, Stanford, Calif.), and TEC 11 (mouse anti-human endoglin; U.S. Pat. No. 5,660,827).

5. Initial Screening

For the initial screening, 96-well ELISA plates (Falcon, Franklin Lakes, N.J.) were coated with 250 ng of either the VEGF peptide or VEGF-Cys-thyroglobulin conjugate and blocked with 5% casein acid hydrolysate (Sigma, St. Louis, Mo.). Supernatants from the anti-gpVEGF hybridomas and the initial anti-human VEGF hybridomas were screened on the antigen coated plates through a dual indirect ELISA technique (Crowther, 1995).

Hybridomas that showed preferential reactivity with VEGF peptide-thyroglobulin but no or weak reactivity with Cys-thyroglobulin were further screened through immunohistochemistry (described below) on frozen sections of tumor tissue.

6. Immunohistochemistry

Guinea pig line 10 hepatocellular carcinoma tumor cells (obtained from Dr. Ronald Neuman, NIH, Bethesda, Md.) were grown in strain 2 guinea pigs (NCI, Bethesda, Md.). The human tumors NCI-H358 non-small cell lung carcinoma (NSCLC), NCI-H460 NSCLC (both obtained from Dr. Adi Gazdar, UT Southwestern, Dallas, Tex.), HT29 colon adenocarcinoma (American Type Culture Collection), and L540CY Hodgkin's lymphoma (obtained from Professor V. Diehl, Cologne, Germany) were grown as xenografts in CB17 SCID mice (Charles River, Wilmington, Mass.).

Tumors were snap frozen in liquid nitrogen and stored at $-70°$ C. Frozen samples of tumor specimens from patients were obtained from the National Cancer Institute Cooperative Human Tissue Network (Southern Division, Birmingham, Ala.). Immunohistochemistry was performed as described by Burrows et al. (1995).

7. ELISA Analysis

Hybridoma supernatants from animals immunized with VEGF were screened through a differential indirect ELISA technique employing three different antigens: human VEGF alone, VEGF:Flk-1/SEAP complex, and Flk-1/SEAP alone. For the human VEGF alone, certain ELISA plates were coated with 100 ng of VEGF.

For Flk-1/SEAP alone, other ELISA plates were coated with 500 ng of Flk-1/SEAP, a soluble form of the mouse VEGF receptor (cells secreting Flk-1/SEAP were obtained from Dr. Ihor Lemischka, Princeton University, Princeton, N.J.). The Flk-1/SEAP protein was produced and purified as described by Tessler et al. (1994). Basically, the extracellular domain of Flk-1 (sFlk-1) was produced in *Spodoptera frugiperda* (Sf9) cells and purified by immunoaffinity techniques utilizing a monoclonal anti-Flk-1 antibody (1A8). sFlk-1 was then biotinylated and bound on avidin-coated plates.

To prepare plates coated with VEGF;Flk-1/SEAP complex, purified sFlk-1 was biotinylated and reacted with VEGF overnight at 4° C. in binding buffer (10MM HEPES, 150 mM NaCl, 20 µg/ml bovine serum albumin and 0.1 µg/ml heparin) at a molar ratio of sFlk-1 to VEGF of 2.5:1 to encourage dimer formation. The VEGF:sFlk-1 complex was then incubated in avidin coated wells of a 96 well microtiter plate to produce plates coated with VEGF associated with its receptor.

The reactivity of the antibodies with VEGF alone, biotinylated sFlk-1 and VEGF:sFlk-1 complex was then determined in controlled studies using the three antigens on avidin-coated plates. The reactivity was determined as described above for the initial screening.

A capture ELISA was also developed. In the capture ELISA, microtiter plates were-coated overnight at 4° C. with 100 ng of the indicated antibody. The wells were washed and blocked as above, then incubated with various concentrations of biotinylated VEGF or VEGF:sFlk-1-biotin. Streptavidin conjugated to peroxidase (Kirkegaard & Perry Laboratories, Inc.), diluted 1:2000, was used as a second layer and developed.

Competition ELISA studies were performed by first labeling the antibodies with peroxidase according to the manufacturer's instructions (EZ-Link Activated Peroxidase, Pierce). The antigen used for the competition studies with 12D7, 3E7, 2C3, and 7G3 was VEGF-biotin captured by avidin on an ELISA plate. Approximately 0.5–2.0 µg/ml of peroxidase labeled test antibody was incubated on the plate in the presence of either buffer alone, an irrelevant IgG, or the other anti-VEGF competing antibodies in a 10–100 fold excess.

The binding of the labeled antibody was assessed by addition of 3,3'5,5'-tetramethylbenzidine (TMB) substrate (Kirkegaard and Perry Laboratories, Inc). Reactions were stopped after 15 min with 1M $H_3PO_4$ and read spectrophotometrically at 450 nM. The assay was done in triplicate at least twice for each combination of labeled and competitor antibody. Two antibodies were considered to be in the same epitope group if they cross-blocked each other's binding by greater than 80%.

GV39M and 11B5 did not retain binding activity after peroxidase labeling but tolerated biotinylation. GV39M and 11B5 were biotinylated and tested against VEGF:sFlk-1 that had either been captured by the anti-Flk-1 antibody (1A8) or coated directly on an ELISA plate.

8. Western Blot Analysis

Purified recombinant VEGF in the presence of 5% fetal calf serum was separated by 12% SDS-PAGE under reducing and non-reducing conditions and transferred to nitrocellulose. The nitrocellulose membrane was blocked using Sea-Block PP82-41 (East Coast Biologics, Berwick, Me.), and probed with primary antibodies using a mini-blotter apparatus (Immunetics, Cambridge, Mass.). The membranes were developed after incubation with the appropriate peroxidase-conjugated secondary antibody by ECL enhanced chemiluminescence.

B. Results 1. 2C3 has a Unique Epitope Specificity

Table 1 summarizes information on the class/subclass of different anti-VEGF antibodies, the epitope groups that they recognize on VEGF, and their preferential binding to VEGF or VEGF:receptor (VEGF:Flk-1) complex. In all instances the antibodies bound to VEGF121 and VEGF165 equally well and produced essentially the same results. The results below are for VEGF 165 unless stipulated otherwise.

TABLE 1

SUMMARY OF ANTI-VEGF ANTIBODY PROPERTIES

| Epitope Group[1] | Clone | Isotype | VEGF Immunogen[2] | Predominant Reactivity[3] |
|---|---|---|---|---|
| 1 | GV39M | IgM, k | Gp N-terminus | VEGF:Flk-1 |
| 1 | 11B5 | IgM, k | Hu N-terminus | VEGF:Flk-1 |
| 2 | 3E7 | IgG1, l | Hu N-terminus | VEGF and VEGF:Flk-1 |

TABLE 1-continued

SUMMARY OF ANTI-VEGF ANTIBODY PROPERTIES

| Epitope Group[1] | Clone | Isotype | VEGF Immunogen[2] | Predominant Reactivity[3] |
|---|---|---|---|---|
| 2 | 7G3 | IgM, k | Hu N-terminus | VEGF and VEGF:Flk-1 |
| 3 | 12D7 | IgG1, k | Hu N-terminus | VEGF |
| 4 | 2C3 | IgG2a, k | rHuVEGF | VEGF |
| [4]centered around aa 89–94 | A4.6.1 | IgG1 | | VEGF |

[1]Epitope groups were determined through competitive ELISA.
[2]Mice were immunized with a synthetic peptide corresponding to either the N-terminal 26 amino acids of human VEGF (11B5, 3E7, 7G3, and 12D7), the N-terminal 25 amino acids of guinea pig VEGF (GV39M), or with full length recombinant human VEGF (2C3).
[3]The antibodies were screened in an indirect and a capture ELISA for reactivity with VEGF alone or with VEGF associated with sFlk-1 (VEGF:Flk-1).
[4]A4.6.1 has a precisely defined epitope, which is distinct from epitope Group 4 recognized by 2C3. The A4.6.1 studies are reported in Kim et al., 1992; Wiesmann et al., 1997; Muller et al., 1998; and Keyt et al., 1996, each incorporated herein by reference.

Competitive binding studies using biotinylated or peroxidase-labeled test antibodies and a 10–100 fold excess of unlabeled competing antibodies showed that 2C3 binds to a unique epitope. These studies first revealed that GV39M and 11B5 cross-blocked each other's binding to VEGF:Flk-1, and that 3E7 and 7G3 cross-blocked each other's binding to VEGF-biotin captured onto avidin. GV39M and 11B5 were arbitrarily assigned to epitope group 1, while 3E7 and 7G3 were assigned to epitope group 2.

2C3 and the remaining antibody, 12D7, did not interfere significantly with each other's binding or the binding of the rest of the antibodies to VEGF or VEGF:receptor. 12D7 was assigned to epitope group 3, and 2C3 was assigned to epitope group 4 (Table 1).

As tabulated above, 2C3 sees a different epitope to the antibody A4.6.1. The inventors' competition studies showed that 2C3 and A4.6.1 are not cross-reactive. The epitope recognized by A4.6.1 has also been precisely defined and is a continuous epitope centered around amino acids 89–94 (Kim et al., 1992; Wiesmann et al, 1997; Muller et al., 1998; Keyt et al., 1996; each incorporated herein by reference). There are also a number known differences between 2C3 and A4.6.1 (see below).

2. 2C3 Can Bind to Free VEGF

There were marked differences in the ability of the antibodies to bind to soluble VEGF in free and complexed form (Table 2). These studies provide further evidence of the unique nature of 2C3. Table 2 shows that GV39M and 11B5 display a strong preference for the VEGF:receptor complex, with half-maximal binding being attained with VEGF:Flk-1 at 5.5 and 2 nM respectively as compared with 400 and 800 nM respectively for free VEGF in solution.

In contrast, 2C3 and 12D7 displayed a preference for free VEGF, with half-maximal binding being attained at 1 and 20 nM respectively as compared with 150 and 250 nM respectively for the VEGF:Flk-1 complex. However, 2C3 localizes to tumor vasculature, as well as tumor stroma, after injection in vivo (see below).

3E7 bound equally well to free VEGF and the VEGF:Flk-1 complex, with half-maximal binding being attained at 1 nM for both.

TABLE 2

ELISA CAPTURE OF VEGF vs. VEGF:FLK-1

| | Concentration giving 50% maximal binding (nM)[1] | | Ratio of |
|---|---|---|---|
| Clone | VEGF | VEGF:Flk-1 | VEGF/VEGF:Flk-1[2] |
| GV39M | 400* | 5.5 | 72.7 |
| 11B5 | 800* | 2 | 400.0 |
| 3E7 | 0.9 | 1 | 0.9 |
| 12D7 | 20 | 250* | 0.1 |
| 2C3 | 1 | 150 | 0.007 |
| Mab 4.6.1[3] | 0.3 | 500* | 0.0006 |
| 1A8 | NR[4] | 1.5 | |
| Control | NR | 600* | |

*Extrapolated value
[1]Half-maximal binding values were determined by titrating biotinylated VEGF and biotinylated sFlk-1 complexed with VEGF in triplicate onto wells coated with the indicated antibody and then developing with peroxidase-labeled avidin.
[2]Ratios greater than 1.0 indicate a preference of antibody for complex (VEGF:Flk-1) while ratios less than 1.0 indicate a preference for VEGF.
[3]Control antibodies used included; 1A8 (mouse anti-Flk-1), Mab 4.6.1 (mouse anti-human VEGF from Genentech), and an irrelevant IgM as a negative control.
[4]NR = no reaction detected.

3. 2C3 Recognizes a Non-Conformationally-Dependent Epitope

Western blot analysis shows that 12D7, 2C3 and 7G3 react with denatured VEGF121 and VEGF 165 under reducing and non-reducing conditions. These antibodies therefore appear to recognize epitopes that are not conformationally-dependent.

In contrast, GV39M, 11B5, and 3E7 did not react with VEGF on western blots, possibly because they recognize an epitope on the N-terminus of VEGF that is conformationally-dependent and is distorted under denaturing conditions.

Western blot analyses of anti-VEGF antibodies were conducted by separating VEGF165 in the presence of 5% FCS using SDS-PAGE on a 12% gel and analyzing by a standard western blotting protocol using ECL detection. The primary antibodies were incubated with the nitrocellulose membrane using a multi-lane mini-blotter apparatus. Control antibodies included: Ab-3, a monoclonal IgG specific for VEGF from Oncogene Science at 1 μg/ml, A-20, a rabbit anti-VEGF antibody from Santa Cruz Biotechnology, Inc. at 5 μg/ml, and an IgG of irrelevant specificity at 10 μg/ml.

A typical western blot for the different antibodies, including 2C3 at 5 μg/ml, showed dimeric VEGF as a large band at approximately 42 kd. A multimer of VEGF at approximately 130kd was also evident with 12D7, 7G3, and a positive control antibody.

4. Tumor Immunohistochemistry

Tumors examined through immunohistochemistry were human tumors of various types from cancer patients, transplantable human tumor xenografts of various types grown in mice, guinea pig Line 10 tumor grown in guinea pig, and mouse 3LL tumor grown in mice (see legend to Table 3 for details).

The immunohistochemical reactivity of 3E7, GV39M, and 11B5 on NCI-H358 human NSCLC xenografts was determined and compared with control antibodies (an IgG of irrelevant specificity; A-20, a rabbit anti-VEGF antibody; and MECA 32, a rat anti-mouse endothelial cell antibody). 8 μm frozen sections of NCI-H358 human NSCLC grown in SCID mice were stained using an indirect immunoperoxidase technique and were counterstained with hematoxylin.

It was determined that GV39M and 11B5, which recognize epitope group 1 on VEGF, stained vascular endothelial cells strongly and perivascular connective tissue moderately in all tumors examined. The epitope group 1 antibodies differed in their reactivity with tumor cells, in that GV39M reacted only weakly with tumor cells while 11B5 reacted more strongly. Approximately 80% of endothelial cells that were stained by MECA 32 (mouse) or TEC 11 (human) were also stained by GV39M and 11B5.

3E7 and 7G3, which recognize VEGF epitope group 2, showed reactivity with vascular endothelial cells, connective tissue, and tumor cells in all tumors examined (Table 3). The intensity of endothelial cell staining was typically stronger than the tumor cell or connective tissue staining, especially when the antibodies were applied at low (1–2 μg/ml) concentrations where there was a noticeably increased selectivity for vascular endothelium.

human tumor sections, suggesting that 3E7 has a lower affinity for mouse VEGF. These results accord with analysis by indirect ELISA, which has shown that all the antibodies except 2C3 react with mouse VEGF.

EXAMPLE II

2C3 Inhibits Endothelial Cell Migration

A. Materials and Methods

Endothelial Cell Growth Assay

Adult bovine aortic endothelial (ABAE) cells were plated into 96-well tissue culture plates at 1500 cells/well and grown in the presence of 0.5 nM human VEGF with the addition of the various sample and control antibodies. Control wells received media with or without VEGF.

After 4 days of incubation, the cells were quantified by an MTS (3-(4,5-dimethylthiazol-2-yl)-5-(3-carboxylmethoxyphenyl)-2-(4-sulfophenyl)-2H-tetrazolium, inner salt) conversion assay, where MTS conversion to a formazan is proportional to cell number and can be followed by absorbance at 490 nM (Cell Titer 96 AQueous One Solution Cell Proliferation Assay, Promega, Madison, Wis.). The assay was performed according to the manufacturer's instructions.

TABLE 3

IMMUNOHISTOCHEMICAL REACTIVITY OF
ANTI-VEGF ANTIBODIES ON TUMOR SECTIONS
Endothelial Cell Staining

| Group | Clone[1] | Reactivity[2] | Xenograft[3] (various) | Hu Tumor[4] (various) | Guinea Pig Tumor[5] (Line 10) | Mouse Tumor[6] (3LL) |
|---|---|---|---|---|---|---|
| 1 | GV39M | EC > CT > TC | 3–4+ | 2–3+ | 4+ | 3+ |
| 1 | 11B5 | EC > CT = TC | 3+ | 3+ | 3+ | 3+ |
| 2 | 3 E7 | EC > CT = TC | 2+ | 2+ | 2+ | 1–2+ |
| 2 | 7G3 | EC > CT = TC | 3+ | 2–3+ | 3+ | 2+ |
| 3 | 12D7 | NR | — | — | — | — |
| 4 | 2C3 | NR | — | — | — | — |

Immunohistochemical analysis was performed on acetone fixed frozen sections of tumor tissues through standard immunohistochemical techniques. The sections were examined microscopically and scored for reactivity as follows: –, negative; +/–, very weak; 1+, weak; 2+, moderate; 3+, strong; 4+, very strong.
[1]2C3 and 12D7 were applied at 20 μg/ml; all other antibodies were at 5–10 μg/ml.
[2]Reactivity definitions: EC = endothelium; CT = connective tissue; TC = tumor cell; NR = no reaction
[3]Human tumor xenografts tested; NCI-H358 NSCLC, NCI-H460 NSCLC, HT29 colon adenocarcinoma, L540 Hodgkin's lymphoma.
[4]Human tumors tested; Soft tissue sarcoma, Hodgkin's lymphoma, Renal, Breast, Parotid, Colon, Lung, and Endometrial carcinomas.
[5]Reactivity with guinea pig VEGF in line 10 guinea pig tumor sections.
[6]Reactivity with mouse VEGF in mouse 3LL Lewis Lung carcinoma tumor sections.

12D7 and 2C3 did not stain frozen sections of any tumor tissues, probably because acetone fixation of the tissue destroyed antibody binding. However, 2C3 localized to tumor tissue after injection in vivo (see below).

GV39M, 11B5, 3E7 and 7G3 reacted with rodent vasculature on frozen sections of guinea pig line 10 tumor grown in guinea pigs and mouse 3LL tumor grown in mice. GV39M, 11B5, and 7G3 reacted as strongly with guinea pig and mouse tumor vasculature as they did with human vasculature in human tumor specimens. 3E7 stained the mouse 3LL tumor less intensely than it did the guinea pig or Cell growth was estimated by subtracting the MTS conversion in cultures to which VEGF was not added. Results were expressed as a percentage of the MTS conversion in control cultures to which only VEGF was added (Buttke et al., 1993).

B. Results

Inhibition of VEGF-Mediated Endothelial Cell Growth

The IgG antibodies 3E7 and 12D7, recognizing epitope groups 1–3 on VEGF, did not inhibit VEGF-mediated growth of ABAE cells (FIG. 1), suggesting that they are non-blocking anti-VEGF antibodies whose epitopes are not involved in the VEGF:KDR interaction. The IgM antibody GV39M, also recognizing epitope groups 1–3 on VEGF, likewise did not inhibit VEGF-mediated growth of ABAE cells and is a non-blocking anti-VEGF antibody.

In contrast, 2C3 against epitope 4 on VEGF and a reference neutralizing anti-VEGF antibody, Mab 4.6.1, inhibited VEGF-mediated ABAE growth by 50% at 3 nM and 1 nM respectively (FIG. 1). This indicates that 2C3 can neutralize the mitogenic activity of VEGF.

The definition of 2C3 as blocking Mab distinguishes 2C3 from a range of other antibodies in addition to GV39M, 3E7 and 12D7. Various anti-VEGF antibodies, such as Ab-3, are known to be non-blocking monoclonals, which are clearly distinct from 2C3.

One of the IgM antibodies, 11B5, was toxic to ABAE cells at a concentration of 8 nM or greater. The cells detached within 30 min and within 24 h took up trypan blue dye. This effect appears to be cell type specific since HUVEC, porcine aortic endothelial cells, and bEND.3 cells were unaffected by 11B5 even at 40 nM. The toxic effect of 11B5 appears to be growth factor-independent as it occurred in the absence of added VEGF and in the presence of basic fibroblast growth factor (bFGF).

EXAMPLE III

2C3 Specifically Localizes to Tumors in Vivo

A. Materials and Methods

In Vivo Localization to Human Tumor Xenografts

Tumors were grown subcutaneously in immunocompromised mice (NCI-H358 NSCLC in nu/nu mice and HT29 colon adenocarcinoma in SCID mice) until the tumor volume was approximately 1 cm$^3$. 100 μg of unlabeled antibody for studies using SCID mice, or 100 μg of biotinylated antibody for studies using nude mice, was injected intravenously via a tail vein. Twenty four hours later, the mice were anesthetized, perfused with PBS, and tumor and organs including heart, lungs, liver, kidneys, intestines and spleen were collected and snap frozen in liquid nitrogen.

The tumor and organs from each mouse were sectioned on a cryostat and stained for antibody immunohistochemically as above, with the exception that sections from the nude mice were developed using peroxidase labeled streptavidin-biotin complex (Dako, Carpinteria, Calif.) and the sections from the SCID mice were developed using two peroxidase-conjugated secondary antibodies, a goat anti-mouse IgG+IgM followed by a rabbit anti-goat IgG.

B. Results

In Vivo Localization in Tumor-Bearing Mice

The in vivo localization of 2C3, 3E7, and GV39M in human tumor xenografts was determined. 100 μg of biotinylated 2C3 or isotype-matched control IgG were injected i.v. into nu/nu mice bearing NCI-H358 human NSCLC. 100 μg of GV39M and 3E7 or isotype-matched control IgG were injected into SCID mice bearing HT29 human colonic adenocarcinomas. Twenty-four hours later, the mice were sacrificed, exsanguinated and the tumors and tissues were removed. Frozen sections of the tumors and tissues were analyzed immunohistochemically to determine the binding and distribution of the antibodies (Table 4).

TABLE 4

TISSUE DISTRIBUTION OF ANTI-VEGF ANTIBODIES IN TUMOR BEARING MICE

| | Immunohistochemical Reactivity | | | | | | |
|---|---|---|---|---|---|---|---|
| Antibody | Heart | Lung | Liver | Kidney[1] | Intestine | Spleen | Tumor[2] |
| 2C3 | — | — | — | — | — | — | 3+ |
| 3E7 | — | — | — | — | — | — | 1–2+ |
| GV39M | — | — | — | 2+ | — | — | 2+ |
| Control[3] | — | — | — | — | — | — | — |

Immunohistochemical analysis was performed on acetone fixed frozen sections of tissues, including the tumor, from tumor-bearing mice that had received 100 mg of the indicated antibody intravenously 24 hours prior to sacrifice. The sections were examined microscopically and scored for specific reactivity as follows: −, negative; +/−, very weak; +, weak; 2+, moderate; 3+, strong; 4+, very strong.
[1]GV39M specifically bound endothelial or mesangial cells in the glomeruli of the kidney
[2]3E7 and GV39M specifically bound tumor vascular endothelium while 2C3 specifically bound tumor stroma.
[3]Control = IgM of irrelevant specificity 3E7 specifically localized to vascular endothelium within the tumors. Approximately 70% of MECA 32 positive blood vessels were stained by 3E7 injected in vivo. The larger blood vessels that feed the microvasculature were 3E7-positive. Small microvessels in both the tracks of stroma and in the tumor nests were also positive for 3E7. The intensity of the staining by 3E7 was increased in and around areas of focal necrosis. In necrotic areas of the tumor, extravascular antibody was evident, but in healthy regions of the tumor there was little evidence of extravascular staining. Vascular endothelium in all normal tissues examined, including the kidney, was unstained by 3E7.

GV39M also specifically localized to vascular endothelium of the tumors. Approximately 80% of the MECA 32 positive blood vessels in the tumor were stained by GV39M. The GV39M positive vessels were distributed evenly throughout the tumor, including large blood vessels, but also small capillaries. As with 3E7, the staining intensity of the GV39M positive blood vessels was increased in areas of focal necrosis in the tumor. However, unlike 3E7, endothelial cells or mesangial cells in the kidney glomeruli were also stained. It appears that the staining of the glomeruli by GV39M is antigen-specific, since a control IgM of irrelevant specificity produced no staining of the glomeruli. Vascular endothelium in tissues other than the kidney was not stained by GV39M.

Biotinylated 2C3 produced intense staining of connective tissue surrounding the vasculature of the H358 human NSCLC tumor after i.v. injection. The large tracks of stromal tissue that connect the tumor cell nests were stained by 2C3, with the most intense localization being observed in the largest tracks of stroma. It was not possible to distinguish the vascular endothelium from the surrounding connective tissue in these regions. However, the endothelial cells in vessels not surrounded by stroma, such as in vessels running through the nests of tumor cells themselves, were stained. There was no detectable staining by 2C3 in any of the normal tissues examined.

In the HT29 human tumor model, 2C3 also localized strongly to the connective tissue but the most intense staining was observed in the necrotic regions of the tumor.

EXAMPLE IV

2C3 Inhibits VEGF Binding to VEGFR2, but not VEGFR1

A. Materials and Methods

1. Cell Lines and Antibodies

Porcine aortic endothelial (PAE) cells transfected with either VEGFR1 (PAE/FLT) or VEGFR2 (PAE/KDR) were obtained from Dr. Johannes Waltenberger (Ulm, Germany), prepared as described in Waltenberger et al. (1994, specifically incorporated herein by reference), and were grown in F-12 medium containing 5% FCS, L-glutamine, penicillin, and streptomycin (GPS). bEND.3 cells were obtained from Dr. Werner Risau (Bad Nauheim, Germany) and were grown in DMEM medium containing 5% FCS and GPS. NCI-H358 NSCLC (obtained from Dr. Adi Gazdar, UT-Southwestern, Dallas, Tex.), A673 human rhabdomyosarcoma, and HT1080 human fibrosarcoma (both from American Type Culture Collection) were grown in DMEM medium containing 10% FCS and GPS.

2C3 and 3E7, anti-VEGF monoclonal antibodies, and 1A8, monoclonal anti-Flk-1 antibody, and T014, a polyclonal anti-Flk-1 antibody are as described above in Example I and in Brekken et al. (1998) and Huang et al. (1998), each specifically incorporated herein by reference. A4.6.1, mouse anti-human VEGF monoclonal antibody, was obtained from Dr. Jin Kim (Genentech Inc., CA) and has been described previously (Kim et al., 1992; specifically incorporated herein by reference). Negative control antibodies used were OX7, a mouse anti-rat Thy1.1 antibody (Bukovsky et. al., 1983), obtained from Dr. A. F. Williams (MRC Cellular Immunology Unit, Oxford, UK) and C44, a mouse anti-colchicine antibody (Rouan et al., 1990, obtained from ATCC).

2. ELISA Analysis

The extracellular domain of VEGFR1 (Flt-1/Fc, R&D Systems, Minneapolis) or VEGFR2 (sFlk-1-biotin) was coated directly on wells of a microtiter plate or captured by NeutrAvidin (Pierce, Rockford, Ill.) coated wells, respectively. VEGF at a concentration of 1 nM (40 ng/ml) was incubated in the wells in the presence or absence of 100–1000 nM (15 μg–150 μg/ml) of control or test antibodies. The wells were then incubated with 1 μg/ml of rabbit anti-VEGF antibody (A-20, Santa Cruz Biotechnology, Santa Cruz, Calif.).

The reactions were developed by the addition of peroxidase-labeled goat anti-rabbit antibody (Dako, Carpinteria, Calif.) and visualized by addition of 3,3'5,5'-tetramethylbenzidine (TMB) substrate (Kirkegaard and Perry Laboratories, Inc.). Reactions were stopped after 15 min with 1 M $H_3PO_4$ and read spectrophotometrically at 450 nM.

The assay was also performed by coating wells of a microtiter plate with either control or test IgG. The wells were then incubated with VEGF:Flt-1/Fc or VEGF:sFlk-1-biotin and developed with either peroxidase-labeled goat anti-human Fc (Kirkegaard and Perry Laboratories, Inc.) or peroxidase-labeled streptavidin, respectively and visualized as above.

3. Coprecipitation Assay 40 ng of VEGF was preincubated with the F(ab')$_2$ of either of 2C3 (20 μg) or A4.6.1 (10 and 1 μg) for 30 min in binding buffer (DMEM with 1 mM $CaCl_2$, 0.1 mM $CuSO_4$, and 0.5% tryptone). 200 ng of soluble forms of VEGFR1 (Flt-1/Fc) or VEGFR2 (KDR/Fc, R&D Systems, Minneapolis, Minn.) were added for a total volume of 50 μl and incubated for 2 hrs. The receptor/Fc constructs were precipitated using Protein A-sepharose beads and the resulting precipitate was washed 4 times with binding buffer.

Reducing sample buffer was added to the pellet and supernatant of each reaction and both were analyzed by 12% SDS-PAGE and transferred to PVDF membranes. The membranes were then probed with 12D7 (1.0 μg/ml), a mouse anti-VEGF antibody and developed after incubation with peroxidase-labeled goat anti-mouse IgG (Kirkegaard & Perry Laboratories, Inc.) by Super Signal chemiluminescence substrate (Pierce, Rockford, Ill.). The soluble receptor/Fc constructs were also detected by using peroxidase-conjugated goat anti-human Fc (Kirkegaard & Perry Laboratories, Inc.)

B. Results 1. 2C3 Blocks VEGF Binding to VEGFR2 but not to VEGFR1 in ELISAs

The anti-VEGF antibody 2C3 blocked VEGF from binding to VEGFR2 (KDR/Flk-1) but not to VEGFR1 (FLT-1) in the ELISA assay. In the presence of a 100-fold and 1000-fold molar excess of 2C3, the amount VEGF that bound to VEGFR2-coated wells was reduced to 26% and 19%, respectively, of the amount that bound in the absence of 2C3 (FIG. 2). In contrast, in the presence of a 100-fold and 1000-fold molar excess of 2C3, the amount VEGF that bound to VEGFR1-coated wells was 92% and 105%, respectively, of the amount that bound in the absence of 2C3 (FIG. 2).

The amounts of VEGF that bound to VEGFR1 or VEGFR2 were unaffected by the presence of a 100–1000 fold excess of the non-blocking monoclonal anti-VEGF antibody 3E7 or of a control IgG of irrelevant specificity (FIG. 2). A4.6.1 blocked VEGF binding to both VEGFR2 (KDR/Flk-1) and VEGFR1 (FLT-1).

2. 2C3 Blocks VEGF Binding to VEGFR2 but not to VEGFR1 in Solution

The ability of 2C3 to block the binding of VEGF to VEGFR1/Fc or VEGFR2/Fc in solution was assessed in co-precipitation assays. 40 ng of VEGF was incubated with 200 ng extracellular domain of VEGFR1 linked to an Fc portion (Flt-1/Fc) or VEGFR2 (KDR/Fc) linked to an in the presence or absence of 2C3 or 4.6.1 F(ab')$_2$. The receptor/Fc constructs were precipitated by incubation with Protein A sepharose beads. The precipitate was washed and resuspended in reducing sample buffer and separated by 12% SDS-PAGE and transferred to PVDF. The membrane was blocked with PP82 and probed with 12D7 (1 μg/ml) mouse anti-VEGF antibody and developed under standard chemiluminescence conditions. VEGF monomer and dimer along with F(ab')$_2$ were detected.

VEGF mixed with either VEGFR1Fc or VEGFR2/Fc was co-precipitated by Protein A sepharose, showing that VEGF binds to both receptors. Addition of 2C3 F(ab')$_2$ blocked the binding of VEGF to VEGFR2/Fc, but not to VEGFR1/Fc. In contrast, 4.6.1 F(ab')$_2$ blocked the binding of VEGF to both VEGFR2/Fc and VEGFR1/Fc. The results affirm that 2C3 inhibits the binding of VEGF to VEGFR2 but not to VEGFR1, whereas the 4.6.1 antibody inhibits the binding of VEGF to both VEGFR2 and VEGFR1.

EXAMPLE V

2C3 Blocks VEGF-Induced Phosphorylation of VEGFR2

A. Materials and Methods

Immunoprecipitation and Western Blot Analysis

PAE/KDR, PAE/FLT, and bEND.3 cells were grown to 80–90% confluency in 100 mm tissue dishes in media containing 5% serum. The cells were then serum starved for 24 hours in media containing 0.1% serum. After pretreatment with 100 nM sodium orthovanadate in PBS for 30 min, the cells were incubated with 5 nM (200 ng/ml) VEGF165, 5 nM (100 ng/ml) bFGF (R&D Systems, Minneapolis, Minn.), or A673 tumor conditioned media in the presence or absence of control or test antibodies for additional 15 min.

The cells were then washed with ice-cold PBS containing 10 mM EDTA, 2 mM sodium fluoride, and 2 mM sodium orthovanadate and lysed in lysis buffer (50 mM Tris, 150 mM NaCl, 1% Nonidet P-40, 0.25% sodium deoxycholate, 0.1% CHAPS, 5 mM EDTA, 1.5 mM $MgCl_2$, 2 mM sodium fluoride, 2 mM sodium orthovanadate, 10% glycerol and protease inhibitors (Complete Protease Inhibitor Cocktail tablets, Boehringer Mannheim)). The lysates were clarified by centrifugation and resulting supernatant used for immunoprecipitation.

VEGFR1 and VEGFR2 were immunoprecipitated by incubating the cell lysates overnight at 4° C. with 5 µg of chicken anti-FLT-1 N-terminus (Upstate Biotechnology, Lake Placid, N.Y.) or 10 µg of T014 (affinity purified anti-Flk-1), respectively. The reactions using the chicken anti-FLT-1 antibody were subsequently incubated with a bridging goat anti-chicken antibody (Kirkegaard and Perry Laboratories, Inc.) for 1 h at 4° C. The immune complex was then precipitated with Protein A/G sepharose, washed multiple times with 10% lysis buffer (with added protease inhibitors) in PBS-tween (0.2%) and boiled in SDS sample buffer containing 100 mM β-mercaptoethanol and 8 M urea.

The samples were then separated by SDS-PAGE and transferred to PVDF membranes. The membranes were blocked for 30–60 min with PP81 (East Coast Biologics, Berwick, Me.) and probed for phosphotyrosine residues with 0.5 µg/ml of 4G10 (Upstate Biotechnology, Lake Placid, N.Y.) overnight at 4° C. The PVDF membranes were developed after incubation with peroxidase-labeled rabbit anti-mouse IgG (Dako, Carpinteria, Calif.) by Super Signal chemiluminescence substrate (Pierce, Rockford, Ill.). The PVDF membranes were then stripped with ImmunoPure Elution buffer (Pierce, Rockford, Ill.) for 30 min at 55° C. and reprobed for receptor levels with either 0.5 µg/ml chicken anti-FLT-1 or 1.0 µg/ml T014 and developed as above after incubation with the appropriate peroxidase-conjugated secondary antibody.

B. Results

Blocking of VEGF-Induced Phosphorylation

In these studies, PAE/KDR cells were stimulated for 15 min. with PBS, bFGF (5 nM, 100 ng/ml), VEGF165 (5 nM, 210 ng/ml), A673 conditioned media (CM), CM in combination with particular antibodies (CNTL, 2C3, 3E7, A4.6.1 separately at 100 nM, 15 µg/ml), or T014 alone (100 nM, 15 µg/ml). PAE/FLT cells were also stimulated for 15 min. with PBS, VEGF165 (5 nM, 210 ng/ml), A673 conditioned media (CM), CM in combination with particular antibodies (2C3, 3E7, A4.6.1 separately at 100 nM, 15 µg/ml), or T014 alone (100 nM, 15 µg/ml). The cells were then incubated in lysis buffer and the receptor was immunoprecipitated, separated by SDS-PAGE under reducing conditions, transferred to PVDF membranes and probed with 4G10 (0.5 µg/ml), mouse anti-phospho-tyrosine antibody, and developed under standard chemiluminescence conditions. The membranes were then stripped and re-probed with the immunoprecipitating IgG to determine the level of receptor protein in each lane.

The results showed that 2C3, along with A4.6.1, a control neutralizing anti-VEGF antibody, block VEGF-induced phosphorylation of VEGFR2 in PAE/KDR cells. This is in agreement with previous results that demonstrated both 2C3 and A4.6.1 block VEGF-mediated growth of endothelial cells (Example II; Brekken et al., 1998). Western blots of VEGFR2 in the immunoprecipitates were conducted to demonstrate the amounts of VEGFR2 protein in each lane. 3E7, which sees an $NH_2$-terminal epitope of VEGF, did not block VEGF-induced phosphorylation of VEGFR2 nor did a control IgG of irrelevant specificity.

The effect of 2C3 on VEGF-induced phosphorylation of VEGFR1 is not clear. As other investigators have shown, VEGF-induced phosphorylation of VEGFR1 in PAE/FLT cells is difficult to demonstrate, possibly due to the low intrinsic kinase activity of VEGFR1 (De Vries et al., 1992; Waltenberger et al., 1994; Davis-Smyth et al., 1996; Landgren et al., 1998).

EXAMPLE VI

2C3 Inhibits VEGF-Induced Permeability

A. Materials and Methods

Miles Permeability Assay

The protocol followed was as described by Murohara, et al. (1998; specifically incorporated herein by reference). Briefly, 400–450 g, male, IAF hairless guinea pigs (Charles River, Wilmington, Mass.) were anesthetized and then injected i.v. with 0.5 ml of 0.5% Evan's blue dye in sterile PBS through an ear vein. Twenty min later 20 ng of VEGF in the presence or absence of control or test antibodies was injected intradermally (i.d.). The resultant blue spots in the back of the guinea pig were photographed and measured with a caliper 30 min after the i.d. injections.

B. Results

2C3 Blocks VEGF-Induced Permeability

To investigate the effects of 2C3 on VEGF-induced permeability, IAF hairless guinea pigs (Hartley strain) 400–450 g in size were anesthetized and injected i.v. with 0.5 ml of 0.5% Evan's blue dye in sterile PBS through an ear vein. Twenty minutes later, 25 ng of VEGF in the presence or absence of control or test antibodies was injected intradermally (i.d.). The resultant blue spots in the back of the guinea pig were photographed and measured with a caliper 30 minutes after the i.d. injections.

Using this Miles permeability assay, it was found that 2C3, which blocks VEGF from activating VEGFR2, inhibited VEGF-induced permeability in the guinea pigs. This effect was evident with 2C3 at a 10-fold, 100-fold, or 1000-fold molar excess over VEGF. A4.6.1, which blocks VEGF from activating both VEGFR1 and VEGFR2, blocked VEGF-induced permeability at 10-fold molar excess (present studies and Kim et al., 1992). 3E7, and a control IgG that do not block VEGF:VEGFR2 interaction also do not block VEGF-induced permeability in the Miles permeability assay in guinea pigs.

These results suggest endothelial permeability mediated by VEGF is mediated, at least in part, through VEGFR2 activation. These results accord with those of other investigators who have shown that the tyrosine kinase activity of VEGFR2 is necessary for VEGF-induced permeability (Murohara et al., 1998; Joukov et al., 1998; Ogawa et al., 1998).

EXAMPLE VII

Anti-Tumor Effects of 2C3

A. Materials and Methods

1. In Vivo Tumor Growth Inhibition

Nu/nu mice were injected subcutaneously with either $1 \times 10^7$ NCI-H358 NSCLC cells or $5 \times 10^6$ A673 rhabdomyosarcoma cells on day 0. On day 1 and subsequently twice per wk the mice were given i.p. injections of 2C3 at 1, 10, or 100 μg or controls as indicated. The tumors were then measured twice per wk for a period of approximately six wk for the NCI-H358 bearing mice and four wk for the A673 bearing mice. Tumor volume was calculated according to the formula: volume=L×W×H, where L=length, W=width, H=height.

2. In Vivo Tumor Therapy

Male nu/nu mice bearing subcutaneous NCI-H358 tumors or HT1080 fibrosarcoma 200–400 mm³ in size were injected i.p. with test or control antibodies. The NCI-H358 bearing mice were treated with 100 μg of antibodies per injection three times a week during the first week and twice a week during the second and third week. The mice were then switched to 50 μg per injection every five days. The HT1080 bearing mice were treated with 100 μg of the indicated antibody or saline every other day throughout the duration of the study. In both studies, mice were sacrificed when their tumors reached 2500 mm³ in size or earlier if tumors began to ulcerate.

B. Results 1. 2C3 Growth Inhibition of Newly-Implanted Human Tumor Xenografts

Figure 3A:
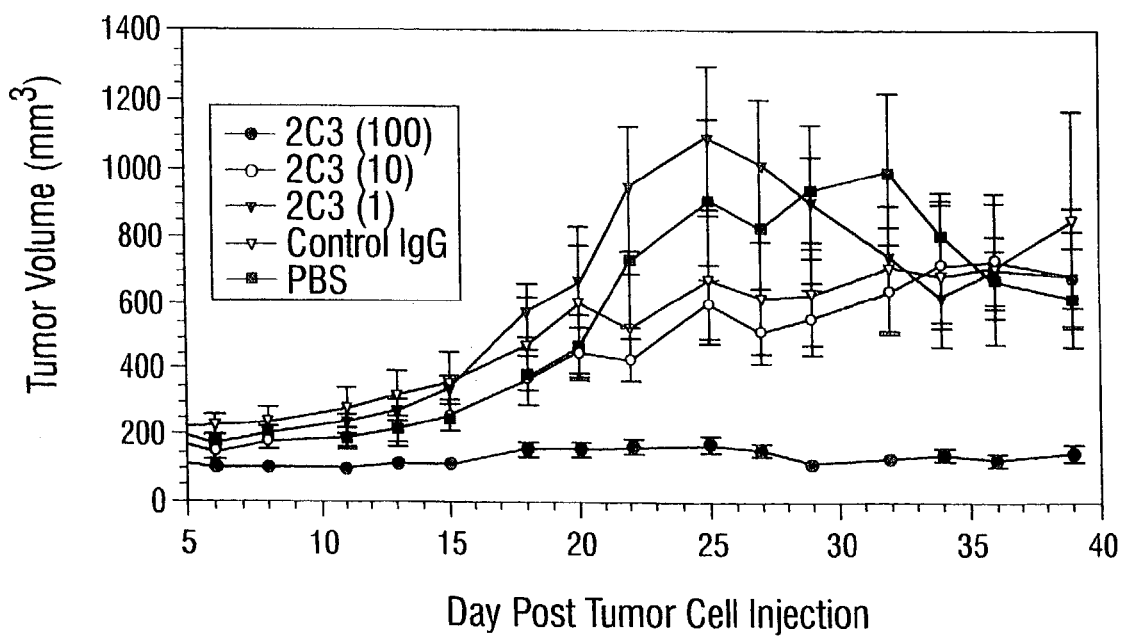
FIG. 3A and FIG. 3B. 2C3 inhibits the in vivo growth of human tumor xenografts.
Figure 3B:
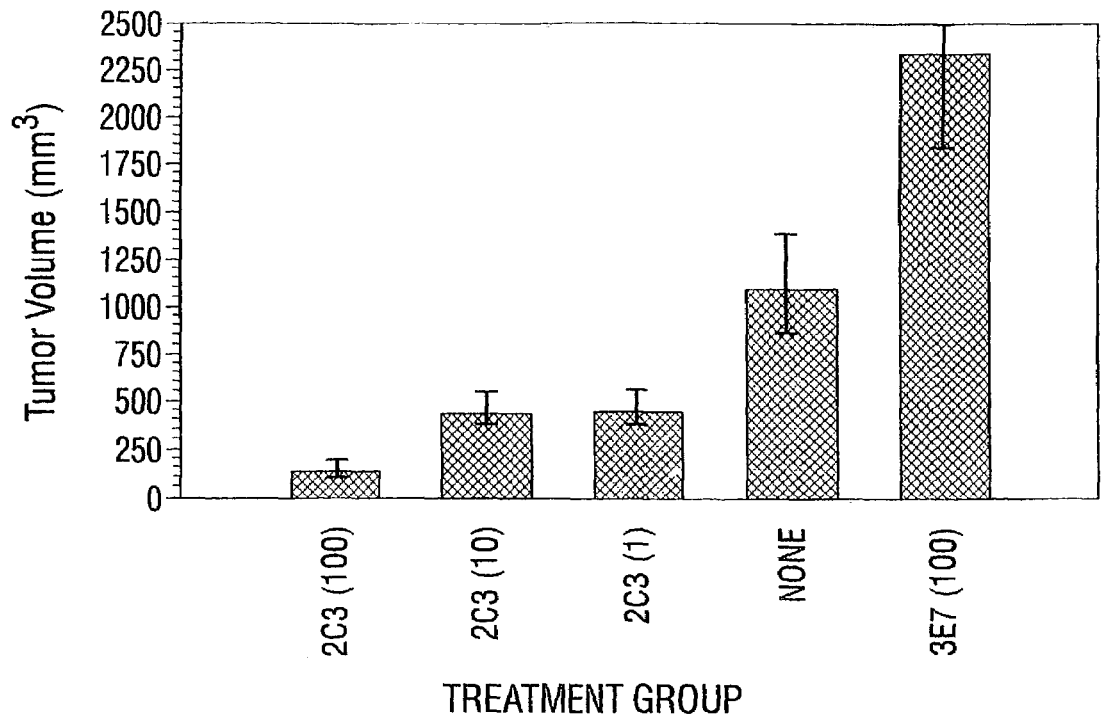

2C3 inhibits the in vivo growth of both NCI-H358 NSCLC and A673 rhabdomyosarcoma in nu/nu mice in a dose dependent manner (FIG. 3A and FIG. 3B). 100 μg of 2C3 given i.p. 2 times per wk to mice that had been injected with tumor cells subcutaneously one day earlier inhibited the growth of both human tumor types. The final tumor volume in the 2C3 recipients was approximately 150 mm³ in both tumor systems, as compared with approximately 1000 mm³ in the recipients of controls.

Treatment with either 10 or 1 μg of 2C3 twice per wk was less effective at preventing tumor growth. However, both lower doses of 2C3 did slow the growth of A673 tumors to a similar degree compared to the untreated mice. The tumor growth retardation caused by a 10 μg dose of 2C3 was less marked in the NCI-H358 tumor model. The differences between these two tumor models and their response to inhibition of VEGFR2 activity by 2C3 correlates with the aggressiveness of the two types of tumors in vivo. NCI-H358 grows in vivo much more slowly than does A673 and appears to be less sensitive to low doses of 2C3, whereas, A673 tumors grow more quickly and aggressively and appear to be more sensitive to lower doses of 2C3.

3E7, which binds to VEGF but does not block its activity, had no effect on the growth of NCI-H358 tumors. However, 3E7 given at a dose of 100 μg twice per wk stimulated the growth of A673 tumors (FIG. 3B), suggesting that it increases the efficiency of VEGF signaling in the tumor.

2. Treatment of Established Human Tumor Xenografts with 2C3

Figure 4:
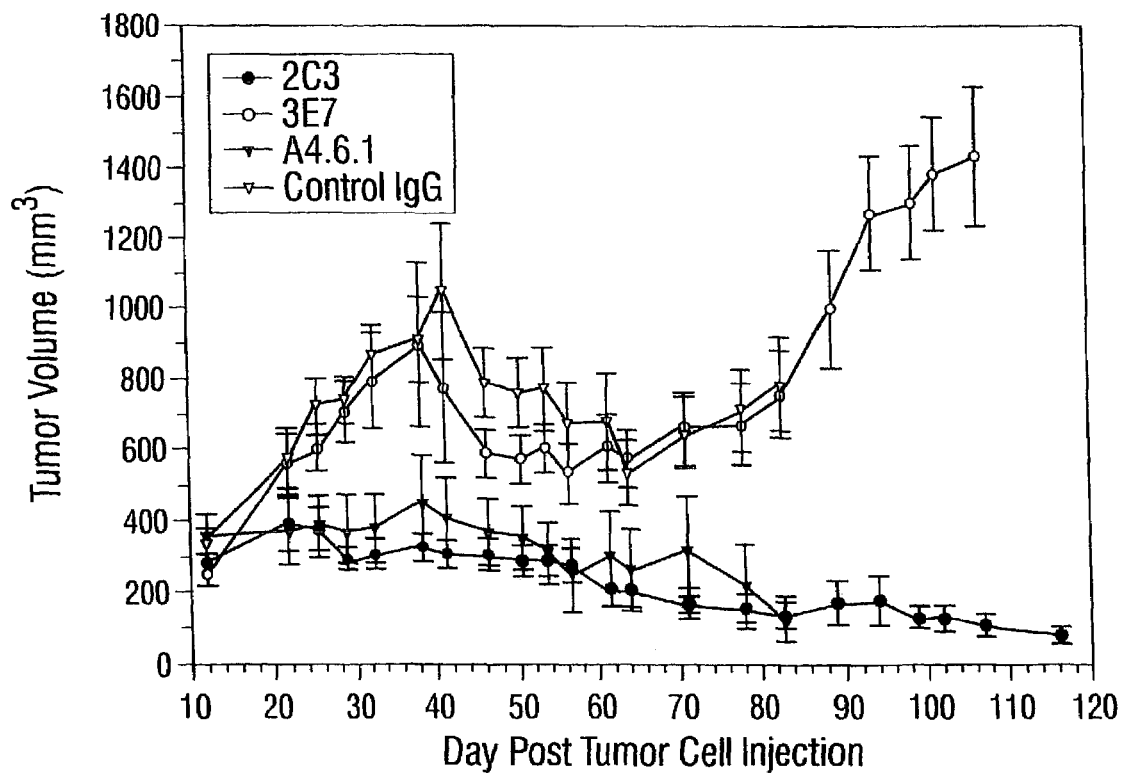
FIG. 4. 2C3 treatment reduces the size of established human NCI-H358 NSCLC tumor xenografts. Mice bearing subcutaneous NCI-H358 tumors, approximately 300–450 mm$^3$ in size, were treated i.p. with 50 µg or 100 µg of 2C3 (n=14), mAb 4.6.1 (n=5), 3E7 (n=12) or a control IgG (n=9) at the indicated time points. Mean tumor volume along with the SEM over 116 days is shown.

Mice bearing subcutaneous NCI-H358 NSCLC tumors that had grown to a size of approximately 300–450 mm³ were injected i.p. with 2C3, A4.6.1, 3E7, or an IgG of irrelevant specificity (FIG. 4). Doses were 50–100 μg every 3–5 days. A4.6.1 was used as a positive control because it has been shown by other investigators to block VEGF activity in vivo resulting in an inhibition of tumor growth (Kim et al., 1993; Mesiano et al., 1998). In addition to measuring mean tumor volume (FIG. 4), photographs of the mice from each treatment group were also taken to show the differences in tumor size and appearance at the end of the study.

Treatment with either 2C3 or A4.6.1 led to a slow regression of the tumors over the course of the study. The mean tumor volumes at the end of the study were 30% (2C3) and 35% (4.6.1) of the initial mean tumor volume (FIG. 4). However, these results are complicated by the fact that spontaneous retardation in tumor growth was observed in the control groups of mice between 40 days and 60 days after tumor cell injection. The results up to 40 days, before the spontaneous retardation in growth was evident, show that treatment with 2C3 and A4.6.1 prevents tumor growth.

Figure 5A:
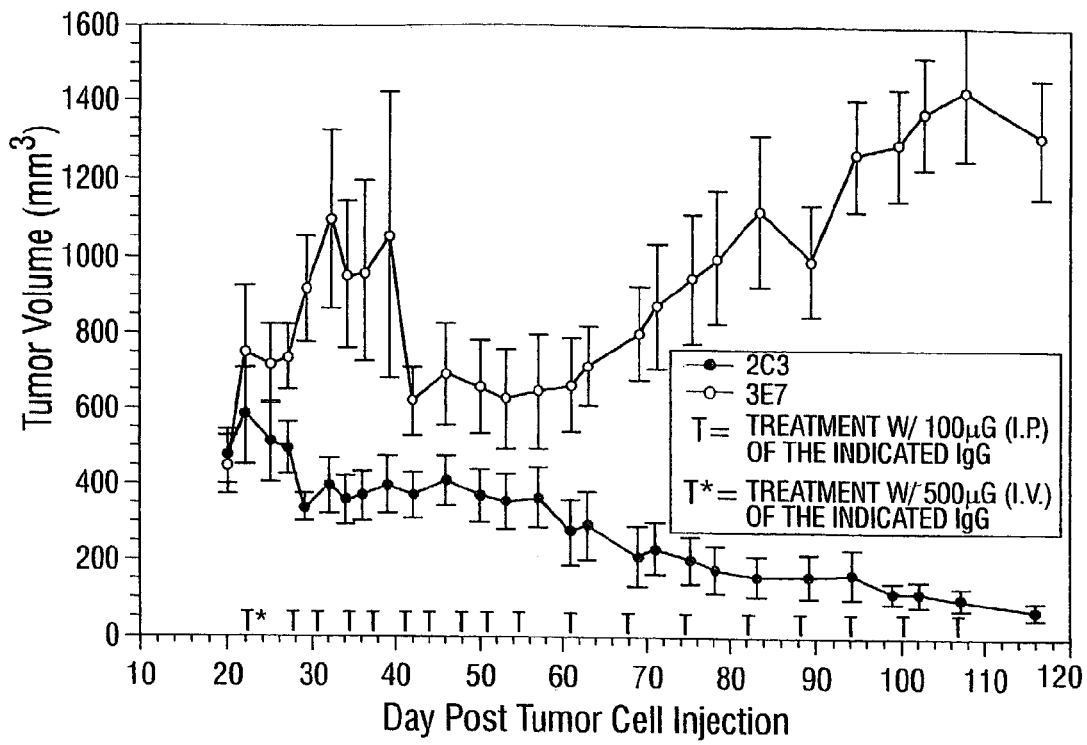
FIG. 5A and FIG. 5B. Comparison of 2C3 and 3E7 treatment of established human tumor xenografts.

FIG. 5A shows a further study in which mice bearing NCI H358 were treated for a prolonged period with 100 μg of either 2C3 or 3E7. In this study, spontaneous regressions were less pronounced. The mean tumor volume of the 2C3 treated mice at the start of treatment was 480 mm³ and after approximately 14 wk of treatment the mean tumor volume dropped to 84 mm³, a decrease of approximately 80% in volume. The 3E7 treated mice began treatment with a mean tumor volume of 428 mm³ and rose to a volume of 1326 mm³ after approximately 14 wk, an increase of 300% in volume.

Figure 5B:
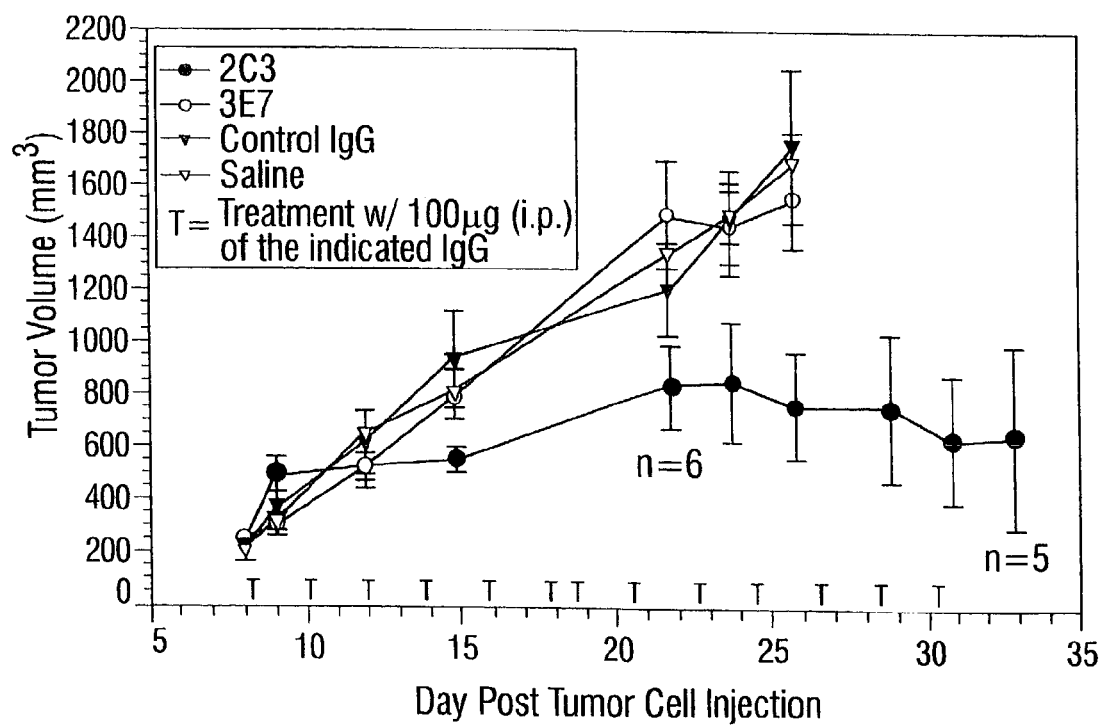

FIG. 5B shows the tumor growth curves of mice bearing a human fibrosarcoma, HT1080, that were every treated every two days with 100 μg of 2C3, 3E7, or a control IgG, or saline. 2C3 arrested the growth of the tumors for as long as treatment was continued. The mice treated with 3E7, control IgG, or saline bore tumors that grew progressively and to a size that required the mice to be sacrificed less than 4 weeks after tumor cell injection.

EXAMPLE VIII

2C3 is Distinct from A4.6.1

There are a number differences between 2C3 and A4.6.1 (e.g., Table 5). The antibodies recognize distinct epitopes on VEGF based upon ELISA cross-blocking studies (Example I). Mutagenesis and X-ray crystallographic studies have earlier shown that A4.6.1 binds to an epitope on VEGF that is centered around amino acids 89–94 (Muller et al., 1998).

Of particular interest is the fact that A4.6.1 blocks VEGF from binding to both VEGFR1 and VEGFR2 (Kim et al., 1992; Wiesmann et al., 1997; Muller et al., 1998; Keyt et al., 1996), while 2C3 only blocks VEGF from binding to VEGFR2 (Example IV). Compelling published evidence that A4.6.1 inhibits VEGF binding to VEGFR2 and VEGFR1 comes from detailed crystallographic and structural studies (Kim et a., 1992; Wiesmann et al., 1997; Muller et al., 1998; Keyt et al., 1996; each incorporated herein by reference). The published data indicate that A4.6.1 inhibits VEGF binding to VEGFR2 by competing for the epitope on VEGF that is critical for binding to VEGFR2, and blocks binding of VEGF to VEGFR1 most probably by steric hindrance (Muller et al., 1998; Keyt et al., 1996).

A humanized version of A4.6.1 is currently in clinical trials (Brem, 1998; Baca et al., 1997; Presta et al., 1997; each incorporated herein by reference). Macrophage/monocyte chemotaxis and other endogenous functions of VEGF that are mediated through VEGFR1 will most likely be impaired in the A4.6.1 trials. In contrast, 2C3 is envisioned to be superior due its ability to specifically block VEGFR2-mediated effects. 2C3 is thus potentially a safer antibody, particularly for long-term administration to humans. The benefits of treatment with 2C3 include the ability of the host to mount a greater anti-tumor response, by allowing macrophage migration to the tumor at the same time it is blocking VEGF-induced tumor vasculature expansion. Also, the many systemic benefits of maintaining macrophage chemotaxis and other effects mediated by VEGFR1 should not overlooked.

TABLE 5

CHARACTERISTICS OF THE ANTI-VEGF ANTIBODIES 2C3 AND A4.6.1

| Characteristic | 2C3 | A4.6.1 |
|---|---|---|
| Isotype | IgG2a, k | IgG1[1] |
| Epitope on VEGF | Undefined, but distinct from A4.6.1[2] | Continuous, centered around amino acids 89–94 |
| Affinity | $1 \times 10^{-9}$ (M)[3] | $8 \times 10^{-10}$ (M) |
| Blocks VEGF from binding to VEGFR1 | No | Yes |
| Blocks VEGF from binding to VEGFR2 | Yes | Yes |
| Blocks VEGF-induced permeability | Yes | Yes |
| Blocks VEGF-induced proliferation | Yes | Yes |
| Direct IHC pattern on frozen tumor sections | NR | Weak reactivity with some BV[4] |
| In vivo tumor localization pattern | Moderate to strong reactivity with CT | Moderate reactivity with a minority of BV, weak to no reactivity with CT |
| In vivo normal mouse tissue localization | None detectable | None detectable |

Abbreviations used: IHC, immunohistochemistry; NR, no reactivity; BV, blood vessels; CT, connective tissue.
[1]References for A4.6.1 data include Kim et al., 1992; Wiesmann et al., 1997; Muller et al., 1998; and Keyt et al., 1996, each incorporated herein by reference
[2]The epitope that 2C3 recognizes on VEGF is undefined but has been shown to be distinct from the epitope that A4.6.1 recognizes through ELISA cross-blocking studies
[3]The affinity of 2C3 for VEGF has been estimated by ELISA and surface plasmon resonance analysis.
[4]A4.6.1 only reacts with lightly fixed acetone fixed frozen sections.

EXAMPLE IX

VEGF Staining in Arthritic Tissue

The relationship between angiogenesis and disease extends beyond that observed in vascularized tumors. For example, the involvement of aberrant angiogenesis is well documented in arthritis. A panel of different anti-VEGF antibodies and antibodies to thymidine phosphorylase have been used to stain arthritic tissue and differentiate this from matched controls. Studies using antibodies against VEGF have shown striking expression in the pannus of rheumatoid arthritis.

EXAMPLE X

2C3-Endostatin Conjugates

A. Cloning and Expression of Endostatin

RNA was isolated from mouse liver and used as the template for RT-PCR™ with the following primers:

5' primer aga cca tgg gtc ata ctc atc agg act ttc a (SEQ ID NO:43);

3' primer ctac cat ggc tat ttg gag aaa gag gtc a (SEQ ID NO:44).

The resultant cDNA fragment has the DNA sequence of SEQ ID NO:12 and the amino acid sequence of SEQ ID NO:13. For reference, the human endostatin amino acid sequence is SEQ ID NO:14. The mouse cDNA fragment was cloned into the expression vector H6pQE60 (Qiagen), which encodes an N-terminal 6×histidine tag, and then expressed in *E. coli* M15 cells. When *E. coli* cell density reached an optical density of 0.6 at 560 nM, 0.1 mM isopropylthiogalactoside (IPTG) was added for 4 hours to induce expression of 6-His endostatin. The cells were harvested by centrifugation and lysed in lysis buffer (B-PER Bacterial Protein Extraction Reagent (Pierce, Rockford, Ill.)).

The inclusion bodies, which contained the 6-His endostatin, were sedimented by centrifugation and dissolved in buffer A (pH 8.0, 6 M guanidine HCl (GuHCL), 100 mM $NaH_2PO_4$, 10 mM Tris, 10 mM imidazol, 10 mM β-2 mercaptoethanol). The solution containing the reduced 6-His endostatin was treated with an excess of 5,5'-dithiobis-(2-nitrobenzoic) acid (Ellman's reagent) (20 mM) and loaded onto a Ni-NTA column. The column was washed with wash buffer (6 M GuHCl, 100 mM $NaH_2PO_4$, 10 mM Tris, 500 mM NaCl, pH 7.3) and 6-His endostatin was eluted from the column with 0.2 M imidazole in wash buffer.

The eluted and insoluble 6-His endostatin was diluted with an equal volume of refolding buffer (3M urea, 1M Tris pH 7.3, 0.5 M L-arginine, 0.5 M NaCl, 0.1 M $Na_2HPO_4$, 1 mM reduced glutathione (GSH)) and incubated overnight at room temperature. Refolded 6-His endostatin was dialyzed extensively against PBS, pH 7.4 at room temperature. The resulting protein, 6-His endostatin was soluble and highly pure based upon SDS-PAGE analysis under non-reducing conditions where it ran as a single 20 kDa band.

B. Functional Activity of Endostatin

In addition to the fact that the expressed protein is fully soluble, other evidence that *E. coli* expressed 6-His endostatin is biologically active includes demonstrated binding to endothelial cells. Biotinylated 6-His endostatin was prepared and incubated with three different endothelial cell types in vitro (Bend3 mouse endothelial cells; ABAE, bovine aortic endothelial cells; and HUVEC, human umbilical vein endothelial cells). Binding was detected using streptavidin-peroxidase in conjunction with O-phenylenediamine (OPD) and the absorbance read at 490 nm.

The direct binding studies showed that (Biotinylated 6-His) endostatin bound in a saturable fashion to these three different types of endothelial cells in vitro. Also, expressed endostatin (without label) was shown to compete with biotinylated endostatin for binding to Bend3 endothelial cells.

C. Conjugation of Endostatin to 2C3 via SMPT and 2-IT

4-Succinimidyloxycarbonyl-α-methyl-α-(2-pyridyldithio)-toluene (SMPT) in N'N-dimethylformamide (DMF) was added to 2C3 IgG at a molar ratio of 5:1 (SMPT:2C3) and incubated at room temperature (RT) for 1 hr in PBS with 5 mM EDTA (PBSE). Free SMPT was removed by G25 size exclusion chromatography run in PBSE. Concurrently, mouse 6-His endostatin was incubated with 2-iminothiolane (2-IT, Traut's reagent) at a molar ratio of 1:5 (endostatin:2-IT) for 1 hour at RT. Free 2-IT was removed by G25 size exclusion chromatography run in PBSE.

SMPT-modified 2C3 was mixed with 2-IT-modified 6-His endostatin, concentrated to 3–5 ml, and incubated for 24 h at RT with gentle shaking. The reaction was analyzed by SDS-PAGE. Unconjugated 2C3-SMPT was removed from the conjugate by heparin affinity chromatography, thus providing 2C3-endostatin.

D. Conjugation of Endostatin to 2C3 via SMCC and SATA

N-Succinimidyl S-acetylthioacetate (SATA) was incubated with 6-His-endostatin at a molar ratio of 6:1 (SATA:endostatin) for 30 min at RT. Free SATA was removed by G25 size exclusion chromatography run in PBSE. SATA modified 6-His endostatin in PBSE was concentrated to 4.0 ml and 0.4 ml deacetylation solution (0.1 M hydroxylamine) was added. The mixture was incubated at RT for 2 hr. Concurrently, 2C3 IgG, in PBSE, was incubated with succinimidyl 4-(N-maleimidomethyl)cyclohexane-1-carboxylate (SMCC) at a molar ratio of 1:5 (2C3:SMCC). Free SMCC was removed by G25 size exclusion chromatography run in PBSE.

Deacetylated SATA modified endostatin was then incubated with SMCC modified 2C3, concentrated to approximately 5 mg/ml total protein under nitrogen, and incubated overnight at RT with gentle stirring. The reaction was analyzed by SDS-PAGE. Unconjugated 2C3-MCC was removed from the 2C3-endostatin conjugate by heparin affinity chromatography in PBSE, thus providing 2C3-endostatin. Successful conjugation was also achieved using 2-iminothiolane rather than SATA as the thiolating agent.

E. Fusion Proteins of 2C3 and Endostatin

As the DNA sequences for mouse and human endostatin, and for 2C3 are available (and provided herein), 2C3-endostatin fusion proteins can readily be prepared. The expression and refolding of endostatin, as described above, shows that successful recombinant expression of this molecule is indeed possible.

The preparation of a 2C3-endostatin fusion protein can be in a form where endostatin is present at the C-terminus of a 2C3 heavy chain or is linked to a 2C3 ScFv fragment. In these cases, recombinant technology makes it straightforward to vary the linkage, and the use of selectively cleavable sequences to join the two functional portions is particularly envisioned. Plasmin-cleavable or MMP-cleavable sequences are currently preferred.

The availability of selectively cleavable sequences and adaptability of recombinant technology also provides for 2C3-endostatin fusion proteins in which the endostatin is substituted at another point of the 2C3 construct. The endostatin will remain embedded within 2C3 until contact with an enzyme that acts on the selectively cleavable sequence, at which point functional endostatin is released from the fusion protein.

EXAMPLE XI

2C3-Ang-2 Conjugates

A. Expression of Ang-2

To construct a 2C3-Ang-2 conjugate, Ang-2 is preferably used in recombinant form, as may be produced in insect cells using a baculovirus expression system. The currently preferred protocol for Ang-2 expression and purification involves cloning Ang-2 cDNA from mouse placenta RNA by RT-PCR™ and cloning the Ang-2 cDNA into pFastBac1 expression vector. Competent DH10Bac E. coli cells are transformed with the recombinant plasmid.

After antibiotic selection, E. coli colonies containing recombinant Bacmid are picked, grown and recombinant Bacmid DNA purified. Insect cells SF9 are transfected with the recombinant Bacmid DNA using the Celifectin reagent. Recombinant baculovirus are harvested from the supernatant of the transfected SF9 cells. Recombinant baculovirus are amplified and used to infect SF9 cells and the infected SF9 cells will express Ang-2. Ang-2 is purified from the supernatant of such infected SF9 cells by affinity purification.

B. Conjugation of Ang-2 to 2C3

Purified 2C3 is conjugated to recombinant Ang-2 using the chemical linker SMPT, generally as described above. SMPT in N'N-dimethylformamide (DMF) is added to 2C3 IgG at a molar ratio of 5:1 (SMPT:2C3) and incubated at room temperature (RT) for 1 hr in PBS with 5 mM EDTA (PBSE). Free SMPT is removed by G25 size exclusion chromatography run in PBSE. Concurrently, recombinant Ang-2 is incubated with 2-IT at RT. Free 2-IT is removed by G25 size exclusion chromatography run in PBSE.

SMPT-modified 2C3 is mixed with 2-IT-modified recombinant Ang-2, concentrated, and incubated for 24 h at RT with gentle shaking. The reaction is analyzed by SDS-PAGE. Unconjugated 2C3-SMPT is removed from the conjugate by gel filtration chromatography, thus providing 2C3-endostatin.

EXAMPLE XII

2C3-Tissue Factor Conjugates

2C3 was modified with SMPT, as described in the foregoing examples. Free SMPT was removed by G25 chromatography as outlined above except that the peak (2C3-SMPT) was collected under nitrogen. 600 μl of 2C3-SMPT was removed to quantitate thiopyridyl groups after addition of dithiothreitol (DTT) to 50 mM. An average of 3 MPT groups were introduced per IgG. Human truncated tissue factor (tTF) having a cysteine residue introduced at the N-terminus was reduced with 5 mM β2-ME. β2-ME was removed by G25 chromatography.

Reduced N-Cys-tTF was pooled with the 2C3-SMPT and incubated at a molar ratio of 2.5:1 (tTF:IgG) for 24 hours at RT. The reaction was concentrated to 1–2 ml using an Amicon with a 50,000 molecular weight cut off (MWCO) membrane. Unconjugated tTF and IgG were separated from conjugates using Superdex 200 size exclusion chromatography, thus providing 2C3-tTF.

EXAMPLE XIII

2C3-CRM107 Conjugates

2C3 was modified with SMPT. The cytotoxic agent, CRM107 (from Dr. Jerry Fulton, Inland Laboratories, DeSoto, Tex.), was modified with 2-IT as described in the foregoing examples. SMPT modified 2C3 was incubated with 2-IT modified CRM107 at a molar ratio of 1:5 (IgG:CRM107) for 24 hr at RT with gentle shaking. Conjugated 2C3 was separated from free reactants by superdex 200 size exclusion chromatography thus providing 2C3-CRM107.

EXAMPLE XIV

2C3 ProDrug Studies

A. Cloning and Expression of β-glucuronidase (GUS)

A plasmid (pBacgus-1) containing the *E. coli* GUS gene was obtained from Novagen, Inc. The plasmid was used a template for PCR to clone the GUS gene into the H6pQE60 expression vector, which encodes an N-terminal 6×histidine tag. *E. coli* M15 cells carrying the plasmid were grown to until the cell density reached an optical density of 0.6 at 560 nM. 0.1 mM isopropylthiogalactoside (IPTG) was added to induce expression of 6 his GUS. After 4 hours, the cells were harvested by centrifugation.

The *E. coli* pellet as lysed in cell lysis buffer (B-PER Bacterial Protein Extraction Reagent (Pierce, Rockford, Ill.)). The solution was loaded onto a Ni-NTA column, the column washed with wash buffer (6 M GuHCl, 100 mM $NaH_2PO_4$, 10 mM Tris, 500 mM NaCl, pH 7.3) and the bound 6-His GUS was eluted with 0.2 M imidazole in the same buffer.

The 6-His GUS was pure based upon SDS-PAGE, where it ran as a single band of 75 kDa band. On gel filtration columns, the 6-His GUS runs as a tetramer of about 300 kDa. The 6-His GUS was enzymatically active as judged by its ability to cleave the substrate p-nitrophenyl-β-D-glucuronide (PNPG).

B. Conjugation of 2C3 to β-glucuronidase (GUS)

N-Succinimidyl S-acetylthioacetate (SATA) was incubated with GUS at a molar ratio of 6:1 (SATA:GUS) for 30 min at RT. Free SATA was removed by G25 size exclusion chromatography run in PBSE. SATA modified GUS in PBSE was concentrated to 4.0 ml and 0.4 ml deacetylation solution (0.1 M hydroxylamine) was added. The mixture was incubated at RT for 2 hr. Concurrently 2C3 IgG, in PBSE, was incubated with succinimidyl 4-(N-maleimidomethyl)cyclohexane-1-carboxylate (SMCC) at a molar ratio of 1:5 (2C3: SMCC). Free SMCC was removed by G25 size exclusion chromatography run in PBSE.

Deacetylated SATA modified GUS was then incubated with SMCC modified 2C3 overnight at RT with gentle stirring. Free GUS was removed by ion-exchange chromatography on Q-Sepharose, with the free 2C3 and the 2C3-GUS conjugate being eluted with 0.5 M NaCl in PBS. The resultant solution was separated by Superdex 200 size exclusion chromatography yielding 2C3-GUS with a purity of 90%.

C. Biological Activity of 2C3-GUS Conjugate

The biological activity of each component of the 2C3-GUS conjugate was confirmed. 2C3-GUS bound specifically to VEGF coated wells in an appropriately controlled ELISA, as detected by a secondary HRP-labelled anti-mouse IgG and OPD. Half maximal binding was observed at 0.1 nM. Thus, the 2C3 binding portion functions correctly. The GUS portion also retained enzymatic activity.

2C3-GUS was radioiodinated with $^{125}I$ to a specific activity of $5\times10^6$ cpm/μg. After intravenous injection into mice, the radioiodinated 2C3-GUS cleared from the blood with a t½ α of about 6 hours and a t½ β of about 25 hours.

D. GUS Cleavable Prodrugs

β-glucuronide prodrugs, such as doxorubicin-β-glucuronide and calcimycin-β-glucuronide were prepared essentially as described in U.S. Pat. No. 5,561,119, specifically incorporated herein by reference. Such prodrugs are designed to release the cytotoxic component, such as doxorubicin or calcimycin, only when degraded by a glycoside enzyme, such as GUS. By attaching GUS to 2C3, GUS is targeted specifically to the tumor vasculature and stroma, thus providing for specific cleavage of the prodrugs and release of the cytotoxic component specifically within the tumor site.

E. Biological Activity of 2C3-GUS Conjugate

2C3-GUS specifically localized to tumor vasculature and surrounding tumor stroma after i.v. injection into SCID mice bearing human NCI-H358 NSCLC tumors in the subcutaneous site. Presence of 2C3-GUS was detected immunohistochemically on frozen sections of tumors with HRP-labeled anti-mouse IgG or with HRP-labeled anti-GUS. Maximal localization was observed 24–48 hours after injection of 2C3-GUS. Normal tissues were unstained. Specific localization of 2C3-GUS to tumor vasculature and surrounding tumor stroma allows for a systemically administered prodrug, such as doxorubicin glucuronide or calcimycin-glucuronide, to be activated only within the tumor.

A hybridoma cell line as described herein has been deposited under the provisions of the Budapest Treaty with the American Type Culture Collection (ATCC), Manassas, Va., USA; and been assigned accession number ATCC No. PTA 1595. The invention described and claimed herein is not limited in scope by the PTA 1595 cell line deposited since the deposited embodiment is an illustration of one aspect of the invention and any equivalent hybridoma cell lines that produce functionally equivalent monoclonal antibodies are within the scope of this invention. Indeed, all of the compositions and methods disclosed and claimed herein can be made and executed without undue experimentation in light of the present disclosure.

While the compositions and methods of this invention have been described in terms of preferred embodiments, it will be apparent to those of skill in the art that variations may be applied to the composition, methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abrams and Oldham, In: *Monoclonal Antibody Therapy of Human Cancer*, Foon and Morgan (Eds.), Martinus Nijhoff Publishing, Boston, pp. 103–120, 1985.

Aiello, Pierce, Foley, Takagi, Chen, Riddle, Ferrara, King, Smith, "Suppression of retinal neovascularization in vivo by inhibition of vascular endothelial growth factor (VEGF) using soluble VEGF-receptor chimeric proteins," *Proc. Natl. Acad. Sci. USA*, 92:10457–10461, 1995.

Akuzawa, Kurabayashi, Ohyama, Arai, Nagai, "Zinc finger transcription factor Egr-1 activates Flt-1 gene expression in THP-1 cells on induction for macrophage differentiation", *Arteriosclerosis, Thrombosis, and Vascular Biology*, 20(2):377–84, 2000.

Alon, Hemo, Itin, Pe'er, Stone, Keshet, "Vascular endothelial growth factor acts as a survival factor for newly formed retinal vessels and has implications for retinopathy of prematurity," *Nature Med.*, 1:1024–1028, 1995.

Antibodies: A Laboratory Manual, Cold Spring Harbor Laboratory, 1988.

Anthony, Wheeler, Elcock, Pickett, Thomas, "Short report: identification of a specific pattern of vascular endothelial growth factor mRNA expression in human placenta and cultured placental fibroblasts", *Placenta*, 15:557–61, 1994.

Asahara et al, "Isolation of putative progenitor endothelial cells for angiogenesis," *Science*, 275(5302):964–967, 1997.

Asahara, Chen, Takahashi, Fujikawa, Kearney, Magner, Yancopoulos, Isner, "Tie2 receptor ligands, angiopoietin-1 and angiopoietin-2, modulate VEGF-induced postnatal neovascularization" *Circ. Res.*, 83(3):233–40, 1998.

Asano, Yukita, Matsumoto, Kondo, Suzuki, "Inhibition of tumor growth and metastasis by an immunoneutralizing monoclonal antibody to human vascular endothelial growth factor/vascular permeability factor," *Cancer Res.*, 55:5296–5301, 1995.

Asano, Yukita, Matsumoto, Hanatani, Suzuki, "An anti-human VEGF monoclonal antibody, MV833, that exhibits potent anti-tumor activity in vivo," *Hybridoma*, 17:185–90, 1998.

Baca et al, "Antibody humanization using monovalent phage display," *J. Biol. Chem.*, 272(16):10678–84, 1997.

Barbas, Kang, Lerner and Benkovic, "Assembly of combinatorial antibody libraries on phage surfaces: the gene III site," *Proc. Natl. Acad. Sci. USA*, 88(18):7978–7982, 1991.

Baxter and Jain, "Transport of fluid and macromolecules in tumors," *Micro. Res.*, 41:5–23, 1991.

Benjamin, Golijanin, Itin, Pode and Keshet, "Selective ablation of immature blood vessels in established human tumors follows vascular endothelial growth factor withdrawal," *J. Clin. Invest.*, 103(2):159–165, 1999.

Berman, Mellis, Pollock, Smith, Suh, Heinke, Kowal, Surti, Chess, Cantor, et al., "Content and organization of the human Ig VH locus: definition of three new VH families and linkage to the Ig CH locus," *EMBO J.*, 7(3):727–738, 1988.

Borgstrom, Hillan, Sriramarao, Ferrara, "Complete inhibition of angiogenesis and growth of microtumors by antivascular endothelial growth factor neutralizing antibody: novel concepts of angiostatic therapy from intravital videomicroscopy," *Cancer Res.*, 56(17):4032–1439, 1996.

Borgstrom, Bourdon, Hillan, Sriramarao, Ferrara, "Neutralizing anti-vascular endothelial growth factor antibody completely inhibits angiogenesis and growth of human prostate carcinoma micro tumors in vivo," *Prostate*, 35(1):1–10, 1998.

Borgstrom, Gold, Hillan, Ferrara, "Importance of VEGF for breast cancer angiogenesis in vivo: implications from intravital microscopy of combination treatments with an anti-VEGF neutralizing monoclonal antibody and doxorubicin," *Anticancer Research*, 19(5B):4203–11, 1999.

Bornstein, "Thrombospondins: structure and regulation of expression," *FASEB J*, 6(14):3290–3299, 1992.

Borrebaeck and Moller, "In vitro immunization. Effect of growth and differentiation factors on antigen-specific B cell activation and production of monoclonal antibodies to autologous antigens and weak immunogens," *J. Immunol.*, 136(10):3710–3715, 1986.

Brekken, Huang, King, Thorpe, "Vascular endothelial growth factor as a marker of tumor endothelium," *Cancer Res.*, 58(9):1952–1959, 1998. Brem, "Angiogenesis antagonists: current clinical trials," *Angiogenesis*, 2: 9–20, 1998.

Bukovsky, Presl, Zidovsky, Mancal, "The localization of Thy-1.1, MRC OX 2 and Ia antigens in the rat ovary and fallopian tube," *Immunology*, 48(3):587–596, 1983.

Burke et al., "Cloning of large segments of exogenous DNA into yeast by means of artificial chromosome vectors", *Science*, 236, 806–812, 1987.

Burke, Lehmann-Bruinsma, Powell, "Vascular endothelial growth factor causes endothelial proliferation after vascular injury," *Biochem. Biophys. Res. Comm.*, 207:348–354, 1995.

Burrows and Thorpe, "Vascular targeting-a new approach to the therapy of solid tumors," *Pharmacol. Ther.*, 64:155–174, 1994a.

Burrows and Thorpe, "Eradication of large solid tumors in mice with an immunotoxin directed against tumor vasculature," *Proc. Natl. Acad. Sci. USA*, 90:8996–9000, 1994b.

Burrows, Watanabe, Thorpe, "A murine model for antibody-directed targeting of vascular endothelial cells in solid tumors," *Cancer Res.*, 52:5954–5962, 1992.

Burrows, Derbyshire, Tazzari, Amlot, Gazdar, King, Letarte, Vitetta, Thorpe, "Endoglin is an endothelial cell proliferation marker that is upregulated in tumor vasculature," *Clin. Cancer Res.*, 1:1623–1634, 1995.

Buttke, McCabrey, Owen, *J. Immunol. Methods*, 157:233–240, 1993.

Campbell, In: *Monoclonal Antibody Technology, Laboratory Techniques in Biochemistry and Molecular Biology*, Vol. 13, Burden and Von Knippenberg (Eds.), Elseview, Amsterdam, pp. 75–83, 1984.

Carmeliet, Ferreira, Breier, Pollefeyt, Kieckens, Gertsenstein, Fahrig, Vandenhoeck, Harpal, Eberhardt, Declercq, Pawling, Moons, Collen, Risau, Nagy, "Abnormal blood vessel development and lethality in embryos lacking a single VEGF allele," *Nature*, 380(6573):435–439, 1996.

Champe et al., *J. Biol. Chem.*, 270:1388–1394, 1995.

Cheng, Huang, Nagane, Ji, Wang, Shih, Arap, Huang, Cavenee, "Suppression of glioblastoma angiogenicity and tumorigenicity by inhibition of endogenous expression of vascular endothelial growth factor," *Proc. Natl. Acad. Sci. USA*, 93:8502–8507, 1996.

Claffey, Brown, del Aguila, Tognazzi, Yeo, Manseau, Dvorak, "Expression of vascular permeability factor/vascular endothelial growth factor by melanoma cells increases tumor growth, angiogenesis, and experimental metastasis," *Cancer Res.*, 56:172–181, 1996.

Clapp et al., "The 16-kilodalton N-terminal fragment of human prolactin is a potent inhibitor of angiogenesis," *Endocrinology*, 133(3):1292–1299, 1993.

Clauss et al., "The vascular endothelial cell growth factor receptor Flt-1 mediates biological activities," *J. Biol. Chem.*, 271(30):17629–17634, 1996.

Connolly, Heuvelman, Nelson, Olander, Eppley, Delfino, Siegel, Leimgruber, Feder, "Tumor vascular permeability factor stimulates endothelial cell growth and angiogenesis," *J. Clin. Invest.*, 84:1470–1478, 1989.

Coughlin et al., "Interleukin-12 and interleukin-18 synergistically induce murine tumor regression which involves inhibition of angiogenesis," *J. Clin. Invest.*, 101(6):1441–1452, 1998.

Couper, Bryant, Eldrup-Jorgensen, Bredenberg, Lindner, "Vascular endothelial growth factor increases the mitogenic response to fibroblast growth factor-2 in vascular smooth muscle cells in vivo via expression of fms-like tyrosine kinase-1," *Circ. Res.*, 81(6):932–939, 1997.

Crowther, In: *ELISA Theory and Practice*, Totowa: Humana Press, 1995.

D'Amato et al., "Thalidomide is an inhibitor of angiogenesis," *Proc. Natl. Acad. Sci. USA*, 91(9):4082–4085, 1994.

D'Angelo et al., "Activation of mitogen-activated protein kinases by vascular endothelial growth factor and basic fibroblast growth factor in capillary endothelial cells is inhibited by the antiangiogenic factor 16-kDa N-terminal fragment of prolactin," *Proc. Natl. Acad. Sci. USA*, 92(14):6374–6378, 1995.

Davis and Yancopoulos, "The angiopoietins: Yin and Yang in angiogenesis", *Curr. Top. Microbiol. Immunol.*, 237:173–85, 1999.

Davis-Smyth, Chen, Park, Presta, Ferrara, "The second immunoglobulin-like domain of the VEGF tyrosine kinase receptor Flt-1 determines ligand binding and may initiate a signal transduction cascade," *EMBO. J.*, 15(18):4919–4927, 1996.

Detmar, Brown, Claffey, Yeo, Kocher, Jackman, Berse, Dvorak, "Overexpression of vascular permeability factor/vascular endothelial growth factor and its receptors in psoriasis," *J. Exp. Med*, 180:1141–1146, 1994.

DeVore et al., "Phase I Study of the Antineovascularization Drug CM101," *Clin. Cancer Res.*, 3(3):365–372, 1997.

deVries, Escobedo, Ueno, Houck, Ferrara, Williams, "The fms-like tyrosine kinase, a receptor for vascular endothelial growth factor," *Science*, 255(5047):989–991, 1992.

Dvorak, Nagy, Dvorak, "Structure of solid tumors and their vasculature: implications for therapy with monoclonal antibodies," *Cancer Cells*, 3:77–85, 1991a.

Dvorak, Sioussat, Brown, Berse, Nagy, Sotrel, Manseau, Vandewater, Senger, "Distribution of vascular permeability factor (vascular endothelial growth factor) in tumors—concentration in tumor blood vessels," *J. Exp. Med*, 174:1275–1278, 1991b.

Ferrara, "The role of vascular endothelial growth factor in pathological angiogenesis," *Breast Cancer Res. Treat.*, 36:127–137, 1995.

Ferrara, Clapp, Weiner, "The 16K fragment of prolactin specifically inhibits basal or fibroblast growth factor stimulated growth of capillary endothelial cells," *Endocrinology*, 129(2):896–900, 1991.

Ferrara, Houck, Jakeman, Winer, Leung, "The vascular endothelial growth factor family of polypeptides," *J. Cell. Biochem.*, 47:211–218, 1991.

Ferrara, Carver-Moore, Chen, Dowd, Lu, O'Shea, Powell-Braxton, Hillan, Moore, "Heterozygous embryonic lethality induced by targeted inactivation of the VEGF gene," *Nature*, 380(6573):439–442, 1996.

Fidler and Ellis, "The implications of angiogenesis for the biology and therapy of cancer metastasis [comment]," *Cell*, 79(2):185–188, 1994.

Fidler, Kumar, Bielenberg, Ellis, "Molecular determinants of angiogenesis in cancer metastasis," *Cancer J. Sci. Am.*, 4 Suppl 1:S58–66, 1998.

Folkman and Shing, "Angiogenesis," *J. Biol. Chem.*, 267:10931–10934, 1992.

Folkman et al., "Angiogenesis inhibition and tumor regression caused by heparin or a heparin fragment in the presence of cortisone," *Science*, 221:719–725, 1983.

Fong, Rossant, Gertsenstein, Breitman, "Role of the Flt-1 receptor tyrosine kinase in regulating the assembly of vascular endothelium," *Nature*, 376:66–70, 1995.

Forsythe, Jiang, Iyer, Agani, Leung, Koos, Semenza, "Activation of vascular endothelial growth factor gene transcription by hypoxia-inducible factor 1," *Mol Cell. Biol.*, 16:4604–4613, 1996.

Fotsis et al, "The endogenous oestrogen metabolite 2-methoxyoestradiol inhibits angiogenesis and suppresses tumour growth," *Nature*, 368(6468):237–239, 1994.

Frank, Hubner, Breier, Longaker, Greenhalgh, Werner, "Regulation of vascular endothelial growth factor expression in cultured growth factor expression in cultured keratinocytes. Implications for normal and impaired wound healing," *J. Biol. Chem.*, 270:12607–12613, 1995.

Frater-Schroder et al., "Tumor necrosis factor type alpha, a potent inhibitor of endothelial cell growth in vitro, is angiogenic in vivo," *Proc. Natl. Acad. Sci. USA*, 84(15):5277–5281, 1987.

Frazier, "Thrombospondins," *Curr. Opin. Cell Biol.*, 3(5):792–799, 1991.

Fujii et al, "Role of nitric oxide, prostaglandins and tyrosine kinase in vascular endothelial growth factor-induced increase in vascular permeability in mouse skin," *Naunyn Schmiedebergs Arch Pharmacol*, 356(4):475–480, 1997.

Gagliardi and Collins, "Inhibition of angiogenesis by antiestrogens," *Cancer Res.*, 53(3):533–535, 1993.

Gagliardi, Hadd, Collins, "Inhibition of angiogenesis by suramin," *Cancer Res.*, 52(18):5073–5075, 1992.

Gagliardi et al., "Antiangiogenic and antiproliferative activity of suramin analogues," *Cancer Chemother. Pharmacol.*, 41(2):117–124, 1998.

Gefter et al., "A simple method for polyethylene glycol-promoted hybridization of mouse myeloma cells," *Somatic Cell Genet.*, 3:231–236, 1977.

Gerber, Condorelli, Park, Ferrara, "Differential transcriptional regulation of the two vascular endothelial growth factor receptor genes," *J. Biol. Chem.*, 272:23659–23667, 1997.

Gerber, Vu, Ryan, Kowalski, Werb, Ferrara, "VEGF couples hypertrophic cartilage remodeling, ossification and angiogenesis during endochondral bone formation"; *Nature Medicine*, 5(6):623–8, 1999.

Glennie, et al., "Preparation and performance of bispecific F(ab' gamma)₂ antibody containing thioether-linked Fab' gamma fragments," *J. Immunol.*, 139:2367–2375, 1987.

Goding, In: *Monoclonal Antibodies: Principles and Practice, 2nd Edition*, Academic Press, Orlando, Fla., pp. 60–61, 65–66, 71–74, 1986.

Good et al., "A tumor suppressor-dependent inhibitor of angiogenesis is immunologically and functionally indistinguishable from a fragment of thrombospondin," *Proc. Natl. Acad. Sci. USA*, 87(17):6624–6628, 1990.

Grant et al., "Fibronectin fragments modulate human retinal capillary cell proliferation and migration," *Diabetes*, 47(8):1335–1340, 1998.

Guo, Jia, Song, Warren, Donner, "Vascular endothelial cell growth factor promotes tyrosine phosphorylation of mediators of signal transduction that contain SH2 domains," *J. Biol. Chem.*, 270:6729–6733, 1995.

Hanahan and Folkman, "Patterns and emerging mechanisms of the angiogenic switch during tumorigenesis," *Cell*, 86(3):353–364, 1996.

Harada, Mitsuyama, Yoshida, Sakisaka, Taniguchi, Kawaguchi, Ariyoshi, Saiki, Sakamoto, Nagata, Sata, Matsuo, Tanikawa, "Vascular endothelial growth factor in patients with rheumatoid arthritis", *Scandinavian J. Rheumatol.*, 27(5):377–80, 1998.

Haran et al., "Tamoxifen enhances cell death in implanted MCF7 breast cancer by inhibiting endothelium growth," *Cancer Res.*, 54(21):5511–5514, 1994.

Hasselaar and Sage, "SPARC antagonizes the effect of basic fibroblast growth factor on the migration of bovine aortic endothelial cells," *J. Cell Biochem.*, 49(3):272–283, 1992.

Hellerqvist et al., "Antitumor effects of GBS toxin: a polysaccharide exotoxin from group B beta-hemolytic streptococcus," *J. Cancer Res. Clin. Oncol.*, 120(1–2): 63–70, 1993.

Hiratsuka, Minowa, Kuno, Noda, Shibuya, "Flt-I lacking the tyrosine kinase domain is sufficient for normal development and angiogenesis in mice," *Proc. Natl. Acad. Sci. USA*, 95(16):9349–9354, 1998.

Hiscox and Jiang, "Interleukin-12, an emerging anti-tumour cytokine," *In Vivo*, 11(2):125–132, 1997.

Holash et al., "Vessel Cooption, Regression, and Growth in Tumors Mediated by Angiopoietins and VEGF", *Science*, 284:1994–1998, 1999.

Hong, Nagy, Senger, Dvorak, Dvorak, "Ultrastructural localization of vascular permeability factor/vascular endothelial growth factor (VPF/VEGF) to the abluminal plasma membrane and vesiculovacuolar organelles of tumor microvascular endothelium," *J. Histochem. Cytochem.*, 43:381–389, 1995.

Hood and Granger, "Protein kinase G mediates vascular endothelial growth factor-induced Raf-1 activation and proliferation in human endothelial cells," *J. Biol. Chem.*, 273(36):23504–23508, 1998.

Hood, Meininger, Ziche, Granger, "VEGF upregulates ecNOS message, protein, and NO production in human endothelial cells," *Am. J. Physiol.*, 274(3 Pt 2):H1054–1058, 1998.

Hori et al., "Differential effects of angiostatic steroids and dexamethasone on angiogenesis and cytokine levels in rat sponge implants," *Br. J. Pharmacol.*, 118(7):1584–1591, 1996.

Houck, Ferrara, Winer, Cachianes, Li, Leung, "The vascular endothelial growth factor family: Identification of a fourth molecular species and characterization of alternative splicing of RNA," *Molec. Endo.*, 5(12):1806–1814, 1991.

Huang, Molema, King, Watkins, Edgington, Thorpe, "Tumor infarction in mice by antibody-directed targeting of tissue factor to tumor vasculature," *Science*, 275: 547–550, 1997.

Huang, Gottstein, Brekken, Thorpe, "Expression of soluble VEGF receptor 2 and characterization of its binding by surface plasmon resonance," *Biochem. Biophys. Res. Commun.*, 252(3):643–648, 1998.

Huse, Sastry, Iverson, Kang, Alting-Mees, Burton, Benkovic and Lerner, *Science*, 246(4935):1275–1281, 1989.

Ingber et al., "Angioinhibins: Synthetic analogues of fumagillin which inhibit angiogenesis and suppress tumor growth," *Nature*, 48:555–557, 1990.

Inoue, Itoh, Ueda, Naruko, Kojima, Komatsu, Doi, Ogawa, Tamura, Takaya, Igaki, Yamashita, Chun, Masatsugu, Becker, Nakao, "Vascular endothelial growth factor (VEGF) expression in human coronary atherosclerotic lesions: possible pathophysiological significance of VEGF in progression of atherosclerosis", *Circulation*, 98(20):2108–16, 1998.

Iwamoto et al., "Inhibition of angiogenesis, tumour growth and experimental metastasis of human fibrosarcoma cells HT1080 by a multimeric form of the laminin sequence Tyr-Ile-Gly-Ser-Arg (YIGSR)," *Br. J. Cancer*, 73(5):589–595, 1996.

Jackson et al., "Stimulation and inhibition of angiogenesis by placental proliferin and proliferin-related protein," *Science*, 266(5190):1581–1584, 1994.

Jendraschak and Sage, "Regulation of angiogenesis by SPARC and angiostatin: implications for tumor cell biology," *Semin. Cancer Biol.*, 7(3):139–146, 1996.

Joukov, Kumar, Sorsa, Arighi, Weich, Saksela, Alitalo, "A recombinant mutant vascular endothelial growth factor-C that has lost vascular endothelial growth factor receptor-2 binding, activation, and vascular permeability activities," *J. Biol. Chem.*, 273(12):6599–6602, 1998.

Kabat et al., "Sequences of Proteins of Immunological Interest" 5th Ed. Public Health Service, National Institutes of Health, Bethesda, Md., 1991, pp 647–669 in particular.

Kang, Barbas, Janda, Benkovic and Lerner, *Proc. Natl. Acad. Sci., U.S.A*, 88(10):4363–4366, 1991.

Keck, Hauser, Krivi, Sanzo, Warren, Feder, Connolly, "Vascular permeability factor, an endothelial cell mitogen related to PDGF," *Science*, 246:1309–1312, 1989.

Kendall and Thomas, "Inhibition of vascular endothelial cell growth factor activity by an endogenously encoded soluble receptor," *Proc. Natl. Acad. Sci. USA*, 90:10705–10709, 1993.

Kenyon, Browne, D'Amato, "Effects of thalidomide and related metabolites in a mouse corneal model of neovascularization," *Exp. Eye Res.*, 64(6):971–978, 1997.

Kerbel, Viloria-Petit, Okada, Rak, "Establishing a link between oncogenes and tumor angiogenesis," *Mol. Med.*, 4(5):286–295, 1998.

Keyt et al., "Identification of vascular endothelial growth factor determinants for binding KDR and FLT-1 receptors. Generation of receptor-selective VEGF variants by site-directed mutagenesis," *J. Biol. Chem.*, 271(10):5638–46, 1996.

Kim, Li, Houck, Winer, Ferrara, "The vascular endothelial growth factor proteins: identification of biologically relevant regions by neutralizing monoclonal antibodies," *Growth Factors*, 7:53–64, 1992.

Kim, Li, Winer, Armanini, Gillett, Phillips, "Inhibition of vascular endothelial growth factor-induced angiogenesis suppresses tumour growth in vivo," *Nature*, 362:841–844, 1993.

Kim, Kwak, Ahn, So, Liu, Koh, Koh, "Molecular cloning and characterization of a novel angiopoietin family protein, angiopoietin-3 ", *FEBS Lett.*, 443(3):353–6, 1999.

Kleinman et al., "The laminins: a family of basement membrane glycoproteins important in cell differentiation and tumor metastases," *Vitam. Horm.*, 47:161–186, 1993.

Kohler and Milstein, "Continuous cultures of fused cells secreting antibody of predefined specificity," *Nature*, 256: 495–497, 1975.

Kohler and Milstein, "Derivation of specific antibody-producing tissue culture and tumor lines by cell fusion," *Eur. J. Immunol.,* 6:511–519, 1976.

Konieczny, Bobrzecka, Laidler and Rybarska, "The combination of IgM subunits and proteolytic IgG fragment by controlled formation of interchain disulphides," *Haematologia,* 14(1):95–99, 1981.

Kondo, Asano, Suzuki, "Significance of vascular endothelial growth factor/vascular permeability factor for solid tumor growth, and its inhibition by the antibody," *Biochem. Biophys. Res. Commun.,* 194:1234–1241, 1993.

Korpelainen and Alitalo, "Signaling angiogenesis and lymphangiogenesis," *Curr. Opin. Cell Biol.,* 10(2):159–164, 1998.

Kremer, Breier, Risau, Plate, "Up-regulation of flk-1/vascular endothelial growth factor receptor 2 by its ligand in a cerebral slice culture system," *Cancer Res.,* 57:3852–3859, 1997.

Kroll and Waltenberger, "The vascular endothelial growth factor receptor KDR activates multiple signal transduction pathways in porcine aortic endothelial cells", *J. Biol. Chem.,* 272:32521–7, 1997.

Kroll and Waltenberger, "VEGF-A induces expression of eNOS and iNOS in endothelial cells via VEGF receptor-2 (KDR)," *Biochem. Biophys. Res. Commun.,* 252(3):743–746, 1998.

Kupprion, Motamed, Sage, "SPARC (BM-40, osteonectin) inhibits the mitogenic effect of vascular endothelial growth factor on microvascular endothelial cells," *J. Biol. Chem.,* 273(45):29635–29640, 1998.

Kyte and Doolittle, "A simple method for displaying the hydropathic character of a protein," *J. Mol. Biol.,* 157(1):105–132, 1982.

Landgren, Schiller, Cao, Claesson-Welsh, "Placenta growth factor stimulates MAP kinase and mitogenicity but not phospholipase C-gamma and migration of endothelial cells expressing Flt 1," *Oncogene,* 16(3):359–367, 1998.

Lane, Iruela-Arispe, Sage, "Regulation of gene expression by SPARC during angiogenesis in vitro. Changes in fibronectin, thrombospondin-1, and plasminogen activator inhibitor-1," *J. Biol. Chem.,* 267(23):16736–16745, 1992.

Lee et al., "Inhibition of urokinase activity by the antiangiogenic factor 16K prolactin: activation of plasminogen activator inhibitor 1 expression," *Endocrinology,* 139(9):3696–3703, 1998.

Lin, Sankar, Shan, Dewhirst, Polyerini, Quinn, Peters, "Inhibition of tumor growth by targeting tumor endothelium using a soluble vascular endothelial growth factor receptor," *Cell Growth Differ.,* 9:49–58, 1998.

Lin, Buxton, Acheson, Radziejewski, Maisonpierre, Yancopoulos, Channon, Hale, Dewhirst, George, Peters, "Anti-angiogenic gene therapy targeting the endothelium-specific receptor tyrosine kinase Tie2", *Proc. Natl. Acad. Sci., USA,* 95(15):8829–34, 1998.

Lin, Nguyen, Mendoza, Escandon, Fei, Meng, Modi, "Preclinical pharmacokinetics, interspecies scaling, and tissue distribution of a humanized monoclonal antibody against vascular endothelial growth factor", *J. Pharmacol. Exp. Therap.,* 288(1):371–8, 1999.

Lindner and Borden, "Effects of tamoxifen and interferon-beta or the combination on tumor-induced angiogenesis," *Int. J. Cancer,* 71(3):456461, 1997.

Lingen, Polyerini, Bouck, "Retinoic acid and interferon alpha act synergistically as antiangiogenic and antitumor agents against human head and neck squamous cell carcinoma," *Cancer Res.,* 58(23):5551–5558, 1998.

Lingen, Polyerini, Bouck, "Inhibition of squamous cell carcinoma angiogenesis by direct interaction of retinoic acid vith endothelial cells," *Lab. Invest.,* 74(2):476–483, 1996.

Lin-Ke, Hong-Qu, Nagy, Eckelhoefer, Masse, Dvorak, Dvorak, "Vascular targeting of solid and ascites tumours with antibodies to vascular endothelial growth factor," *Eur. J. Cancer,* 32A(14):2467–2473, 1996.

Luo, Toyoda, Shibuya, "Differential inhibition of fluid accumulation and tumor growth in two mouse ascites tumors by an antivascular endothelial growth factor/permeability factor neutralizing antibody," *Cancer Res.,* 58(12):2594–2600, 1998a.

Luo, Yamaguchi, Shinkai, Shitara, Shibuya, "Significant expression of vascular endothelial growth factor/vascular permeability factor in mouse ascites tumors," *Cancer Res.,* 58(12):2652–2660, 1998b.

Majewski et al., "Vitamin D3 is a potent inhibitor of tumor cell-induced angiogenesis," *J. Investig. Dermatol. Symp. Proc.,* 1(1):97–101, 1996.

Malecaze, Clamens, Simorre-Pinatel, Mathis, Chollet, Favard, Bayard, Plouet, "Detection of vascular endothelial growth factor messenger RNA and vascular endothelial growth factor-like activity in proliferative diabetic retinopathy," *Arch. Ophthalmol.,* 112:1476–1482, 1994.

Mandriota and Pepper, "Regulation of angiopoietin-2 mRNA levels in bovine microvascular endothelial cells by cytokines and hypoxia", *Circ. Res.,* 83(8):852–9, 1998.

Manetti et al., "Synthesis and binding mode of heterocyclic analogues of suramin inhibiting the human basic fibroblast growth factor," *Bioorg. Med. Chem.,* 6(7):947–958, 1998.

Massey et al., *Nature,* 328:457–458, 1987.

Mazure, Chen, Yeh, Laderoute, Giaccia, "Oncogenic transformation and hypoxia synergistically act to modulate vascular endothelial growth factor expression," *Cancer Res.,* 56:3436–3440, 1996.

McNamara, Harmey, Walsh, Redmond, Bouchier-Hayes, "Significance of angiogenesis in cancer therapy [published erratum appears in Br J. Surg., October;85(10):1449, 1998," *Br. J. Surg,* 85(8):1044–1055. 1998.

Mesiano, Ferrara, Jaffe, "Role of vascular endothelial growth factor in ovarian cancer: inhibition of ascites formation by immunoneutralization," *Am. J. Pathol.,* 153(4):1249–1256, 1998.

Meyer, Clauss, Lepple-Wienhues, Waltenberger, Augustin, Ziche, Lanz, Buttner, Rziha, Dehio, "A novel vascular endothelial growth factor encoded by Orf virus, VEGF-E, mediates angiogenesis via signalling through VEGFR-2 (KDR) but not VEGFR-1 (Flt-1) receptor tyrosine kinases, *EMBO J,* 18:363–74, 1999.

Millauer, Longhi, Plate, Shawver, Risau, Ullrich, Strawn, "Dominant-negative inhibition of Flk-1 suppresses the growth of many tumor types in vivo," *Cancer Res.,* 56:1615–1620, 1996.

Mills, Brooker and Camerini-Otero, "Sequences of human immunoglobulin switch regions: implications for recombination and transcription," *Nucl. Acids Res.,* 18:7305–7316, 1990.

Moore et al., "Tumor angiogenesis is regulated by CXC chemokines," *J. Lab. Clin. Med.,* 132(2):97–103, 1998.

Mordenti, Thomsen, Licko, Chen, Meng, Ferrara, "Efficacy and concentration-response of murine anti-VEGF monoclonal antibody in tumor-bearing mice and extrapolation to humans", *Toxicologic Pathology,* 27(1):14–21, 1999.

Morrison, Johnson, Herzenberg and Oi, "Chimeric human antibody molecules: mouse antigen-binding domains with human constant region domains," *Proc. Natl. Acad. Sci. USA,* 81(21):6851–6855, 1984.

Morrison, Wims, Kobrin and Oi, "Production of novel immunoglobulin molecules by gene transfection," *Mt. Sinai J. Med.,* 53(3):175, 1986.

Morrow, Unuvar, King, Mleczko, "Techniques for the production of monoclonal and polyclonal antibodies," In: *Colloidal Gold: Principles, Methods and Applications*, M. A. Hayat (ed.), Orlando: Academic Press, pp. 31–57, 1990.

Muller, Li, Christinger, Wells, Cunningham, De Vos, "Vascular Endothelial growth factor: Crystal structure and functional mapping of the kinase domain receptor binding site", *Proc. Natl. Acad. Sci. USA.,* 94:7192–7197, 1997.

Muller, Chen, Christinger, Li, Cunningham, Lowman, de Vos, "VEGF and the Fab fragment of a humanized neutralizing antibody: crystal structure of the complex at 2.4 A resolution and mutational analysis of the interface," *Structure,* 6(9):1153–67, 1998.

Murohara, Horowitz, Silver, Tsurumi, Chen, Sullivan, Isner, "Vascular endothelial growth factor/vascular permeability factor enhances vascular permeability via nitric oxide and prostacyclin," *Circulation,* 97(1):99–107, 1998.

Mustonen and Alitalo, "Endothelial receptor tyrosine kinases involved in angiogenesis," *J. Cell Biol.,* 129: 895–898, 1995.

Nagashima, Yoshino, Aono, Takai, Sasano, "Inhibitory effects of anti-rheumatic drugs on vascular endothelial growth factor in cultured rheumatoid synovial cells", *Clin. Exp. Immunol.,* 116(2):360–5, 1999.

Nagler, Feferman, Shoshan, "Reduction in basic fibroblast growth factor mediated angiogenesis in vivo by linomide," *Connect Tissue Res.,* 37(1–2):61–68, 1998.

Nakamura et al., Enzyme Immunoassays: Heterogeneous and Homogeneous Systems, Chapter 27.

Neufeld, Cohen, Gengrinovitch, Poltorak, "Vascular endothelial growth factor (VEGF) and its receptors," *FASEB J.,* 13(1):9–22, 1999.

Niida, Kaku, Amano, Yoshida, Kataoka, Nishikawa, Tanne, Maeda, Nishikawa, Kodama, "Vascular endothelial growth factor can substitute for macrophage colony-stimulating factor in the support of osteoclastic bone resorption", *J. Exp. Med,* 190(2):293–8, 1999.

Ogawa, Oku, Sawano, Yamaguchi, Yazaki, Shibuya, "A novel type of vascular endothelial growth factor, VEGF-E (NZ-7 VEGF), preferentially utilizes KDR/Flk-1 receptor and carries a potent mitotic activity without heparin-binding domain," *J. Biol. Chem.,* 273(47):31273–31282, 1998.

Oikawa et al., "A highly potent antiangiogenic activity of retinoids," *Cancer Lett.,* 48(2):157–162, 1989.

Olander, Connolly, DeLarco, "Specific binding of vascular permeability factor to endothelial cells," *Biochem. Biophys. Res. Comm.,* 175:68–76, 1991.

O'Reilly et al., "Angiostatin: a novel angiogenesis inhibitor that mediates the suppression of metastases by a Lewis lung carcinoma," *Cell,* 79:315–328, 1994.

O'Reilly et al., "Endostatin: an endogenous inhibitor of angiogenesis and tumor growth," *Cell,* 88(2):277–285, 1997.

Papapetropoulos, Garcia-Cardena, Dengler, Maisonpierre, Yancopoulos, Sessa, "Direct actions of angiopoietin-1 on human endothelium: evidence for network stabilization, cell survival, and interaction with other angiogenic growth factors", *Lab. Invest.,* 79(2):213–23, 1999.

Parenti et al., "Nitric oxide is an upstream signal of vascular endothelial growth factor-induced extracellular signal-regulated kinase½ activation in postcapillary endothelium," *J. Biol. Chem.,* 273(7):4220–4226, 1998.

Parmley and Smith, "Antibody-selectable filamentous fd phage vectors: affinity purification of target genes," *Gene,* 73(2):305–318, 1988.

Pepper et al., "Leukemia inhibitory factor (LIF) inhibits angiogenesis in vitro," *J. Cell Sci.,* 108(Pt 1):73–83, 1995.

Plate, Breier, Weich, Mennel, Risau, "Vascular endothelial growth factor and glioma angiogenesis: coordinate induction of VEGF receptors, distribution of VEGF protein and possible in vivo regulatory mechanisms," *Int. J. Cancer,* 59:520–529, 1994.

Potgens, Westphal, DeWaal, Ruiter, "The role of vascular permeability factor and basic fibroblast growth factor in tumor angiogenesis," *In: Growth Factors in Tumor Angiogenesis*, Berlin: Walter de Gruyer & Co. pp. 57–70, 1995.

Presta, Chen, O'Connor, Chisholm, Meng, Krunimmen, Winkler, Ferrara, "Humanization of an anti-vascular endothelial growth factor monoclonal antibody for the therapy of solid tumors and other disorders," *Cancer Res.,* 57:4593–4599, 1997.

Quinn et al., CM101, a polysaccharide antitumor agent, does not inhibit wound healing in murine models," *J. Cancer Res. Clin. Oncol.,* 121(4):253–256, 1995.

RayChaudhury and D'Amore, "Endothelial cell regulation by transforming growth factor-beta," *J. Cell Biochem.,* 47(3):224–229, 1991.

Richer and Lo, "Introduction of human DNA into mouse eggs by injection of dissected human chromosome fragments", *Science* 245, 175–177, 1989.

Riechmann, Clark, Waldmann and Winter, "Reshaping human antibodies for therapy," *Nature,* 332(6162):323–327, 1988.

Rouan, Ottemess, Cunningham, Holden, Rhodes, "Reversal of colchicine-induced mitotic arrest in Chinese hamster cells with a colchicine-specific monoclonal antibody," *Am. J. Pathol.,* 137(4):779–787, 1990.

Ryan, Eppler, Hagler, Bruner, Thomford, Hall, Shopp, O'Neill, "Preclinical safety evaluation of rhuMAbVEGF, an antiangiogenic humanized monoclonal antibody", *Toxicologic Pathology,* 27(1):78–86, 1999.

Sakamoto et al., "Heparin plus cortisone acetate inhibit tumor growth by blocking endothelial cell proliferation," *Canc. J.,* 1:55–58, 1986.

Saleh, Stacker, Wilks, "Inhibition of growth of C6 glioma cells in vivo by expression of antisense vascular endothelial growth factor sequence," *Cancer Res.,* 56:393–401, 1996.

Sambrook, Fritsch and Maniatis, *Molecular Cloning: A Laboratory Manual,* 2nd Ed., Cold Spring Harbor Press, Cold Spring Harbor, N.Y., 1989.

Sang, "Complex role of matrix metalloproteinases in angiogenesis," *Cell Res.,* 8(3):171–177, 1998.

Sawano, Takahashi, Yamaguchi, Aonuma, Shibuya, "Flt-1 but not KDR/Flk-1 tyrosine kinase is a receptor for placenta growth factor, which is related to vascular endothelial growth factor," *Cell Growth Differ,* 7(2):213–221, 1996.

Senger, Galli, Dvorak, Perruzzi, Harvey, Dvorak, "Tumor cells secrete a vascular permeability factor that promotes accumulation of ascites fluid," *Science,* 219:983–985, 1983.

Senger, Perruzzi, Feder, Dvorak, "A highly conserved vascular permeability factor secreted by a variety of human and rodent tumor cell lines," *Cancer Res.,* 46:5629–5632, 1986.

Senger, Connolly, Vandewater, Feder, Dvorak, "Purification and NH2-terminal amino acid sequence of guinea pig tumor secreted vascular permeability factor," *Cancer Res.*, 50:1774–1778, 1990.

Shalaby, Rossant, Yamaguchi, Gertsenstein, Wu, Breitman, Schuh, "Failure of blood-island formation and vasculogenesis in Flk-1-deficient mice," *Nature*, 376:62–66, 1995.

Sheibani and Frazier, "Thrombospondin 1 expression in transformed endothelial cells restores a normal phenotype and suppresses their tumorigenesis," *Proc. Natl. Acad. Sci. USA*, 92(15):6788–6792, 1995.

Sheu et al., "Inhibition of angiogenesis in vitro and in vivo: comparison of the relative activities of triflavin, an Arg-Gly-Asp-containing peptide and anti-alpha(v)beta3 integrin monoclonal antibody," *Biochim. Biophys. Acta*, 1336 (3):445–454, 1997.

Shyu, Manor, Magner, Yancopoulos, Isner, "Direct intramuscular injection of plasmid DNA encoding angiopoietin-1 but not angiopoietin-2 augments revascularization in the rabbit ischemic hindlimb", *Circulation*, 98(19): 2081–7, 1998.

Sideras, Mizuta, Kanamori, Suzuki, Okamoto, Kuze, Ohno, Doi, Fukuhara, Hassan, et al., "Production of sterile transcripts of C gamma genes in an IgM-producing human neoplastic B cell line that switches to IgG-producing cells," *Intl. Immunol.*, 1(6):631–642, 1989.

Siemeister, Martiny-Baron, Marme, "The pivotal role of VEGF in tumor angiogenesis: molecular facts and therapeutic opportunities," *Cancer Metastasis Rev.*, 17(2):241–248., 1998

Sioussat, Dvorak, Brock, Senger, "Inhibition of vascular permeability factor (vascular endothelial growth factor) with antipeptide antibodies," *Arch. Biochem. Biophys.*, 301:15–20, 1993.

Sipos et al., "Inhibition of tumor angiogenesis," *Ann. NY Acad. Sci.*, 732:263–272, 1994.

Skobe, Rockwell, Goldstein, Vosseler, Fusenig, "Halting angiogenesis suppresses carcinoma cell invasion", *Nat. Med.*, 3:1222–7, 1997.

Soff et al., "Expression of plasminogen activator inhibitor type 1 by human prostate carcinoma cells inhibits primary tumor growth, tumor-associated angiogenesis, and metastasis to lung and liver in an athymic mouse model," *J. Clin. Invest.*, 96(6):2593–2600, 1995.

Soker, Takashima, Miao, Neufeld, Klagsbrun, "Neuropilin-1 is expressed by endothelial and tumor cells as an isoform-specific receptor for vascular endothelial growth factor," *Cell*, 92(6):735–745, 1998.

Springer, Chen, Kraft, Bednarski, Blau, "VEGF gene delivery to muscle: potential role for vasculogenesis in adults," *Mol. Cell*, 2(5):549–558, 1998.

Stella et al., "Prodrugs: A chemical approach to targeted drug delivery", *Directed Drug Delivery*, Borchardt et al., Eds. Human Press, 1985, pp 247–267.

Stratmann, Risau, Plate, "Cell type-specific expression of angiopoietin-1 and angiopoietin-2 suggests a role in glioblastoma angiogenesis", *Am. J. Pathol.*, 153(5):1333–9, 1998.

Tada et al., "Inhibition of tubular morphogenesis in human microvascular endothelial cells by co-culture with chondrocytes and involvement of transforming growth factor beta: a model for avascularity in human cartilage," *Biochim. Biophys. Acta*, 1201(2):135–142, 1994.

Takahashi, Shirasawa, Miyake, Yahagi, Maruyama, Kasahara, Kawamura, Matsumura, Mitarai, Sakai, "Protein tyrosine kinases expressed in glomeruli and cultured glomerular cells: Flt-1 and VEGF expression in renal mesangial cells," *Biochem. Biophys. Res. Comm.*, 209: 218–226, 1995.

Takano et al., "Suramin, an anticancer and angiosuppressive agent, inhibits endothelial cell binding of basic fibroblast growth factor, migration, proliferation, and induction of urokinase-type plasminogen activator," *Cancer Res.*, 54(10):2654–2660, 1994.

Tanaka, Mori, Sakamoto, Makuuchi, Sugimachi, Wands, "Biologic significance of angiopoietin-2 expression in human hepatocellular carcinoma", *J. Clin. Invest.*, 103 (3):341–5, 1999.

Tanaka et al., "Viral vector-mediated transduction of a modified platelet factor 4 cDNA inhibits angiogenesis and tumor growth," *Nat. Med.*, 3(4):437–442, 1997.

Terman, Dougher-Vermazen, Carrion, Dimitrov, Armellino, Gospodarowicz, Bohlen, "Identification of the KDR tyrosine kinase as a receptor for vascular endothelial cell growth factor," *Biochem. Biophys. Res. Comm.*, 187: 1579–1586, 1992.

Terman, Khandke, Dougher-Vermazan, Maglione, Lassam, Gospodarowicz, Persico, Bohlen, Eisinger, "VEGF receptor subtypes KDR and FLT1 show different sensitivities to heparin and placenta growth factor," *Growth Factors*, 11 (3):187–195, 1994.

Tessler, Rockwell, Hicklin, Cohen, Levi, Witte, Lemischka, Neufeld, "Heparin modulates the interaction of VEGF 165 with soluble and cell associated flk-1 receptors," *J. Biol. Chem.*, 269:12456–12461, 1994.

Thomas, "Vascular endothelial growth factor, a potent and selective angiogenic agent," *J. Biol. Chem.*, 271:603–606, 1996.

Thorpe et al., "Heparin-Steroid Conjugates: New Angiogenesis Inhibitors with Antitumor Activity in Mice;" *Cancer Res.*, 53:3000–3007, 1993.

Tischer, Mitchell, Hartman, Silva, Gospodarowicz, Fiddes, Abraham, "The human gene for vascular endothelial growth factor," *J. Biol. Chem.*, 266:11947–11954, 1991.

Tolsma et al., "Peptides derived from two separate domains of the matrix protein thrombospondin-1 have anti-angiogenic activity," *J. Cell Biol.*, 122(2):497–511, 1993.

Tryggvason, "The laminin family," *Curr. Opin. Cell Biol.*, 5(5):877–882, 1993.

Valenzuela, Griffiths, Rojas, Aldrich, Jones, Zhou, McClain, Copeland, Gilbert, Jenkins, Huang, Papadopoulos, Maisonpierre, Davis, Yancopoulos, "Angiopoietins 3 and 4: diverging gene counterparts in mice and humans", *Proc. Natl. Acad. Sci., USA*, 96(5):1904–9, 1999.

van Dijk, Wamaar, van Eendenburg, Thienpont, Braakman, Boot, Fleuren and Bolhuis, "Induction of tumor-cell lysis by bi-specific monoclonal antibodies recognizing renal-cell carcinoma and CD3 antigen," *Int. J. Cancer*, 43:344–349, 1989.

Volpert, Lawler, Bouck, "A human fibrosarcoma inhibits systemic angiogenesis and the growth of experimental metastases via thrombospondin-1," *Proc. Natl. Acad. Sci. USA*, 95(11):6343–6348, 1998.

Vukanovic et al, "Antiangiogenic effects of the quinoline-3-carboxamide linomide," *Cancer Res.*, 53(8):1833–1837, 1993.

Waltenberger, Claesson-Welsh, Siegbahn, Shibuya, Heldin, "Different signal transduction properties of KDR and Flt1, two receptors for vascular endothelial growth factor," *J. Biol. Chem.*, 269(43):26988–26995, 1994.

Waltenberger, Mayr, Pentz, Hombach, "Functional upregulation of the vascular endothelial growth factor receptor KDR by hypoxia," *Circulation*, 94:1647–1654, 1996.

Waltenberger et al., "Suramin is a potent inhibitor of vascular endothelial growth factor. A contribution to the molecular basis of its antiangiogenic action," *J. Mol Cell Cardiol.*, 28(7):1523–1529, 1996.

Warnil et al., "Soluble E-selectin in cancer patients as a marker of the therapeutic efficacy of CM101, a tumor-inhibiting anti-neovascularization agent, evaluated in phase I clinical trail," *J. Cancer Res. Clin. Oncol.*, 123(3):173–179, 1997.

Wells, "Starving cancer into submission", *Chem. Biol.*, 5(4):R87–88, 1998.

Wiesmann, Fuh, Christinger, Eigenbrot, Wells, de Vos, "Crystal structure at 1.7 A resolution of VEGF in complex with domain 2 of the Flt-1 receptor," *Cell*, 91(5):695–704, 1997.

Willman et al., "Prodrugs in cancer therapy", *Biochem. Soc. Trans.*, 14:375–382, 1988.

Winter and Milstein, "Man-made antibodies," *Nature*, 349:293–299, 1991.

Wolff et al., "Dexamethasone inhibits glioma-induced formation of capillary like structures in vitro and angiogenesis in vivo," *Klin. Padiatr.*, 209(4):275–277, 1997.

Yoon et al., "Inhibitory effect of Korean mistletoe (Viscum album coloratum) extract on tumour angiogenesis and metastasis of haematogenous and non-haematogenous tumour cells in mice," *Cancer Lett*, 97(1):83–91, 1995.

Yoshida et al., "Suppression of hepatoma growth and angiogenesis by a fumagillin derivative TNP470: possible involvement of nitric oxide synthase," *Cancer Res.*, 58(16):3751–3756, 1998.

Yuan, Chen, Dellian, Safabakhsh, Ferrara, Jain, "Time-dependent vascular regression and permeability changes in established human tumor xenografts induced by an anti-vascular endothelial growth factor/vascular permeabilty factor antibody," *Proc. Natl. Acad. Sci. USA*, 93:14765–14770, 1996.

Yamamura et al., "Effect of Matrigel and laminin peptide YIGSR on tumor growth and metastasis," *Semin. Cancer Biol.*, 4(4):259–265, 1993.

Zachary, "Vascular endothelial growth factor: how it transmits its signal," *Exp. Nephrol.*, 6(6):480–487, 1998.

Zapata et al., Protein Eng., 8(10):1057–1062, 1995.

Ziche et al., "Linomide blocks angiogenesis by breast carcinoma vascular endothelial growth factor transfectants," *Br. J. Cancer*, 77(7):1123–1129, 1998.

What is claimed is:

1. A method of neutralizing the survival signal of VEGF, the method comprising contacting a cell population including cells that express VEGFR2 (KDR/Flk-1) with a composition comprising a biologically effective amount of at least a first anti-VEGF antibody that binds to substantially the same epitope as the inonoclonal antibody 2C3 produced by hybridorna ATCC PTA 1595, or an antigen-binding fragment of said antibody; wherein said anti-VEGF antibody neutralizes the survival signal of VEGF, which is mediated through VEGFR2.

2. A method of inhibiting VEGF-induced endothelial cell differentiation or migration, comprising contacting a biological tissue comprising a population of endothelial cells with a composition comprising a biologically effective amount of at least a first anti-VEGF antibody that binds to substantially the same epitope as the monoclonal antibody 2C3 produced by hybridoma ATCC PTA 1595, or an antigen-binding fragment of said antibody.

3. A method of reducing a vascular network, comprising contacting a vascular network with a composition comprising at least a first anti-VEGF antibody, or antigen-binding fragment thereof, that binds to substantially the same epitope as the monoclonal antibody 2C3, produced by hybridoma ATCC PTA 1595, in an amount effective to neutralize VEGF in said vascular network.

4. A method of inhibiting blood vessel fonnation or invasion or ingrowth of new blood vessels, comprising contacting a population of blood vessels with at least a first composition comprising a biologically effective amount of at least a first anti-VEGF antibody, or antigen-binding fragment thereof, that binds to substantially the same epitope as the monoclonal. antibody 2C3 produced by hybridoma ATCC PTA 1595.

5. The method of claim 4, wherein said at least a first antibody is a monoclonal antibody or an antigen-binding fragment thereof.

6. The method of claim 1, wherein said cell population includes cells that express VEGFR2 (KDR/Flk-1) and cells that express VEGFR1 (Flt-1).

7. The method of claim 5, wherein said at least a first anti body is an scFv, Fv, Fab', Fab, diabody, linear antibody or F(ab')$_2$ antigen-binding fragment of an antibody.

8. The method of claim 1, wherein said cell population is located within a population of blood vessels.

9. The method of claim 4, wherein said at least a first antibody is a human, humanized or part-human antibody or antigen-binding fragment thereof.

10. The method of claim 4, wherein said at least a first antibody is a chimeric antibody or a recombinant antibody.

11. The method of claim 1, wherein said cell population is located within an animal and said composition that comprises said anti-VEGF antibody is administered to said animal.

12. The method of claim 3, wherein s&d vascular network is located within an animal and said composition that comprises said anti-VEGF antibody is administered to said animal.

13. The method of claim 4, wherein said at least a first antibody is the monoclonal antibody 2C3 produced by bybridoma ATCC PTA 1595.

14. The method of claim 4, wherein said population of blood vessels is located within an animal and said at least a first composition is administered to said animal.

15. The method of claim 14, wherein said at least a first composition is administered to said animal intravenously.

16. The method of claim 14, wherein said animal has, or is at risk for developing, a vaseularized solid tumor, metastases from a primary tumor, ocular neovascular disease, macular degeneration, age-related macular degeneration, arthritis, rheumatoid arthritis, osteoarthritis, atherosclerosis, diabetic retinopathy, thyroid hyperplasia, Grave's disease, hemangioma, neovascular glaucoma or psonasis.

17. The method of claim 14, wherein said at least a first anti-VEGF antibody, or antigen-binding fragment thereat binds to the same epitope as the monoclonal antibody 2C3 produced by hybridoma ATCC PTA 1595.

18. The method of claim 14, further comprising administering to said animal a therapeutically effective amount of at least a second therapeutic agent.

19. The method of claim 14, wherein said animal is a human patient.

20. A method for inhibiting blood vessel formation or invasion or ingrowib of new blood vessels, comprising contacting a population of blood vessels with at least a first composition comprising a biologically ciThetive amount of at least a first anti-VEGF antibody, or an antigen-hinding fragment thereof, that binds to the same epitope as the monoclonal antibody 2C3 produced by hybridoma ATCC PTA 1595 and that significantly inhibits VEGF binding to the VEGF receptor VEGFR2 (KDR/Flk-1) without significantly inhibiting VEGF binding to the VEGF receptor VEGFR1 (Flt-1).

21. A method for inhibiting blood vessel formation or invasion or ingrowth of new blood vessels, comprising contacting a population of blood vessels with at least a first composition comprising a biologically effective amount of at least a first anti-VEGF antibody, or antigen-binding fragment thereof, that effectively competes with the monoelonal antibody 2C3, produced by hybridoma ATCC PTA 1595, for binding to VEGF.

22. A method for treating an animal that has, or is at risk for developing, a vascularized solid tumor, metastases from a primary tumor, macular degeneration, age-related macular degeneration, ocular neovaseular disease, arthritis, rheumatoid arthritis, osteoarthritis, atherosclerosis, diabetic retinopathy, thyroid hyperplasia, Grave's disease, hemangioma, neovascular glaucoma or psoriasis, comprising administering to said animal a composition comprising a therapeutically effective amount of at least a first anti-VEGF antibody, or an antigen-binding fragment thereof, that binds to substantially the same epitope as the monoclonal antibody 2C3 produced by hybridoma ATCC PTA 1595.

* * * * *

UNITED STATES PATENT AND TRADEMARK OFFICE
CERTIFICATE OF CORRECTION

PATENT NO. : 7,056,509 B2
APPLICATION NO. : 10/373561
DATED : June 6, 2006
INVENTOR(S) : Philip E. Thorpe and Rolf A. Brekken It is certified that error appears in the above-identified patent and that said Letters Patent is hereby corrected as shown below:

On the title page, correct the name of the Assignee (73) to insert a comma, as: --Board of Regents, The University of Texas System--.

On the title page, item (56), page 1, column 1, after "6,524,583 B1 2/2003 Thorpe et at.", insert --*.--

Claim 1, column 195, line 46, delete "thc" and insert --the-- therefor.

Claim 1, column 195, line 46, delete "inonoclonal" and insert --monoclonal-- therefor.

Claim 1, column 195, line 47, delete "hybridorna" and insert --hybridoma-- therefor.

Claim 4, column 195, line 66, delete "fonnation" and insert --formation-- therefor.

Claim 7, column 196, lines 53 and 54, delete "anti body" and insert --antibody-- therefor.

Claim 12, column 197, line 1, delete "s&d" and insert --said-- therefor.

Claim 13, column 197, line 7, delete "bybridoma" and insert --hybridoma-- therefor.

Claim 16, column 197, line 14, delete "vaseularized" and insert --vascularized-- therefor.

Claim 16, column 197, line 19, delete "psonasis" and insert --psoriasis-- therefor.

Claim 17, column 197, line 21 delete "thereat" and insert --thereof-- therefor.

Claim 20, column 197, line 30, delete "ingrowib" and insert --ingrowth-- therefor.

Claim 20, column 198, line 1, delete "ciThetive" and insert --effective-- therefor.

Claim 20, column 198, line 2, delete "hinding" and insert --binding-- therefor.

Claim 21, column 198, lines 14 and 15, delete "monoelonal" and insert --monoclonal-- therefor.

UNITED STATES PATENT AND TRADEMARK OFFICE
CERTIFICATE OF CORRECTION

PATENT NO. : 7,056,509 B2
APPLICATION NO. : 10/373561
DATED : June 6, 2006
INVENTOR(S) : Philip E. Thorpe and Rolf A. Brekken It is certified that error appears in the above-identified patent and that said Letters Patent is hereby corrected as shown below:

Claim 22, column 198, line 20, delete "neovaseular" and insert --neovascular-- therefor.

Signed and Sealed this

Twenty-seventh Day of February, 2007

JON W. DUDAS
*Director of the United States Patent and Trademark Office*

SEQUENCE LISTING

<160> NUMBER OF SEQ ID NOS: 44

<210> SEQ ID NO 1
<211> LENGTH: 2149
<212> TYPE: DNA
<213> ORGANISM: Homo sapiens

<400> SEQUENCE: 1

```
cagctgactc aggcaggctc catgctgaac ggtcacacag agaggaaaca ataaatctca      60
gctactatgc aataaatatc tcaagtttta acgaagaaaa acatcattgc agtgaaataa     120
aaaattttaa aattttagaa caaagctaac aaatggctag ttttctatga ttcttcttca     180
aacgctttct ttgaggggga aagagtcaaa caaacaagca gttttacctg aaataaagaa     240
ctagttttag aggtcagaag aaaggagcaa gttttgcgag aggcacggaa ggagtgtgct     300
ggcagtacaa tgcagtttt cctttccttt gctttcctcg ctgccattct gactcacata      360
gggtgcagca atcagcgccg aagtccagaa aacagtggga gaagatataa ccggattcaa     420
catgggcaat gtgcctacac tttcattctt ccagaacacg atggcaactg tcgtgagagt     480
acgacagacc agtacaacac aaacgctctg cagagagatg ctccacacgt ggaaccggat     540
ttctcttccc agaaacttca acatctggaa catgtgatgg aaaattatac tcagtggctg     600
caaaaacttg agaattacat tgtggaaaac atgaagtcgg agatggccca gatacagcag     660
aatgcagttc agaaccacac ggctaccatg ctggagatag gaaccagcct cctctctcag     720
actgcagagc agaccagaaa gctgacagat gttgagaccc aggtactaaa tcaaacttct     780
cgacttgaga tacagctgct ggagaattca ttatccacct acaagctaga gaagcaactt     840
cttcaacaga caaatgaaat cttgaagatc catgaaaaaa acagtttatt agaacataaa     900
atcttagaaa tggaaggaaa acacaaggaa gagttggaca ccttaaagga agagaaagag     960
aaccttcaag gcttggttac tcgtcaaaca tatataatcc aggagctgga aaagcaatta    1020
aacagagcta ccaccaacaa cagtgtcctt cagaagcagc aactggagct gatggacaca    1080
```

-continued

```
gtccacaacc ttgtcaatct ttgcactaaa gaaggtgttt tactaaaggg aggaaaaaga    1140
gaggaagaga aaccatttag agactgtgca gatgtatatc aagctggttt taataaaagt    1200
ggaatctaca ctatttatat taataatatg ccagaaccca aaaaggtgtt ttgcaatatg    1260
gatgtcaatg ggggaggttg gactgtaata caacatcgtg aagatggaag tctagatttc    1320
caaagaggct ggaaggaata taaaatgggt tttggaaatc cctccggtga atattggctg    1380
gggaatgagt ttatttttgc cattaccagt cagaggcagt acatgctaag aattgagtta    1440
atggactggg aagggaaccg agcctattca cagtatgaca gattccacat aggaaatgaa    1500
aagcaaaact ataggttgta tttaaaaggt cacactggga cagcaggaaa acagagcagc    1560
ctgatcttac acggtgctga tttcagcact aaagatgctg ataatgacaa ctgtatgtgc    1620
aaatgtgccc tcatgttaac aggaggatgg tggtttgatg cttgtggccc ctccaatcta    1680
aatggaatgt tctatactgc gggacaaaac catggaaaac tgaatgggat aaagtggcac    1740
tacttcaaag ggcccagtta ctccttacgt tccacaacta tgatgattcg acctttagat    1800
ttttgaaagc gcaatgtcag aagcgattat gaaagcaaca agaaatccg gagaagctgc    1860 caggtgagaa actgtttgaa aacttcagaa gcaaacaata ttgtctccct tccagcaata    1920
agtggtagtt atgtgaagtc accaaggttc ttgaccgtga atctggagcc gtttgagttc    1980
acaagagtct ctacttgggg tgacagtgct cacgtggctc gactatagaa aactccactg    2040
actgtcgggc tttaaaaagg gaagaaactg ctgagcttgc tgtgcttcaa actactactg    2100
gaccttattt tggaactatg gtagccagat gataaatatg gttaatttc                2149
```

<210> SEQ ID NO 2
<211> LENGTH: 498
<212> TYPE: PRT
<213> ORGANISM: Homo sapiens

<400> SEQUENCE: 2

```
Met Thr Val Phe Leu Ser Phe Ala Phe Leu Ala Ala Ile Leu Thr His
 1               5                  10                  15

Ile Gly Cys Ser Asn Gln Arg Arg Ser Pro Glu Asn Ser Gly Arg Arg
                20                  25                  30

Tyr Asn Arg Ile Gln His Gly Gln Cys Ala Tyr Thr Phe Ile Leu Pro
            35                  40                  45

Glu His Asp Gly Asn Cys Arg Glu Ser Thr Thr Asp Gln Tyr Asn Thr
        50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190
```

-continued

Leu Leu Glu His Lys Ile Leu Glu Met Glu Gly Lys His Lys Glu Glu
                195                 200                 205

Leu Asp Thr Leu Lys Glu Glu Lys Glu Asn Leu Gln Gly Leu Val Thr
        210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270

Lys Gly Gly Lys Arg Glu Glu Lys Pro Phe Arg Asp Cys Ala Asp
            275                 280                 285

Val Tyr Gln Ala Gly Phe Asn Lys Ser Gly Ile Tyr Thr Ile Tyr Ile
        290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
        355                 360                 365

Arg Gln Tyr Met Leu Arg Ile Glu Leu Met Asp Trp Glu Gly Asn Arg
370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
            435                 440                 445

Phe Asp Ala Cys Gly Pro Ser Asn Leu Asn Gly Met Phe Tyr Thr Ala
        450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495
Asp Phe

<210> SEQ ID NO 3
<211> LENGTH: 2269
<212> TYPE: DNA
<213> ORGANISM: Homo sapiens

<400> SEQUENCE: 3
tgggttggtg tttatctcct cccagccttg agggagggaa caacactgta ggatctgggg     60
agagaggaac aaaggaccgt gaaagctgct ctgtaaaagc tgacacagcc ctcccaagtg    120
agcaggactg ttcttcccac tgcaatctga cagtttactg catgcctgga gagaacacag    180
cagtaaaaac caggtttgct actggaaaaa gaggaaagag aagactttca ttgacggacc    240
cagccatggc agcgtagcag ccctgcgttt cagacggcag cagctcggga ctctggacgt    300
gtgtttgccc tcaagtttgc taagctgctg gtttattact gaagaaagaa tgtggcagat    360

-continued

```
tgttttctttt actctgagct gtgatcttgt cttggccgca gcctataaca actttcggaa      420
gagcatggac agcataggaa agaagcaata tcaggtccag catgggtcct gcagctacac      480
tttcctcctg ccagagatgg acaactgccg ctcttcctcc agccctacg tgtccaatgc       540 tgtgcagagg gacgcgccgc tcgaatacga tgactcggtg cagaggctgc aagtgctgga      600
gaacatcatg gaaacaaca ctcagtggct aatgaagctt gagaattata tccaggacaa      660
catgaagaaa gaaatggtag agatacagca gaatgcagta cagaaccaga cggctgtgat      720
gatagaaata gggacaaacc tgttgaacca acagctgag caaacgcgga agttaactga       780
tgtggaagcc caagtattaa atcagaccac gagacttgaa cttcagctct ggaacactc       840 cctctcgaca aacaaattgg aaaaacagat tttggaccag accagtgaaa taaacaaatt      900
gcaagataag aacagtttcc tagaaaagaa ggtgctagct atggaagaca agcacatcat      960
ccaactacag tcaataaaag aagagaaaga tcagctacag gtgttagtat ccaagcaaaa      1020
ttccatcatt gaagaactag aaaaaaaaat agtgactgcc acggtgaata attcagttct      1080
tcaaaagcag caacatgatc tcatggagac agttaataac ttactgacta tgatgtccac      1140
atcaaactca gctaaggacc ccactgttgc taaagaagaa caaatcagct tcagagactg      1200
tgctgaagta ttcaaatcag acacaccac aaatggcatc tacacgttaa cattccctaa      1260
ttctacagaa gagatcaagg cctactgtga catggaagct ggaggaggcg ggtgacaat      1320 tattcagcga cgtgaggatg gcagcgttga ttttcagagg acttggaaag aatataaagt      1380
gggatttggt aacccttcag gagaatattg gctgggaaat gagtttgttt cgcaactgac      1440
taatcagcaa cgctatgtgc ttaaaatac ccttaaagac tgggaaggga atgaggctta      1500
ctcattgtat gaacatttct atctctcaag tgaagaactc aattatagga ttcaccttaa      1560
aggacttaca gggacagccg gcaaaataag cagcatcagc caaccaggaa atgattttag      1620
cacaaaggat ggagacaacg acaaatgtat ttgcaaatgt tcacaaatgc taacaggagg      1680
ctggtggttt gatgcatgtg gtccttccaa cttgaacgga atgtactatc cacagaggca      1740
gaacacaaat aagttcaacg gcattaaatg gtactactgg aaaggctcag gctattcgct      1800
caaggccaca accatgatga tccgaccagc agatttctaa acatcccagt ccacctgagg      1860
aactgtctcg aactattttc aaagacttaa gcccagtgca ctgaaagtca cggctgcgca      1920
ctgtgtcctc ttccaccaca gagggcgtgt gctcggtgct gacgggaccc acatgctcca      1980
gattagagcc tgtaaacttt atcacttaaa cttgcatcac ttaacggacc aaagcaagac      2040
cctaaacatc cataattgtg attagacaga acacctatgc aaagatgaac ccgaggctga      2100
gaatcagact gacagtttac agacgctgct gtcacaacca agaatgttat gtgcaagttt      2160
atcagtaaat aactggaaaa cagaacactt atgttataca atacagatca tcttggaact      2220
gcattcttct gagcactgtt tatacactgt gtaaataccc atatgtcct                   2269
```

<210> SEQ ID NO 4
<211> LENGTH: 496
<212> TYPE: PRT
<213> ORGANISM: Homo sapiens

<400> SEQUENCE: 4

Met Trp Gln Ile Val Phe Phe Thr Leu Ser Cys Asp Leu Val Leu Ala
 1               5                  10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro

-continued

```
                35                  40                  45
Glu Met Asp Asn Cys Arg Ser Ser Ser Pro Tyr Val Ser Asn Ala
 50                  55                  60

Val Gln Arg Asp Ala Pro Leu Glu Tyr Asp Asp Ser Val Gln Arg Leu
 65                  70                  75                  80

Gln Val Leu Glu Asn Ile Met Glu Asn Asn Thr Gln Trp Leu Met Lys
                 85                  90                  95

Leu Glu Asn Tyr Ile Gln Asp Asn Met Lys Lys Glu Met Val Glu Ile
                100                 105                 110

Gln Gln Asn Ala Val Gln Asn Gln Thr Ala Val Met Ile Glu Ile Gly
                115                 120                 125

Thr Asn Leu Leu Asn Gln Thr Ala Glu Gln Thr Arg Lys Leu Thr Asp
130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
                180                 185                 190

Lys Lys Val Leu Ala Met Glu Asp Lys His Ile Ile Gln Leu Gln Ser
                195                 200                 205

Ile Lys Glu Glu Lys Asp Gln Leu Gln Val Leu Val Ser Lys Gln Asn
                210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
                260                 265                 270

Val Ala Lys Glu Glu Gln Ile Ser Phe Arg Asp Cys Ala Glu Val Phe
                275                 280                 285

Lys Ser Gly His Thr Thr Asn Gly Ile Tyr Thr Leu Thr Phe Pro Asn
                290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
                340                 345                 350

Tyr Trp Leu Gly Asn Glu Phe Val Ser Gln Leu Thr Asn Gln Gln Arg
                355                 360                 365

Tyr Val Leu Lys Ile His Leu Lys Asp Trp Glu Gly Asn Glu Ala Tyr
                370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
                420                 425                 430

Cys Ile Cys Lys Cys Ser Gln Met Leu Thr Gly Gly Trp Trp Phe Asp
                435                 440                 445

Ala Cys Gly Pro Ser Asn Leu Asn Gly Met Tyr Tyr Pro Gln Arg Gln
450                 455                 460
```

```
Asn Thr Asn Lys Phe Asn Gly Ile Lys Trp Tyr Trp Lys Gly Ser
465                 470                 475                 480

Gly Tyr Ser Leu Lys Ala Thr Thr Met Met Ile Arg Pro Ala Asp Phe
                485                 490                 495
```

<210> SEQ ID NO 5
<211> LENGTH: 495
<212> TYPE: PRT
<213> ORGANISM: Homo sapiens

<400> SEQUENCE: 5

```
Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Phe Ser Ser Gln Lys Leu
65                  70                  75                  80

Gln His Leu Glu His Val Met Glu Asn Tyr Thr Gln Trp Leu Gln Lys
                85                  90                  95

Leu Glu Asn Tyr Ile Val Glu Asn Met Lys Ser Glu Met Ala Gln Ile
            100                 105                 110

Gln Gln Asn Ala Val Gln Asn His Thr Ala Thr Met Leu Glu Ile Gly
        115                 120                 125

Thr Ser Leu Leu Ser Gln Thr Ala Glu Gln Thr Arg Lys Leu Thr Asp
    130                 135                 140

Val Glu Thr Gln Val Leu Asn Gln Thr Ser Arg Leu Glu Ile Gln Leu
145                 150                 155                 160

Leu Glu Asn Ser Leu Ser Thr Tyr Lys Leu Glu Lys Gln Leu Leu Gln
                165                 170                 175

Gln Thr Asn Glu Ile Leu Lys Ile His Glu Lys Asn Ser Leu Leu Glu
            180                 185                 190

His Lys Ile Leu Glu Met Glu Gly Lys His Lys Glu Glu Leu Asp Thr
        195                 200                 205

Leu Lys Glu Glu Lys Glu Asn Leu Gln Gly Leu Val Thr Arg Gln Thr
    210                 215                 220

Tyr Ile Ile Gln Glu Leu Glu Lys Gln Leu Asn Arg Ala Thr Thr Asn
225                 230                 235                 240

Asn Ser Val Leu Gln Lys Gln Gln Leu Glu Leu Met Asp Thr Val His
                245                 250                 255

Asn Leu Val Asn Leu Ser Thr Lys Glu Gly Val Leu Leu Lys Gly Gly
            260                 265                 270

Lys Arg Glu Glu Glu Lys Pro Phe Arg Asp Cys Ala Asp Val Tyr Gln
        275                 280                 285

Ala Gly Phe Asn Lys Ser Gly Ile Tyr Thr Ile Tyr Ile Asn Asn Met
    290                 295                 300

Pro Glu Pro Lys Lys Val Phe Cys Asn Met Asp Val Asn Gly Gly Gly
305                 310                 315                 320

Trp Thr Val Ile Gln His Arg Glu Asp Gly Ser Leu Asp Phe Gln Arg
                325                 330                 335

Gly Trp Lys Glu Tyr Lys Met Gly Phe Gly Asn Pro Ser Gly Glu Tyr
```

```
                      340                 345                 350
Trp Leu Gly Asn Glu Phe Ile Phe Ala Ile Thr Ser Gln Arg Gln Tyr
            355                 360                 365

Met Leu Arg Ile Glu Leu Met Asp Trp Glu Gly Asn Arg Ala Tyr Ser
        370                 375                 380

Gln Tyr Asp Arg Phe His Ile Gly Asn Glu Lys Gln Asn Tyr Arg Leu
385                 390                 395                 400

Tyr Leu Lys Gly His Thr Gly Thr Ala Gly Lys Gln Ser Ser Leu Ile
                405                 410                 415

Leu His Gly Ala Asp Phe Ser Thr Lys Asp Ala Asp Asn Asp Asn Cys
            420                 425                 430

Met Cys Lys Cys Ala Leu Met Leu Thr Gly Gly Trp Trp Phe Asp Ala
        435                 440                 445

Cys Gly Pro Ser Asn Leu Asn Gly Met Phe Tyr Thr Ala Gly Gln Asn
        450                 455                 460

His Gly Lys Leu Asn Gly Ile Lys Trp His Tyr Phe Lys Gly Pro Ser
465                 470                 475                 480

Tyr Ser Leu Arg Ser Thr Thr Met Met Ile Arg Pro Leu Asp Phe
                485                 490                 495

<210> SEQ ID NO 6
<211> LENGTH: 381
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 6
aagcttcagg tgcaactgca ggagtctgga cctgagctgg taaagcctgg ggcttcagtg      60
aagatgtcct gcaaggcttc tggatacaca ttcactagct atgttttcca ctgggtgaag     120
cagaaacctg gcagggcct tgagtggatt ggatatatta atccttacaa tgatgttact     180
aagtacaatg agaagttcaa aggcaaggcc acactgactt cagacaaatc ctccagcaca     240
gcctacatgg agctcagcag cctgacctct gaggactctg cggtctatta ctgtgcaagc     300
tactacggta gtagttacgg atactatgct atggacgact ggggccaagg gaccacggtc     360
accgtttcct ctggcggtgg c                                               381

<210> SEQ ID NO 7
<211> LENGTH: 127
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 7

Lys Leu Gln Val Gln Leu Gln Glu Ser Gly Pro Glu Leu Val Lys Pro
  1               5                  10                  15

Gly Ala Ser Val Lys Met Ser Cys Lys Ala Ser Gly Tyr Thr Phe Thr
            20                  25                  30

Ser Tyr Val Phe His Trp Val Lys Gln Lys Pro Gly Gln Gly Leu Glu
        35                  40                  45

Trp Ile Gly Tyr Ile Asn Pro Tyr Asn Asp Val Thr Lys Tyr Asn Glu
    50                  55                  60

Lys Phe Lys Gly Lys Ala Thr Leu Thr Ser Asp Lys Ser Ser Ser Thr
65                  70                  75                  80
```

```
Ala Tyr Met Glu Leu Ser Ser Leu Thr Ser Glu Asp Ser Ala Val Tyr
             85                  90                  95

Tyr Cys Ala Ser Tyr Tyr Gly Ser Ser Tyr Gly Tyr Tyr Ala Met Asp
            100                 105                 110

Asp Trp Gly Gln Gly Thr Thr Val Thr Val Ser Ser Gly Gly Gly
            115                 120                 125
```

<210> SEQ ID NO 8
<211> LENGTH: 347
<212> TYPE: DNA
<213> ORGANISM: Artificial Sequence
<220> FEATURE:
<223> OTHER INFORMATION: Description of Artificial Sequence: SYNTHETIC OLIGONUCLEOTIDE

<400> SEQUENCE: 8

```
gacatccagc tgacgcagtc tccagcatcc ctgagtgtgt cagcaggaga gaaggtcact      60
atgagctgca agtccagtca gagtctgtta aacagtggaa atcaaaagaa ctacttggcc     120
tggtatcagc agaaaccagg gcagcctcct aaactgttga tccacggggc atccactagg     180
gaatctgggg tccctgatcg cttcacaggc agtggatctg gaaccgattt cactcttacc     240
atcagcagtg tgcaggctga agacctggca gtttattact gtcagaatga ttatagttat     300
cctctcacgt tcggtgctgg caccaagctg gaactgaaac gtctaga                   347
```

<210> SEQ ID NO 9
<211> LENGTH: 115
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 9

```
Asp Ile Gln Leu Thr Gln Ser Pro Ala Ser Leu Ser Val Ser Ala Gly
  1               5                  10                  15

Glu Lys Val Thr Met Ser Cys Lys Ser Ser Gln Ser Leu Leu Asn Ser
             20                  25                  30

Gly Asn Gln Lys Asn Tyr Leu Ala Trp Tyr Gln Gln Lys Pro Gly Gln
         35                  40                  45

Pro Pro Lys Leu Leu Ile His Gly Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
             85                  90                  95

Asp Tyr Ser Tyr Pro Leu Thr Phe Gly Ala Gly Thr Lys Leu Glu Leu
            100                 105                 110

Lys Arg Leu
        115
```

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence: SYNTHETIC PEPTIDE

<400> SEQUENCE: 10

```
Ala Pro Met Ala Glu Gly Gly Gln Asn His His Glu Val Val Lys
 1               5                  10                  15

Phe Met Asp Val Tyr Gln Arg Ser Tyr Cys
            20                  25
```

<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 11

```
Ala Pro Met Ala Glu Gly Glu Gln Lys Pro Arg Glu Val Val Lys Phe
 1               5                  10                  15

Met Asp Val Tyr Lys Arg Ser Tyr Cys
            20                  25
```

<210> SEQ ID NO 12
<211> LENGTH: 573
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE
<220> FEATURE:
<221> NAME/KEY: CDS
<222> LOCATION: (1)..(573)

<400> SEQUENCE: 12

```
atg cat cac cat cac cat cac cat act cat cag gac ttt cag cca gtg      48
Met His His His His His His His Thr His Gln Asp Phe Gln Pro Val
 1               5                  10                  15 ctc cac ctg gtg gca ctg aac acc ccc ctg tct gga ggc atg cgt ggt      96
Leu His Leu Val Ala Leu Asn Thr Pro Leu Ser Gly Gly Met Arg Gly
            20                  25                  30 atc cgt gga gca gat ttc cag tgc ttc cag caa gcc cga gcc gtg ggg     144
Ile Arg Gly Ala Asp Phe Gln Cys Phe Gln Gln Ala Arg Ala Val Gly
        35                  40                  45 ctg tcg ggc acc ttc cgg gct ttc ctg tcc tct agg ctg cag gat ctc     192
Leu Ser Gly Thr Phe Arg Ala Phe Leu Ser Ser Arg Leu Gln Asp Leu
    50                  55                  60 tat agc atc gtg cgc cgt gct gac cgg ggg tct gtg ccc atc gtc aac     240
Tyr Ser Ile Val Arg Arg Ala Asp Arg Gly Ser Val Pro Ile Val Asn
65                  70                  75                  80 ctg aag gac gag gtg cta tct ccc agc tgg gac tcc ctg ttt tct ggc     288
Leu Lys Asp Glu Val Leu Ser Pro Ser Trp Asp Ser Leu Phe Ser Gly
                85                  90                  95 tcc cag ggt caa ctg caa ccc ggg gcc cgc atc ttt tct ttt gac ggc     336
Ser Gln Gly Gln Leu Gln Pro Gly Ala Arg Ile Phe Ser Phe Asp Gly
            100                 105                 110 aga gat gtc ctg aga cac cca gcc tgg ccg cag aag agc gta tgg cac     384
Arg Asp Val Leu Arg His Pro Ala Trp Pro Gln Lys Ser Val Trp His
        115                 120                 125 ggc tcg gac ccc agt ggg cgg agg ctg atg gag agt tac tgt gag aca     432
Gly Ser Asp Pro Ser Gly Arg Arg Leu Met Glu Ser Tyr Cys Glu Thr
    130                 135                 140 tgg cga act gaa act act ggg gct aca ggt cag gcc tcc tcc ctg ctg     480
Trp Arg Thr Glu Thr Thr Gly Ala Thr Gly Gln Ala Ser Ser Leu Leu
145                 150                 155                 160 tca ggc agg ctc ctg gaa cag aaa gct gcg agc tgc cac aac agc tac     528
Ser Gly Arg Leu Leu Glu Gln Lys Ala Ala Ser Cys His Asn Ser Tyr
```

```
                        165                 170                 175
atc gtc ctg tgc att gag aat agc ttc atg acc tct ttc tcc aaa         573
Ile Val Leu Cys Ile Glu Asn Ser Phe Met Thr Ser Phe Ser Lys
        180                 185                 190
```

<210> SEQ ID NO 13
<211> LENGTH: 191
<212> TYPE: PRT
<213> ORGANISM: Artificial Sequence
<220> FEATURE:
<223> OTHER INFORMATION: Description of Artificial Sequence: SYNTHETIC

<400> SEQUENCE: 13

```
Met His His His His His His Thr His Gln Asp Phe Gln Pro Val
 1               5                  10                  15

Leu His Leu Val Ala Leu Asn Thr Pro Leu Ser Gly Gly Met Arg Gly
                20                  25                  30

Ile Arg Gly Ala Asp Phe Gln Cys Phe Gln Gln Ala Arg Ala Val Gly
        35                  40                  45

Leu Ser Gly Thr Phe Arg Ala Phe Leu Ser Ser Arg Leu Gln Asp Leu
    50                  55                  60

Tyr Ser Ile Val Arg Arg Ala Asp Arg Gly Ser Val Pro Ile Val Asn
65                  70                  75                  80

Leu Lys Asp Glu Val Leu Ser Pro Ser Trp Asp Ser Leu Phe Ser Gly
                85                  90                  95

Ser Gln Gly Gln Leu Gln Pro Gly Ala Arg Ile Phe Ser Phe Asp Gly
                100                 105                 110

Arg Asp Val Leu Arg His Pro Ala Trp Pro Gln Lys Ser Val Trp His
        115                 120                 125

Gly Ser Asp Pro Ser Gly Arg Arg Leu Met Glu Ser Tyr Cys Glu Thr
    130                 135                 140

Trp Arg Thr Glu Thr Thr Gly Ala Thr Gly Gln Ala Ser Ser Leu Leu
145                 150                 155                 160

Ser Gly Arg Leu Leu Glu Gln Lys Ala Ala Ser Cys His Asn Ser Tyr
                165                 170                 175

Ile Val Leu Cys Ile Glu Asn Ser Phe Met Thr Ser Phe Ser Lys
        180                 185                 190
```

<210> SEQ ID NO 14
<211> LENGTH: 182
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 14

```
His Ser His Arg Asp Phe Gln Pro Val Leu His Leu Val Ala Leu Asn
 1               5                  10                  15

Ser Pro Leu Ser Gly Gly Met Arg Gly Ile Arg Gly Ala Asp Phe Gln
                20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
```

```
                    85                  90                  95
Gly Ala Arg Ile Phe Ser Phe Asp Gly Lys Asp Val Leu Arg His Pro
            100                 105                 110
Thr Trp Pro Gln Lys Ser Val Trp His Gly Ser Asp Pro Asn Gly Arg
        115                 120                 125
Arg Leu Thr Glu Ser Tyr Cys Glu Thr Trp Arg Thr Glu Ala Pro Ser
    130                 135                 140
Ala Thr Gly Gln Ala Ser Ser Leu Leu Gly Gly Arg Leu Leu Gly Gln
145                 150                 155                 160
Ser Ala Ala Ser Cys His His Ala Tyr Ile Val Leu Cys Ile Glu Asn
                165                 170                 175
Ser Phe Met Thr Ala Ser
            180

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 15

Pro Arg Phe Lys Ile Ile Gly Gly
 1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 16

Pro Arg Phe Arg Ile Ile Gly Gly
 1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 17

Ser Ser Arg His Arg Arg Ala Leu Asp
 1               5

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 18

Arg Lys Ser Ser Ile Ile Ile Arg Met Arg Asp Val Val Leu
 1               5                  10

<210> SEQ ID NO 19
<211> LENGTH: 15
```

```
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 19

Ser Ser Ser Phe Asp Lys Gly Lys Tyr Lys Lys Gly Asp Asp Ala
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 20

Ser Ser Ser Phe Asp Lys Gly Lys Tyr Lys Arg Gly Asp Asp Ala
 1               5                  10                  15

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 21

Ile Glu Gly Arg
 1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 22

Ile Asp Gly Arg
 1

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 23

Gly Gly Ser Ile Asp Gly Arg
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 24

Pro Leu Gly Leu Trp Ala
```

```
   1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 25

Gly Pro Gln Gly Ile Ala Gly Gln
  1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 26

Gly Pro Gln Gly Leu Leu Gly Ala
  1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 27

Gly Ile Ala Gly Gln
  1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 28

Gly Pro Leu Gly Ile Ala Gly Ile
  1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 29

Gly Pro Glu Gly Leu Arg Val Gly
  1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: SYNTHETIC
```

```
              PEPTIDE

<400> SEQUENCE: 30

Tyr Gly Ala Gly Leu Gly Val Val
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 31

Ala Gly Leu Gly Val Val Glu Arg
 1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 32

Ala Gly Leu Gly Ile Ser Ser Thr
 1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 33

Glu Pro Gln Ala Leu Ala Met Ser
 1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 34

Gln Ala Leu Ala Met Ser Ala Ile
 1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 35

Ala Ala Tyr His Leu Val Ser Gln
 1               5

<210> SEQ ID NO 36
```

```
<211> LENGTH: 8
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 36

Met Asp Ala Phe Leu Glu Ser Ser
 1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 37

Glu Ser Leu Pro Val Val Ala Val
 1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 38

Ser Ala Pro Ala Val Glu Ser Glu
 1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 39

Asp Val Ala Gln Phe Val Leu Thr
 1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 40

Val Ala Gln Phe Val Leu Thr Glu
 1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 41
```

-continued

```
Ala Gln Phe Val Leu Thr Glu Gly
  1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 42

Pro Val Gln Pro Ile Gly Pro Gln
  1               5

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence:  SYNTHETIC
      OLIGONUCLEOTIDE

<400> SEQUENCE: 43
agaccatggg tcatactcat caggactttc a                                         31

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence:  SYNTHETIC
      OLIGONUCLEOTIDE

<400> SEQUENCE: 44
ctaccatggc tatttggaga aagaggtca                                            29
```